(12) United States Patent
Heartlein et al.

(10) Patent No.: US 10,420,791 B2
(45) Date of Patent: *Sep. 24, 2019

(54) CFTR MRNA COMPOSITIONS AND RELATED METHODS AND USES

(71) Applicants: Translate Bio, Inc., Lexington, MA (US); Ethris GmbH, Planegg (DE)

(72) Inventors: Michael Heartlein, Cambridge, MA (US); Braydon Charles Guild, Concord, MA (US); Frank DeRosa, Cambridge, MA (US); Carsten Rudolph, Planegg (DE); Christian Plank, Planegg (DE); Lianne Smith, Cambridge, MA (US)

(73) Assignee: Translate Bio, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/625,648

(22) Filed: Jun. 16, 2017

(65) Prior Publication Data

US 2018/0015116 A1    Jan. 18, 2018

Related U.S. Application Data

(60) Division of application No. 14/876,071, filed on Oct. 6, 2015, now Pat. No. 9,713,626, which is a division of application No. 14/307,322, filed on Jun. 17, 2014, now Pat. No. 9,181,321, which is a continuation of application No. PCT/US2014/028849, filed on Mar. 14, 2014.

(60) Provisional application No. 61/783,663, filed on Mar. 14, 2013.

(51) Int. Cl.
| | | |
|---|---|---|
| *A61K 48/00* | (2006.01) | |
| *C12N 15/63* | (2006.01) | |
| *C07H 21/04* | (2006.01) | |
| *A61K 31/713* | (2006.01) | |
| *C07K 14/705* | (2006.01) | |
| *A61K 31/7105* | (2006.01) | |
| *A61K 31/7115* | (2006.01) | |
| *A61K 9/00* | (2006.01) | |
| *A61K 9/51* | (2006.01) | |
| *A61K 9/127* | (2006.01) | |
| *C12N 9/14* | (2006.01) | |
| *A61K 47/69* | (2017.01) | |
| *C07H 21/02* | (2006.01) | |
| *C07K 14/47* | (2006.01) | |
| *C12N 15/88* | (2006.01) | |

(52) U.S. Cl.
CPC .......... *A61K 31/713* (2013.01); *A61K 9/0073* (2013.01); *A61K 9/0078* (2013.01); *A61K 9/1271* (2013.01); *A61K 9/5123* (2013.01); *A61K 31/7105* (2013.01); *A61K 31/7115* (2013.01); *A61K 47/6935* (2017.08); *A61K 48/005* (2013.01); *C07K 14/705* (2013.01); *C12N 9/14* (2013.01); *A61K 9/127* (2013.01); *A61K 48/00* (2013.01); *C07H 21/02* (2013.01); *C07K 14/4712* (2013.01); *C12N 15/63* (2013.01); *C12N 15/88* (2013.01); *C12Y 306/03049* (2013.01)

(58) Field of Classification Search
CPC .. A61K 9/0073; A61K 9/1271; A61K 48/005; C12N 15/63; C07H 21/02
USPC ........................ 514/44 R; 435/455; 536/23.5
See application file for complete search history.

(56) References Cited

U.S. PATENT DOCUMENTS

| | | | |
|---|---|---|---|
| 2,647,121 | A | 7/1953 | Jacoby |
| 2,717,909 | A | 9/1955 | Kosmin |
| 2,819,718 | A | 1/1958 | Goldman |
| 2,844,629 | A | 7/1958 | William et al. |
| 3,096,560 | A | 7/1963 | Liebig |
| 3,535,289 | A | 10/1970 | Yoshihara et al. |
| 3,614,954 | A | 10/1971 | Mirowski et al. |
| 3,614,955 | A | 10/1971 | Mirowski |
| 3,656,185 | A | 4/1972 | Carpentier |
| 3,805,301 | A | 4/1974 | Liebig |
| 3,945,052 | A | 3/1976 | Liebig |
| 3,995,623 | A | 12/1976 | Blake et al. |
| 4,013,507 | A | 3/1977 | Rembaum |
| 4,072,146 | A | 2/1978 | Howes |
| 4,096,860 | A | 6/1978 | McLaughlin |
| 4,099,528 | A | 7/1978 | Sorenson et al. |
| 4,106,129 | A | 8/1978 | Carpentier et al. |
| 4,134,402 | A | 1/1979 | Mahurkar |
| 4,140,126 | A | 2/1979 | Choudhury |
| 4,180,068 | A | 12/1979 | Jacobsen et al. |
| 4,182,833 | A | 1/1980 | Hicks |
| 4,227,533 | A | 10/1980 | Godfrey |
| 4,284,459 | A | 8/1981 | Patel et al. |
| 4,308,085 | A | 12/1981 | Horhold et al. |

(Continued)

FOREIGN PATENT DOCUMENTS

| | | |
|---|---|---|
| CA | 2518132 A1 | 3/2006 |
| CA | 2807552 A1 | 2/2012 |

(Continued)

OTHER PUBLICATIONS

U.S. Appl. No. 60/083,294, filed Apr. 28, 1998, Chen et al.

(Continued)

*Primary Examiner* — Shin Lin Chen
(74) *Attorney, Agent, or Firm* — Proskauer Rose LLP; Fangli Chen; Julio J. Mendez

(57) ABSTRACT

The present invention is particularly useful for treating cystic fibrosis. The disclosure concerns method and compositions for treating cystic fibrosis. The method comprises inducing CFTR expression in epithelial cells in a lung of a mammal by contacting the epithelial cells in the lung of the mammal with a composition, where the composition is a pharmaceutical composition comprising in vitro transcribed mRNA.

13 Claims, 58 Drawing Sheets

Specification includes a Sequence Listing.

(56) References Cited

U.S. PATENT DOCUMENTS

| | | |
|---|---|---|
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,375,817 A | 3/1983 | Engle et al. |
| 4,385,631 A | 5/1983 | Uthmann |
| 4,401,472 A | 8/1983 | Gerber |
| 4,406,656 A | 9/1983 | Hattler et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,737,323 A | 4/1988 | Martin et al. |
| 4,762,915 A | 8/1988 | Kung et al. |
| 4,782,836 A | 11/1988 | Alt |
| 4,856,521 A | 8/1989 | Irnich |
| 4,860,751 A | 8/1989 | Callaghan |
| 4,878,908 A | 11/1989 | Martin et al. |
| 4,892,540 A | 1/1990 | Vallana |
| 4,897,355 A | 1/1990 | Eppstein et al. |
| 4,920,016 A | 4/1990 | Allen et al. |
| 4,946,683 A | 8/1990 | Forssen |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,171,678 A | 12/1992 | Behr et al. |
| 5,176,661 A | 1/1993 | Evard et al. |
| 5,194,654 A | 3/1993 | Hostetler et al. |
| 5,200,395 A | 4/1993 | Eto et al. |
| 5,223,263 A | 6/1993 | Hostetler et al. |
| 5,261,419 A | 11/1993 | Osypka |
| 5,264,618 A | 11/1993 | Felgner et al. |
| 5,279,833 A | 1/1994 | Rose |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,552,155 A | 9/1996 | Bailey et al. |
| 5,595,756 A | 1/1997 | Bally et al. |
| 5,607,385 A | 3/1997 | Francischelli et al. |
| 5,609,624 A | 3/1997 | Kalis |
| 5,610,283 A | 3/1997 | Buechler |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,677,124 A | 10/1997 | DuBois et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,705,385 A | 1/1998 | Bally et al. |
| 5,736,573 A | 4/1998 | Galat |
| 5,744,335 A | 4/1998 | Wolff et al. |
| 5,772,694 A | 6/1998 | Bokros et al. |
| 5,776,165 A | 7/1998 | Ripart |
| 5,776,747 A | 7/1998 | Schinstine et al. |
| 5,783,383 A | 7/1998 | Kondo et al. |
| 5,844,107 A | 12/1998 | Hanson et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,965,434 A | 10/1999 | Wolff et al. |
| 5,976,567 A | 11/1999 | Wheeler et al. |
| 5,976,569 A | 11/1999 | Milstein |
| 5,981,501 A | 11/1999 | Wheeler et al. |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,147,055 A | 11/2000 | Hobart et al. |
| 6,152,955 A | 11/2000 | KenKnight et al. |
| 6,165,763 A | 12/2000 | Brown et al. |
| 6,169,923 B1 | 1/2001 | Kroll |
| 6,176,877 B1 | 1/2001 | Buchanan et al. |
| 6,204,297 B1 | 3/2001 | Tracy et al. |
| 6,210,892 B1 | 4/2001 | Bennett et al. |
| 6,214,804 B1 | 4/2001 | Felgner et al. |
| 6,271,208 B1 | 8/2001 | Bischoff |
| 6,271,209 B1 | 8/2001 | Smith et al. |
| 6,287,591 B1 | 9/2001 | Semple et al. |
| 6,299,604 B1 | 10/2001 | Ragheb et al. |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,417,326 B1 | 7/2002 | Cullis et al. |
| 6,485,726 B1 | 11/2002 | Blumberg et al. |
| 6,534,484 B1 | 3/2003 | Wheeler et al. |
| 6,585,410 B1 | 7/2003 | Ryan |
| 6,586,410 B1 | 7/2003 | Wheeler et al. |
| 6,670,178 B1 | 12/2003 | Selden et al. |
| 6,696,424 B1 | 2/2004 | Wheeler |
| 6,733,777 B2 | 5/2004 | Erbacher et al. |
| 6,743,823 B1 | 6/2004 | Summar et al. |
| 6,756,055 B2 | 6/2004 | McDonald et al. |
| 6,790,838 B2 | 9/2004 | Alison et al. |
| 6,815,432 B2 | 11/2004 | Wheeler et al. |
| 6,821,530 B2 | 11/2004 | Koob et al. |
| 6,835,395 B1 | 12/2004 | Semple et al. |
| 6,858,224 B2 | 2/2005 | Wheeler et al. |
| 6,858,225 B2 | 2/2005 | Semple et al. |
| 6,887,665 B2 | 5/2005 | Trulson et al. |
| 6,998,115 B2 | 2/2006 | Langer et al. |
| 7,022,214 B2 | 4/2006 | Olech |
| 7,067,697 B2 | 6/2006 | Gao |
| 7,084,303 B2 | 8/2006 | Watanabe et al. |
| 7,341,738 B2 | 3/2008 | Semple et al. |
| 7,422,902 B1 | 9/2008 | Wheeler et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,901,708 B2 | 3/2011 | MacLachlan et al. |
| 7,972,435 B2 | 7/2011 | Bury et al. |
| 8,021,686 B2 | 9/2011 | Semple et al. |
| 8,071,082 B2 | 12/2011 | Zugates et al. |
| 8,101,741 B2 | 1/2012 | MacLachlan et al. |
| 8,106,022 B2 | 1/2012 | Manoharan et al. |
| 8,158,601 B2 | 4/2012 | Chen et al. |
| 8,188,263 B2 | 5/2012 | MacLachlan et al. |
| RE43,612 E | 8/2012 | Anderson et al. |
| 8,236,943 B2 | 8/2012 | Lee et al. |
| 8,278,036 B2 | 10/2012 | Kariko et al. |
| 8,287,849 B2 | 10/2012 | Langer et al. |

(56) References Cited

U.S. PATENT DOCUMENTS

| | | |
|---|---|---|
| 8,329,070 B2 | 12/2012 | MacLachlan et al. |
| 8,389,238 B2 | 3/2013 | Cooper et al. |
| 8,450,298 B2 | 5/2013 | Mahon et al. |
| 8,450,467 B2 | 5/2013 | Manoharan et al. |
| 8,513,403 B2 | 8/2013 | MacLachlan et al. |
| 8,557,231 B2 | 10/2013 | Langer et al. |
| 8,562,966 B2 | 10/2013 | Zugates et al. |
| 8,569,256 B2 | 10/2013 | Heyes et al. |
| 8,652,512 B2 | 2/2014 | Schmehl et al. |
| 8,691,966 B2 | 4/2014 | Kariko et al. |
| 8,710,200 B2 | 4/2014 | Schrum et al. |
| 8,748,089 B2 | 6/2014 | Kariko et al. |
| 8,802,644 B2 | 8/2014 | Chen et al. |
| 8,808,681 B2 | 8/2014 | Anderson et al. |
| 8,808,982 B2 | 8/2014 | Dahl et al. |
| 8,822,663 B2 | 9/2014 | Schrum et al. |
| 8,828,956 B2 | 9/2014 | Manoharan et al. |
| 8,835,108 B2 | 9/2014 | Kariko et al. |
| 8,846,348 B2 | 9/2014 | Jendrisak et al. |
| 8,853,377 B2 | 10/2014 | Guild et al. |
| 8,859,229 B2 | 10/2014 | Rabinovich et al. |
| 8,883,202 B2 | 11/2014 | Manoharan et al. |
| 8,936,942 B2 | 1/2015 | Heyes et al. |
| 8,969,353 B2 | 3/2015 | Mahon et al. |
| 8,980,864 B2 | 3/2015 | Hoge et al. |
| 8,999,351 B2 | 4/2015 | Manoharan et al. |
| 8,999,950 B2 | 4/2015 | MacLachlan et al. |
| 9,005,930 B2 | 4/2015 | Jendrisak et al. |
| 9,012,219 B2 | 4/2015 | Kariko et al. |
| 9,012,498 B2 | 4/2015 | Manoharan et al. |
| 9,018,187 B2 | 4/2015 | Heyes et al. |
| 9,040,256 B2 | 5/2015 | Grunenwald et al. |
| 9,051,567 B2 | 6/2015 | Fitzgerald et al. |
| 9,061,021 B2 | 6/2015 | Guild et al. |
| 9,061,059 B2 | 6/2015 | Chakraborty et al. |
| 9,074,208 B2 | 7/2015 | MacLachlan et al. |
| 9,080,211 B2 | 7/2015 | Grunenwald et al. |
| 9,085,801 B2 | 7/2015 | Grunenwald et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,181,321 B2 | 11/2015 | Heartlein et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,220,682 B2 | 12/2015 | Manoharan et al. |
| 9,220,683 B2 | 12/2015 | Manoharan et al. |
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,394,234 B2 | 7/2016 | Chen et al. |
| 9,404,127 B2 | 8/2016 | Yaworski et al. |
| 9,428,751 B2 | 8/2016 | MacDonald et al. |
| 9,464,124 B2 | 10/2016 | Bancel et al. |
| 9,492,386 B2 | 11/2016 | MacLachlan et al. |
| 9,504,651 B2 | 11/2016 | MacLachlan et al. |
| 9,504,734 B2 | 11/2016 | Bancel et al. |
| 9,518,272 B2 | 12/2016 | Yaworski et al. |
| 9,572,874 B2 | 2/2017 | Fotin-Mleczek et al. |
| 9,587,003 B2 | 3/2017 | Bancel et al. |
| 9,616,084 B2 | 4/2017 | Mutzke |
| 2002/0022721 A1 | 2/2002 | Trulson et al. |
| 2002/0094528 A1 | 7/2002 | Salafsky |
| 2002/0192651 A1 | 12/2002 | Wheeler et al. |
| 2002/0192721 A1 | 12/2002 | Rizzuto et al. |
| 2002/0193622 A1 | 12/2002 | Watanabe et al. |
| 2003/0082154 A1 | 5/2003 | Leamon |
| 2003/0083272 A1 | 5/2003 | Wiederholt et al. |
| 2003/0104044 A1 | 6/2003 | Semple et al. |
| 2003/0181410 A1 | 9/2003 | Wheeler et al. |
| 2003/0215395 A1 | 11/2003 | Yu et al. |
| 2004/0110709 A1 | 6/2004 | Li et al. |
| 2004/0132683 A1 | 7/2004 | Felgner et al. |
| 2004/0142025 A1 | 7/2004 | MacLachlan et al. |
| 2004/0224912 A1 | 11/2004 | Dobie et al. |
| 2004/0235982 A1 | 11/2004 | Rabasco et al. |
| 2005/0004058 A1 | 1/2005 | Benoit et al. |
| 2005/0008689 A1 | 1/2005 | Semple et al. |
| 2005/0032730 A1 | 2/2005 | Von Der Mulbe et al. |
| 2005/0054026 A1 | 3/2005 | Atsushi et al. |
| 2005/0059005 A1 | 3/2005 | Tuschl et al. |
| 2005/0059624 A1 | 3/2005 | Hoerr et al. |
| 2005/0065107 A1 | 3/2005 | Hobart et al. |
| 2005/0069590 A1 | 3/2005 | Buehler et al. |
| 2005/0079212 A1 | 4/2005 | Wheeler et al. |
| 2005/0143332 A1 | 6/2005 | Monahan et al. |
| 2005/0148786 A1 | 7/2005 | Ikeda et al. |
| 2005/0158302 A1 | 7/2005 | Faustman et al. |
| 2005/0244961 A1 | 11/2005 | Short et al. |
| 2005/0250723 A1 | 11/2005 | Hoerr et al. |
| 2006/0008910 A1 | 1/2006 | MacLachlan et al. |
| 2006/0059576 A1 | 3/2006 | Pasinetti et al. |
| 2006/0069225 A1 | 3/2006 | Wintermantel et al. |
| 2006/0083780 A1 | 4/2006 | Heyes et al. |
| 2006/0172003 A1 | 8/2006 | Meers et al. |
| 2006/0204566 A1 | 9/2006 | Smyth-Templeton et al. |
| 2006/0216343 A1 | 9/2006 | Panzner et al. |
| 2006/0223939 A1 | 10/2006 | Lange et al. |
| 2006/0228404 A1 | 10/2006 | Anderson et al. |
| 2006/0241071 A1 | 10/2006 | Grinstaff et al. |
| 2007/0135372 A1 | 6/2007 | MacLachlan et al. |
| 2007/0142628 A1 | 6/2007 | Ghoshal et al. |
| 2007/0172950 A1 | 7/2007 | Wheeler et al. |
| 2007/0252295 A1 | 11/2007 | Panzner et al. |
| 2007/0275923 A1 | 11/2007 | Chen et al. |
| 2007/0281336 A1 | 12/2007 | Jendrisak et al. |
| 2008/0145338 A1 | 6/2008 | Anderson et al. |
| 2008/0160048 A1 | 7/2008 | Fuller |
| 2008/0242626 A1 | 10/2008 | Zugates et al. |
| 2008/0260706 A1 | 10/2008 | Rabinovich et al. |
| 2009/0023673 A1 | 1/2009 | Manoharan et al. |
| 2009/0093433 A1 | 4/2009 | Woolf et al. |
| 2009/0163705 A1 | 6/2009 | Manoharan et al. |
| 2009/0186805 A1 | 7/2009 | Tabor et al. |
| 2009/0221684 A1 | 9/2009 | Grinstaff et al. |
| 2009/0263407 A1 | 10/2009 | Dande et al. |
| 2009/0270481 A1 | 10/2009 | MacLachlan et al. |
| 2009/0286852 A1 | 11/2009 | Kariko et al. |
| 2009/0326051 A1 | 12/2009 | Corey et al. |
| 2010/0028943 A1 | 2/2010 | Thomas et al. |
| 2010/0035249 A1 | 2/2010 | Hayashizaki et al. |
| 2010/0036084 A1 | 2/2010 | Langer et al. |
| 2010/0041152 A1 | 2/2010 | Wheeler et al. |
| 2010/0047261 A1 | 2/2010 | Hoerr et al. |
| 2010/0120129 A1 | 5/2010 | Amshey et al. |
| 2010/0178699 A1 | 7/2010 | Gao et al. |
| 2010/0189729 A1 | 7/2010 | Hoerr et al. |
| 2010/0267806 A1 | 10/2010 | Bumcrot et al. |
| 2010/0323356 A1 | 12/2010 | Inoue et al. |
| 2010/0331234 A1 | 12/2010 | Mahon et al. |
| 2011/0009641 A1 | 1/2011 | Anderson et al. |
| 2011/0035819 A1 | 2/2011 | Cooper et al. |
| 2011/0038941 A1 | 2/2011 | Lee et al. |
| 2011/0092739 A1 | 4/2011 | Chen et al. |
| 2011/0143397 A1 | 6/2011 | Kariko et al. |
| 2011/0200582 A1 | 8/2011 | Baryza et al. |
| 2011/0244026 A1 | 10/2011 | Guild et al. |
| 2011/0256175 A1 | 10/2011 | Hope et al. |
| 2011/0287435 A1 | 11/2011 | Grunenwald et al. |
| 2011/0293703 A1 | 12/2011 | Mahon et al. |
| 2011/0311583 A1 | 12/2011 | Manoharan et al. |
| 2012/0007803 A1 | 1/2012 | Takatsuka |

(56) References Cited

U.S. PATENT DOCUMENTS

| | | |
|---|---|---|
| 2012/0009222 A1 | 1/2012 | Nguyen et al. |
| 2012/0065252 A1 | 3/2012 | Schrum et al. |
| 2012/0065358 A1 | 3/2012 | Langer et al. |
| 2012/0114831 A1 | 5/2012 | Semple et al. |
| 2012/0128760 A1 | 5/2012 | Manoharan et al. |
| 2012/0129910 A1 | 5/2012 | Thompson et al. |
| 2012/0142756 A1 | 6/2012 | Guild et al. |
| 2012/0195936 A1 | 8/2012 | Rudolph et al. |
| 2012/0202871 A1 | 8/2012 | Heyes et al. |
| 2012/0237975 A1 | 9/2012 | Schrum et al. |
| 2012/0251560 A1 | 10/2012 | Dahlman et al. |
| 2012/0251618 A1 | 10/2012 | Schrum et al. |
| 2012/0328668 A1 | 12/2012 | MacLachlan et al. |
| 2013/0017223 A1 | 1/2013 | Hope et al. |
| 2013/0158021 A1 | 6/2013 | Dong et al. |
| 2013/0195967 A1 | 8/2013 | Guild et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0302401 A1 | 11/2013 | Ma et al. |
| 2014/0010861 A1 | 1/2014 | Bancel et al. |
| 2014/0044772 A1 | 2/2014 | MacLachlan et al. |
| 2014/0094399 A1 | 4/2014 | Langer et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161830 A1 | 6/2014 | Anderson et al. |
| 2014/0162897 A1 | 6/2014 | Grunenwald et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200163 A1 | 7/2014 | Mikkelsen et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221248 A1 | 8/2014 | Jendrisak et al. |
| 2014/0221465 A1 | 8/2014 | Bancel et al. |
| 2014/0227300 A1 | 8/2014 | Chin et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294937 A1 | 10/2014 | MacLachlan et al. |
| 2014/0294938 A1 | 10/2014 | Guild et al. |
| 2014/0294939 A1 | 10/2014 | Guild et al. |
| 2014/0294940 A1 | 10/2014 | Guild et al. |
| 2014/0329884 A1 | 11/2014 | Dong et al. |
| 2014/0343129 A1 | 11/2014 | de Fougerolles et al. |
| 2014/0363876 A1 | 12/2014 | Jendrisak et al. |
| 2015/0004217 A1 | 1/2015 | Guild et al. |
| 2015/0005372 A1 | 1/2015 | Hoge et al. |
| 2015/0011615 A1 | 1/2015 | Manoharan et al. |
| 2015/0011633 A1 | 1/2015 | Shorr et al. |
| 2015/0017211 A1 | 1/2015 | de Fougerolles et al. |
| 2015/0038556 A1 | 2/2015 | Heartlein et al. |
| 2015/0038558 A1 | 2/2015 | Kariko et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0110857 A1 | 4/2015 | DeRosa et al. |
| 2015/0110858 A1 | 4/2015 | DeRosa et al. |
| 2015/0110859 A1 | 4/2015 | Heartlein et al. |
| 2015/0111248 A1 | 4/2015 | Bancel et al. |
| 2015/0111945 A1 | 4/2015 | Geisbert et al. |
| 2015/0119444 A1 | 4/2015 | Manoharan et al. |
| 2015/0119445 A1 | 4/2015 | Manoharan et al. |
| 2015/0157565 A1 | 6/2015 | Heartlein et al. |
| 2015/0166465 A1 | 6/2015 | Chen et al. |
| 2015/0190515 A1 | 7/2015 | Manoharan et al. |
| 2015/0191760 A1 | 7/2015 | Jendrisak et al. |
| 2015/0265708 A1 | 9/2015 | Manoharan et al. |
| 2015/0267192 A1 | 9/2015 | Heartlein et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0256573 A1 | 9/2016 | de Fougerolles et al. |
| 2016/0264971 A1 | 9/2016 | Geisbert et al. |
| 2016/0264975 A1 | 9/2016 | Schrum et al. |
| 2016/0274089 A1 | 9/2016 | Ciufolini et al. |
| 2016/0304552 A1 | 10/2016 | Roy et al. |
| 2016/0317647 A1 | 11/2016 | Ciaramella et al. |
| 2016/0317676 A1 | 11/2016 | Hope et al. |
| 2016/0331828 A1 | 11/2016 | Ciaramella et al. |
| 2016/0348099 A1 | 12/2016 | Roy et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2016/0367687 A1 | 12/2016 | Manoharan et al. |
| 2016/0367702 A1 | 12/2016 | Hoge et al. |
| 2016/0375134 A1 | 12/2016 | Bancel et al. |
| 2016/0375137 A9 | 12/2016 | Manoharan et al. |
| 2017/0000858 A1 | 1/2017 | Fotin-Mleczek et al. |
| 2017/0000870 A1 | 1/2017 | Hoerr et al. |
| 2017/0000871 A1 | 1/2017 | Probst et al. |
| 2017/0002060 A1 | 1/2017 | Bolen et al. |
| 2017/0007702 A1 | 1/2017 | Heyes et al. |
| 2017/0014496 A1 | 1/2017 | Fotin-Mleczek et al. |
| 2017/0028059 A1 | 2/2017 | Baumhof et al. |
| 2017/0029847 A1 | 2/2017 | Thess |
| 2017/0056528 A1 | 3/2017 | De Fougerolles et al. |
| 2017/0056529 A1 | 3/2017 | Thess et al. |
| 2017/0065727 A1 | 3/2017 | Fotin-Mleczek et al. |

FOREIGN PATENT DOCUMENTS

| | | |
|---|---|---|
| CN | 100569877 C | 12/2009 |
| CN | 101863544 A | 10/2010 |
| DE | 2520814 A1 | 11/1976 |
| EP | 6 73 637 A1 | 9/1995 |
| EP | 0783297 A1 | 7/1997 |

(56) References Cited

FOREIGN PATENT DOCUMENTS

| | | |
|---|---|---|
| EP | 0853123 A1 | 7/1998 |
| EP | 0959092 A1 | 11/1999 |
| EP | 1519714 B1 | 4/2005 |
| EP | 1979364 A2 | 10/2008 |
| EP | 2045251 A1 | 4/2009 |
| EP | 2338478 B1 | 6/2011 |
| EP | 2338520 A1 | 6/2011 |
| EP | 2449106 A1 | 5/2012 |
| EP | 2532649 A1 | 12/2012 |
| EP | 2578685 A2 | 4/2013 |
| EP | 2823809 A1 | 1/2015 |
| FR | 2 235 112 A1 | 1/1975 |
| GB | 1072118 A | 6/1967 |
| GB | 1602085 A | 11/1981 |
| JP | H07-053535 | 2/1955 |
| JP | S48-022365 | 3/1973 |
| JP | S49-127908 A | 12/1974 |
| JP | S51-023537 | 2/1976 |
| JP | 51-125144 | 11/1976 |
| JP | S52-010847 | 1/1977 |
| JP | S63125144 A | 5/1988 |
| JP | 63-154788 | 6/1988 |
| JP | H09-505593 A | 6/1997 |
| JP | H10-197978 A | 7/1998 |
| JP | 11-005786 A | 1/1999 |
| JP | 11-080142 | 3/1999 |
| JP | 2001-523215 A | 11/2001 |
| JP | 2002-167368 A | 6/2002 |
| JP | 2003-519199 A | 6/2003 |
| JP | 4-108173 B2 | 6/2008 |
| JP | 2008-247749 A | 10/2008 |
| JP | 50-24216 B2 | 9/2012 |
| WO | WO-90/11092 A1 | 10/1990 |
| WO | WO-93/18229 A1 | 9/1993 |
| WO | WO-93/18754 A1 | 9/1993 |
| WO | WO-95/11004 A1 | 4/1995 |
| WO | WO-95/14651 A1 | 6/1995 |
| WO | WO-95/27478 A1 | 10/1995 |
| WO | WO-96/18372 A2 | 6/1996 |
| WO | WO-96/26179 A1 | 8/1996 |
| WO | WO-96/37211 A1 | 11/1996 |
| WO | WO-96/40964 A2 | 12/1996 |
| WO | WO-97/46223 A1 | 12/1997 |
| WO | WO-98/10748 A1 | 3/1998 |
| WO | WO-98/16202 A2 | 4/1998 |
| WO | WO-98/51278 A2 | 11/1998 |
| WO | WO-99/14346 A2 | 3/1999 |
| WO | WO-00/03044 A1 | 1/2000 |
| WO | WO-00/62813 A2 | 10/2000 |
| WO | WO-00/64484 A2 | 11/2000 |
| WO | WO-00/69913 A1 | 11/2000 |
| WO | WO-01/05375 A1 | 1/2001 |
| WO | WO-01/07599 A1 | 2/2001 |
| WO | WO-02/00870 A2 | 1/2002 |
| WO | WO-02/22709 A1 | 3/2002 |
| WO | WO-02/31025 A2 | 4/2002 |
| WO | WO-02/34236 A2 | 5/2002 |
| WO | WO-02/42317 A2 | 5/2002 |
| WO | WO-03/040288 A2 | 5/2003 |
| WO | WO-03/070735 A2 | 8/2003 |
| WO | WO-2004/043588 A2 | 5/2004 |
| WO | WO-2004/048345 A2 | 6/2004 |
| WO | WO-2004/106411 A2 | 12/2004 |
| WO | WO-2005/026372 A1 | 3/2005 |
| WO | WO-2005/028619 A2 | 3/2005 |
| WO | WO-2005/037226 A2 | 4/2005 |
| WO | WO-2005/121348 A1 | 12/2005 |
| WO | WO-2006/000448 A2 | 1/2006 |
| WO | WO-2006/016097 A2 | 2/2006 |
| WO | WO-2006/082088 A1 | 8/2006 |
| WO | WO-2006/105043 A2 | 10/2006 |
| WO | WO-2006/138380 A2 | 12/2006 |
| WO | WO-2007/024708 A2 | 3/2007 |
| WO | WO-2007/031091 A2 | 3/2007 |
| WO | WO-2007/120863 A2 | 10/2007 |
| WO | WO-2007/126386 A1 | 11/2007 |
| WO | WO-2007/143659 A2 | 12/2007 |
| WO | WO-2008/011561 A2 | 1/2008 |
| WO | WO-2008/042973 A2 | 4/2008 |
| WO | WO-2008/045548 A2 | 4/2008 |
| WO | WO-2008/083949 A2 | 7/2008 |
| WO | WO-2008/113364 A2 | 9/2008 |
| WO | WO-2009/046220 A2 | 4/2009 |
| WO | WO-2009/127060 A1 | 10/2009 |
| WO | WO-2009/127230 A1 | 10/2009 |
| WO | WO-2010/037408 A1 | 4/2010 |
| WO | WO-2010/042877 A1 | 4/2010 |
| WO | WO-2010/045512 A2 | 4/2010 |
| WO | WO-2010/053572 A2 | 5/2010 |
| WO | WO-2010/054401 A1 | 5/2010 |
| WO | WO-2010/054405 A1 | 5/2010 |
| WO | WO-2010/056403 A1 | 5/2010 |
| WO | WO-2010/099387 A1 | 9/2010 |
| WO | WO-2010/114789 A1 | 10/2010 |
| WO | WO-2010/119256 A1 | 10/2010 |
| WO | WO-2010/129709 A1 | 11/2010 |
| WO | WO-2010/144740 A1 | 12/2010 |
| WO | WO-2010/147992 A1 | 12/2010 |
| WO | WO-2010/148013 A2 | 12/2010 |
| WO | WO-2011/012316 A2 | 2/2011 |
| WO | WO-2011/012746 A2 | 2/2011 |
| WO | WO-2011/039144 A1 | 4/2011 |
| WO | WO-2011/068810 A1 | 6/2011 |
| WO | WO-2011/075656 A1 | 6/2011 |
| WO | WO-2011/141705 A1 | 11/2011 |
| WO | WO-2012/019168 A2 | 2/2012 |
| WO | WO-2012/019630 A1 | 2/2012 |
| WO | WO-2012/019780 A1 | 2/2012 |
| WO | WO-2012/027675 A2 | 3/2012 |
| WO | WO-2012/045075 A1 | 4/2012 |
| WO | WO-2012/045082 A2 | 4/2012 |
| WO | WO-2012/075040 A2 | 6/2012 |
| WO | WO-2012/133737 A1 | 10/2012 |
| WO | WO-2012/135025 A2 | 10/2012 |
| WO | WO-2012/135805 A2 | 10/2012 |
| WO | WO-2012/170889 A1 | 12/2012 |
| WO | WO-2012/170930 A1 | 12/2012 |
| WO | WO-2013/039857 A1 | 3/2013 |
| WO | WO-2013/039861 A2 | 3/2013 |
| WO | WO-2013/063468 A1 | 5/2013 |
| WO | WO2013/090186 | 6/2013 |
| WO | WO-2013/101690 A1 | 7/2013 |
| WO | WO-2013/102203 A1 | 7/2013 |
| WO | WO-2013/126803 A1 | 8/2013 |
| WO | WO-2013/130161 A1 | 9/2013 |
| WO | WO-2013/149140 A1 | 10/2013 |
| WO | WO-2013/149141 A1 | 10/2013 |
| WO | WO-2013/151663 A1 | 10/2013 |
| WO | WO-2013/151664 A1 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2013/182683 A1 | 12/2013 |
| WO | WO-2013/185067 A1 | 12/2013 |
| WO | WO-2013/185069 A1 | 12/2013 |
| WO | WO-2014/028487 A1 | 2/2014 |
| WO | WO-2014/089486 A1 | 6/2014 |
| WO | WO-2014/113089 A2 | 7/2014 |
| WO | WO-2014/144039 A1 | 9/2014 |
| WO | WO-2014/144196 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |

(56) References Cited

FOREIGN PATENT DOCUMENTS

| | | |
|---|---|---|
| WO | WO-2014/152774 A1 | 9/2014 |
| WO | WO-2014/152940 A1 | 9/2014 |
| WO | WO-2014/152966 A1 | 9/2014 |
| WO | WO-2014/153052 A2 | 9/2014 |
| WO | WO-2014/158795 A1 | 10/2014 |
| WO | WO-2014/159813 A1 | 10/2014 |
| WO | WO-2014/179562 A1 | 11/2014 |
| WO | WO-2014/210356 A1 | 12/2014 |
| WO | WO-2015/006747 A2 | 1/2015 |
| WO | WO-2015/011633 A1 | 1/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/058069 A1 | 4/2015 |
| WO | WO2015/085318 | 6/2015 |
| WO | WO2015/089511 | 6/2015 |
| WO | WO2016/054421 | 4/2016 |
| WO | WO2016/071857 | 5/2016 |
| WO | WO2016/077123 | 5/2016 |
| WO | WO2016/077125 | 5/2016 |
| WO | WO2016/118724 | 7/2016 |
| WO | WO2016/118725 | 7/2016 |
| WO | WO2016/154127 | 9/2016 |
| WO | WO2016/164762 | 10/2016 |
| WO | WO2016/183366 A2 | 11/2016 |
| WO | WO2016/197132 A1 | 12/2016 |
| WO | WO2016/197133 A1 | 12/2016 |
| WO | WO2016/201377 A1 | 12/2016 |
| WO | WO2016/197133 A2 | 2/2017 |
| WO | WO2017/049074 A1 | 3/2017 |
| WO | WO2017/049275 A2 | 3/2017 |
| WO | WO2017/049286 A1 | 3/2017 |

OTHER PUBLICATIONS

U.S. Appl. No. 61/494,714, filed Jun. 8, 2011, Guild.
Adami, R.C. et al., An amino acid-based amphoteric liposomal delivery system for systemic administration of siRNA. Molecular Therapy 19(6):1141-1151 (2011).
Akinc, A. et al., A combinatorial library of lipid-like materials for delivery of RNAi therapeutics. Nature Biotechnology 26(5):561-569 (2008).
Akinc, A. et al., Development of lipidoid-siRNA formulations for systemic delivery to the liver. Molecular Therapy 17(5):872-879 (2009).
Alton, E.W.F.W. et al., Cationic Lipid-Mediated CFR Gene Transfer to the Lungs and Nose of Patients with Cystic Fibrosis: a Double-Blind Placebo-Controlled Trial, Lancet, 353:947-954 (1999).
Anderson, D.G. et al., Structure/property studies of polymeric gene delivery using a library of poly(beta-amino esters). Molecular Therapy 11(3):426-434 (2005).
Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).
Anderson, J. Biological Responses to Materials. Annual Review of Materials Research 31:81-110 (2001).
Anderson, W. French, Human gene therapy, Nature, 392, 25-30 (1998).
Andries, O. et al., Comparison of the Gene Transfer Efficiency of mRNA/GL67 and pDNA/GL67 Complexes in Respiratory Cells, Mol. Pharmaceut., 9: 2136-2145 (2012).
Auffray, C. et al., Purification of Mouse Immunoglubulin Heavy-Chain Messenger RNAs from Total Myeloma Tumor RNA, European Journal of Biochemistry, 107(2):303-314 (1980).
Author Unknown, Blood Proteins, published by WikiPedia, San Francisco, CA, 2 pages, <http://en.wikipedia.org/wiki/Biood_proteins> downloaded May 17, 2015.
Bahlke, M. A. et al., Progress towards in vivo use of siRNAs, Molecular Therapy, 13:644-670 (2006).

Bajaj, A. et al., Synthesis and gene transfection efficacies of PEI-cholesterol-based lipopolymers. Bioconjugate Chemistry 19(8):1640-516511 (2008).
Barreau, C. et al., Liposome-mediated RNA transfection should be used with caution, RNA, 12:1790-1793 (2006).
Behr, J. et al., Efficient Gene Transfer into Mammalian Primary Endocrine Cells with Lipo Polyamine-Coated DNA, Proc. Nat.'l Acad. Sci., 86: 6982-6986 (1989).
Bennett, J. Immune response following intraocular delivery of recombinant viral vectors, Gene Therapy, 10: 977-982 (2003).
Bhaduri, S. et al., Procedure for the preparation of milligram quantities of adenovirus messenger ribonucleic acid, J. Virol., 10(6): 1126-1129 (1972).
Bloomfield, V.A., Quasi-Elastic Light Scattering Applications in Biochemistry and Biology, Ann. Rev. Biophys. Bioeng. 10:421-450 (1981).
Boussif, O. et al., A versatile vector for gene and oligonucleotide transfer into cells in culture and in vivo: polyethylenimine. Proceedings of the National Academy of Sciences of the USA. 92(16):7297-7301 (1995).
Braun, C.S. et al., ucture/function relationships of polyamidoamine/DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the U S A. 104(36):14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).
Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3):731-741 (2007).
Budker, V. et al., Protein/Amphipathic Polyamine Complexes Enable Highly Efficient Transfection with Minimal Toxicity, BioTechniques, 23: 139-147 (1997).
Burger, G. et al., Sequencing complete mitochondrial and plastid genomes, Nature Protocols, 2: 603-614 (2007).
Burnett, J.C. et al., Current progress of siRNA/shRNA therapeutics in clinical trials. Biotechnology Journal 6(9):1130-1146 (2011).
Byk, G. et al., Synthesis, activity, and structure—activity relationship studies of novel cationic lipids for DNA transfer. Journal of Medical Chemistry 41(2):224-235 (1998).
Caplen, N.J. et al., In vitro liposome-mediated DNA transfection of epithelial cell lines using the cationic liposome DC-Chol/DOPE, Gene Therapy, 2:603-613 (1995).
Cassiman, D. Gene transfer for inborn errors of metabolism of the liver: the clinical perspective, Current Pharmaceutical Design, 17(24):2550-2557 (2011).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chandler, R. et al., Liver-directed adeno-associated virus serotype 8 gene transfer rescues a lethal murine model of citrullinemmia type 1, Gene Therapy, 20:1188-1191 (2013).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).

(56) References Cited

OTHER PUBLICATIONS

Chiou, H.C. et al., Enhanced resistance to nuclease degradation of nucleic acids complexed to; asialoglycoprotein-polylysine carriers, Nucleic Acids Research, 22(24):5439-5446 (1994).

Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).

Conese, M. et al., Gene and Cell Therapy for Cystic Fibrosis: From Bench to Bedside, J. Cyst. Fibros., 10 Suppl 2:S114-s128 (2011).

Cotten, M. et al., Receptor-mediated transport of DNA into eukaryotic cells. Methods in Enzymology 217 (H):618-644 (1993).

Cowling, V.H., Regulation of mRNA cap methylation, Biochemical Journal, 425:295-302 (2010).

Creusat, G. et al., Proton sponge trick for pH-sensitive disassembly of polyethylenimine-based siRNA delivery systems. Bioconjugate Chemistry 21(5):994-1002 (2010).

Crooke, S.T. Molecular mechanisms of action of antisense drugs. Biochimica et Biophysica Acta 1489(1):31-44. Review (1999).

Crystal, R.G. Transfer of genes to humans: early lessons and obstacles to success. Science 270(5235):404-410. Review (1995).

Damen, M. et al., Delivery of DNA and siRNA by novel gemini-like amphiphilic peptides. Journal of Controlled Release 145(1):33-39 (2010).

Dande, P. et al., Improving RNA interference in mammalian cells by 4'-thio-modified small interfering RNA (siRNA): effect on siRNA activity and nuclease stability when used in combination with 2'-0-alkyl modifications, Journal of Medicinal Chemistry, 49(5):1624-1634 (2006).

Davis, M. E., The first targeted delivery of siRNA in humans via a self-assembling, cyclodextrin polymer-based nanoparticle: from concept to clinic. Molecular Pharmacuetics 6(3):659-668 (2009).

Davis, M.E. et al., Evidence of RNAi in humans from systemically administered siRNA via targeted nanoparticles. Nature 464(7291):1067-1070 (2010).

Debus, H. et al., Delivery of Messenger RNA Using Poly(ethylene imine)-poly(ethylene glycol)-Copolymer Blends for Polyplex Formation: Biophysical Characterization and In Vitro Transfection Properties, J. Control. Rel., 148:334-343 (2010).

Decher, G. Fuzzy Nanoassemblies: Toward Layered Polymeric Multicomposites. Science 277: 1232-1237 (1997).

Demeshkina, N. et al., Interactions of the ribosome with mRNA and tRNA, Current Opinion in Structural Biology, 20(3):325-332 (2010).

Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N'',N'''-Tetraacetic Acid (DOTA)-Peptide versus 2IT-DOTA Monoclonal Antibody Linkage for RIT1, Clin. Cancer Res., 9: 3665s (2003).

Dern, R.J. et al., Toxicity studies of pyrimethamine (daraprim). The American Journal of Tropical Medicine and Hygiene 4(2):217-220 (1955).

Deshmukh, H. M and Huang, L., Liposome and polylysine mediated gene therapy. New Journal of Chemistry 21:113-124 (1997).

Discher, B.M. et al., Polymersomes: tough vesicles made from diblock copolymers. Science 284(5417):1143-1146 (1999).

Discher, D.E. and Eisenberg, A., Polymer vesicles. Science 297(5583):967-973. Review (2002).

Dong, Y. et al., Lipopeptide nanoparticles for potent and selective siRNA delivery in rodents and nonhuman primates, Proceedings of the National Academy of Sciences, 111(11): 3955-3960 (2014).

Driscoll, K.E. et al., Intratracheal instillation as an exposure technique for the evaluation of respiratory tract toxicity: uses and limitations, Toxicol. Sci., 55(1): 24-35 (2000).

Drummond, D.C. et al., Optimizing Liposomes for Delivery of Chemotherapeutic Agents to Solid Tumors, Pharmacological Reviews, 51(4): 691-743 (1999).

Dwarki, V. et al., Cationic liposome-mediated RNA transfection, Methods in Enzymology, 217:644-654 (1993).

Elbashir, S.M. et al., RNA interference is mediated by 21- and 22-nucleotide RNAs. Genes & Development 15: 188-200 (2001).

Elton, C., The Next Next Big Thing, Boston Magazine, 106-118 (Mar. 2013).

Emlen, W. et al., Effect of DNA size and strandedness on the in vivo clearance and organ localization of DNA, Clinical & Experimental Immunology, 56:185-192 (1984).

Eon-Duval, A. et al., Removal of RNA impurities by tangential flow filtration in an RNase-free plasmid DNA purification process, Analytical Biochemistry, 316(1):66-73 (2003).

Ernst, N. et al., Interaction of Liposomal and Polycationic Transfection Complexes with Pulmonary Surfactant, J. Gene. Med., 1:331-340 (1999).

Estimated Number of Animal and Plant Species on Earth, http://www.factmonster.com/ipka/A0934288.html, 2000-2014, 3 pages, (Retrieved Aug. 2, 2014).

Ewert, K. et al., Cationic lipid-DNA complexes for gene therapy: understanding the relationship between complex structure and gene delivery pathways at the molecular level. Current Medicinal Chemistry 11(2): 133-149 (2004).

Fath, S. et al., Multiparameter RNA and Codon Optimization: A Standardized Tool to Assess and Enhance Autologous Mammalian Gene Expression, PLoS One, 6(3):e17596 (14 pages) 2011.

Fechter, P. and Brownlee, G. G., Recognition of mRNA cap structures by viral and cellular proteins, Journal of General Virology, 86:1239-1249 (2005).

Felgner, P.L. and Ringold, G.M., Cationic liposome-mediated transfection, Nature, 337(6205):387-388 (1989).

Felgner, P.L. et al., Lipofection: A Highly Efficient, Lipid-Mediated DNA-Transfection Procedure, Proc. Natl. Acad., 84:7413-7417 (1987).

Fenske, D.B. and Cullis, P., Liposomal nanomedicines. Expert Opinion on Drug Delivery 5(1):25-44 (2008).

Fernandez, V. et al., Cross Flow Filtration of RNA Extracts by Hollow Fiber Membrane, Acta Biotechnologica, 12(1):49-56 (1992).

Ferruti, P.F. and Barbucci, R., Linear amino polymers: Synthesis, protonation and complex formation. Advances in Polymer Science 58:55-92 (1984).

Ferruti, P.F. et al., A novel modification of poly(l-lysine) leading to a soluble cationic polymer with reduced toxicity and with potential as a transfection agent. Macromolecular Chemistry and Physics 199:2565-2575 (1998).

Fire, A. et al., Potent and specific genetic interference by double-stranded RNA in Caenorhabditis elegans. Nature 391(6669):806-811 (1998).

Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-992 (2004).

Fumoto, S. et al., Targeted Gene Delivery: Importance of Administration Routes, Novel Gene Therapy Approaches, 3-31 (2013).

Furgeson, D.Y. et al., Modified linear polyethylenimine-cholesterol conjugates for DNA complexation. Bioconjugate Chemistry 14(4):840-847 (2003).

Furgeson, D.Y. et al., Novel water insoluble lipoparticulates for gene delivery. Pharmaceutical Research 19(4): 382-390 (2002).

Galipon, J. et al., Stress-induced lncRNAs evade nuclear degradation and enter the translational machinery, Genes to Cells, 18(5):353-368 (2013).

Gao, X. and Huang, L., A novel cationic liposome reagent for efficient transfection of mammalian cells, Biochem. Biophys. Res. Comm., 179(1): 280-285 (1991).

Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).

Geraerts, M. et al., Upscaling of lentiviral vector production by tangential flow filtration, Journal of Gene Medicine, 7(10):1299-1310 (2005).

Godbey, W.T. et al., Size matters: molecular weight affects the efficiency of poly(ethylenimine) as a gene delivery vehicle. Journal of Biomedical Materials Research 45(3):268-275 (1998).

Gonzalez, H. et al., New class of polymers for the delivery of macromolecular therapeutics. Bioconjugate Chemistry 10(6):1068-1074 (1999).

(56) References Cited

OTHER PUBLICATIONS

Gonzalez-Aseguinolaza, G. et al., Gene therapy of liver diseases: A 2011 perspective, Clinics and Research in Hepatology and Gastroenterology, 35(11):699-708 (2011).
Gordon, N. Ornithine transcarbamylase deficiency: a urea cycle defect, European Journal of Paediatric Neurology, 7:115-121 (2003).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA Biology, 10(9):1479-1487 (2004).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).
Gust, T.C. et al., RNA-containing adenovirus/polyethylenimine transfer complexes effectively transduce dendritic cells and induce antigen-specific T cell responses, The Journal of Gene Medicine, 6(4): 464-470 (2004).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Harada-Shiba, M. et al., Polyion complex micelles as vectors in gene therapy—pharmacokinetics and in vivo; gene transfer, Gene Therapy, 9(6):407-414 (2002).
Haskins M., Gene Therapy for Lysosomal Storage Disorders (LDSs) in Large Animal Models, ILAR J., 50(2):112-121 (2009).
Hata, A. et al., Isolation and Characterization of the Human Ornithine Transcarbamylase Gene: Structure of the 5'-End Region, Journal of Biochemistry, 100:717-725 (1986).
Hecker, J. et al., Advances in Self-Limited Gene Expression of Protective Intracellular Proteins In-Vivo in Rat Brain Using mRNA / Cationic Lipid Complexes, Anesthesia and Analgesia, 86(2S):346S (1994).
Heidenreich, O. et al., High Activity and Stability of Hammerhead Ribozymes Containing 2'-Modified Pyrimidine Nucleosides and Phosphorothioates, The Journal of Biological Chemistry, 269(3):2131-2138 (1994).
Henkin, R. I. et al., Inhaled Insulin—Intrapulmonary, intranasal, and other routes of administration: Mechanisms of action, Nutrition, 26: 33-39 (2010).
Hess, P. R. et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy:CII, 55(6): 672-683 (2006).
Heyes, J. et al., Cationic Lipid Saturation Influences Intracellular Delivery of Encapsulated Nucleic Acids, J. Controlled Release, 107:276-287 (2005).
Higman, M.A. et al., The mRNA (Guanine-7-)methyltransferase Domain of the Vaccinia Virus mRNA Capping Enzyme, The Journal of Biological Chemistry, 269(21):14974-14981 (1994).
Hill, I.R.C. et al., In vitro cytotoxicity of poly(amidoamine)s: relevance to DNA delivery. Biochimica et Biophysica Acta 1427: 161-174 (1999).
Hill, J.G. et al., Enantioselective Epoxidation of Allylic Alcohols: (2S,3S)-3-Propyloxiranemethanol. Organic Syntheses Collection 7: 461 (1990) and 63: 66 (1985) (8 pages).
Hillery, A.M. et al., Drug Delivery and Targeting for Pharmacists and Pharmaceutical Scientists, Taylor and Francis (2005).
Hoerr, I. et al., In Vivo Application of RNA Leads to Induction of Specific Cytotoxic T Lymphocytes and Antibodies, European Journal of Immunology, 30(1):1-7 (2000).

Hofland, H.E.J et al., Formation of stable cationic lipid/DNA complexes for gene transfer. Proceedings of the National Academy of Sciences of the USA 93 (14): 7305-7309 (1996).
*Homo sapiens* galactosidase, alpha (GLA) mRNA, NCBI Reference Sequence NM_000169.1, Modification Date: Nov. 17, 2006.
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hope, M.J. et al., Reduction of Liposome Size and Preparation of Unilamellar Vesicles by Extrusion Techniques, In: Liposome Technology, 1:123-139 (1993).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Horwich, A.L. et al., Structure and Expression of a Complementary DNA for the Nuclear Coded Precursor of Human Mitochondrial Ornithine Transcarbamylase, Science, 224(4653):1068-1074 (1984).
Horwich, A.L. et al., Targeting of Pre-Ornithine Transcarbamylase to Mitochondria: Definition of Critical Regions and Residues in the Leader Peptide, Cell, 44:451-459 (1986).
Howard, K.A. Delivery of RNA interference therapeutics using polycation-based nanoparticles. Advanced Drug Delivery Reviews 61: 710-720 (2009).
Huang, Z. et al., Thiocholesterol-based lipids for ordered assembly of bioresponsive gene carriers, Molecular Therapy, 11(3):409-417 (2005).
Huttenhofer, A. and Noller, H., Footprinting mRNA-ribosome complexes with chemical probes, The EMBO Journal, 13(16):3892-3901 (1994).
Incani, V. et al., Lipid and hydrophobic modification of cationic carriers on route to superior gene vectors. Soft Matter 6: 2124-2138 (2010).
International Preliminary Report on Patentability for PCT/US2010/058457, 12 pages (dated Jun. 14, 2012).
International Search Report for PCT/US15/27563, 5 pages (dated Sep. 18, 2015).
International Search Report for PCT/US2010/058457, 4 pages (dated May 6, 2011).
International Search Report for PCT/US2011/062459, 3 pages (dated Apr. 11, 2012).
International Search Report for PCT/US2012/041663, 4 pages (dated Oct. 8, 2012).
International Search Report for PCT/US2012/041724, 5 pages (dated Oct. 25, 2012).
International Search Report for PCT/US2013/034602, 2 pages (dated Jun. 17, 2013).
International Search Report for PCT/US2013/034604, 4 pages (dated Jun. 17, 2013).
International Search Report for PCT/US2013/044769, 4 pages (dated Nov. 12, 2013).
International Search Report for PCT/US2013/044771, 6 pages (dated Nov. 1, 2013).
International Search Report for PCT/US2013/073672, 6 pages (dated Mar. 3, 2014).
International Search Report for PCT/US2014/027422, 5 pages (dated Jul. 31, 2014).
International Search Report for PCT/US2014/027585, 3 pages (dated Jul. 14, 2014).
International Search Report for PCT/US2014/027587, 6 pages (dated Jul. 24, 2014).
International Search Report for PCT/US2014/027602, 6 pages (dated Jul. 28, 2014).
International Search Report for PCT/US2014/027717, 5 pages (dated Jul. 16, 2014).
International Search Report for PCT/US2014/028330, 5 pages (dated Jul. 22, 2014).
International Search Report for PCT/US2014/028441, 6 pages (dated Jul. 22, 2014).
International Search Report for PCT/US2014/028498, 5 pages (dated Jul. 28, 2014).
International Search Report for PCT/US2014/028849, 6 pages (dated Jul. 17, 2015).

(56) References Cited

OTHER PUBLICATIONS

International Search Report for PCT/US2014/061786, 6 pages (dated Feb. 6, 2015).
International Search Report for PCT/US2014/061793, 4 pages (dated Feb. 6, 2015).
International Search Report for PCT/US2014/061830, 5 pages (dated Feb. 4, 2015).
International Search Report for PCT/US2014/061841, 6 pages (dated Feb. 24, 2015).
International Search Report for PCT/US2015/039004, 4 pages (dated Oct. 6, 2015).
International Search Report for PCT/US2015/21403 (4 pages) dated Jun. 15, 2015.
Jakobsen, K. et al., Purification of MRNA Directly From Crude Plant Tissues in 15 Minutes Using Magnetic Oligo DT Microsheres, Nucleic Acids Research, 18(12):3669 (1990).
Jeffs, L.B. et al., A scalable, extrusion-free method for efficient liposomal encapsulation of plasmid DNA, Pharmacol. Res., 22(3): 362-372 (2005).
Jemielity, J. et al., Novel "anti-reverse" cap analogs with superior translational properties, Cold Spring Harbor Laboratory Press, 9(9):1108-1122 (2003).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21(5):807-810 (2010).
Jon, S. et al., Degradable poly(amino alcohol esters) as potential DNA vectors with low cytotoxicity. Biomacromolecules 4(6):1759-1762 (2003).
Jones, G. et al., Duplex- and Triplex-Forming Properties of 4'-Thio-Modified Oligodeoxynucleotides, Bioorganic & Medicinal Chemistry Letters, 7(10):1275-1278 (1997).
Kabanov, A.V. and Kabanov, V.A., DNA complexes with polycations for the delivery of genetic material into cells. Bioconjugate Chemistry 6(1): 7-20 (1995).
Kamath, S. et al., Surface chemistry influences implant-mediated host tissue responses. Journal of Biomedical Materials Research A 86(3):617-626 (2007).
Kariko, K. et al., In vivo protein expression from mRNA delivered into adult rat brain, Journal of Neuroscience Methods, 105:77-86 (2001).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kasuya, T. et al., In Vivo Delivery of Bionanocapsules Displaying *Phaseolus vulgaris* Agglutinin-L₄ Isolectin to Malignant Tumors Overexpressing N-Acetylglucosaminyltransferase V, Human Gene Therapy, 19:887-895 (2008).
Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kaur, T. et al., Addressing the Challenge: Current and Future Directions in Ovarian Cancer THerapy, Current Gene Therapy, 9: 434-458 (2009).
Kiew, L.V. et al., Effect of antisense oligodeoxynucleotides for ICAM-1 on renal ischaemia-reperfusion injury in the anaesthetised rat, The Journal of Physiology, 557(3):981-989 (2004).
Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).
Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).
Klibanov, A.L. et al., Amphipathic polyethyleneglycols effectively prolong the circulation time of liposomes, FEBS, 268(1): 235-237 (1990).
Kober, L. et al., Optimized Signal Peptides for the Development of High Expressing CHO Cell Lines, Biotechnol. Bioeng., 110:1164-1173 (2012).
Kodama, K. et al., The Features and Shortcomings for Gene Delivery of Current Non-Viral Carriers, Current Medicinal Chemistry, 13: 2155-2161 (2006).
Kore, A. and Charles, I., Synthesis and evaluation of 2'-O-allyl substituted dinucleotide cap analog for mRNA translation, Bioorganics & Medicinal Chemistry, 18:8061-8065 (2010).
Kore, A. and Shanmugasundaram, M., Synthesis and biological evaluation of trimethyl-substituted cap analogs, Bioorganic & Medicinal Chemistry, 18:880-884 (2008).
Kormann, M.S.D. et al., Expression of therapeutic proteins after delivery of chemically modified mRNA in mice, Nature Biotechnology, 29(2):154-157 (2011).
Kozak, M. An analysis of 5'-noncoding sequences from 699 vertebrate messenger RNAs, Nucleic Acid Research, 15(20):8125-8148 (1987).
Krieg, P.A. et al., In vitro RNA synthesis with SP6 RNA polymerase, Methods in Enzymology, 155:397-415 (1987).
Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).
Lam, J.K.W et al., Pulmonary delivery of therapeutic siRNA, Advanced Drug Delivery Reviews (2011).
Lasic, D.D. et al., Gelation of liposome interior: A novel method for drug encapsulation, FEBS, 312(2,3):255-258 (1992).
Lasic, D.D. Novel applications of liposomes, Trends in Biotechnology, 16:307-321 (1998).
Lee, S. et al., Stability and cellular uptake of polymerized siRNA (poly-siRNA)/polyethylenimine (PEI) complexes for efficient gene silencing. Journal of Controlled Release 141: 339-346 (2010).
Li, L. et al., Preparation and Gene Delivery of Alkaline Amino Acids-Based Cationic Liposomes, Archives of Pharmaceutical Research, 31(7):924-931 (2008).
Li, S. et al., In vivo gene transfer via intravenous administration of cationic lipid-protamine-DNA (LPD) complexes, Gene Therapy, 4:891-900 (1997).
Li, W. et al., Lipid-based Nanoparticles for Nucleic Acid Delivery, Pharmaceutical Research, 24(3):438-449 (2007).
Liebhaber, S.A. et al., Translation inhibition by an mRNA coding region secondary structure is determined by its proximity to the AUG initiation codon, Journal of Molecular Biology, 226(3):609-621 (1992).
Lim, Y. et al., A self-destroying polycationic polymer: biodegradable poly(4-hydroxy-l-proline ester). Journal of American Chemical Society 121: 5633-5639 (1999).
Lindgren, V. et al., Human Ornithine Transcarbamylase Locus Mapped to Band Xp21.1 Near the Duchenne Muscular Dystrophy Locus, Science, 226(2675):698-700 (1984).
Liu, X. et al., COStar: a D-star Lite-based Dynamic Search Algorithm for Codon Optimization, Journal of Theoretical Biology, 344:19-30 (2014).
Liu, Y. and Huang, L., Designer Lipids Advance Systematic siRNA Delivery, Molecular Therapy, 18(4):669-670 (2010).
Liu, Y. et al., Factors influencing the efficiency of cationic liposome-mediated intravenous gene delivery, Nature Biotechnology, 15:167-173 (1997).
Lo, K-M et al., High level expression and secretion of Fc-X fusion proteins in mammalian cells, Protein Engineering, 11(6):495-500 (1998).
Lorenzi, J. C. C. et al., Intranasal Vaccination with Messenger RNA as a New Approach in Gene Therapy: Use Against Tuberculosis, BMC Biotechnology, 10(77):1-11 (2010).
Love, K.T. et al., Lipid-like materials for low-dose, in vivo gene silencing, PNAS, 107(5):1864-1869 (2010).

(56) References Cited

OTHER PUBLICATIONS

Lu, D. et al., Optimization of methods to achieve mRNA-mediated transfection of tumor cells in vitro and in vivo employing cationic liposome vectors, Cancer Gene Therapy, 1(4):245-252 (1994).
Lukyanov, A.N. and Torchilin, V.P., Micelles from lipid derivatives of water-soluble polymers as delivery systems for poorly soluble drugs. Advanced Drug Delivery Reviews 56: 1273-1289 (2004).
Luo, D. and Saltzman, M., Synthetic DNA delivery systems. Nature Biotechnology 18: 33-37. Review (2000).
Lynn, D.M. and Langer, R., Degradable Poly(β-amino esters):? Synthesis, Characterization, and Self-Assembly with Plasmid DNA. Journal of American Chemical Society 122(44): 10761-10768 (2000).
Lynn, D.M. et al., Accelerated discovery of synthetic transfection vectors: parallel synthesis and screening of a degradable polymer library. Journal of American Chemical Society 123(33): 8155-8156 (2001).
Lynn, D.M. et al., pH-Responsive Polymer Microspheres: Rapid Release of Encapsulated Material within the Range of Intracellular pH. Angewandte Chemie International Edition 40(9): 1707-1710 (2001).
Ma, M. et al., Development of Cationic Polymer Coatings to Regulate Foreign Body Responses. Advanced Healthcare Materials 23: H189-H194. Reviews (2011).
MacLachlan, I., Lipid nanoparticle-mediated delivery of messenger RNA, 1st International mRNA Health Conference; Tubingen Germany, (Oct. 24, 2013) Retrieved from the Internet: URL: <http://files.shareholder.com/downloads/ABEA-50QJTB/2628241206x0x699789/47543d12-db34-4e6e-88a9-f3ae5d97b1d2/MacLachlan_mRNA_Conf_2013>.
Maeda-Mamiya, R. et al., In vivo gene delivery by cationic tetraamino; fullerene. Proceedings of National Academy of Sciences U S A, 107(12):5339-5344 (2010).
Malone, R.W., et al., Cationic liposome-mediated RNA transfection, PNAS, 86:6077-6081 (1989).
Mammal, http://en.wikipedia.org/wiki/Mammal, 2007, Pearson Education, NY, NY, Author unkown (Source: The international union for conservation of nature and natural resources), 2 pages, (Retrieved Aug. 2, 2014).
Mansour, H.M. et al., Nanomedicine in pulmonary delivery, International Journal of Nanomedicine, 4:299-319 (2009).
Margus, H. et al., Cell-penetrating peptides as versatile vehicles for oligonucleotide delivery. Molecular Therapy 20 (3): 525-533 (2012).
Martell, A.E. and Chaberek, S., The Preparation and the Properties of Some N,N'-Disubstituted-ethylenediaminedipropionic Acids. Journal of the American Chemical Society 72: 5357-5361 (1950).
Martinon, F. et al., Induction of Virus-Specific Cytotoxic T Lymphocytes in Vivo by Liposome-Entrapped mRNA, European Journal of Immunology, 23(7):1719-1722 (1993).
Mathiowitz, E. and Langer, R., Polyanhydride microspheres as drug carriers I. Hot-melt microencapsulation. Journal of Controlled Release 5: 13-22 (1987).
Mathiowitz, E. et al., Novel microcapsules for delivery systems. Reactive Polymers 6: 275-283 (1987).
Mathiowitz, E. et al., Polyanhydride microspheres as drug carriers II. Microencapsulation by solvent removal. Journal of Applied Polymer Sciences 35: 755-774 (1988).
McCracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).
McIvor, R. S., Therapeutic Delivery of mRNA: The Medium is the Message, Molecular Therapy, 19(5):822-823 (2011).
Melton, D.A. et al., Efficient in vitro synthesis of biologically active RNA and RNA hybridization probes from; plasmids containing a bacteriophage SP6 promoter, Nucleic Acids Research, 12(18):7035-7056 (1984).
Mendelsohn, J.D. et al., Rational design of cytophilic and cytophobic polyelectrolyte multilayer thin films. Biomacromolecules 4(1): 96-106 (2003).

Merkel, O.M. and Kissel, T., Nonviral Pulmonary Delivery of siRNA, Accounts of Chemical Research, 45(7):961-970 (2012).
Merten, O. et al., Large-Scale Manufacture and Characterization of a Lentiviral Vector Produced for Clinical Ex Vivo Gene Therapy Application, Human Gene Therapy, 22(3):343-356 (2011).
Miller, A. Cationic Liposomes for Gene Therapy. Angewandte Chemie International Edition 37: 1768-1785 (1998).
Monia, B.P. et al., Evaluation of 2'-Modified Oligonucleotides Containing 2'-Deoxy Gaps as Antisense Inhibitors of Gene Epression, The Journal of Biological Chemistry, 268(19):14514-14522 (1993).
Morrissey, D.V. et al., Potent and Persistent in vivo Anti-HBV Activity of Chemically Modified siRNAs, Nat. Biotechnol., 23(8): 1003-1007 (2005).
Narang, A.S. et al., Cationic lipids with increased DNA binding affinity for nonviral gene transfer in dividing and nondividing cells. Bioconjugate Chemistry 16(1): 156-168 (2005).
Navarro, G. et al., Phospholipid-polyethylenimine conjugate-based micelle-like nanoparticles for siRNA delivery. Drug Delivery and Translational Research 1: 25-33 (2011).
Neamnark, A. et al., Aliphatic lipid substitution on 2 kDa polyethylenimine improves plasmid delivery and transgene expression. Molecular Pharmaceutics 6(6): 1798-1815 (2009).
Ng, J. et al., LincRNAs join the pluripotency alliance, Nature Genetics, 42:1035-1036 (2010).
Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nojima, T. et al., The Interaction between Cap-binding Complex and RNA Export Factor is Required for Intronless mRNA Export, Journal of Biological Chemistry, 282(21):15645-15651 (2007).
Nori, A. et al., Tat-conjugated synthetic macromolecules facilitate cytoplasmic drug delivery to human ovarian carcinoma cells, Bioconj. Chem., 14(1): 44-50 (2003).
Okumura, K. et al., Bax mRNA therapy using cationic liposomes for human malignant melanoma, The Journal of Gene Medicine, 10:910-917 (2008).
Otsuka, Y. et al., Identification of a Cytoplasmic Complex That Adds a Cap onto 5'-Monophosphate RNA, Molecular and Cellular Biology, 29(8):2155-2167 (2009).
Ozer, A., Alternative applications for drug delivery: nasal and pulmonary routes, Nanomaterials and Nanosystems for Biomedical Applications, M.R. Mozafari (ed.): 99-112 (2007).
Painter, H. et al, Topical Delivery of mRNA to the Murine Lung and Nasal Epithelium, Gene Medicine Group and the Medical Informatics Unit, Nuffield Department of Clinical Laboratory Sciences, University of Oxford, 1 page.
Painter, H. et al., Topical Delivery of mRNA to the Murine Lung and Nasal Epithelium, Molecular Therapy, 9:S187 (2004).
Painter, H., An Investigation of mRNA as a Gene Transfer Agent, Gene Medicine Research Group Nuffield Department of Clinical Laboratory Sciences and Merton College, University of Oxford, 1-282 (2007).
Painter, H., An Investigation of mRNA as a Gene Transfer Agent, Oxford University GeneMedicine, Abstract Only, 1 page. (2007).
Parrish, D.A. and Mathias, L.J., Five- and six-membered ring opening of pyroglutamic diketopiperazine. Journal of Organic Chemistry 67(6): 1820-1826 (2002).
Patton, J., Market Trends in Pulmonary Therapies, Trends and Opportunities, VI: 372-377.
Paulus, C. and Nevels, M., The Human Cytomegalovirus Major Immediate-Early Proteins as Antagonists of Intrinsic and Innate Antiviral Host Responses, Viruses, 1:760-779 (2009).
Pearson, H., One Gene, Twenty Years, Nature 460:165-169 (2009).
Peppas, N.A. et al., Hydrogels in Biology and Medicine: From Molecular Principles to Bionanotechnology. Advanced Materials 18: 1345-1360 (2006).
Philipp, A. et al., Hydrophobically modified oligoethylenimines as highly efficient transfection agents for siRNA delivery. Bioconjugate Chemistry 20(11): 2055-2061 (2009).

(56) References Cited

OTHER PUBLICATIONS

Pons, M. et al., Liposomes obtained by the ethanol injection method, Int. J. Pharm., 95: 51-56. (1993).
Prata, C.A. et al., Lipophilic peptides for gene delivery. Bioconjugate Chemistry 19(2): 418-420 (2008).
Probst, J. et al., Spontaneous cellular uptake of exogenous messenger RNA in vivo is nucleic acid-specific, saturable and ion dependent, Gene Therapy, 14:1175-1180 (2007).
Promega, PolyATtract mRNA Isolation Systems, Instructions for Use of Products Z5200, Z5210, Z2300 and Z5310, Technical Manual (2012).
Putnam, D. Polymers for gene delivery across length scales. Nature Materials 5: 439-451 (2006).
Putnam, D. and Langer, R., Poly(4-hydroxy-l-proline ester): Low-Temperature Polycondensation and Plasmid DNA Complexation. Macromolecules 32(11): 3658-3662 (1999).
Qiagen, Oligotex Handbook, Second Edition (2002).
Rabinovich, P.M. et al., Synthetic Messenger RNA as a Tool for Gene Therapy, Human Gene Therapy, 17:1027-1035 (2006).
Raper, S.E. et al., Developing adenoviral-mediated in vivo gene therapy for ornithine transcarbamylase deficiency, Journal of Inherited Metabolic Disease, 21:119-137 (1998).
Ratajczak, J. et al., Membrane-derived microvesicles: important and underappreciated mediators of cell-to-cell communication, Leukemia, 20:1487-1495 (2006).
Ratner, B.D. and Bryant, S., Biomaterials: where we have been and where we are going. Annual Review of Biomedical Engineering 6: 41-75 (2004).
Reddy, A. et al., The Effect of Labour and Placental Separation on the Shedding of Syncytiotrophoblast Microparticles, Cell-free DNA and mRNA in Normal Pregnancy and Pre-eclampsia, Placenta, 29: 942-949 (2008).
Rejman, J. et al., Characterization and transfection properties of lipoplexes stabilized with novel exchangeable polyethylene glycol-lipid conjugates, Biochimica et Biophysica Acta, 1660:41-52 (2004).
Remington: The Science and Practice of Pharmacy, 21st Edition, Philadelphia, PA. Lippincott Williams & Wilkins (2005).
Rosenecker, J. et al., Gene Therapy for Cystic Fibrosis Lung Disease: Current Status and Future Perspectives, Curr. Opin. Mol. Ther., 8:439-445 (2006).
Rosenecker, J. et al., Interaction of Bronchoalveolar Lavage Fluid with Polyplexes and Lipoplexes: Analysing the Role of Proteins and Glycoproteins, J. Gene. Med., 5:49-60 (2003).
Rowe, S.M. et al., Cystic Fibrosis, New Engl. J. Med. 352:1992-2001 (2005).
Rudolph, C. et al., Aerosolized Nanogram Quantities of Plasmid DNA Mediate Highly Efficient Gene Delivery to Mouse Airway Epithelium, Molecular Therapy, 12(3): 493-501 (2005).
Rudolph, C. et al., Methodological optimization of polyethylenimine (PEI)-based gene delivery to the lungs of mice via aerosol application, Journal of Gene Medicine, 7(1): 59-66 (2005).
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).
Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31: 183-201 (2001).
Schnierle, B.S. et al., Cap-specific mRNA (nucleoside-O2'-)-methyltransferase and poly(A) polymerase stimulatory activities of vaccinia virus are mediated by a single protein, Proceedings of the National Academy of Sciences, 89:2897-2901 (1992).
Schreier, H., The new frontier: gene and oligonucleotide therapy, Pharmaceutica Acta Helvetiae, 68(3):145-159 (1994).
Semple, S.C. et al., Rational design of cationic lipids for siRNA delivery, Nature Biotechnology, 28(2): 172-176 (2010).
Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Shimada, A. et al., Translocation Pathway of the Intratracheally Instilled Ultrafine Particles from the Lung into the Blood Circulation in the Mouse, Toxicologic Pathology, 34:949-957 (2006).
Siegwart, D.J. et al., Combinatorial synthesis of chemically diverse core-shell nanoparticles for intracellular delivery. Proceedings of the National Academy of the Sciences of the USA 108(32):12996-123001 (2011).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).
Stern, L. et al., A novel antitumor prodrug platform designed to be cleaved by the endoprotease legumain, Bioconj. Chem., 20: 500-510 (2009).
Su, X. et al., Cytosolic Delivery Mediated Via Electrostatic Surface Binding of mRNA to Degradable Lipid-Coated Polymeric Nanoparticles, Polymer Preprints, 51(2):668-669 (2010).
Su, X. et al., In Vitro and in Vivo mRNA Delivery Using Lipid-Enveloped pH-Responsive Polymer Nanoparticles, Molecular Pharmaceutics, 8(3):774-787 (2011).
Suri, M. et al., Genetics for Pediatricians, Remedica Publishing, (2005).
Szoka, F. and Papahadjopoulos, D., Comparative properties and methods of preparation of lipid vesicles (liposomes). Annual Review of Biophysics Bioengineering 9: 467-508 (1980).
Tagawa, M. et al., Gene expression and active virus replication in the liver after injection of duck hepatitis B virus DNA into the peripheral vein of ducklings, Journal of Hepatology, 24:328-334 (1996).
Takahashi, Y. et al., Development of safe and effective nonviral gene therapy by eliminating CpG motifs from plasmid DNA vector, Frontiers in Bioscience, S4: 133-141 (2012).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Tavernier, G. et al., mRNA as gene therapeutic: How to control protein expression, Journal of Controlled Release, 150:238-247 (2011).
Tcherepanova, I. et al., Ectopic expression of a truncated CD40L protein from synthetic post-transcriptionally capped RNA in dendritic cells induces high levels of IL-12 secretion, BMC Molecular Biology, 9(1):pp. 1-13 (2008).
Theus, S. and Liarakos, C., A Simple Assay for Determining the Capping Efficiencies of RNA Polymerases Used for In Vitro Transcription, BioChromatography, 9(5):610-614 (1990).
Third Party Preissuance Submission Under 37 CFR § 1.290 (Oct. 25, 2013).
Thomas, C. E. et al., Progress and problems with the use of viral vectors for gene therapy, Nature Reviews/Genetics, 4: 346-358 (2003).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).

(56) References Cited

OTHER PUBLICATIONS

Tsui, N.B. et al., Stability of endogenous and added RNA in blood specimens, serum, and plasma, Clinical Chemistry, 48(10):1647-1653 (2002).
Tsvetkov, D.E. et al., Neoglycoconjugates based on dendrimeric poly(aminoamides). Russian Journal of Bioorganic Chemistry 28(6): 470-486 (2002).
Tuschl, T. et al., Targeted mRNA degradation by double-stranded RNA in vitro, Genes and Development, 13(24):3191-3197 (1999).
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).
Van De Wetering, P. et al., Structure-activity relationships of water-soluble cationic methacrylate/methacrylamide polymers for nonviral gene delivery. Bioconjugate Chemistry 10(4): 589-597 (1999).
Van Der Gun, B.T.F et al., Serum insensitive, intranuclear protein delivery by the multipurpose cationic lipid Saint-2, Journal of Controlled Release, 123:228-238 (2007).
Van Tendeloo, V.F.I et al., mRNA-based gene transfer as a tool for gene and cell therapy, Current Opinion in Molecular Therapeutics, 9(5):423-431 (2007).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Varambally, S. et al., Genomic Loss of microRNA-101 Leads to Overexpression of Histone Methyltransferase EZH2 in Cancer, Science, 322:1695-1699 (2008).
Veronese, F.M. et al., PEG-doxorubicin conjugates: influence of polymer structure on drug release, in vitro cytotoxicity, biodistribution, and antitumor activity, Bioconj. Chem., 16(4):775-784 (2005).
Viecelli, H. et al., Gene Therapy for Hepatic Diseases Using Non-Viral Minicircle-DNA Vector, Journal of Inherited Metabolic Disease, 35(1):S144 (2012).
Viecelli, H. et al., Gene therapy for liver diseases using non-viral minicircle-DNA vector, Human Gene Therapy, 23(10):A145 (2012).
Viecelli, H. et al., Gene therapy for liver diseases using non-viral minicircle-DNA vector, Molecular Therapy, 21(1):S136 (2013).
Vomelova, I. et al., Methods of RNA Purification. All Ways (Should) Lead to Rome, Folia Biologica, 55(6):242-251 (2009).
Von Harpe et al., Characterization of commercially available and synthesized polyethylenimines for gene delivery. Journal of Controlled Release 69(2):309-322 (2000).
Walde, P. et al., Preparation of Vesicles (Liposomes). Encyclopedia of Nanoscience and Nanotechnology. Nalwa, ed. American Scientific Publishers, Los Angeles 9:43-79 (2004).
Wang, H. et al., N-acetylgalactosamine functionalized mixed micellar nanoparticles for targeted delivery of siRNA to liver, Journal of Controlled Release, 166(2):106-114 (2013).
Wang, Y. et al., Systemic delivery of modified mRNA encoding herpes simplex virus 1 thymidine kinase for targeted cancer gene therapy, Molecular Therapy, 21(2):358-367 (2013).
Webb, M. et al., Sphingomyeline-cholesterol liposomes significantly enhance the pharmacokinetic and therapeutic properties of vincristine in murine and human tumour models, British Journal of Cancer, 72(4):896-904 (1995).
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al., Reducible cationic lipids for gene transfer, Biochem. J., 356:747-756 (2001).
White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10,11-epoxyundecanoic acid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wiehe, J.M. et al., mRNA-mediated gene delivery into human progenitor cells promotes highly efficient protein expression, Journal of Cellular and Molecular Medicine, 11(3):521-530 (2007).
Williams, D. et al., A simple, highly efficient method for heterologous expression in mammalian primary neurons using cationic lipid-mediated mRNA transfection, Frontiers in Neuroscience, 4(181):1-20 (2010).
Written Opinion for PCT/US15/27563, 12 pages (dated Sep. 18, 2015).
Written Opinion for PCT/US2010/058457, 14 pages (dated May 6, 2011).
Written Opinion for PCT/US2011/062459, 9 pages (dated Apr. 11, 2012).
Written Opinion for PCT/US2012/041663, 7 pages (dated Oct. 8, 2012).
Written Opinion for PCT/US2012/041724, 11 pages (dated Oct. 25, 2012).
Written Opinion for PCT/US2013/034602, 4 pages (dated Jun. 17, 2013).
Written Opinion for PCT/US2013/034604, 9 pages (dated Jun. 17, 2013).
Written Opinion for PCT/US2013/044769, 8 pages (dated Nov. 12, 2013).
Written Opinion for PCT/US2013/044771, 7 pages (dated Nov. 1, 2013).
Written Opinion for PCT/US2013/073672, 7 pages (dated Mar. 3, 2014).
Written Opinion for PCT/US2014/027422, 6 pages (dated Jul. 31, 2014).
Written Opinion for PCT/US2014/027587, 5 pages (dated Jul. 24, 2014).
Written Opinion for PCT/US2014/027602, 7 pages (dated Jul. 28, 2014).
Written Opinion for PCT/US2014/027717, 5 pages (dated Jul. 16, 2014).
Written Opinion for PCT/US2014/028330, 7 pages (dated Jul. 22, 2014).
Written Opinion for PCT/US2014/028441, 6 pages (dated Jul. 22, 2014).
Written Opinion for PCT/US2014/028498, 6 pages (dated Jul. 28, 2014).
Written Opinion for PCT/US2014/028849, 7 pages (dated Jul. 17, 2015).
Written Opinion for PCT/US2014/061786, 5 pages (dated Feb. 6, 2015).
Written Opinion for PCT/US2014/061793, 4 pages (dated Feb. 6, 2015).
Written Opinion for PCT/US2014/061830, 7 pages (dated Feb. 4, 2015).
Written Opinion for PCT/US2014/061841, 8 pages (dated Feb. 24, 2015).
Written Opinion for PCT/US2015/039004, 8 pages (dated Oct. 6, 2015).
Written Opinion for PCT/US2015/21403 (7 pages) dated Jun. 15, 2015.
Wu, J. and Zern, M., Modification of liposomes for liver targeting, Journal of Hepatology, 24(6):757-763 (1996).
Wu, J. et al., Cationic lipid polymerization as a novel approach for constructing new DNA delivery agents. Bioconjugate Chemistry 12(2): 251-257 (2001).
Wurdinger, T. et al., A secreted luciferase for ex-vivo monitoring of in vivo processes, Nat. Methods, 5(2):171-173 (2008).
Yamamoto, A. et al., Current prospects for mRNA gene delivery, European Journal of Pharmaceutics and Biopharmaceutics, 71(3): 484-489 (2009).

(56) References Cited

OTHER PUBLICATIONS

Yamamoto, Y. et al., Important Role of the Proline Residue in the Signal Sequence that Directs the Secretion of Human Lysozyme in *Saccharomyces cerevisiae*, Biochemistry, 28:2728-2732 (1989).

Yasuda, M. et al., Fabry Disease: Novel [alpha]-Galactosidase A 3-terminal Mutations Result in Multiple Transcripts Due to Aberrant 3-End Formation, American Journal of Human Genetics, 73:162-173 (2003).

Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).

Yokoe, H. et al., Spatial dynamics of GFP-tagged proteins investigated by local fluorescence enhancement, Nature Biotechnology, 14(10):1252-1256 (1996).

Yoneda et al., A cell-penetrating peptidic GRP78 ligand for tumor cell-specific prodrug therapy, Bioorg. Med. Chem. Lett., 18(5): 1632-1636 (2008).

Yoshioka, Y. and Calvert, P., Epoxy-based Electroactive Polymer Gels. Experimental Mechanics 42(4): 404-408 (2002).

Zagridullin, P.H. et al., Monobasic amines. II. Cycloalkylation and hydroxyalkylation of cyclic and acyclic di- and polyamines. Journal of Organic Chemistry, 26(1):184-88. Russian (1990).

Zaugg, H.E. et al., 3-Carboxy-2,5-piperazinedione and Derivatives. Journal of American Chemical Society 78(11):2626-2631 (1956).

Zauner, W. et al., Polylysine-based transfection systems utilizing receptor-mediated delivery. Advanced Drug Delivery Reviews 30(1-3):97-113(1998).

Zintchenko, A. et al., Simple modifications of branched PEI lead to highly efficient siRNA carriers with low toxicity. Bioconjugate Chemistry 19(7):1448-1455 (2008).

Zou, S. et al., Lipid-mediated delivery of RNA is more efficient than delivery of DNA in non-dividing cells, International Journal of Pharmaceutics, 389(1-2):232-243 (2010).

Brown, M.D. et al., Gene Delivery with synthetic (non viral) carriers, Int. J. Pharm., 1-21 (2001).

Eck, et al., Goodman & Gilman's The Pharmacological Basis of Therapeutics, McGraw-Hill, New York, 77-101 (1996).

Gorecki, et al., Prospects and problems of gene therapy: an update, Expert Opin. Emerging Drugs, 6(2): 187-198 (2001).

Lechardeur, et al., Metabolic instability of plasmid DNA in the cytosol: a potential barrier to gene transfer, Gene Therapy, 6: 482-497 (1999).

A 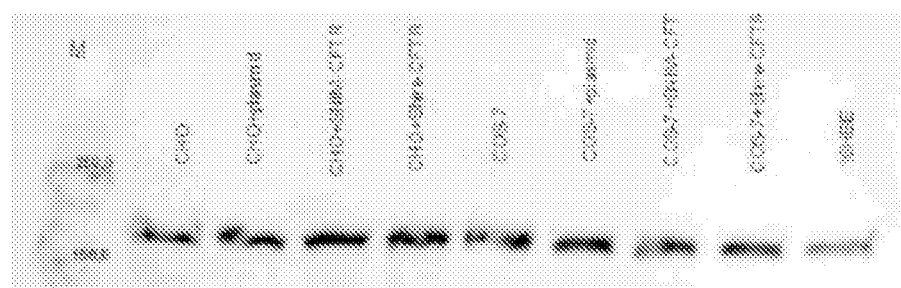
B 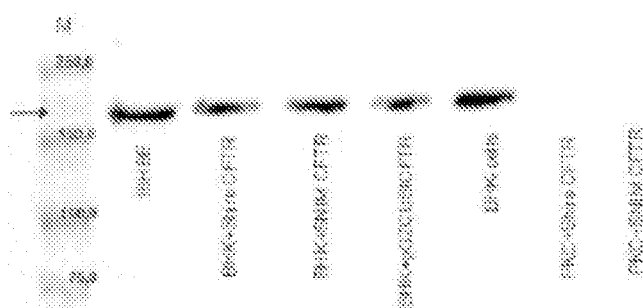
Figures 12 A & B

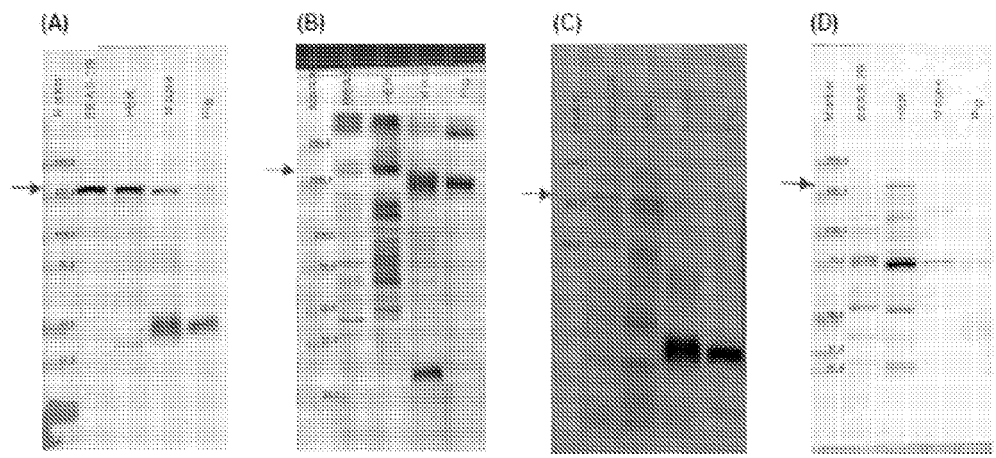
Figures 13 A-D

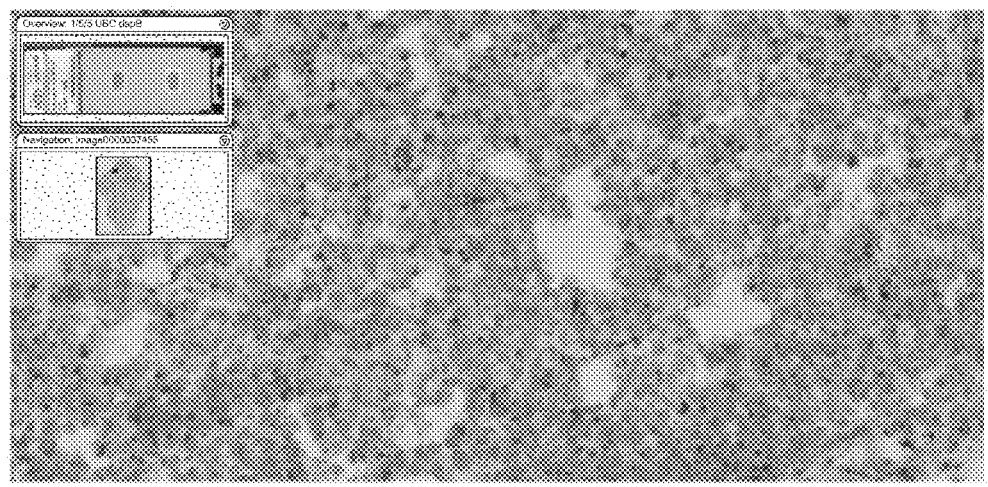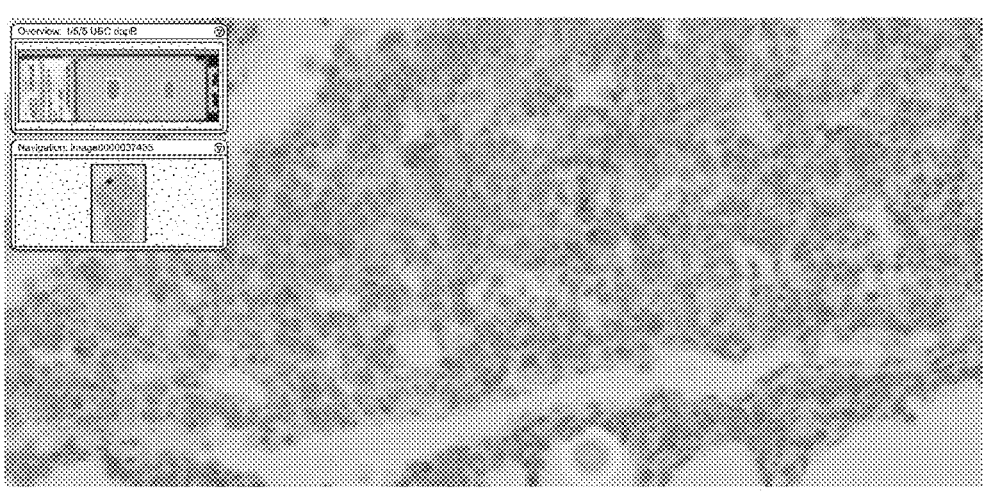
Figure 47 A&B

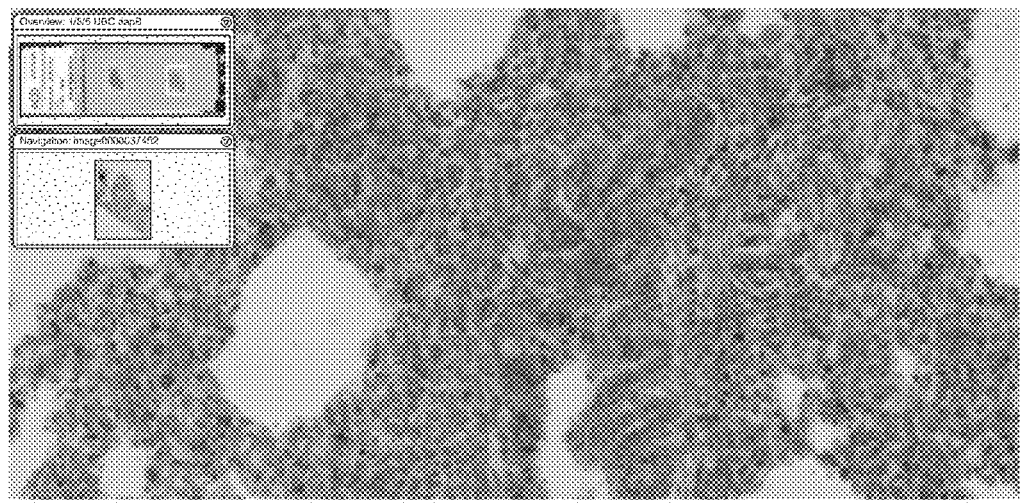
Figure 48 A&B

A
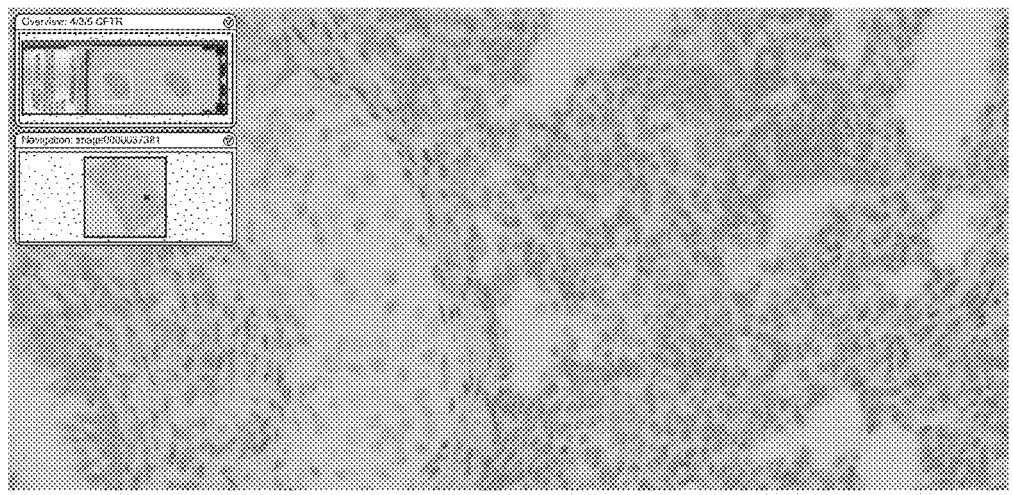
B
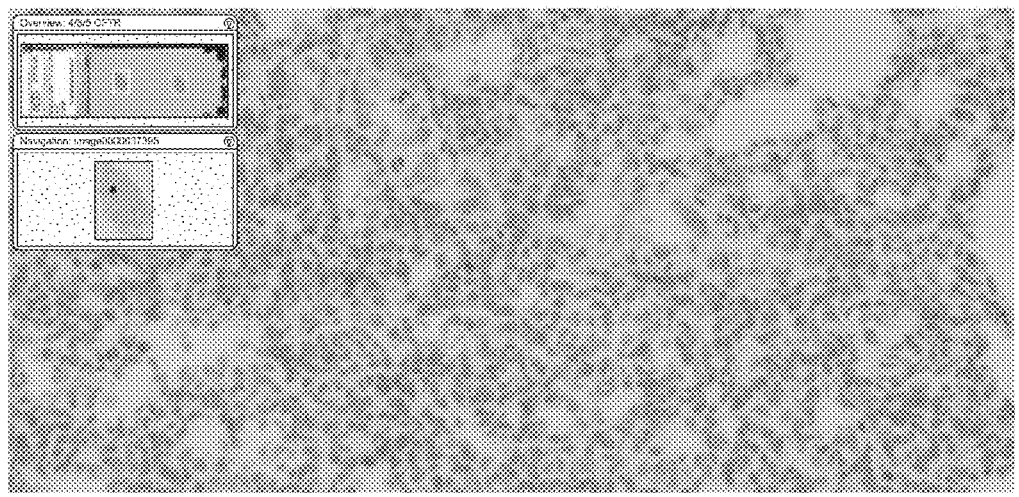
Figure 49 A&B

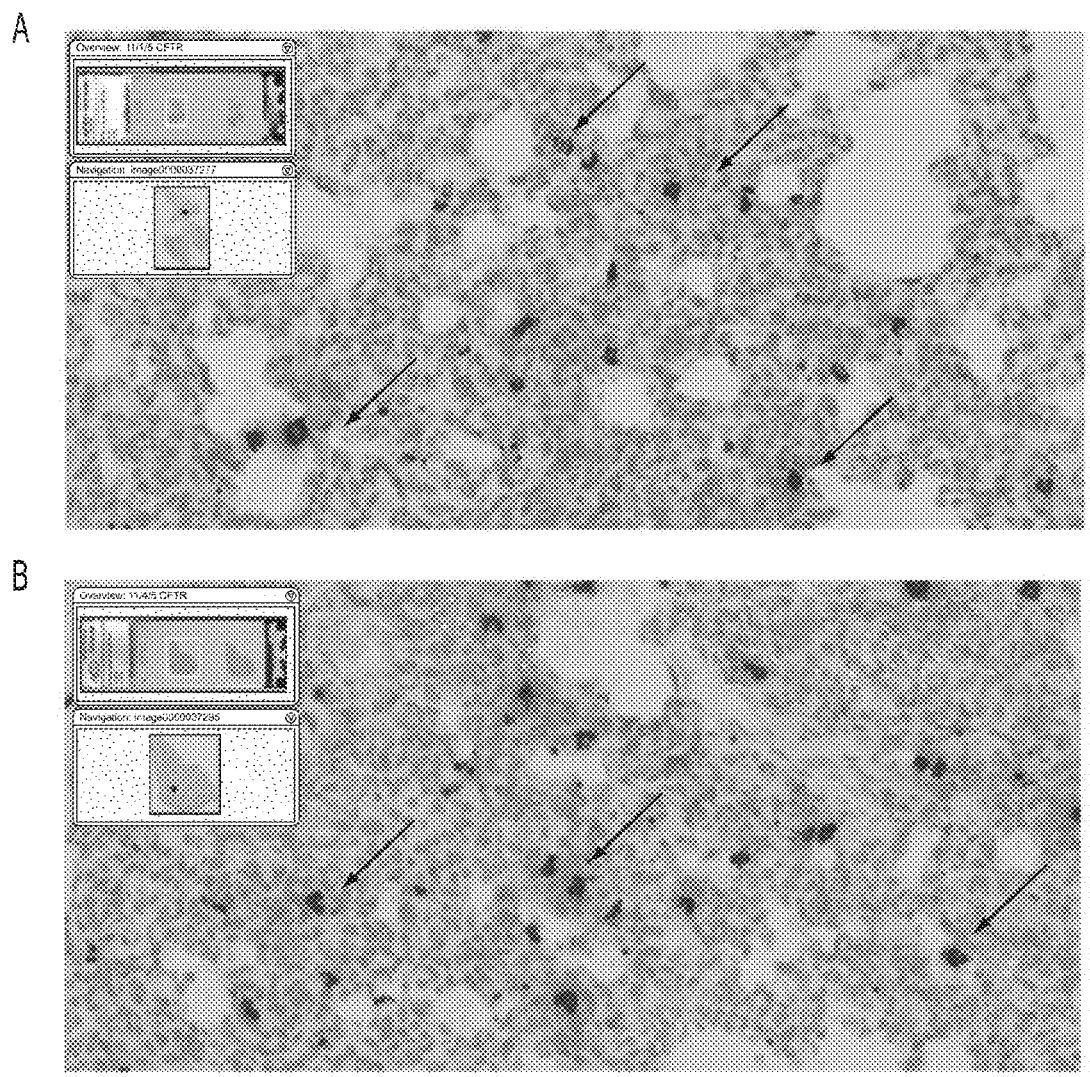
Figure 50 A&B

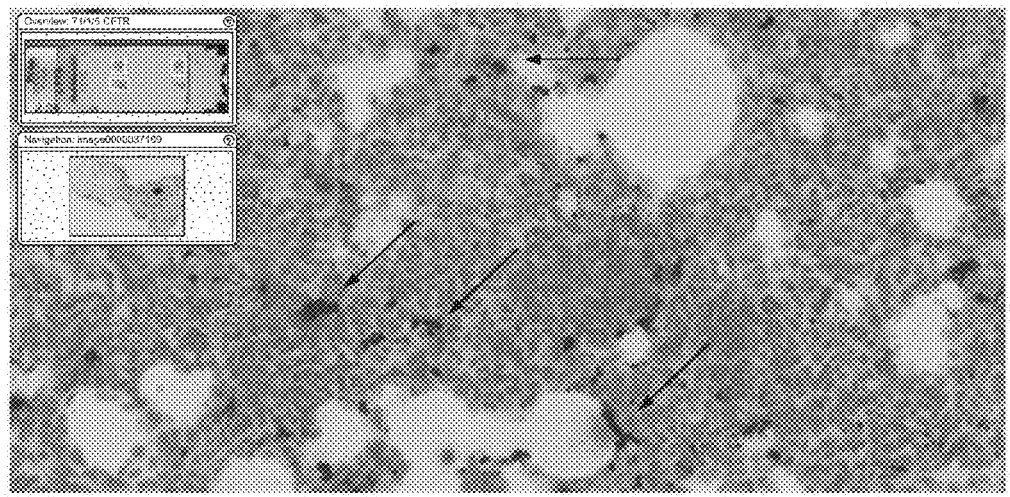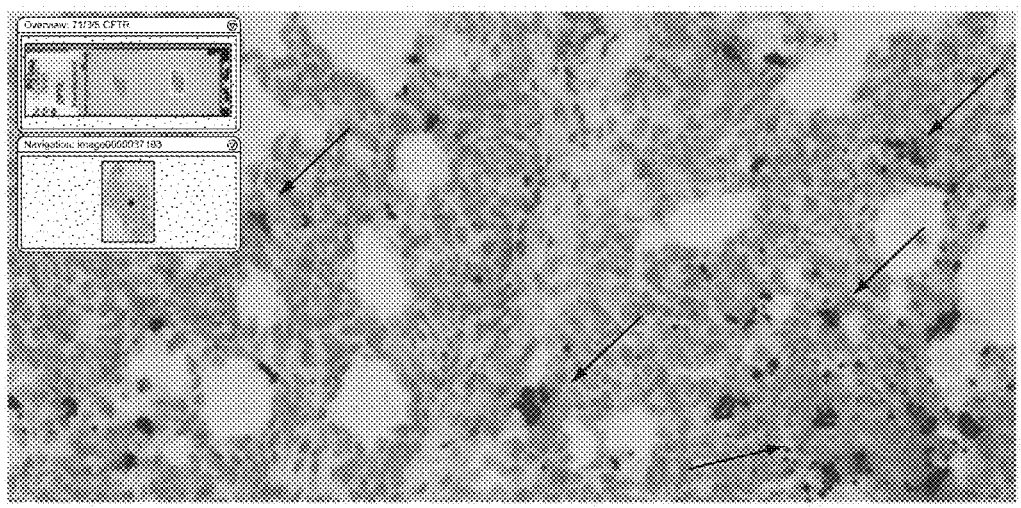
Figure 51 A&B

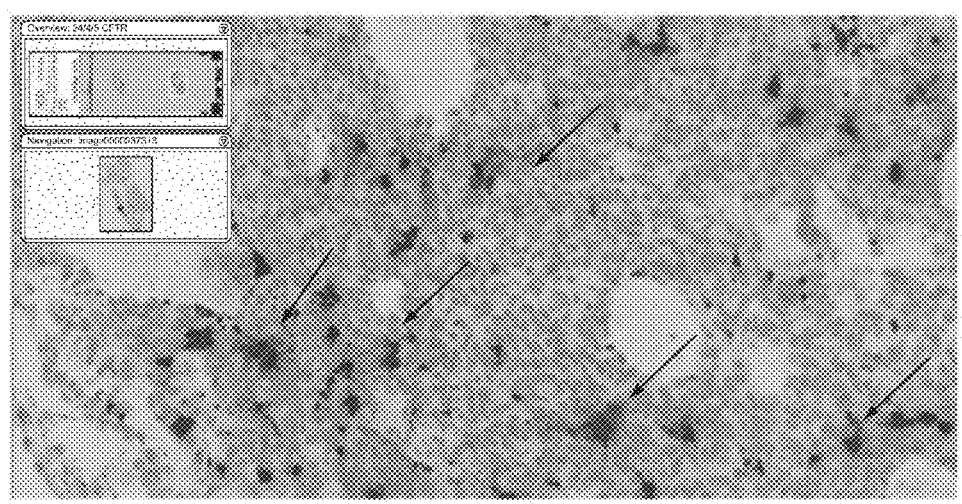
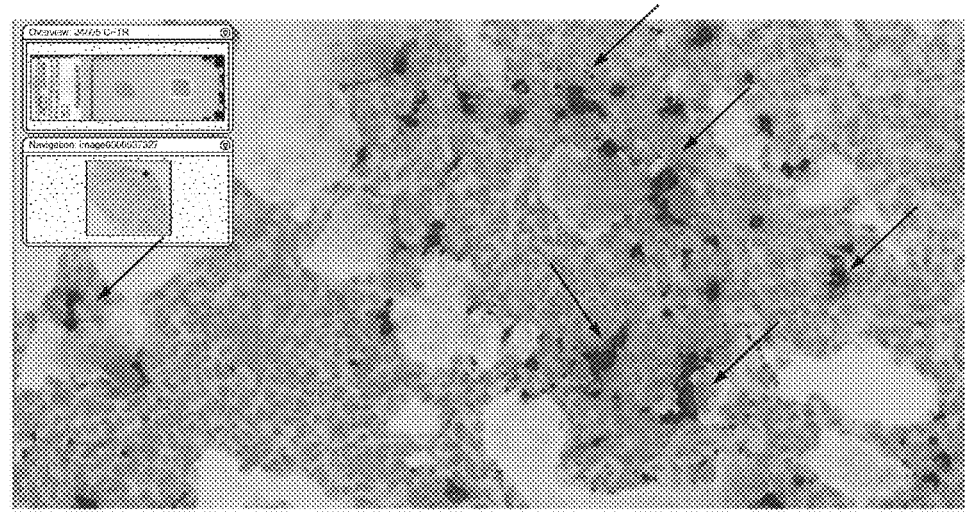
Figure 52 A&B

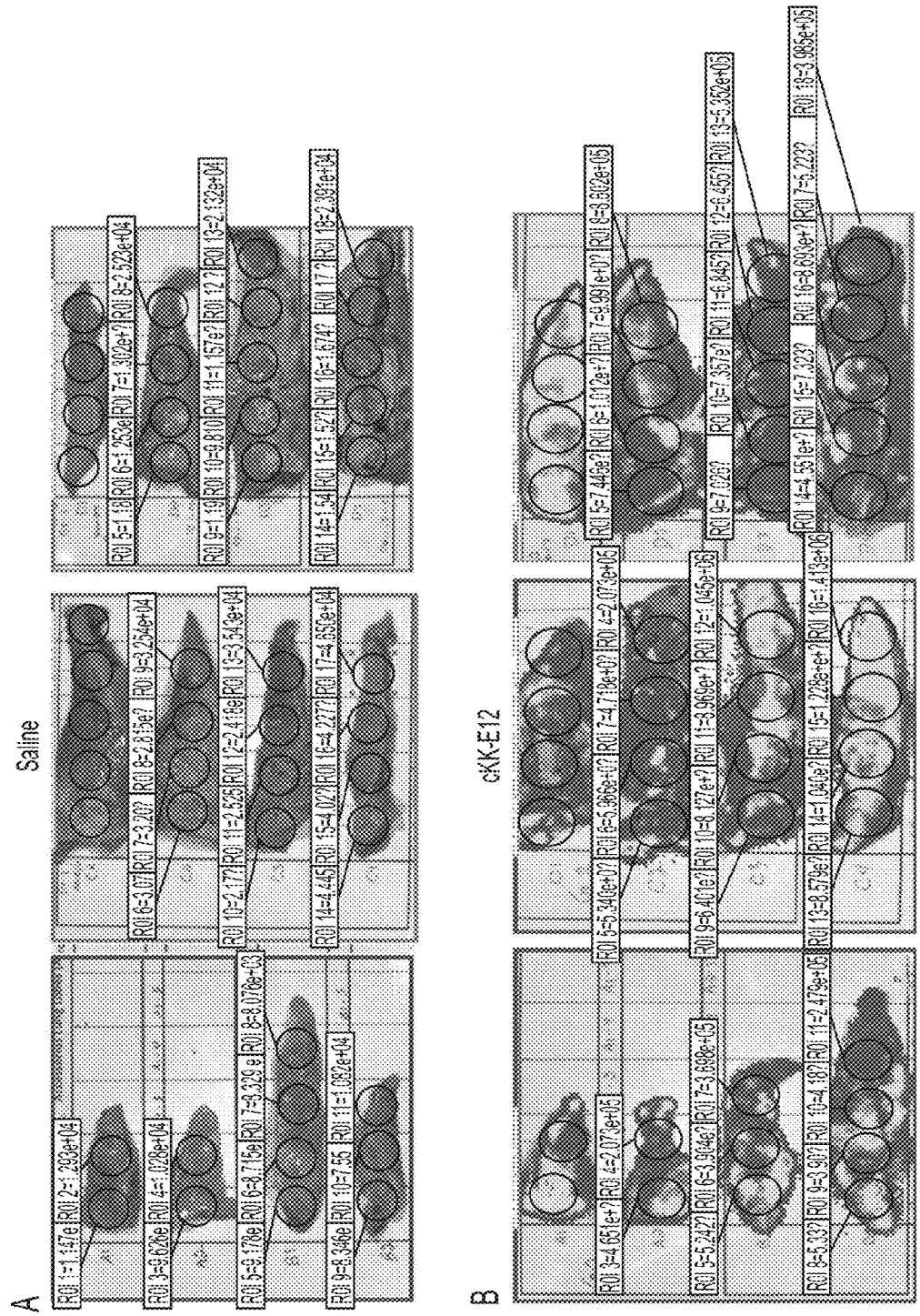
Figure 53 A&B

HEK cells transfected using complexes given to Pigs 10, 11 and 12 (1mg Dose).
HEK-UT – untransfected HEK cells HEK cells transfected using complexes given to Pigs 13, 14 and 15 (5mg Dose)
HEK cells transfected using complexes given to Pigs 19, 20 and 21 (10mg Dose)

HEK-UT – untransfected HEK cells used for complexes from Pigs 19-21
HEK-UT – untransfected HEK cells used for complexes from Pigs 13-15

HEK cells transfected using complexes given to Pigs 16 (5 mg Dose), 22 (10 mg Dose) and 67 (1mg Dose)

HEK-UT 16– untransfected HEK cells used for complexes from Pigs 16, 22 and 67

HEK cells transfected using complexes given to Pigs 17-18 (5 mg Doses), 23-24 (10 mg Doses) and 68-69 (1mg Doses)

HEK-UT – untransfected HEK cells

```
                         SEQUENCE LISTING

<160> NUMBER OF SEQ ID NOS: 20

<210> SEQ ID NO 1
<211> LENGTH: 1480
<212> TYPE: PRT
<213> ORGANISM: Homo sapiens

<400> SEQUENCE: 1

Met Gln Arg Ser Pro Leu Glu Lys Ala Ser Val Val Ser Lys Leu Phe
1               5                  10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255
```

-continued

```
Glu Arg Leu Val Ile Thr Ser Glu Met Ile Glu Asn Ile Gln Ser Val
            260                 265                 270
Lys Ala Tyr Cys Trp Glu Ala Met Glu Lys Met Ile Glu Asn Leu
        275                 280                 285
Arg Gln Thr Glu Leu Lys Leu Thr Arg Lys Ala Ala Tyr Val Arg Tyr
        290                 295                 300
Phe Asn Ser Ser Ala Phe Phe Phe Ser Gly Phe Val Val Phe Leu
305                 310                 315                 320
Ser Val Leu Pro Tyr Ala Leu Ile Lys Gly Ile Ile Leu Arg Lys Ile
                325                 330                 335
Phe Thr Thr Ile Ser Phe Cys Ile Val Leu Arg Met Ala Val Thr Arg
                340                 345                 350
Gln Phe Pro Trp Ala Val Gln Thr Trp Tyr Asp Ser Leu Gly Ala Ile
        355                 360                 365
Asn Lys Ile Gln Asp Phe Leu Gln Lys Gln Glu Tyr Lys Thr Leu Glu
        370                 375                 380
Tyr Asn Leu Thr Thr Thr Glu Val Val Met Glu Asn Val Thr Ala Phe
385                 390                 395                 400
Trp Glu Glu Gly Phe Gly Glu Leu Phe Glu Lys Ala Lys Gln Asn Asn
                405                 410                 415
Asn Asn Arg Lys Thr Ser Asn Gly Asp Asp Ser Leu Phe Phe Ser Asn
            420                 425                 430
Phe Ser Leu Leu Gly Thr Pro Val Leu Lys Asp Ile Asn Phe Lys Ile
            435                 440                 445
Glu Arg Gly Gln Leu Leu Ala Val Ala Gly Ser Thr Gly Ala Gly Lys
        450                 455                 460
Thr Ser Leu Leu Met Val Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
            500                 505                 510
Asp Glu Tyr Arg Tyr Arg Ser Val Ile Lys Ala Cys Gln Leu Glu Glu
        515                 520                 525
Asp Ile Ser Lys Phe Ala Glu Lys Asp Asn Ile Val Leu Gly Glu Gly
        530                 535                 540
Gly Ile Thr Leu Ser Gly Gly Gln Arg Ala Arg Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
            595                 600                 605
His Leu Lys Lys Ala Asp Lys Ile Leu Ile Leu His Glu Gly Ser Ser
        610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
            660                 665                 670
```

```
Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
            690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Gly Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
            755                 760                 765

Val Leu Asn Leu Met Thr His Ser Val Asn Gln Gly Gln Asn Ile His
            770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Phe Phe Asp Asp Met Glu Ser Ile Pro Ala Val Thr Thr Trp Asn Thr
            835                 840                 845

Tyr Leu Arg Tyr Ile Thr Val His Lys Ser Leu Ile Phe Val Leu Ile
            850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
            915                 920                 925

Met Gly Phe Phe Arg Gly Leu Pro Leu Val His Thr Leu Ile Thr Val
            930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Leu Leu Pro Leu Thr Ile Phe
            980                 985                 990

Asp Phe Ile Gln Leu Leu Leu Ile Val Ile Gly Ala Ile Ala Val Val
            995                 1000                1005

Ala Val Leu Gln Pro Tyr Ile Phe Val Ala Thr Val Pro Val Ile
    1010                1015                1020

Val Ala Phe Ile Met Leu Arg Ala Tyr Phe Leu Gln Thr Ser Gln
    1025                1030                1035

Gln Leu Lys Gln Leu Glu Ser Glu Gly Arg Ser Pro Ile Phe Thr
    1040                1045                1050

His Leu Val Thr Ser Leu Lys Gly Leu Trp Thr Leu Arg Ala Phe
    1055                1060                1065
```

-continued

Gly Arg Gln Pro Tyr Phe Glu Thr Leu Phe His Lys Ala Leu Asn
1070             1075             1080

Leu His Thr Ala Asn Trp Phe Leu Tyr Leu Ser Thr Leu Arg Trp
1085             1090             1095

Phe Gln Met Arg Ile Glu Met Ile Phe Val Ile Phe Phe Ile Ala
1100             1105             1110

Val Thr Phe Ile Ser Ile Leu Thr Thr Gly Glu Gly Glu Gly Arg
1115             1120             1125

Val Gly Ile Ile Leu Thr Leu Ala Met Asn Ile Met Ser Thr Leu
1130             1135             1140

Gln Trp Ala Val Asn Ser Ser Ile Asp Val Asp Ser Leu Met Arg
1145             1150             1155

Ser Val Ser Arg Val Phe Lys Phe Ile Asp Met Pro Thr Glu Gly
1160             1165             1170

Lys Pro Thr Lys Ser Thr Lys Pro Tyr Lys Asn Gly Gln Leu Ser
1175             1180             1185

Lys Val Met Ile Ile Glu Asn Ser His Val Lys Lys Asp Asp Ile
1190             1195             1200

Trp Pro Ser Gly Gly Gln Met Thr Val Lys Asp Leu Thr Ala Lys
1205             1210             1215

Tyr Thr Glu Gly Gly Asn Ala Ile Leu Glu Asn Ile Ser Phe Ser
1220             1225             1230

Ile Ser Pro Gly Gln Arg Val Gly Leu Leu Gly Arg Thr Gly Ser
1235             1240             1245

Gly Lys Ser Thr Leu Leu Ser Ala Phe Leu Arg Leu Leu Asn Thr
1250             1255             1260

Glu Gly Glu Ile Gln Ile Asp Gly Val Ser Trp Asp Ser Ile Thr
1265             1270             1275

Leu Gln Gln Trp Arg Lys Ala Phe Gly Val Ile Pro Gln Lys Val
1280             1285             1290

Phe Ile Phe Ser Gly Thr Phe Arg Lys Asn Leu Asp Pro Tyr Glu
1295             1300             1305

Gln Trp Ser Asp Gln Glu Ile Trp Lys Val Ala Asp Glu Val Gly
1310             1315             1320

Leu Arg Ser Val Ile Glu Gln Phe Pro Gly Lys Leu Asp Phe Val
1325             1330             1335

Leu Val Asp Gly Gly Cys Val Leu Ser His Gly His Lys Gln Leu
1340             1345             1350

Met Cys Leu Ala Arg Ser Val Leu Ser Lys Ala Lys Ile Leu Leu
1355             1360             1365

Leu Asp Glu Pro Ser Ala His Leu Asp Pro Val Thr Tyr Gln Ile
1370             1375             1380

Ile Arg Arg Thr Leu Lys Gln Ala Phe Ala Asp Cys Thr Val Ile
1385             1390             1395

Leu Cys Glu His Arg Ile Glu Ala Met Leu Glu Cys Gln Gln Phe
1400             1405             1410

Leu Val Ile Glu Glu Asn Lys Val Arg Gln Tyr Asp Ser Ile Gln
1415             1420             1425

Lys Leu Leu Asn Glu Arg Ser Leu Phe Arg Gln Ala Ile Ser Pro
1430             1435             1440

Ser Asp Arg Val Lys Leu Phe Pro His Arg Asn Ser Ser Lys Cys
1445             1450             1455

```
Lys Ser Lys Pro Gln Ile Ala Ala Leu Lys Glu Glu Thr Glu Glu
    1460            1465                1470

Glu Val Gln Asp Thr Arg Leu
    1475            1480

<210> SEQ ID NO 2
<211> LENGTH: 4443
<212> TYPE: RNA
<213> ORGANISM: Homo sapiens

<400> SEQUENCE: 2
augcagaggu cgccucugga aaaggccagc guugucucca acuuuuuuu cagcuggacc      60 agaccaauuu ugaggaaagg auacagacag cgccuggaau ugucagacau auaccaaauc    120
ccuucuguug auucugcuga caaucuaucu gaaaaauugg aaagagaaug ggauagagag    180
cuggcuucaa agaaaaaucc uaaacucauu aaugcccuuc ggcgauguuu uuucggaga     240 uuuauguucu auggaaucuu uuuauauuua ggggaaguca ccaaagcagu acagccucuc    300
uuacugggaa gaaucauagc uuccuaugac ccggauaaca aggaggaacg ucuaucgcg     360 auuuaucuag gcauaggcuu augccuucuc uuuauuguga ggacacugcu ccuacaccca    420
gccauuuuug gccuucauca cauuggaaug cagaugagaa uagcuauguu uaguuugauu    480
uauaagaaga cuuuaaagcu gucaagccgu guucuagaua aaauuaaguau uggacaacuu   540 guuagucucc uuuccaacaa ccugaacaaa uuugaugaag acuugcauu ggcacauuuc     600 gugggaucg ucccuuugca guggcacuc ucaugggc uaaucuggga guuguuacag         660
gcgucugccu ucuggacu ugguuuccug auaguccuug cccuuuuuca ggcugggcua       720
gggagaauga ugaugaagua cagagaucag agagcuggga agaucaguga aagacuugug    780
auuaccucag aaaugauuga aaauaccaa ucuguuaagg cauacugcug gaagaagca      840 augggaaaaaa ugauugaaaa cuuaagacaa acagaacuga acugacucg gaaggcagcc    900 uaugugagau acuucaauag cucagccuuc uucuucucag gguucuuugu ggguuuuua     960 ucugugcuuc ccuaugcacu aaucaaagga aucauccucc ggaaaauauu caccaccauc   1020
ucauucugca uuguucugcg cauggcgguc acucggcaau ucccuggc guacaaaca      1080 ugguaugacu cucuuggagc aauaaacaaa uacaggauu ucuuacaaaa gcaagaauau     1140
aagacauugg aauauaacuu aacgacuaca gaaguaguga uggagaaugu aacagccuuc   1200
ugggaggagg gauuugggga auuauuugag aaagcaaaac aaaacaauaa caauagaaaa   1260
acuucuaaug gugaugacag ccucuucuuc aguaauuucu cacuucuggg uacuccuguc   1320
cugaaagaua uuaauuucaa gauagaaaga ggacaguugu uggcgguugc uggauccacu   1380
ggagcaggca agacuucacu ucuaaugaug auuauggga aacuggagcc uucagagggu   1440
aaaauuaagc acagugaag aauuucauuc uguucuagu uuccuggau uaugccuggc    1500 accauuaaag aaaauaucau cuuuggugu uccauaaug auauagaua cagaagcguc      1560 aucaaagcau gccaacuaga agaggacauc uccaaguuu cagagaaaga caauauaguu    1620
cuuggagaag guggaaucac acugagugga ggucaacgag caagaauuuc uuuagcaaga   1680
gcaguauaca aagaugcuga uuuguauuua uuagacuccuc cuuuuggaua ccuagauguu   1740
uuaacagaaa aagaaauauu ugaaagcugu gucuguaaac ugauggcuaa caaaacuagg   1800 auuuuggcuca cucuaaaau ggaacauuua agaaagcug acaaauauau aauuuugaau    1860
gaagguagca gcuauuuuua ugggacauuu ucagaacucc aaaaucuaca gccagacuuu    1920 agcucaaaaac ucaugggau ugauucuuuu gaccaauuua gugcagaaag aagaaauuca    1980
```

```
auccuaacug agaccuuaca ccguuucuca uuagaaggag augcuccugu cuccuggaca    2040
gaaacaaaaa aacaaucuuu uaaacagacu ggagaguuug gggaaaaaag gaagaauucu    2100
auucucaauc caaucaacuc uauacgaaaa uuuuccauug ugcaaaagac ucccuuacaa    2160
augaauggca ucgaagagga uucugaugag ccuuuagaga gaaggcuguc cuuaguacca    2220
gauucugagc agggagaggc gauacugccu cgcaucagcg ugaucagcac uggccccacg    2280
cuucaggcac gaaggaggca gucuguccug aaccugauga cacacucagu uaaccaaggu    2340
cagaacauuc accgaaagac aacagcaucc acacgaaaag ugucacuggc cccucaggca    2400
aacuugacug aacuggauau auauucaaga agguuaucuc aagaaacugg cuuggaaaua    2460
agugaagaaa uuaacgaaga agacuuaaag gagugccuuu ugaugauau ggagagcaua     2520 ccagcaguga cuacauggaa cacauaccuu cgauauauua cuguccacaa gagcuuaauu    2580
uuugugcuaa uuuggugcuu aguaauuuuu cuggcagagg uggcugcuuc uuugguugug    2640
cuguggcucc uuggaaacac uccucuucaa gacaaaggga auaguacuca aguagaaau    2700 aacagcuaug cagugauuau caccagcacc aguucguauu auguguuuua cauuuacgug    2760
ggaguagccg acacuuugcu ugcuauggga uucuucagag gucuaccacu ggugcauacu    2820 cuaucacag ugucgaaaau uuuacaccac aaaauguuac auucuguucu ucaagccaccu    2880 augucaaccc ucaacacguu gaaagcaggu gggauucuua auagauucuc caaagauaua    2940
gcaauuuugg augaccuucu gcccuuuacc auauuugacu ucauccaguu guuauuaauu    3000
gugauuggag cuauagcagu ugucgcaguu uuacaacccu acaucuuugu ugcaacagug    3060
ccagugauag uggcuuuuau uauguugaga gcauauuucc uccaaaccuc acagcaacuc    3120
aaacaacugg aaucugaagg caggagucca auuuucacuc aucuuguuac aagcuuaaaa    3180
ggacuaugga cacuucgugc cuucggacgg cagccuuacu uugaaacucu guuccacaaa    3240
gcucugaauu uacauacugc caacugguuc uuguaccugu caacacugcg cuugguccaa    3300 augaaauag aaaugauuuu ugucaucuuc uucauugcug uuaccuucau uccauuuua     3360 acaacaggag aaggagaagg aagaguuggu auuauccuga cuuuagccau gaauaucaug    3420
aguacauugc aguggcuguu aaacuccagc auagaugugg auagcuugau gcgaucugug    3480
agccgagucu uuaaguucau ugacaugcca acagaaggua aaccuaccaa gucaaccaaa    3540
ccauacaaga auggccaacu cucgaaaguu augauuauug agaauucaca cgugaagaaa    3600
gaugacaucu ggcccucagg gggccaaaug acugucaaag aucucacagc aaaauacaca    3660
gaaggcggaa augccauauu agagaacauu uccuucucaa uaaguccugg ccagaggdgug    3720 ggccucuugg gaagaacugg aucagggaag aguacuuugu uaucagcuuu uuugagacua    3780
cugaacacug aaggagaaau ccagaucgau ggugugucuu gggauucaau aacuuugcaa    3840
caguggagga aagccuuugg agugauacca cagaaaguau uauuuuuuc uggaacauuu    3900 agaaaaaacu uggaucccua ugaacagugg agugaucaag aaauauggaa aguugcagau    3960
gagguugggc ucagaucugu gauagaacag uuuccgggga agcuugacuu uguccuuguу    4020 gauggggggcu ugugucuaag ccauggccac aagcaguuga ugugcuuggc uagaucuguu    4080
cucaguaagg cgaagaucuu gcugcuugau gaacccagug ucauuuugga uccaguaaca    4140
uaccaaauaa uuagaagaac ucuaaaacaa gcauuugcug auugcacagu aauucucugu    4200
gaacacagga uagaagcaau gcuggaaugc caacaauuuu uggucauaga agaaacaaa    4260 gugcggcagu acgauuccau ccagaaacug cugaacgaga ggagcucuuu ccggcaagcc    4320
aucagccccu ccgacagggu gaagcucuuu ccccaccgga acucaagcaa gugcaagucu    4380
```

```
aagccccaga uugcugcucu gaaagaggag acagaagaag aggugcaaga uacaaggcuu   4440
uag                                                                4443

<210> SEQ ID NO 3
<211> LENGTH: 4443
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 3
augcagcggu ccccgcucga aaaggccagu gucgugucca acucuucuu cucauggacu     60 cggccuaucc uuagaaaggg guaucggcag aggcuugagu ugucugacau cuaccagauc   120
cccucgguag auucggcgga uaaccucucg gagaagcucg aacgggaaug ggaccgcgaa   180
cucgcgucua agaaaaaccc gaagcucauc aacgcacuga gaaggugcuu cuucuggcgg   240
uucauguucu acgguaucuu cuuguaucuc ggggaggucc aaaaagcagu ccaaccccug   300 uuguggguc gcauuaucgc cucguacgac cccgauaaca agaagaacg gagcaucgcg    360 aucuaccucg ggaucggacu uguuugcuu ucaucguca gaacacuuuu guugcaucca    420
gcaaucuucg gccuccauca caucgguaug cagaugcgaa ucgcuauguu uagcuugauc   480
uacaaaaaga cacugaaacu cucgucgcgg guguuggaua agauuuccau cggucaguug   540 guguccccugc uuaguaauaa cccuaacaaa uucgaugagg acuggcgcu ggcacauuuc    600 gugugggauug ccccguugca agucgcccuu ugaugggcc uuauugggga gcuguugcag    660
gcaucugccu uuuguggccu gggauuucug auugugguugg cauuguuuca ggcugggcuu   720
gggcggauga ugaugaagua cgcgaccag agagcgggua aaaucucgga agacucguc     780 aucacuucgg aaaugaucga aaacaucag ucggucaaag ccuauugcug ggaagaagcu    840
auggagaaga ugauugaaaa ccuccgccaa acugagcuga aacugacccg caaggcggcg   900 uaugccggu auucaauuc gucagcguuc ucuuuuccg gguucuucgu ugucuuucuc     960 ucgguuugc cuuaugccuu gauuaggggg auuauccucc gcaagauuuu caccacgauu   1020
ucguucugca uuguauugcg cauggcagug acacggcaau uccguggc cgucagaca    1080 ugguaugacu cgcuuggagc gaucaacaaa auccaagacu ucuugcaaaa gcaagaguac   1140
aagacccugg aguacaaucu acuacuacg gagguaguaa uggagaaugu gacggcuuuu   1200
ugggaagagg guuuuggaga acuguuugag aaagcaaagc agaauaacaa caaccgcaag   1260
accucaaaug gggacgauuc ccuguuuuuc ucgaacuucu cccugcucgg aacacccgug   1320
uugaaggaca ucaauuucaa gauugagagg ggacagcuuc ucgcgguagc gggaagcacu   1380
ggugcgggaa aaacuagccu cuugaugguug auuauggggg agcuugagcc cagcgagggg   1440
aagauuaaac acuccggcg uaucucauuc uguagccagu uuucauggau caugcccgga   1500
accauuaaag agaacaucau uuucggagua uccuaugaug aguaccgaua cagaucgguc   1560
auuaaggcgu gccaguugga agaggacauu ucuaaguucg ccgagaagga uaacaucguc   1620
uugggagaag ggguauuac auugucggga ggcagcgag cgcggaucag ccucgcgaga    1680
gcgguauaca agaugcaga uuguaucug cuugauucac cguuuggaua ccucgacgua    1740
uugacagaaa agaaaaucuu cgagucgugc guguguaaac uuauggcuaa uaagacgaga   1800
auccuggugu caucaaaaau ggaacaccuu aagaaggcgg acaagauccu gauccuccac   1860
gaaggaucgu ccuacuuuua cggcacuuuc ucagaguugc aaaacuugca gccggacuuc   1920
```

```
ucaagcaaac ucauggggug ugacucauuc gaccaguuca gcgcggaacg gcggaacucg    1980
aucuugacgg aaacgcugca ccgauucucg cuugagggug augccccggu aucguggacc    2040
gagacaaaga agcagucguu uaagcagaca ggagaauuug gugagaaaag aaagaacagu    2100
aucuugaauc cuauuaacuc aauucgcaag uucucaaucg uccagaaaac uccacugcag    2160
augaauggaa uugaagagga uucggacgaa ccccuggagc gcaggcuuag ccucgugccg    2220
gauucagagc aaggggaggc cauucuuccc cggauuucgg ugauuucaac cggaccuaca    2280
cuucaggcga ggcgaaggca auccgugcuc aaccucauga cgcauucggu aaaccagggg    2340
caaaacauuc accgcaaaac gacggcccuca acgagaaaag ugucacugc accccaggcg    2400 aauuugacug aacucgacau cuacagccgu aggcuuucgc aagaaaccgg acuugagauc    2460
agcgaagaaa ucaaugaaga agauuugaaa gaguguuucu uugaugacau ggaaucaauc    2520
ccagcgguga caacguggaa cacauacuug cguuacauca cggugcacaa guccuugauu    2580
uucguccuca ucuggugucu cgugaucuuu cucgcugagg ucgcagcguc acuugugguc    2640
cucuggcugc uugguaauac gcccuugcaa gacaaaggca auucuacaca cucaagaaac    2700
aauuccuaug ccgugauuau cacuucuaca agcucguauu acguguuuua caucuacgua    2760
ggaguggccg acacucugcu cgcgaugggu uucuuccgag gacucccacu cguucacacg    2820
cuuaucacug ucuccaagau ucuccaccau aagaugcuuc auagcguacu gcaggcucccc    2880 auguccaccu ugaauacgcu caaggcggga gguauuuuga aucgcuucuc aaaagauauu    2940
gcaauuuugg augaccuucu gccccugacg aucuucgacu ucauccaguu guugcugauc    3000
gugauugggg cuauugcagu agucgcuguc cuccagccuu acauuuuugu cgcgaccguu    3060
ccggugaucg uggcguuuau caugcugcgg gccuauuucu gcagacguc acagcagcuu    3120 aagcaacugg agucugaagg gaggucgccu aucuuuacgc aucuugugac caguuugaag    3180
ggauugugga cguugcgcgc cuuuggcagg cagcccuacu uugaaacacu guccacaaa    3240 gcgcugaauc uccauacggc aaauugguuu uguauuuga guaccuccg augguuucag    3300 augcgcauug agaugauuuu ugugaucuuc uuuaucgcgg ugacuuuuau cuccaucuug    3360
accacgggag agggcgaggg acgggucggu auuauccuga cacucgccau gaacauuaug    3420
agcacuuugc aguggggcagu gaacagcucg auugaugugg auagccugau gagguccguu    3480
ucgagggucu uuaaguucau cgacaugccg acgagggaa agcccacaaa aaguacgaaa    3540
cccuauaaga augggcaauu gaguaaggua augaucaucg agaacaguca cgugaagaag    3600
gaugacaucu ggccuagcgg gggucagaug accgugaagg accugacggc aaaauacacc    3660
gagggaggga acgcaauccu ugaaaacauc ucguucagca uuagcccggg ucagcgugug    3720
ggguugcucg ggaggaccgg gucaggaaaa ucgacguugc ugucggccuu cuugagacuu    3780
cugaauacag agggugagau ccagaucgac ggcguuucgu gggauagcau caccuugcag    3840
caguggcgga aagcguuugg aguaauccccc caaaaggucu uuaucuuuag cggaaccuuc    3900
cgaaagaauc ucgauccuua ugaacagugg ucagaucaag agauuuggaa agucgcggac    3960
gagguuggcc uucggagugu aaucgagcag uuuccgggaa aacucgacuu uguccuugua    4020 gauggggggau cguccugguc gcaugggcac aagcagcuca ugugccuggc cgauccgguc    4080
cucucuaaag cgaaaauucu ucucuuggau gaaccuucgg cccaucugga cccgguaacg    4140
uaucagauca ucagaggac acuuaagcag gcguuugccg acugcacggu gauucucugu    4200
gagcaucgua ucgaggccau gcucgaaugc cagcaauuuc uugucaucga agagaauaag    4260
guccgccagu acgacuccau ccagaagcug cuuaaugaga gaucauuguu ccggcaggcg    4320
```

```
auuucaccau ccgauagggu gaaacuuuuu ccacacagaa auucgucgaa gugcaaguuc    4380
aaaccgcaga ucgcggccuu gaaagaagag acugaagaag aaguucaaga cacgcgucuu    4440
uaa                                                                 4443

<210> SEQ ID NO 4
<211> LENGTH: 140
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 4
ggacagaucg ccuggagacg ccauccacgc uguuugacc uccauagaag acaccgggac      60
cgauccagcc uccgcggccg ggaacggugc auggaacgc ggauuccccg ugccaagagu    120
gacucaccgu ccuugacacg                                                140

<210> SEQ ID NO 5
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 5
cggguggcau cccugugacc ccucccagu gccucuccug gcccuggaag uugccacucc      60
agugcccacc agccuugucc uaauaaaauu aaguugcauc                          100

<210> SEQ ID NO 6
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gggauccuac c                                                          11

<210> SEQ ID NO 7
<211> LENGTH: 1652
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 7
auggaagaug ccaaaaacau uaagaagggc ccagcgccau ucuacccacu cgaagacggg      60
accgccggcg agcagcugca caaagccaug aagcgcuacg cccuggugcc cggcaccauc    120
gccuuuaccg acgcacauau cgagguggac auuaccuacg ccgaguacuu cgagaugagc    180
guucggcugg cagaagcuau gaagcgcuau gggcugaaua caaaccaucg gaucguggug    240
ugcagcgaga auagcuugca guucuucaug cccguguugg gugcccuguu caucggugug    300
gcugugggcc cagcuaacga caucuacaac gagcgcgagc ugcugaacag caugggcauc    360
agccagccca ccgucguauu cgugagcaag aaagggcugc aaaagauccu caacgugcaa    420
aagaagcuac cgaucauaca aaagaucauc aucauggaua gcaagaccga cuaccagggc    480
uuccaaagca uguacaccuu cgugacuucc cauuugccac ccggcuucaa cgaguacgac    540
```

```
uucgugcccg agagcuucga ccgggacaaa accaucgccc ugaucaugaa caguaguggc    600
aguaccggau ugcccaaggg cguagcccua ccgcaccgca ccgcuugugu ccgauucagu    660
caugcccgcg accccaucuu cggcaaccag aucaucccg acaccgcuau ccucagcgug     720
gugccauuuc accacggcuu cggcauguuc accacgcugg cuacuugau cugcggcuuu     780 cggucgugc ucauguaccg cuucgaggag gagcuauucu ugcgcagcuu gcaagacuau    840
aagauucaau cugcccugcu ggugcccaca cuauuuagcu ucuucgcuaa gagcacucuc    900
aucgacaagu acgaccuaag caacuugcac gagaucgcca gcggcggggc gccgcucagc    960
aaggagguag gugaggccgu ggccaaacgc uuccaccuac caggcauccg ccagggcuac    1020
ggccugacag aaacaaccag cgccauucug aucaccccg aaggggacga caagccuggc    1080
gcaguaggca aggugugcc cuucuucgag gcuaagguog uggacuugga caccgguaag    1140
acacggguug ugaaccagcg cggcgagcug ugcguccgug gccccaugau caugagcggc    1200
uacguuaaca cccccgaggc uacaaacgcu cucaucgaca aggacggcug gcugcacagc    1260
ggcgacaucg ccuacuggga cgaggacgag cacuucuuca ucguggaccg gcugaagagc    1320
cugaucaaau acaagggcua ccagguagcc ccagccgaac uggagagcau ccugcugcaa    1380
caccccaaca ucuucgacgc cggggucgcc ggccugcccg acgacgaugc cggcgagcug    1440
cccgccgcag ucgucgugcu ggaacacggu aaaaccauga ccgagaagga gaucguggac    1500
uauguggcca gccagguuac aaccgccaag aagcugcgcg ugguguugu guucguggac    1560 gaggugccua aggacugac cggcaaguug gacgcccgca agauccgcga gauucucauu    1620
aaggccaaga agggcggcaa gaucgccgug ua                                  1652

<210> SEQ ID NO 8
<211> LENGTH: 8
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8 uuugaauu                                                               8

<210> SEQ ID NO 9
<211> LENGTH: 4443
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9
augcagagaa gccccccugga aaaggccagc guguguccca agcuguucuu cagcuggacc    60
agacccaucc ugagaaaggg cuacagacag agacuggaac ugagcgacau cuaccagauc    120
cccagcgugg acagcgccga caaccugagc gagaagcugg aaagagagug ggacagagag    180
cuggcuagca agaagaaccc caagcugauc aacgcccuga ggcggugcuu cuucuggcgg    240 uuuaugucu acggcaucuu ccuguaccug ggcgaaguga caaaggccgu gcagccccug    300
cuccugggca gaaucauugc cagcuacgac cccgacaaca agaggaaag aucuaucgcc    360 aucuaccugg gcaucggccu ugccugcug uucaucgugc ggacacugcu gcugcacccc    420
gccaucuucg gccugcacca caucggcaug cagaugagaa ucgccauguu cagccugauc    480
uacaagaaaa cccugaagcu gagcagcagg gugcuggaca agaucagcau cggacagcug    540
```

```
gugucccugc ugagcaacaa ccugaacaag uucgacgagg acuggcccu ggcucacuuc      600 guguggaucg cuccacugca ggucgcccug cugauggcc ugaucuggga gcugcugcag      660
gccagcgcuu ucugcggccu gggcuuucug auugugcugg cccuguuuca ggcuggccug      720
ggcaggauga ugaugaagua cagggaccag agagccggca agaucagcga gagacugguc      780
aucaccagcg agaugaucga gaacauccag agcgugaagg ccuacugcug ggaagaggcc      840
auggaaaaga ugaucgaaaa accugagaca accgagcuga agcugaccag aaaggccgcc      900
uacgugcggu acuucaacag cagcgccuuc uucuucuccg gcuucuucgu gguguuccug      960
uccgugcugc ccuacgcccu gaucaagggc aucauccuga ggaagaucuu caccaccauu    1020
ucuuucugca ucgugcugag aauggccgug accagacagu uccccugggc cgugcagacu    1080
ugguacgaca gccugggcgc caucaacaag uccaggacu ccugcagaa gcaggaguac      1140 aagacccucg aguacaaccu gaccaccacc gaggugguca uggaaaacgu gaccgccuuc    1200
ugggaggaag cuucggcga gcuguucgag aaggccaagc agaacaacaa caacagaaag    1260
accagcaacg gcgacgacuc ccuguucuuc uccaacuucu cccugcuggg cacccccgug    1320
cugaaggaca ucaacuucaa gaucgagaga ggccagcugc ucgccgugc cggcucuaca    1380 ggcgcuggca agaccucucu gcugaugguc aucaugggcg agcuggaacc cagcgagggc    1440
aagaucaagc acagcggcag aaucagcuuc ugcagccagu ucagcuggau caugcccggc    1500
accaucaaag agaacaucau cuucggcgug uccuacgacg aguacagaua cagaagcgug    1560
aucaaggccu gccagcugga agaggacauc agcaaguucg ccgagaagga caacaucgug    1620
cugggcgagg cggcaucac ccugucuggc ggccagagag ccagaaucag ccuggccaga    1680
gccguguaca aggacgccga ccuguaccug cuggacagcc ccuucggcua ccuggacgug    1740
cugaccgaga aagagaucuu cgagagcgc guguccaagc ugauggccaa caagaccaga    1800
auccugguca ccagcaagau ggaacaccug aagaaggccg acaagaauccu gauccugcac    1860 gagggcagca gcuacuucua cggcacauuc agcgagcugc agaaccugca gcccgacuuc    1920
agcagcaaac ugauggggcug cgacagcuuc gaccaguuca gcgccgagag aagaaacagc    1980
auccugaccg agacacugca cagauucagc cuggaaggcg acgcccccgu gucuuggacc    2040
gagacaaaga agcagagcuu caagcagacc ggcgaguucg gcgagaagag aaagaacucc    2100
auccugaacc ccaucaacag cauccggaag uucagcaucg ugcagaaaac cccccugcag    2160
augaacggca ucgaagagga cagcgacgag ccccuggaaa acggcugag ccuggugccu    2220 gacagcgagc agggcgaggc cauccugccu agaaucagcg ugaucagcac cggcccacc    2280 cugcaggcua aaggcggca gagcgugcug aaccugauga cccacagcgu gaaccagggc    2340
cagaacaucc accgcaagac caccgccagc accagaaagg uguccccggc ccucaggcc    2400 aaccugaccg agcuggacau cuacagcaga aggcugagcc aggaaccggg ccuggaaauc    2460
agcgaggaaa ucaacgaaga ggaccugaaa gagugcuucu cgacgacau ggaauccauc    2520 cccgccguga ccaccggaa caccuaccug cgguacauca ccgugcacaa gagccugauc    2580
uucgugcuga ucugggugccu ggcaucuuc cuggccgagg uggccgccag ccugguggug    2640
cuguggcucc ugggaaacac cccucuggag gacaagggca acagcaccca gcagaaac    2700 aacagcuacg ccgugaucau caccuccacc agcucuacu acguguuca ucaucuacgug    2760 ggcgugggccg acaccugccu ggcuaugggc uucuucagag gccugcccu ggugcacacc    2820 cugauccgg ugccaagau ccugcaccau aagaugcugc acagcgugcu gcaggcccc    2880 augagcaccc ugaacacacu gaaggcuggc ggcauccuga acagguucag caaggauauc    2940
```

| | |
|---|---:|
| gccauccugg acgaccugcu gccucugacc aucuucgacu ucauccagcu gcugcugauc | 3000 |
| gugaucggcg cuaucgccgu ggguggccgug cugcagcccu acaucuucgu ggccaccgug | 3060 |
| cccgugaucg uggccuucau uaugcugaga gccacuuuc ugcagaccag ccagcagcug | 3120 |
| aagcagcugg aaagcgaggg cagaagcccc aucuucaccc accucgugac cagccugaag | 3180 |
| ggccugugga cccugagagc cuucggcaga cagcccuacu ucgagacacu guuccacaag | 3240 |
| gcccugaacc ugcacaccgc caacugguuu cuguaccugu ccacccugag augguuccag | 3300 |
| augaggaucg agaugaucuu cgucaucuuc uuuaucgccg ugaccuucau ucuauccug | 3360 |
| accaccggcg agggcgaggg aagagugga aucauccuga cccuggccau gaacaucaug | 3420 |
| agcacacugc agugggccgu gaacagcagc aucgacgugg acagccugau gagaagcgug | 3480 |
| uccagagugu ucaaguucau cgacaugccu accgagggca agcccaccaa gagcaccaag | 3540 |
| cccuacaaga acggccagcu gagcaaagug augaucaucg agaacagcca cgucaagaag | 3600 |
| gacgacaucu ggcccagcgg cggacagaug accgugaagg accugaccgc caaguacaca | 3660 |
| gagggcggca acgcuauccu ggaaaacauc agcuucagca ucagcccagg ccagagagug | 3720 |
| ggccugcugg ggagaacagg cagcggcaag ucuacccugc ugucogccuu ccugagacug | 3780 |
| cugaacaccg agggcgagau ccagaucgau ggcguguccu gggacuccau cacccugcag | 3840 |
| caguggcgca aggccuucgg cgugauccc cagaaggugu caucuucag cggcaccuuc | 3900 |
| agaaagaacc uggaccccua cgagcagugg uccgaccagg aaaucuggaa ggucgccgau | 3960 |
| gaagugggcc ugagauccgu gaucgagcag uucccggca agcuggacuu cgugcuggug | 4020 |
| gacggcggcu gcgugcugag ccacggccac aagcagcuga ugugucuggc cgcuccgug | 4080 |
| cugagcaagg cuaagauucu gcugcuggac gagccuagcg ccaccugga cccugugacc | 4140 |
| uaccagauca ucgaaggac ccugaagcag gccuucgccg acugaccgu gauccugugc | 4200 |
| gagcacagaa ucgaggccau gcuggaaugc cagcaguucc uggucaucga agagaacaaa | 4260 |
| gugcggcagu acgacagcau ccagaagcug cugaacgaga gaagccuguu cagacaggcc | 4320 |
| aucagcccca gcgacagagu gaagcuguuc ccccaccgca acagcagcaa gugcaagagc | 4380 |
| aagcccagga ucgccgcccu gaaagaagag acugaggaag aggugcagga caccagacug | 4440 |
| uga | 4443 |

<210> SEQ ID NO 10
<211> LENGTH: 4443
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 10

| | |
|---|---:|
| augcagcggu ccccgcucga aaaggccagu gucgugucca acucuucucuu cucauggacu | 60 |
| cggccuaucc uuagaaaggg guaucggcag aggcuugagu gucugacau cuaccagauc | 120 |
| cccucgguag auucggcgga uaaccucucg gagaagcucg aacgggaaug ggaccgcgaa | 180 |
| cucgcgucua agaaaaaccc gaagcucauc aacgcacuga aaggugcuu cuucggcgg | 240 |
| uucauguucu acgguaucuu cuuguaucuc ggggaggucaa caaagcagu ccaaccccug | 300 |
| uguugggguc gcauuaucgc cucguacgac cccgauaaca agaagaacg gagcaucgcg | 360 |
| aucuaccucg ggaucggacu guguuugcuu uucaucguca gaacacuuu guugcaucca | 420 |
| gcaaucuucg gccuccauca caucgguaug cagaugcgaa ucgcuauguu uagcuugauc | 480 |

-continued

```
uacaaaaaga cacugaaacu cucgucgcgg guguuggaua agauuuccau cggucaguug    540
guguccccugc uuaguaauaa ccucaacaaa uucgaugagg gacuggcgcu ggcacauuuc   600
guguggauug ccccgcugca agucgcacug cuuaugggac ugauuuggga acuguugcag    660
gccagcgccu uuugcggccu gggauuucuc auugugcuug cacuuuucca agcagggcuc    720
ggcagaauga ugaugaagua cagggaccag agagccggaa agaucucaga acggcucgug    780
auuacuucag aaaugaucga gaacauucaa ucggugaaag cguacugcug ggaagaggcg    840
auggaaaaga ugaucgaaaa ccucagacag accgaguuga agcugacccg gaaggccgcg    900
uacgucagau acuucaacag cagcgcuuuc uucuucucgg gcuucuucgu cguguuccug    960
ucggugcugc cguaugcccu cauuaaggga auuaucuugc ggaagaucuu uacuacuauc   1020
ucauuuugca ucguccuucg gauggcgguc acucggcagu ucccgugggc cgugcagacc   1080
ugguacgaca gccucggggc caucaacaag auccaagacu uucuccaaaa gcaagaguac   1140
aaaacccucg aauacaaccu caccacuacu gaagugguca uggaaaacgu gaccgccuuu   1200
ugggaagaag gcuucggaga acuguucgag aaggcgaagc aaaacaacaa uaaucgcaag   1260
acuagcaacg ggaugacuc acuguucuuc agcaauuucu cacugcucgg caccccggug    1320
cuuaaggaca ucaacuucaa gauugaacgc ggacagcucu uggcggugc cggauccacc    1380
ggagcaggaa agacuagccu gcugauggug aucaugggug agcuggaacc guccgaaggc   1440
aaaaucaagc acuccggcag aaucagcuuc ugcucgcagu uuucguggau caugccagga   1500
accaucaaag agaacaucau cuuuggaguc ucauacgaug aguaccgcua cagaagcgug   1560
auuaaggccu gccagcuuga agaggacauc uccaaguucg cggaaaagga caacaucgug   1620
cugggugagg gagggaucac guugucgggc ggucagagag cccgcauuuc gcuggcacgg   1680
gcuguguaca aggaugcgga ucuuuaccuu cuggacucgc cauucgguua ccucgacgug   1740
cugaccgaaa aagaaaucuu cgagagcugc guguguaagc ugauggcuaa uaagacuaga   1800
auccucguga cguccaaaau ggaacaucuu aagaaggcgg auaagauucu cauucuucac   1860
gaggggucga gcuacuucua cgggacuuuu agcgagcugc agaauuugca gccggacuuc   1920
agcucaaagc ucaugggcug cgacucguuc gaucaguuca gcgccgaacg gcgcaauucg   1980
aucuugacgg aaacccugca cagauucucg cuggagggag augcaccugu cucguggacc   2040
gaaaccaaga agcaguccuu caagcagacg ggagaguucg gagaaaagcg gaagaacuca   2100
auccucaacc caaucaacuc cauucgcaaa uucucaaucg ugcagaaaac uccacugcag   2160
augaacggua ucgaagagga uucggacgag ccacuugagc ggagacuguc gcuggugcca   2220
gauucagaac agggggaggc aauccugccg cgcauuuccg ugaucagcac ugggccgacc   2280
cuccaagcua gacgcaggca aucagugcug aaucucauga cccacuccgu caaccaggga   2340
cagaauaucc accgcaagac caccgcgucg acuagaaagg ugucauuggc accgcaagca   2400
aauuugacug aacuugacau cuacucacgg cgccucuccc aagaaaccgg auuggaaauc   2460
uccgaagaga uuaacgaaga agauuugaaa gaguguuucu ucgacgauau ggagucgauc   2520
cccgcaguga ccacuuggaa uacguaucuu cgguacauca ccgugcacaa gagccugauc   2580
uucguccuca ucuggugccu ggugaucuuu cuggccgaag ucgccgcuuc gcuggucgug   2640
cuguggcugc ucgguaauac ccccgcuccaa gacaaaggca auuccacuca cucgcgcaac  2700
aacagcuacg cugugauuau cacgucaacc ucgucguacu auguguucua caucuacgug   2760
ggagucgcgg acacucugcu cgcuaugggc uucuuucgcg gacugccccu gguccacacu   2820
cucaucacgg ugagcaagau ccuccaucau aagaugcucc auuccgugcu gcaggccccg   2880
```

| | |
|---|---|
| augagcacuc ucaacacucu gaaggcgggu ggaaucuuga acagauuuuc caaagacauc | 2940 |
| gcgauucugg acgaucugcu cccacucacu aucuucgacu ucauccaacu gcugcugauc | 3000 |
| gucaucggag cuaucgccgu gguggcuguc uccagccgu auaucuucgu ggccacugug | 3060 |
| ccggugauug ucgcuuucau cauguucgc gcgacuucu ugcaaaccuc gcagcaacuc | 3120 |
| aagcaacugg aguccgaggg ccggagccca aucuuuaccc aucuggugac uucacugaaa | 3180 |
| ggucugugga ccucccgcgc cuuuggucgc cagccuuacu cgaaacucu cuuucacaaa | 3240 |
| gcacugaauc uccacacugc aaacugguuc uuguaccugu ccacccugcg gugguuccaa | 3300 |
| augcggaucg agaugaucuu ugucaucuuc uucaucgccg ugacuuuuau ucccauccuc | 3360 |
| accaccggcg agggagaggg gagagugga auccuccuga cgcuggcgau gaauaucaug | 3420 |
| uccacuuugc aguggccgu caauucgagc aucgacgugg auucgcugau gcgcagcgug | 3480 |
| ucgcgcgugu ucaaguucau cgauaugccc accgaaggua aacccaccaa gagcacgaag | 3540 |
| ccuuacaaga acgggcagcu cucaaaggug augauuaucg agaacuccca ugugaagaag | 3600 |
| gacgacaucu ggccauccgg aggacagaug accgugaagg accugaccgc caaauacacg | 3660 |
| gagggcggaa augcaauccu cgaaaacauc ucguucucca ucucgccugg ccaaagggug | 3720 |
| ggacuuuugg gacgcacugg auccggaaag agcacccugc uuagcgccuu cuugaggcuc | 3780 |
| uugaacaccg agggcgaaau ccagaucgau ggcgugucgu gggaucgau cacccugcag | 3840 |
| caguggagaa aggccuucgg ggugauccg caaaaagugu caucuucuc cggaacguuu | 3900 |
| cggaaaaacc uugacccaua cgaacaaugg ucggaucaag agauuggaa ggucgccgac | 3960 |
| gaaguggggc ugcgcuccgu gaucgagcag uuuccgggaa aacuggacuu cgucuugguc | 4020 |
| gacggcggau cgugccuguc ccacggacau aagcagcuga ugugccuggc ccgcagcguc | 4080 |
| cuuucaaaag cuaagauccu gcugcuggau gaaccuucag cacaccccga cccggucacc | 4140 |
| uaccagauca ucagacggac ccugaaacag gccuuugcgg auuguacugu gaucuugugu | 4200 |
| gaacaccgca uugaagccau gcuggagugc cagcaguucc uggucaucga agagaacaaa | 4260 |
| gugcggcagu acgauuccau ccaaaaacug cucaaugagc gguccccuguu cagacaggca | 4320 |
| auuagcccga cgacagggu caaauuguuc ccccauagaa auucgucgaa auguaaguca | 4380 |
| aagccucaga ucgcggcacu gaaagaagaa acugaagaag aggugcaaga caccagacug | 4440 |
| uga | 4443 |

<210> SEQ ID NO 11
<211> LENGTH: 4443
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 11

| | |
|---|---|
| augcagagaa gcccacugga aaaggcgucg guggugucaa agcuguucuu uagcuggacc | 60 |
| agaccuaucu ugcggaaggg auaccgccaa cgccuggagc ugucggacau cuaccagauu | 120 |
| ccgucagugg auucagcaga caaucucucc gaaaagcugg aacgcgaaug ggacagagag | 180 |
| uuggcgucaa agaagaaccc aaaguugauc aaugcccugc gccgcugcuu cuucuggcgg | 240 |
| uucauguucu acgaaucuu ucuguacccc ggcgaaguca ccaaggcugu gcaaccgcuu | 300 |
| cugcugggac gcaucaucgc cucauacgac ccggacaaca aggaagaacg cuccaucgca | 360 |
| aucuaccucg ggaucggccu cugccugcug uuuaucgugc ggacgcugcu gcuccauccca | 420 |

```
gccauuuucg gacugcacca cauuggcaug caaaugcgga ucgccauguu cagccugauc    480
uacaaaaaga cccugaaguu gagcucacgg guguuggaua agauuucgau cggacagcug    540
gugucgcugc ucuccaacaa ccucaacaag uuugacgaag gccuggcacu ggcccacuuc    600
guguggauug ccccguugca agucgcccuu uugaugggcc uuauuuggga gcuguugcag    660
gcaucugccu uuuguggccu gggauuucug auugucuugg cauuguuuca ggcugggcuu    720
gggcggauga ugaugaagua ucgcgaccag agagcgggua aaaucucgga agacucguc     780 aucacuucgg aaaugaucga aaacauccag ucggucaaag ccuauugcug ggaagaagcu    840
auggagaaga ugauugaaaa ccuccgccaa acugagcuga aacugacccg caaggcggcg    900
uauguccggu auuucaauuc gucagcguuc ucuuuuccg gguucuucgu ugucuuucuc     960
ucgguuuugc cuuaugccuu gauuaagggg auuauccucc gcaagauuuu caccacgauu   1020
ucguucugca uuguauugcg cauggcagug acacggcaau uccgugggc cgugcagaca    1080 ugguaugacu cgcuuggagc gaucaacaaa uccaagacu cuugcaaaa gcaagaguac    1140 aagacccugg aguacaaucu acuacuacg gagguaguaa uggagaaugu gacggcuuuu    1200
ugggaggaag gauucggcga auuguucgaa aaggcuaagc agaacaacaa caaucggaaa   1260
accuccaaug gggacgauuc gcuguucuuc ucgaauuucu cccugcuggg aacgcccgug   1320
cuuaaagaca ucaacuucaa gaucgaacgg ggccagcugc ucgcggucgc gggcagcacu   1380
ggagcgggaa agacuucccu gcucauggcu aucauggag agcuggagcc cucggagggc    1440
aaaaucaagc acucggggag gaucucauuu ugcagccagu ucucguggau caugcccggu   1500
acuaucaaag aaaacaucau cuuuggaguc agcaugacg aguaccgcua ccggucggug    1560
aucaaggccu gccagcugga agaagauauc ccaaguucg ccgaaaagga caacauugug   1620 cuggagaag guggaaucac ucucucggga ggccagcgcg cacgaucuc acucgcaagg    1680 gccguguaca aggaugccga uuuguaccug uuggauucgc cguucgguua ucuugauguc   1740
cucacugaga aagagauuuu ugagucgcgc gucuguaagc ugauggccaa caaaacccgc   1800
auccugguga ccucgaagau ggagcacuug aagaaggccg acaaaaauccu uauccuccau   1860 gagggguagcu cauacuucua cggcaccuuu ucggaacugc agaaucugca gcccgacuuc   1920
ucaucaaaac ugaugggaug ugacucguuc gaucaguucu cggcggagcg gcggaacucg   1980
auccucaccg aaacucucca ccgguucagc cucagggag augccccagu cagcuggacc    2040
gaaacuaaga agcaguccuu caaacagacc ggagaguucg gagaaaaacg caagaacucc    2100
auccucaauc caaucaacag cauccgcaag uucagcaucg ugcagaaaac uccacuucag    2160
augaacggaa ucgaagagga uagcgacgag ccgcuugagc ggagauuguc acuggugccg   2220
gacagcgagc aagggaagc gauucugccg cggaucuccg ugaucucgac uggcccuacc    2280
cuccaagcuc gcagacgcca gagcgugcug aaucucauga cccacucagu caaccaggga   2340
caaaacaucc auagaaagac caccgcuuca cccggaaaag ugucacuugc accgcaggca    2400
aaccugaccg aacucgacau cuacagcaga cggcucucac aagaaacugg auuggagauc    2460
agcgaagaga ucaacgaaga agaucucaaa gaaugcuucu cgacgauau ggaguccauc    2520 ccagcaguca cuacguggaa uaccuacccuc cgcuacauca cugugcacaa gagccugauu    2580
uucguguuga ucuggugccu ggucaucuuc uuggccgagg uggccgcgag ccucgugguc    2640
cucuggcugc ucggcaauac gccgcugcaa gauaagggaa auuccacgca uagcagaaac    2700
aacucauacg cagugaucau cacuagcacu ucaucgucacu acguuucua caucuacgug    2760 gggguggccg auacucuguu ggcaauggga auucuuagag ggcugccucu ggugcauacu   2820
```

| | |
|---|---:|
| cugaucacug uguccaagau ccuccaccac aagaugcucc acuccgugcu ucaggcsccu | 2880 |
| augucaacuc ucaacacccu caaggccgga gguauucuua aucgcuuuuc caaggacauc | 2940 |
| gccauucucg augacuugcu uccccugacu aucuucgacu uuauccaguu gcugcugauu | 3000 |
| gugaucggcg cuauugccgu cgucgcagug cugcaaccgu acaucuuugu ggcuaccguc | 3060 |
| ccagucauug uggccuucau caugcucagg gcauacuuuc uccagaccag ccagcagcuc | 3120 |
| aagcagcucg aauccgaagg cagaucgccg aucuucaccc accucgucac uucgcucaag | 3180 |
| ggccucugga cccugcgcgc cuucggucgc cagccguauu ucgaaacccu guuccauaaa | 3240 |
| gcacugaacc uccauacugc gaacgguuuu cucuaccuuu caacccugag gugguuccag | 3300 |
| augagaaucg agaugaucuu ugugaucuuc uuuaucgcug ugacguucau cuccauucuc | 3360 |
| acuaccggcg agggagaggg cagaguggg auuauccuca cgcuggccau gaauaucaug | 3420 |
| agcacgcugc aguggccgu caauagcagc aucgacgugg acuccugau gcggaccgug | 3480 |
| ucgagagugu uuaaguucau cgauaugccu acugaaggga aaccgaccaa gucgaccaag | 3540 |
| ccguacaaga augggcagcu gagcaaggug augauuaug agaacccca ugugaagaag | 3600 |
| gacgacaucu ggcccagcgg aggccagaug accgugaagg acuugaccgc uaaguacacu | 3660 |
| gaggguggaa augccauucu ugagaauauc agcuucucga ucucgccggg acaacgcgug | 3720 |
| ggauugcucg ggcgcacugg cagcggcaaa uccacccugc uuagcgcuuu ucugaggcug | 3780 |
| cugaacacug aaggugaaau ucaaaucgau ggagugcgu gggauagcau caccccuucaa | 3840 |
| caguggcgca aggccuucgg cgugacccu caaaaggucu uuaucuucuc ggggacguuc | 3900 |
| cggaaaaauc ucgacccucua cgaacagugg ucagaccaag agauuuggaa agucgcagau | 3960 |
| gaggucggac ugcgcucagu gaucgaacag uuuccgggua aacuugacuu cgugcucguc | 4020 |
| gauggagguu gcguccuguc ccacggacau aagcagcuga ugugucuggc gcgcucgguc | 4080 |
| cucuccaaag cgaagauccu gcugcucgau gaaccguccg cccaccuuga uccagugacc | 4140 |
| uaucagauca uucggagaac uuugaagcaa gccuucgcug acugaccgu caucucugc | 4200 |
| gaacaccgga ucgaggcaau gcuggagugc caacaguuuc uggucaucga agaaaacaaa | 4260 |
| gugcgccagu augacucgau ccaaaaacuu cugaacgagc gcucccucuu ccggcaggca | 4320 |
| aucagcccau ccgaccgcgu gaaguuguuc ccucaucgga auagcuccaa augcaaaucg | 4380 |
| aagccgcaga ucgcugccuu gaaagaagaa accgaagaag aaguccaaga cacuagguug | 4440 |
| uag | 4443 |

<210> SEQ ID NO 12
<211> LENGTH: 4443
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 12

| | |
|---|---:|
| augcagcggu cccucugga gaaggcuucc gguucagca agcuguucuu cucguggacc | 60 |
| agaccuaucc uccgcaaggg auaccgccag cgccuggagc ugucagauau cuaccagauc | 120 |
| ccaagcgugg acucagccga caaucugagc gaaaagcugg aacgggagug ggaccgggag | 180 |
| cucgccuca agaagaaucc gaaguugauc aaucgcugc gcagaugcuu cuucuggcgg | 240 |
| uuuauguuuu acggcaucuu ucuguaucuc ggagaaguga ccaaagccgu gcagccgcug | 300 |
| cucuuggua ggaucauugc uucguacgac ccggacaaca agaagaacg cucccaucgcc | 360 |

```
aucuaccucg gaaucggucu gugccugcuc uuuaucgugc gcacucuccu gcugcauccg    420
gcgaucuucg gacugcacca caucggcaug caaaugcgga ucgcaauguu cucacugauc    480
uacaaaaaga cucugaagcu cagcccagag ugucuggaua agaucucgau cgggcaacuc    540
gucagccugc ugucgaacaa ucugaauaag uucgacgaag gguuggcccu cgcacauuuc    600
guguggaucg caccgcugca aguggcgcuc cugaugggac ucauuuggga acugcuccaa    660
gccagcgcgu uuugcggacu cggauuccug aucgugcucg cccuguucca agccggacug    720
gggcgcauga ugaugaagua ccgcgaucag cgggcaggaa agauccccga gcgguuggug    780
aucacuuccg aaaugaucga gaauauucag uccgugaagg ccuacugcug ggaagaagcu    840
auggaaaaga ugauugaaaa cuugcggcaa acugagcuga aauugacucg caaagcggca    900
uacguccgcu acuucaauag cagcgccuuc ucuuuucgg gcuuuucgu gguguuucug    960 agcgugcugc ccuacgcucu gaucaaggga aucauccucc ggaaaaucuu caccaccauu   1020
ucguucugua ucguguugcg cauggccgug acucgccagu uccccugggc ggugcagacc   1080
ugguacgaca gcuuggggc aaucaauaag auucaagacu cuugcaaaa gcaggaguac   1140 aagacucugg aguacaaccu gaccaccacu gaagucguga uggagaacgu gaccgcccuuu   1200 ugggaagagg guuuuggaga acuguuugag aaagcaaagc agaauaacaa caaccgcaag   1260
accucaaaug gggacgauuc ccuguuuuuc ucgaacuucu cccugcucgg aacacccgug   1320
uugaaggaca ucaauuucaa gauugagagg ggacagcuuc ucgcgguagc gggaagcacu   1380
ggugcgggaa aaacuagccu cuugauggug auuaugggg agcuugagcc cagcgagggg   1440
aagauuaaac acucccggcg uaucucauuc uguagccagu uucauggau caugcccgga   1500 accauuaaag agaacaucau uucggaguga uccuaugaug aguaccgaua cagaucgguc   1560
auuaaggcgu gccaguugga agaggacauu ucuaaguucg ccgagaagga uaacaucguc   1620
uugggagaag ggguauuac auugucggga gggcagcgag cgcggaucag ccucgcgaga   1680
gcgguauaca aagaugcaga uuuguacugu cuugauucac cguuuggaua ccucgacgua   1740
uugacagaaa aagaaaucuu cgagucgugc guguguaaac uuauggcuaa uaagacgaga   1800
auccugguga cuuccaaaau ggagcaucuc aagaaggcgg acaagauccu gauucugcau   1860
gagggaucaa gcuauuucua cggaacuuuu ccgagcugc agaaccucca gccggauuuu   1920
agcuccaagc ugaugggguug cgacucauuc gaccaauucu cggcgagcg gcggaacuca   1980 auccugaccg aaaccccugca ucgcuucucc cuugagggag augccccggu gucguggacu   2040
gagacuaaaa agcagucguu uaagcaaacu ggcgaauucg gcgaaaagcg gaagaauagc   2100
auccucaacc caaucaacag cauucggaag uucagcaucg uccaaaagac cccgcuccag   2160
augaacggca uugaagagga cucagacgag ccauuggaaa gacgccuguc acuggucccca   2220 gauucggagc agggugaagc aauucugccu cggaucucgg ucaucgac uggccccacu   2280 cuccaagcuc ggcggagaca gagcgugcuu aacuugauga cccacuccgu gaaccagggu   2340
cagaacaucc accgcaaaac caccgccucc accaggaagg ugucacuggc cccucaagcc   2400
aaucugacug aguuggauau cuaccucaga aggcucagcc aggaaaccgg acuggaaauc   2460
ucggaagaga ucaacgaaga ggaucucaaa gaguguuucu cgacgacau ggaaucaauc   2520 ccugcugcuca cuacuuggaa caccuaucuc cgcuacauua ccgugcacaa gucacucauc   2580
uucguccuga ucugguguccu cgugaucuuc cuggccgagg ucgcagcauc gcugucugug   2640
cuguggcugc ucgcaacac cccacuccaa gacaaaggca acagcaccca uucccgcaac   2700
aacuccuacg cggugaucau cacuucaacu ucguccuacu acgucuuuua caucuacgug   2760
```

```
ggcguggcgg acacgcuccu ggcuaugggg uucuuucgcg ggcugccucu uguccacacg    2820
cucaucacug ugucaaagau ucuccaccac aaaaugcugc acuccgugcu ccaggccccu    2880
augucgacuu ugaacacgcu uaaggccgga ggcauccuua acagauucuc gaaagauauc    2940
gcgaucuugg acgaucuucu gccgcugacu aucuuugacu ucauccaacu ccugcugauc    3000
gucaucggug ccaucgcagu ggucgcggug cuccaaccgu acauuuucgu ggcgacugug    3060
ccggugaucg uggcguucau caugcugcgg gcuuacuuuc uucagaccuc acagcagcug    3120
aagcaacucg aaucggaggg uagaucacca aucuuuaccc accucgucac cucgcugaag    3180
ggacucugga cccugcgcgc auuuggacgg caaccguacu ucgagacucu cuuccauaag    3240
gcccugaauc ugcauacggc gaauugguuu cuuuaccucu cgacgcuccg cugguuccag    3300
augcgcauug agaugauuuu cgucaucuuu uucaucgcgg ugaccuucau cuccauccuc    3360 accacggguq agggagaggg cagagucgga auuauccuca cucuggccau gaacaucaug    3420
uccacucugc aguqggccgu caacucaucc auugacgugg acucgcugau gcgcuccgug    3480
ucgagagugu caaguucau cgauaugccg accgaggaa agccaacuaa gucgaccaag    3540
ccguacaaaa acggacagcu gagcaagguc augaucaucg aaaacuccca cgugaaaaag    3600
gaugacaucu ggccgccgg uggacagaug acggugaagg aucugacgc gaaguacacu    3660 gagggaggga augccauccu cgaaaacauc ucauucuaa ucuccccugg acagaggguc    3720
gggcugcugg gccgcacugg cucggggaag ucgacucuuc uuucggcauu ucugcgcuug    3780
cucaauaccg agggagaaau ccagaucgau ggagugucau gggacucgau caccccugcag    3840 cagugqcgca aggcuuuugg cgucaucccg caaaaggugu caucuucuc gggcacuuuu    3900 agaaagaauc uggaucccua cgaacagugg ucagaucaag agauuggaa agucgcagac    3960 gaagugggcc uccggucgu gauugaacag uuuccgggaa agcucgacuu cgucuugu    4020 gacggaggau gugugcugag ccacggccac aaacagcuca ugugccuggc ucggucgguc    4080
cugucgaaag caaagauccu gcugcuggac gaaccgucgg cacaccucga uccagugacg    4140
uaccagauca uccggcggac ccugaagcag gccuucgcag acugcacugu cauuugugu    4200 gaacacagaa ucgaagcuau guuggagugc cagcaguucc uggucaucga agaaaacaaa    4260
guccgccagu acgauucgau ucagaagcug cugaacgaac ggagccucuu cagacaggcg    4320
aucagcccca gcgaucgggu caaguuguuc ccgcaucgga acagcagcaa guguaagca    4380 aagcccucaga ucgcugcacu caaagaagag acugaagaag aagugcaaga caccagacuc    4440
uga                                                                 4443

<210> SEQ ID NO 13
<211> LENGTH: 4443
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 13
augcagcgcu cgcccucugga gaaagccuca gucgugucaa aacuguucuu uagcuggacu      60
cgcccgauuc uccggaaggg uuauagacag cgcuuggagc ucuccgacau cuaccaaauc     120
ccuuccgugg acuccgccga caaccugucg gagaagcucg aacgcgagug ggaccgggaa     180
cucgcgucca aaagaaaucc aaaacucauu aaugcacugc gccgcugcuu cucuggcgc      240 uuuauguuuu acgguaucuu ucucuaccug ggcgagguga cgaaagcagu gcagccgcuc     300
```

```
cugcuuggca gaauuaucgc cucguacgau ccggauaaca aagaagaacg cucaaucgcu    360
aucuaccucg guaucggauu gugccugcuu uucaucgugc gcacccuguu gcugcacccg    420
gcgauuuucg gacuccacca caucggaaug caaaugagaa uugcaauguu ucauugauc     480 uacaaaaaga cccuuaaacu gucgucccgc guccucgaca agauuucaau cggccagcug    540
gugucgcuuc uuucgaauaa ucuuaacaag uucgaugaag gacucgcgcu cgcccauuuc    600
guguggaucg caccacuuca agucgcacug cucaugggac ugauuuggga guugcugcag    660
gcuuccgccu uuugcggccu gggauuccug aucguccugg cuuuguucca ggcuggacug    720
ggcagaauga ugaugaagua ccgggaccag cgggcaggaa agaucagcga aaggcucgug    780
aucacuagcg aaaugaucga gaacauccaa uccgucaagg cguacugcug ggaagaagcg    840
auggagaaga ugaucgaaaa ucuucgccaa accgaacuca aacucacuag aaaggcugcc    900
uacgugcgcu acuuuaacag cucagcauuu ucuucuccg gauuuucgu ggguguuccug    960 ucggugcugc cauacgcccu gaucaagggg aucauucuuc gcaaaaucuu caccacgauc   1020
ucauucugca uugccuccg gauggccgug acgcggcagu cccuugggc agugcaaacu    1080 ugguacgauu cgcuggggggc cauuaacaag auucaagauu ucuucaaaa gcaggaguac   1140 aaacccugg aguacaaucu gaccacuacg gaagucguga uggaaaacgu gacugcuuuu    1200
ugggaggaag gcuucggcga acuuuuugaa aaggcaaagc aaaacaauaa caacagaaag    1260
acgucaaacg gcgaugacuc gcuguucuuc uccaauuucu cccugcucgg caccccugug    1320
cugaaggaca ucaacuucaa aauugaacgc ggacagcugc uggccguggc gggaucgacc    1380
ggggcuggga aaaccucguu guugaugug aucaugggag aacucgaacc cucggaggga    1440
aagauuaagc auagcggacg gaucagcuuc uguucccagu ucucguggau caugccggga    1500
accauuaagg aaaacaucau cuuccggcgug uccuacgacg aguaccggua uaggucggug    1560
aucaaggccu gccaguugga agaggacauc uccaaguucg cugagaagga caacaucgug    1620
cucgugaagg ggggcauuac ucuguccggu ggccagcgcg cgagaauuuc gcuggcucgc    1680
gcgguguaca aagaugcgga ucucuaucug cuggauucgc ccuucggaua ccucgauguc    1740
cucacggaga aggagaucuu cgaaucgcgc gugugcaagu ugaauggcgaa caagacuagg    1800 auccugguca cuuccaagau ggagcacuug aagaaggccg auaagaucuu gauccuccau    1860
gaaggaucga gcuacuuuua cggaacuuuc ucagagcugc agaacuugca gccggacuuc    1920
ucaagcaaac ugaugggguug cgacucguuc gaccaguuuu cggcagaacg gcggaacucg    1980
auccugacug agacucugca ucgcuuuucg cuggaaggcg augccccugu guccuggacu    2040
gaaaccaaga agcaauccuu caaacaaacu ggagaauucg gagaaaagcg gaagaacucc    2100
auccuuaacc ccaucaauag cauccggaag uucuucaaucg uccaaaagac cccgcugcag    2160
augaauggca ucgaagaaga uagcgacgaa ccucuugaaa gacggcuguc cuuggugcca    2220
gacucagaac agggagaagc uauccugccg cggaucuccg ugaucagcac cggaccgacu    2280
cugcaggcuc gcagacgcca gagcgugcuc aaccugauga cccacuccgu gaaccaggga    2340
caaaacaucc auagaaagac cacggccucc accagaaaag ucucccuggc accgcaagcc    2400
aaccugacug aacuggacau cuacagcaga aggcucagcc aagaaaccgg acuggagauu    2460
ucagaagaaa ucaacgagga agaucuuaaa gagugcuucu cgacgacau ggaaucgauc    2520 ccagccguga ccacuuggaa uaccuacucg agauacauca ccgugcacaa auccucgauc    2580
uucgugcuga ucuggugccu ggugaucuuc ccuggugagg uggccgccuc acugguggug    2640 cuuuggguugc ugggaauac gccgcuccaa gacaagggaa acuccacgca cuccagaaac    2700
```

| | |
|---|---|
| aacucguacg ccgugaucau cacgucgacu ucgucguacu acguuucua caucuacguc | 2760 |
| gguguggcag acacucucuu ggcgaugggc uuuuuccggg gacugccacu gguccacacc | 2820 |
| cugaucaccg uguccaaaau cuugcaccac aagaugcucc acagcgugcu gcaagccccg | 2880 |
| augagcaccc ugaauacccu caaagcggga ggcauccuca acagauucag caaggacauc | 2940 |
| gccauccucg acgaccuguu gccccugacc aucuucgauu ucauccagcu ucuucucauc | 3000 |
| gugaucgggg caaucgcugu cguggcggug cugcagccgu acaucuucgu ggcgacugug | 3060 |
| ccagugaucg ucgccuuuau caugcugcgg gccuacuuuc uccaaacuuc ccaacagcug | 3120 |
| aaacaacugg agucgagggg ccgcagcccu aucuucaccc aucuggugac cagccucaaa | 3180 |
| ggacugugga cucugagggc uuucgggagg cagccauacu ucgagacucu cuuucacaag | 3240 |
| gcccugaauc uccauacggc aaauugguuu uguauuuga guaccuccg augguuucag | 3300 |
| augcgcauug agaugauuuu ugugaucuuc uuuaucgcgg ugacuuuuau cuccaucuug | 3360 |
| accacgggag agggcgaggg acgggucggu auuauccuga cacucgccau gaacauuaug | 3420 |
| agcacuuugc aguggcagu gaacagcucg auugaugugg auagccugau gaggucgcuu | 3480 |
| ucgagggucu uaaguucau cgacaugccg acggaggaa agcccacaaa aaguacgaaa | 3540 |
| cccuauaaga auggcaauu gaguaaggua augaucaucg agaacaguca cgugaagaag | 3600 |
| gaugacaucu ggccuagcgg ggucagaug accgugaagg accgacggc aaaauacacc | 3660 |
| gagggaggga acgcaauccu ugaaaacauc ucguucagca uuagccccgg ucagcgugug | 3720 |
| ggguugcucg ggaggaccgg gucaggaaaa ucgacguugc ugucggccuu cuugagacuu | 3780 |
| cugaauacag agggugagau ccagaucgac ggcguuucgu gggauagcau caccuugcag | 3840 |
| cagugcgca aggcguucgg agucauuccc caaaaggugu ucaucuuuuc gggaaccuuc | 3900 |
| cgcaagaauc uggauccgua cgaacagugg agcgaccaag agauuuggaa aguggcagau | 3960 |
| gaaguggau ugcggagcgu caucgaacag uuuccgggaa agcucgauuu cguccuugug | 4020 |
| gacgguggau gugugcuguc gcacggccau aagcagcuga ugucucgc ccgcucgguu | 4080 |
| cugucaaagg cgaagauccu cuugcuggau gagccaucag cccaucugga cccggugacg | 4140 |
| uaccagauca uuagacggac gcugaaacag gcauucgcgg acugcacugu gauccucugu | 4200 |
| gaacaucgga ucgaggccau gcuggagugu caacaauucu ggucaucga agagaacaaa | 4260 |
| gugcggcagu acgacagcau ccaaaagcug cugaacgaga gguccccucuu ccgccaggcc | 4320 |
| aucuccccau ccgaccgggu caagcuguuc ccucaccgca acagcucaaa gugcaaaucc | 4380 |
| aaaccccaga ucgcagcgcu gaaagaagaa acugaagaag aagugcaaga cacuagacug | 4440 |
| uga | 4443 |

<210> SEQ ID NO 14
<211> LENGTH: 4443
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 14

| | |
|---|---|
| augcaaaggu ccccauugga gaaggccuca guggugucga agcuguucuu cucguggacc | 60 |
| aggccuaucc uccggaaggg auacagacag cggcuggaac uguccgauau cuaccagauc | 120 |
| cccagcgugg acagcgccga uaaucucagc gaaaagcugg aacgggaaug ggaccgcgaa | 180 |
| cucgcuucga agaagaaccc gaagcugauu aaugcucugc ggagauguuu cuuuuggcgg | 240 |

```
uucauguuuu acggaaucuu ucuguacuug ggagagguca cgaaggcugu gcagccucug      300
cugcugggac ggauuaucgc gucguaugac cccgacaaua aggaagaacg cagcaucgca      360
aucuaccugg gcaucggauu gugccugcug uucaucguga gaacucuccu gcugcaucca     420
gccaucuucg gacuccacca cauuggaaug cagaugagaa ucgcaauguu cucccugauc      480
uacaagaaaa cgcucaagcu cagcagccgc gugcucgaua agaucagcau cggucaauug      540 gucccugc ugucgaauaa cccaacaag uucgacgaag gguuggcccu cgcucacuuc          600
guguggaucg caccucugca aguggcccug cugaugggac ugauuggga gcugcugcag        660 gcuuccgcuu ucugcggccu gggauuucuu aucgugcuug cucuguucca ggcgggacug       720
ggacgcauga ugaugaagua ccgggaccaa cgggcuggaa agaucagcga acggcuggug       780
aucacuuccg aaaugauuga gaauauccag ucagucaagg cguacugcug ggaagaggcu       840
auggaaaaga ugauugaaaa ucugacaca accgagcuga agcugacucg gaaagcggcc       900
uacgucagau acuucaauag gucagcuuuc uuuucucgg gguuuucgu cguguuccug         960 ucggugcuuc ccuaugcccu gauuaagggc aucauucugc gcaagaucuu cacuacgauc      1020
ucauucugca ucgugcugcg cauggcugug accagacaau ucccgugggc cgugcaaaacc     1080 ugguacgauu cacugggagc caucaacaag auccaagacu uucuccaaaa acaggaguau      1140 aagaccccugg aguacaaccu gacuacuacc gagguggugu ggagaacgu gacugcguuu     1200 ugggaagaag gguucggcga acuguuugaa aaggccaagc agaacaauaa caacagaaag     1260
acuucaaacg gagaugacuc gcuguucuuu ucgaacuuca gccugcuggg uaccccagug      1320
uugaaagaua ucaacuucaa gauugagaga ggacagcugc uggcugugc gggauccacc       1380 ggagcaggaa aaacuucacu ccugauggug aucaugggag aacucgaacc gucagagggg     1440
aagauuaaac acucgggaag aaucucauuu ugcucccaau uucauggau uaugccggga       1500 accauuaaag aaaacauuau cuucggcgug uccuacgacg aguaccgcua cagaucggug     1560
aucaaagcau gccagcugga gaggacauc ucgaaauucg cugaaaaaga caauaucgug        1620
cucggggaag gcggcaucac ccucagcgga ggacaacggg cacggauuc gcucgcacgc       1680 gcagucuaca aagacgccga ucucuaccuc uuggacagcc cauucgggua ucuggacgug     1740
cucaccgaga aagagaucuu cgaaagcugc gucugcaagc ucauggccaa caagacccgc      1800
auccucguga cgucgaagau ggaacaucuu aagaaggcug acaagauucu cauuccccau     1860
gaagggagcu cauacuucua cggcaccuuu uccgagcucc agaaucugca accggacuuc      1920
ucguccaagc ugaugggcug cgauucguuu gaucaguucu ccgccgagcg gagaaacagc     1980
auucugacgg aaaccugca ccgguucucg cuggaaggcg augcaccggu gucguggacc       2040
gaaacuaaga agcaaucguu caagcagacg ggagaguuug gagagaagcg gaaaaacucc     2100 auccucaaacc gaucaacag caucggaag uucagcaucg ugcaaaagac cccgcuccag        2160
augaauggca uugaagagga cuccgacgaa ccuuuggaac gcagacugag ccucgugccg      2220
gauucagaac agggagaagc cauucugcca cggauuccg ugaucagcac ugggccaacu       2280
cuccaagcac ggcggaggca guccgugcug aaucuuauga cgcacagcgu gaaccaaggg      2340
cagaacaucc auagaaaaac gaccgcuucg accaggaaag ucccccucgc cccacaagcu      2400
aaccucacgg aacuggauau cuacucccgc agacugcgc aagagacugg ccuugagauc       2460
uccgaagaga uuaacgaaga agaucucaaa gaauguuucu cgaugauau ggaaucaauc       2520 ccggcaguga ccacuuggaa caccuacuug cgcuauauca cuguugcacaa aagccuuauc     2580 uucgucccuca ucuggugccu cgucaucuuc cuggcugagg ucgcagcccuc gcuggucgug    2640
```

| | |
|---|---:|
| cucugguugc ucggaaacac uccgcugcag gauaagggga auucgacuca cucgcggaac | 2700 |
| aauucguacg cugucauuau caccucgacg ucgucauacu acguguuuua caucuacgug | 2760 |
| ggaguggcug acacucuguu ggcuaugggg uucuucgcg gccugccacu gguccauacu | 2820 |
| cucauuacug uguccaaaau ccuucaucac aagauguugc auucagugcu gcaagcaccg | 2880 |
| auguccaccc ucaauacccu uaaggcuggc gggauucuca accgcuucuc gaaagacauc | 2940 |
| gccauccucg augaucuucu gccucucacc aucuuugauu ucauccagcu gcuccugauc | 3000 |
| gugaucggag cgauugccgu ggugcagug uugcagccgu acaucuuugu cgcaacugug | 3060 |
| ccggucaucg ucgccuucau caugcugcgc gccuacuucu ugcaaacguc acagcaacug | 3120 |
| aagcagcuug aauccgaggg aagaucaccu aucuucaccc accucgugac uucgcugaag | 3180 |
| gggcugugga cgcugcgcgc auuuggaagg caaccguacu ucgagacuuu guuccacaag | 3240 |
| gcgcucaauc uucacacugc caauugguuc uuguaccugu caacgcugag augguuucag | 3300 |
| augcggaucg aaaugaucuu cgugaucuuc uuuaucgcgg ugacuuucau cucgauccug | 3360 |
| acuaccggag agggagaagg acggugggu auuauccuca cucuggcgau gaacaucaug | 3420 |
| ucgacgcuuc agugggcggu gaauagcuca aucgaugucg acucgcugau gcgcuccgug | 3480 |
| agccgggugu uuaaguucau cgacaugcca acugaaggga agccgaccaa gucgaccaaa | 3540 |
| ccguacaaaa acggacagcu cuccaaggug augauuaucg agaauccca cgugaaaaag | 3600 |
| gacgacaucu ggccauccgg uggacagaug accgugaagg accugaccgc gaaguacacu | 3660 |
| gagggaggca acgcaauccu ugagaacauc agcuucucca ucucgcccgg ucagagggug | 3720 |
| ggccuucuug gccggaccgg aucgggaaag uccacucuuc ugucggccuu ucuucgccuc | 3780 |
| uugaauacug aaggggaaau ccagaucgac ggagugucgu gggauagcau cacucugcag | 3840 |
| caguggcgga aagcguuugg aguaaucccc caaaaggucu uuaucuuuag cggaaccuuc | 3900 |
| cgaaagaauc ucgauccuua ugaacagugg ucagaucaag agauuggaa agucgcggac | 3960 |
| gagguuggcc uucggagugu aaucgagcag uuuccgggaa aacucgacuu gcccuugua | 4020 |
| gauggggau cguccugc gcaugggcac aagcagcuca ugugccuggc gcgauccguc | 4080 |
| cucucuaaag cgaaaauucu ucucuuggau gaaccuucgg cccaucugga cccgguaacg | 4140 |
| uaucagauca ucagaaggac acuuaagcag gcguuugccg acugcacggu gauucucugu | 4200 |
| gagcaucgua ucgaggccau gcucgaaugc cagcaauuuc uugcaucga agagaauaag | 4260 |
| guccgccagu acgacuccau ccagaagcug cuuaaugaga gaucauuguu ccggcaggcg | 4320 |
| auuucaccau ccgauagggu gaaacuuuuu ccacacagaa auucgucgaa gugcaaguccc | 4380 |
| aaaccgcaga ucgcggccuu gaaagaagag acugaagaag aaguucaaga cacgcgucuu | 4440 |
| uaa | 4443 |

<210> SEQ ID NO 15
<211> LENGTH: 4473
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 15

| | |
|---|---:|
| augcagcggu ccccgcucga aaaggccagu gucgugucca aacucuucuu cucauggacu | 60 |
| cggccuauce uuagaaaggg guaucggcag aggcuugagu ugucugacau cuaccagauc | 120 |
| cccucgguag auucggcgga uaaccucucg gagaagcucg aacgggaaug ggaccgcgaa | 180 |

-continued

| | |
|---|---|
| cucgcgucua agaaaaaccc gaagcucauc aacgcacuga gaaggugcuu cuucuggcgg | 240 |
| uucauguucu acgguaucuu cuuguaucuc ggggagguca caaaagcagu ccaaccccug | 300 |
| uuguugqguc gcauuaucgc cucguacgac cccgauaaca aagaagaacg gagcaucgcg | 360 |
| aucuaccucg ggaucggacu guguuugcuu ucaucguca gaacacuuuu guugcaucca | 420 |
| gcaaucuucg gccuccauca caucgguaug cagaugcgaa ucgcuauguu uagcuugauc | 480 |
| uacaaaaaga cacugaaacu cucgcgcgg guguuggaua agauuuccau cggucaguug | 540 |
| gugucccugc uuaguaauaa ccucaacaaa uucgaugagg gacuggcgcu ggcacauuuc | 600 |
| guguggauug ccccguugca agucgcccuu ugauggggcc uuauuuggga gcuguugcag | 660 |
| gcaucugccu uuuguggccu gggauuucug auuguguugg cauuguuuca ggcugggcuu | 720 |
| gggcggauga ugaugaagua ucgcgaccag agagcgggua aaaucucgga agacucguc | 780 |
| aucacuucgg aaaugaucga aaacauccag ucggucaaag ccuauugcug ggaagaagcu | 840 |
| auggagaaga ugauugaaaa ccuccgccaa acugagcuga aacugacccg caaggcggcg | 900 |
| uauguccggu auucaauuc gucagcguuc uucuuuccg gguucuucgu ugucuuucuc | 960 |
| ucgguuugc cuuaugccuu gauuaagggg auuauccucc gcaagauuuu caccacgauu | 1020 |
| ucguucugca uuguauugcg cauggcagug acacggcaau uccgugggc cgucagaca | 1080 |
| ugguaugacu cgcuggagc gaucaacaaa auccaagacu ucuugcaaaa gcaagaguac | 1140 |
| aagacccugg aguacaaucu acuacuacg gagguaguaa uggagaaugu gacggcuuuu | 1200 |
| ugggaagagg guuuggaga acuguuugag aaagcaaagc agaauaacaa caaccgcaag | 1260 |
| accucaaaug gggacgauuc ccuguuuuuc ucgaacuucu cccugcucgg aacacccgug | 1320 |
| uugaaggaca ucaauuucaa gauugagagg ggacagcuuc ucgcgguagc gggaagcacu | 1380 |
| ggugcgggaa aaacuagccu cuugauggug auuauggggg agcuugagcc cagcgagggg | 1440 |
| aagauuaaac acuccgggcg uaucucauuc uguagccagu uucauggau caugcccgga | 1500 |
| accauuaaag agaacaucau uuucggagua uccuaugaug aguaccgaua cagaucgguc | 1560 |
| auuaaggcgu gccaguugga agaggacauu ucuaaguucg ccgagaagga uaacaucguc | 1620 |
| uugggagaag gggguauuac auugucggga gggcagcgag cgcggaucag ccucgcgaga | 1680 |
| gcgguauaca aagaugcaga uuuguaucug cuugauucac cguuggaua ccucgacgua | 1740 |
| uugacagaaa agaaaucuu cgagucgugc gugguaaac uuauggcuaa uaagacgaga | 1800 |
| auccugguga caucaaaaau ggaacaccuu aagaaggcgg acaagauccu gauccuccac | 1860 |
| gaaggaucgu ccuacuuuua cggcacuuuc ucagaguugc aaaacuugca gccgacuuc | 1920 |
| ucaagcaaac ucaugggggu ugacucauuc gaccaguuca gcgcggaacg gcggaacucg | 1980 |
| aucuugacgg aaacgcugca ccgauucucg cuugagggug augccccggu aucguggacc | 2040 |
| gagacaaaga agcagucguu uaagcagaca ggagaauuug gugagaaaag aaagaacagu | 2100 |
| aucuugaauc cuauuaacuc aauucgcaag uucucaaucg uccagaaaac uccacugcag | 2160 |
| augaauggaa uugaagagga uucggacgaa ccccuggagc gcaggcuuag ccucgugccg | 2220 |
| gauucagagc aaggggaggc cauucuuccc cggauucgg ugauuucaac cggaccuaca | 2280 |
| cuucaggcga ggcgaaggca auccgugcuc aaccucauga cgcauucggu aaaccagggg | 2340 |
| caaaacauuc accgcaaaac gacggccuca acgagaaaag ugucacuugc ccccaggcg | 2400 |
| aauuugacug aacucgacau cuacagccgu aggcuuucgc aagaaaccgg acuugagauc | 2460 |
| agcgaagaaa ucaugaaga agauuugaaa gaguguuucu uugaugacau ggaaucaauc | 2520 |
| ccagcgguga caacguggaa cacauacuug cguuacauca cggugcacaa guccuugauu | 2580 |

```
uucgccuca ucuggugucu cgugaucuuu cucgcugagg ucgcagcguc acuugugguc      2640
cucuggcugc uugguaauac gcccuugcaa gacaaaggca auucuacaca cucaagaaac      2700
aauuccuaug ccgugauuau cacuucuaca agcucguauu acguguuuua caucuacgua      2760
ggaguggccg acacucugcu cgcgaugggu uucuuccgag gacucccacu cguucacacg      2820
cuuaucacug ucuccaagau ucuccaccau aagaugcuuc auagcguacu gcaggcuccc      2880
auguccaccu ugaauacgcu caaggcggga gguauuuuga aucgcuucuc aaaagauauu      2940
gcaauuuugg augaccuucu gccccugacg aucuucgacu ucauccaguu guugcugauc      3000
gugauugggg cuauugcagu agucgcuguc uccagccuu acauuuuugu cgcgaccguu       3060
ccggugaucg uggcguuuau caugcugcgg gccuauuucu gcagacguc acagcagcuu       3120
aagcaacugg agcugaagg gaggucgccu aucuuuacgc aucuugugac caguuugaag      3180
ggauugugga cguugcgcgc cuuggcagg cagcccuacu uugaaacacu guuccacaaa       3240
gcgcugaauc uccauacggc aaauggguu uguauuuga guaccuccg augguuucag        3300
augcgcauug agaugauuuu ugugaucuuc uuuaucgcgg ugacuuuuau cuccaucuug     3360
accacgggag agggcgaggg acggucggu auuauccuga cacucgccau gaacauuaug      3420
agcacuuugc aguggcagu gaacagcucg auugaugugg auagccugau gaggucggu       3480
ucgagggucu uuaaguucau cgacaugccg acggaggaa agcccacaaa aagauacgaaa    3540
cccuauaaga augggcaauu gaguaaggua augaucaucg agaacaguca cgugaagaag     3600
gaugacaucu ggccuagcgg gggucagaug accgugaagg accugacggc aaaauacacc    3660
gagggaggga acgcaauccu ugaaaacauc cguucagca uuagcccggg ucagcgugug      3720
ggguugcucg ggaggaccgg gucaggaaaa ucgacguugc ugucggccuu cuugagacuu    3780
cugaauacag agggugagau ccagaucgac ggcguuucgu gggauagcau caccuugcag    3840
caguggcgga aagcguuugg aguaauccccc caaaaggucu uuaucuuuag cggaaccuuc    3900
cgaaagaauc ucgauccuua ugaacagugg ucagaucaag agauuuggaa agucgcggac    3960
gagguuggcc uucggagugu aaucgagcag uuuccgggaa aacucgacuu ugccuugua    4020
gauggggau gccuccuguc gcaugggcac aagcagcuca ugccccuggc gcgaucccguc    4080
cucucaaag cgaaaauucu ucucuuggau gaaccuucgg cccaucugga cccgguaacg    4140
uaucagauca ucagaaggac acuuaagcag gcguuugccg acugcacggu gauucucugu    4200
gagcaucgua ucgaggccau gcucgaaugc cagcaauuuc uugucaucga agagaauaag    4260
guccgccagu acgacuccau ccagaagcug cuuaaugaga gaucauuguu ccggcaggcg     4320
auuucaccau ccgauagggu gaaacuuuuu ccacacagaa auccgucgaa gugcaagucc    4380
aaaccgcaga ucgcggccuu gaaagaagag acugaagaag aaguucaaga cacgcgucuu    4440
caccaucacc aucaccauca ccaucaccau uaa                                 4473

<210> SEQ ID NO 16
<211> LENGTH: 4542
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 16
auggccacug gaucaagaac cucacugcug cucgcuuuug gacugcuuug ccugcccugg      60
uugcaagaag gaucggcuuu cccgaccauc ccacucucca ugcagcgguc cccgcucgaa     120
```

| | |
|---|---|
| aaggccagug ucguguccaa acucuucuuc ucauggacuc ggccuauccu uagaaagggg | 180 |
| uaucggcaga ggcuugaguu gucugacauc uaccagaucc ccucgguaga uucggcggau | 240 |
| aaccucucgg agaagcucga acgggaaugg gaccgcgaac ucgcgucuaa gaaaaacccg | 300 |
| aagcucauca acgcacugag aaggugcuuc uucggcgguu ucauguucua cgguaucuuc | 360 |
| uuguaucucg gggaggucac aaaagcaguc caaccccugu uguugggucg cauuaucgcc | 420 |
| ucguacgacc ccgauaacaa agaagaacgg agcaucgcga cuaccucgg gaucggacug | 480 |
| uguuugcuuu ucaucgucag aacacuuuug uugcauccag caaucuucgg ccuccaucac | 540 |
| aucgguaugc agaugcgaau cgcuauguuu agcuugaucu acaaaaagac acugaaacuc | 600 |
| ucgucgcggg uguggauaa gauuuccauc ggucaguugg ugcccugcu uaguaauaac | 660 |
| cucaacaaau ucgaugaggg acuggcgcug gcacauuucg ugggauugc cccguugcaa | 720 |
| gucgcccuuu ugauggcccu uauuugggag cuguugcagg caucugccuu uuguggccug | 780 |
| ggauuucuga uugucuuggc auuguuucag gcugggcuug gcggaugau gaugaaguau | 840 |
| cgcgaccaga gagcgggaa aaucucgaa agacucguca ucacuucgga aaugaucgaa | 900 |
| aacauccagu cggucaaagc cuauugcugg gaagaagcua uggagaagau gauugaaaac | 960 |
| cuccgccaaa cugagcugaa acugacccgc aaggcggcgu auguccggua uuucaauucg | 1020 |
| ucagcguucu ucuuuuccgg guucuucguu gucuuucucu cgguuuugcc uuaugccuug | 1080 |
| auuaagggga uuauccuccg caagauuuuc accacgauuu cguucugcau uguauugcgc | 1140 |
| auggcaguga cacggcaauu uccguggcc gugcagacau gguaugacuc gcuuggagcg | 1200 |
| aucaacaaaa uccaagacuu cuugcaaaag caagaguaca agacccugga guacaaucuu | 1260 |
| acuacuacgg agguaguaau ggagaaugug acggcuuuuu gggaagaggg uuuuggagaa | 1320 |
| cuguuugaga aagcaaagca gaauaacaac aaccgcaaga ccucaaaugg ggacgauucc | 1380 |
| cuguuuuucu cgaacuucuc ccugcucgga acaccgugu ugaaggacau caauuucaag | 1440 |
| auugagaggg gacagcuucu cgcgguagcg ggaagcacug gugcgggaaa aacuagccuc | 1500 |
| uugauggugu uuauggggga gcuugagccc agcgagggga agauuaaaca cuccgggcgu | 1560 |
| aucucauucu guagccaguu ucauggauc augcccggaa ccauuaaaga gaacaucauu | 1620 |
| uucggaguau ccuaugauga guaccgauac agaucggucc uuaaggcgug ccaguuggaa | 1680 |
| gaggacauuu cuaaguucgc cgagaaggau aacaucgucu ugggagaagg ggguauuaca | 1740 |
| uugucgggag ggcagcgagc gcggaucagc cucgcgagag cgguauacaa agaugcagau | 1800 |
| uuguaucugc uugauucacc guuggauac cucgacguau ugacagaaaa agaaaucuuc | 1860 |
| gagucgugcg uguguaaacu uauggcuaau aagacgagaa uccggugac aucaaaaaug | 1920 |
| gaacaccuua agaaggcgga caagauccug auccuccacg aaggaucguc cuacuuuuac | 1980 |
| ggcacuuucu cagaguugca aaacuugcag ccggacuucu caagcaaacu caugggugu | 2040 |
| gacucauucg accaguucag cgcggaacgg cggaacucga cuugacgga aacgcugcac | 2100 |
| cgauucucgc uugaggguga ugccccggua ucguggaccg agacaaagaa gcagucguuu | 2160 |
| aagcagacag gagaauuugg ugagaaaaga aagaacagua ucuugaaucc uauuaacuca | 2220 |
| auucgcaagu ucucaaucgu ccagaaaacu ccacugcaga ugaauggaau ugaagaggau | 2280 |
| ucggacgaac cccuggagcg caggcuuagc cucgugccgg auucagagca aggggaggcc | 2340 |
| auucuucccc ggauuucggu gauuucaacc ggaccuacac uucaggcgag gcgaaggcaa | 2400 |
| uccgugcuca accucaugac gcauucggua aaccaggggc aaaacauuca ccgcaaaacg | 2460 |

```
acggccucaa cgagaaaagu gucacuugca ccccaggcga auuugacuga acucgacauc    2520
uacagccgua ggcuuucgca agaaaccgga cuugagauca gcgaagaaau caaugaagaa    2580
gauuugaaag aguguuucuu ugaugacaug gaaucaaucc cagcggugac aacguggaac    2640
acauacuugc guuacaucac ggugcacaag uccuugauuu ucguccucau cuggugucuc    2700
gugaucuuuc ucgcugaggu cgcagcguca cuuguggucc ucuggcugcu ugguaauacg    2760
cccuugcaag acaaaggcaa uucuacacac ucaagaaaca auuccuaugc cgugauuauc    2820
acuucuacaa gcucguauua cguguuuuac aucuacguag gaguggccga cacucugcuc    2880 gcgaugggu ucuuccgagg acucccacuc guucacacgc uuaucacugu uccaagauu     2940 cuccaccaua agaugcuuca uagcguacug caggcuccca uguccaccuu gaauacgcuc    3000
aaggcgggag guauuuugaa ucgcuucuca aaagauauug caauuuugga ugaccuucug    3060
ccccugacga ucuucgacuu cauccaguug uugcugaucg ugauugggc uauugcagua     3120 gucgcugucc uccagccuua cauuuuuguc gcgaccguuc cggugaucgu ggcguuuauc    3180
augcugcggg ccuauuucuu gcagacguca cagcagcuua agcaacugga gucugaaggg    3240
aggucgccua ucuuuacgca ucuugugacc aguuugaagg gauuguggac guugcgcgcc    3300
uuuggcaggc agcccuacuu ugaaacacug uuccacaaag cgcugaaucu ccauacggca    3360
aauugguuuu uguauuugag uaccccucga ugguucaga ugcgcauuga gaugauuuuu     3420
gugaucuucu uuaucgcggu gacuuuuauc uccaucuuga ccacgggaga gggcgaggga    3480
cgggucggua uuauccugac acucgccaug aacauuauga gcacuuugca gugggcagug    3540
aacagcucga uugaugugga uagccugaug aggccguuu cgagggucuu uaaguucauc     3600
gacaugccga cggagggaaa gcccacaaaa aguacgaaac ccuauaagaa ugggcaauug    3660
aguaagguaa ugaucaucga gaacagucac gugaagaagg augacaucug gccuagcggg    3720
ggucagauga ccgugaagga ccugacggca aaauacaccg agggagggaa cgcaauccuu    3780
gaaaacaucu cguucagcau uagccccggu cagcgugugg gguugcucgg gaggaccggg    3840
ucaggaaaau cgacguugcu gucggccuuc uuugagacuu ugaauacaga gggugagauc    3900
cagaucgacg gcguuucgug ggauagcauc accuugcagc aguggcggaa agcguuugga    3960 guaaucccc aaaaggucuu uaucuuuagc ggaaccuucc gaaagaaucu cgauccuuau     4020
gaacaguggu cagaucaaga gauuuggaaa gucgcggacg agguuggccu ucggagugua    4080
aucgagcagu uucgggaaa acucgacuuu guccuuguag auggggaug cguccugucg     4140 caugggcaca agcagcucau gugccuggcg cgauccgucc ucucuaaagc gaaaauucuu    4200
cucuuggaug aaccuucggc ccaucuggac ccgguaacgu aucagaucau cagaaggaca    4260
cuuaagcagg cguugccga cugcacggug auucucugug agcaucguau cgaggccaug     4320
cucgaaugcc agcaauuucu ugcaucgaa gagaauaagg uccgccagua cgacuccauc     4380
cagaagcugc uuaaugagag ucauuguuc cggcaggcga uuucaccauc cgauagggug     4440
aaacuuuuuc cacacagaaa uucgucgaag ugcaagucca aaccgcagau cgcggccuug    4500
aaagaagaga cugaagaaga aguucaagac acgcgucuuu aa                      4542

<210> SEQ ID NO 17
<211> LENGTH: 4443
<212> TYPE: RNA
<213> ORGANISM: Artificial Sequence
<220> FEATURE:
<223> OTHER INFORMATION: Description of Artificial Sequence: Synthetic
      polynucleotide
```

<400> SEQUENCE: 17

```
augcagcggu ccccgcucga aaaggccagu gucgugucca aacucuucuu cucauggacu    60
cggccuaucc uuagaaaggg guaucggcag aggcuugagu ugucugacau cuaccagauc   120
cccucgguag auucggcgga uaaccucucg gagaagcucg aacgggaaug ggaccgcgaa   180
cucgcgucua agaaaaaccc gaagcucauc aacgcacuga gaaggugcuu cuucuggcgg   240
uucauguucu acgguaucuu cuuguaucuc ggggaggauca caaaagcagu ccaaccccug   300
uuguggguc gcauuaucgc cucguacgac cccgauaaca agaagaacg gagcaucgcg    360
aucuaccucg ggaucggacu guguuugcuu uucaucguca gaacacuuuu guugcaucca   420
gcaaucuucg gccuccauca caucggauag cagaugcgaa ucgcuauguu uagcuugauc   480
uacaaaaaga cacugaaacu cucgucgcgg guguuggaua agauuuccau cggucaguug   540
gugucccugc uuaguaauaa ccucaacaaa uucgaugagg gacuggcgcu ggcacauuuc   600
guguggauug ccccguugca agucgcccuu uugauggggcc uuauuuggga gcuguugcag   660
gcaucugccu uuugugggccu gggauuucug auugugguug cauuguuuca ggcuggggcuu   720
gggcggauga ugaugaagua ucgcgaccag agagcgggua aaaucucgga aagacucguc   780
aucacuucgg aaaaugaucga aaacaauccag ucggucaaag ccuauugcug ggaagaagcu   840
auggagaaga ugauugaaaa ccuccgccaa acugagcuga aacugacccg caaggcggcg   900
uaugucccggu auuucaauuc gucagcguuc uucuuuuccg gguucuucgu ugucuuucuc   960
ucgguuuugc cuuaugccuu gauuaagggg auuauccucc gcaagauuuu caccacgauu  1020
ucguucugca uuguauugcg cauggcagug acacggcaau uccgugggc cgucagacuca  1080
ugguaugacu cgcuuggagc gaucaacaaa auccaagacu ucuugcaaaa gcaagaguac  1140
aagacccugg aguacaaucu acuacuacg gagguaguaa uggagaaugu gacggcuuuu  1200
ugggaagagg guuuggaga acuguuugag aaagcaaagc agaauaacaa caaccgcaag  1260
accucaaaug gggacgauuc ccuguuuuuc ucgaacuucu cccugcucgg aacacccgug  1320
uugaaggaca ucaauuucaa gauugagagg ggacagcuuc ucgcgguagc gggaagcacu  1380
ggugcgggaa aaacuagccu cuugauggug auuauggggg agcuugagcc cagcgagggg  1440
aagauuaaac acuccgggcg uaucucauuc uguagccagu uucauggau caugcccgga  1500
accauuaaag agaacaucau uuucggagua uccuaugaug aguaccgaua cagaucgguc  1560
auuaaggcgu gccaguugga agaggacauu ucuaaguucg ccgagaagga uaacaucguc  1620
uugggagaag gggguauuac auugucggga gggcagcgag cgcggaucag ccucgcgaga  1680
gcgguauaca aagaugcaga uuuguaucug cuugauucac cguuuggaua ccucgacgua  1740
uugacagaaa aagaaaucuu cgagucgugc guguguaaac uuauggcuaa uaagacgaga  1800
auccggguga caucaaaaau ggaacaccuu aagaaggcgg acaagauccu gauccuccac  1860
gaaggaucgu ccuacuuuua cggcacuuuc ucagaguugc aaaacuugca gccggacuuc  1920
ucaagcaaac ucauggggug ugacucauuc gaccaguuca gcgcggaacg gcggaacucg  1980
aucuugacgg aaaacgcugca ccgauucucg cuugagggug augcccccggu aucguggacc  2040
gagacaaaga agcagucguu uaagcagaca ggagaauuug gugagaaaag aaagaacagu  2100
aucuugaauc cuauuaacuc aauucgcaag uucuaaucg uccagaaaac uccacugcag  2160
augaauggaa uugaagagga uucggacgaa ccccuggagc gcaggcuuag ccucgugccg  2220
gauucagagc aaggggaggc cauucuuccc cggauucgg uugauucaac cggaccuaca  2280
cuucaggcga ggcgaaggca auccgugcuc aaccucauga cgcauucggu aaaccagggg  2340
```

| | |
|---|---|
| caaaacauuc accgcaaaac gacgccuca acgagaaaag ugucacuugc accccaggcg | 2400 |
| aauuugacug aacucgacau cuacagccgu aggcuuucgc aagaaaccgg acuugagauc | 2460 |
| agcgaagaaa ucaaugaaga agauuugaaa gaguguuucu uugaugacau ggaaucaauc | 2520 |
| ccagcgguga caacguggaa cacauacuug cguuacauca cggugcacaa guccuugauu | 2580 |
| uucguccuca ucuggugucu cgugaucuuu ucgcugagg ucgcagcguc acuugugguc | 2640 |
| cucuggcugc uugguaauac gcccuugcaa gacaaaggca auucuacaca cucaagaaac | 2700 |
| aauuccuaug ccgugauuau cacuucuaca agcucguauu acguguuuua caucacgua | 2760 |
| ggaguggccg acacucugcu cgcgaugggu uucuuccgag acucccacu cguucacacg | 2820 |
| cuuaucacug ucuccaagau ucuccaccau aagaugcuuc auagcguacu gcaggcuccc | 2880 |
| auguccaccu ugaauacgcu caaggcggga gguauuuuga aucgcuucuc aaaagauauu | 2940 |
| gcaauuuugg augaccuucu gccccugacg aucuucgacu ucauccaguu guugcugauc | 3000 |
| gugauuggg cuauugcagu agucgcguc cuccagccuu acauuuugu cgcgaccguu | 3060 |
| ccggugaucg uggcguuuau caugcugcgg gccuauuucu gcagacguc acagcagcuu | 3120 |
| aagcaacugg agucugaagg gaggucgccu aucuuuacgc aucugugac caguuugaag | 3180 |
| ggauguggga cguugcgcgc cuuuggcagg cagcccuacu ugaaacacu guccacaaa | 3240 |
| gcgcugaauc uccauacggc aaauugguuu uguauuuga guacccuccg augguucag | 3300 |
| augcgcauug agaugauuuu ugugaucuuc uuuaucgcgg ugacuuuau ucccaucuug | 3360 |
| accacgggag agggcgaggg acgggucggu auuauccuga cacucgccau gaacauuaug | 3420 |
| agcacuuugc aguggcagu gaacagcucg auugauguggu auagccugau gaggucccguu | 3480 |
| ucgagggucu uuaaguucau cgacaugccg acggagggaa agccccacaaa aaguacgaaa | 3540 |
| cccuauaaga augggcaauu gaguaaggua augaucaucg agaacaguca cgugaagaag | 3600 |
| gaugacaucu ggccuagcgg gggucagaug accgugaagg accugacggc aaaauacacc | 3660 |
| gagggaggga acgcaauccu ugaaaacauc ucguucagca uuagccccgg ucagcgugug | 3720 |
| ggguugcucg gaggaccgg gucaggaaaa ucgacguugc ugucggccuu cuugagacuu | 3780 |
| cugaauacag agggugagau ccagaucgac ggcguuucgu gggauagcau caccuugcag | 3840 |
| caguggcgga aagcguuugg aguaauccccc caaaagguccu uuaucuuag cggaaccuuc | 3900 |
| cgaaagaauc ucgauccuua ugaacagugg ucagaucaag agauuggaa agucgcggac | 3960 |
| gagguuggcc uucggagugu aaucgagcag uuuccgggaa aacucgacuu uguccuugua | 4020 |
| gauggggau gcguccuguc gcaugggcac aagcagcuca ugugccuggc gcgauccguc | 4080 |
| cucucuaaag cgaaaauucu ucucuuggau gaaccuucgg cccaucugga cccgguaacg | 4140 |
| uaucagauca ucagaaggac acuuaagcag gcguuugccg acugcacggu gauucucugu | 4200 |
| gagcaucgua ucgaggccau gcucgaaugc cagcaauuuc uugucaucga agagaauaag | 4260 |
| guccgccagu acgacuccau ccagaagcug cuuaaugaga gaucauuguu ccggcaggcg | 4320 |
| auuucaccau ccgauagggu gaaacuuuuu ccacacagaa auucgucgaa gugcaaguccc | 4380 |
| aaaccgcaga ucgcggccuu gaaagaagag acugaagaag aaguucaaga cacgcgucuu | 4440 |
| uaa | 4443 |

<210> SEQ ID NO 18
<211> LENGTH: 99
<212> TYPE: RNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 18
auggccacug gaucaagaac cucacugcug cucgcuuuug gacugcuuug ccugcccugg     60
uugcaagaag gaucggcuuu cccgaccauc ccacucucc                            99

<210> SEQ ID NO 19
<211> LENGTH: 99
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
auggcaacug gaucaagaac cucccuccug cucgcauucg gccugcucug ucucccaugg     60
cuccaagaag gaagcgcguu ccccacuauc ccccucucg                            99

<210> SEQ ID NO 20
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 20
cggguggcau cccugugacc ccuccccagu gccucuccug gcccuggaag uugccacucc     60
agugcccacc agccuugucc uaauaaaauu aaguugcauc aagcu                    105
```

CFTR MRNA COMPOSITIONS AND RELATED METHODS AND USES

CROSS REFERENCE TO RELATED APPLICATIONS

The present application division of U.S. application Ser. No. 14/876,071 filed on Oct. 6, 2016, which is a division of U.S. application Ser. No. 14/307,322 filed on Jun. 17, 2014, which is a continuation of International Application PCT/US2014/028849 filed on Mar. 14, 2014, which claims priority to U.S. Provisional Application Ser. No. 61/783,663, filed Mar. 14, 2013, the disclosures of which are hereby incorporated by reference.

SEQUENCE LISTING

The present specification makes reference to a Sequence Listing (submitted electronically as a .txt file named "SL_MRT-1100US3" on Jun. 16, 2017). The .txt file was generated on Jun. 16, 2017 and is 82 bytes in size. The entire contents of the Sequence Listing are herein incorporated by reference.

BACKGROUND

The present invention relates to cystic fibrosis transmembrane regulator (CFTR) mRNA compositions, uses of same, and methods of making and using same.

Cystic fibrosis is an autosomal inherited disorder resulting from mutation of the CFTR gene, which encodes a chloride ion channel believed to be involved in regulation of multiple other ion channels and transport systems in epithelial cells. Loss of function of CFTR results in chronic lung disease, aberrant mucus production, and dramatically reduced life expectancy. See generally Rowe et al., New Engl. J. Med. 352, 1992-2001 (2005).

Despite cloning of the CFTR gene in 1989, effective therapy for replacing CFTR for the treatment of cystic fibrosis has yet to be developed. The literature has documented numerous difficulties encountered in attempting to induce expression of CFTR in the lung. For example, viral vectors comprising CFTR DNA triggered immune responses and CF symptoms persisted after administration. Conese et al., J. Cyst. Fibros. 10 Suppl 2, S114-28 (2011); Rosenecker et al., Curr. Opin. Mol. Ther. 8, 439-45 (2006). Non-viral delivery of DNA, including CFTR DNA, has also been reported to trigger immune responses. Alton et al., Lancet 353, 947-54 (1999); Rosenecker et al., J Gene Med. 5, 49-60 (2003). Furthermore, non-viral DNA vectors encounter the additional problem that the machinery of the nuclear pore complex does not ordinarily import DNA into the nucleus, where transcription would occur. Pearson, Nature 460, 164-69 (2009).

Another source of difficulties in inducing CFTR expression in the lung is the lung environment itself. Pulmonary surfactant has been reported to reduce transfection efficiency for cationic lipid transfer vehicles such as Lipofectamine (DOSPA:DOPE). Ernst et al., J. Gene Med. 1, 331-40 (1999).

Also, Rosenecker et al., 2003, supra, identified multiple inhibitory components present in the airway surface liquid which can interfere with either polymer-mediated or lipid-mediated transfection. Messenger RNA therapy has been proposed as a general approach for inducing expression of a therapeutic or replacement protein. The concept of introduction of messenger RNA (mRNA) as a means of protein production within a host has been reported previously (Yamamoto, A. et al. Eur. J. Pharm. 2009, 71, 484-489; Debus, H. et al. J. Control Rel. 2010, 148, 334-343). However, apparent lung-specific difficulties have been reported for mRNA delivery using certain lipoplexes formulations. For example, a comparison of in vitro and in vivo performance of lipoplexes carrying mRNA or DNA revealed that even though the mRNA composition gave higher expression in cultured cells, measureable expression was detected only with the DNA composition when administered intranasally to mouse lung. Andries et al., Mol. Pharmaceut. 9, 2136-45 (2012).

It should also be noted that CFTR is a relatively large gene relative to model or reporter genes such as firefly luciferase (FFL). Compare the lengths of the wild-type CFTR coding sequence (SEQ ID NO: 2) and the FFL coding sequence (SEQ ID NO: 7). The difference in length can impact stability under some circumstances, and therefore whether and how much protein expression any given dose of mRNA will produce. Furthermore, although in vitro synthesis of mRNA is generally preferable to synthesis by cells due to the absence of normal cellular mRNA and other cellular components which constitute undesirable contaminants, in vitro synthesis of mRNA with a long coding sequence, such as CFTR mRNA, is substantially more difficult to achieve than in vitro synthesis of mRNA with a relatively short coding sequence such as FFL.

PCT patent publication WO2007/024708 and US patent publications US2010/0203627 and US2011/0035819 discuss the therapeutic administration of CFTR mRNA but provide neither a demonstrated reduction to practice of production of functional CFTR in the lung following administration of CFTR mRNA or sufficient guidance for overcoming the difficulties associated with inducing CFTR expression in the lung using in vitro-transcribed CFTR mRNA. These include difficulties with achieving in vitro synthesis of the mRNA and difficulties specific to the interactions of mRNA compositions with lung-specific substances that investigators such as Andries et al., supra, have found to render mRNA compositions ineffective for induction of expression even while corresponding DNA-based compositions did provide some level of expression.

Thus, there is a need for improved materials, formulations, production methods, and methods for delivery of CFTR mRNA for induction of CFTR expression, including in the mammalian lung, for the treatment of cystic fibrosis.

SUMMARY OF THE INVENTION

The present invention is based, in part, on the development of formulations of CFTR mRNA and non-naturally occurring CFTR mRNA and methods of administration thereof that can induce functional CFTR expression in vivo. The compositions, methods, and uses according to the invention can provide CFTR expression in the lung of a large mammal with a favorable safety profile suitable for effective treatment of cystic fibrosis.

Thus, in one aspect, the present invention provides a method of in vivo production of CFTR, in particular, in the lung of a subject (e.g., a mammal) in need of delivery by delivering an mRNA encoding a CFTR protein. In some embodiments, the mRNA encoding a CFTR protein is delivered directly to the lung of the subject. As used herein, a "CFTR protein" encompasses any full length, fragment or portion of a CFTR protein which can be used to substitute for naturally-occurring CFTR protein activity and/or reduce the intensity, severity, and/or frequency of one or more symptoms associated with Cystic fibrosis. For example, a suitable CFTR protein according to the present invention may have an amino acid sequence identical to the wild-type human CFTR protein (SEQ ID NO: 1). In some embodiments, a suitable CFTR protein according to the present invention may have an amino acid sequence at least about 70%, 75%, 80%, 85%, 90%, 95%, 96%, 97%, 98%, or 99% identical to the wild-type human CFTR protein (SEQ ID NO: 1).

In one embodiment, the invention provides a method of inducing CFTR expression in epithelial cells in a lung of a mammal, the method comprising contacting the epithelial cells in the lung of the mammal with a composition, wherein: the composition is a pharmaceutical composition comprising an in vitro transcribed mRNA; the in vitro transcribed mRNA comprises a coding sequence which encodes SEQ ID NO: 1. In another embodiment, the in vitro transcribed mRNA comprises a coding sequence which encodes an amino acid sequence at least about 70%, 75%, 80%, 85%, 90%, 95%, 96%, 97%, 98%, or 99% identical to SEQ ID NO: 1.

In one embodiment, the invention provides a method of inducing CFTR expression in a mammalian target cell, the method comprising contacting the mammalian target cell with a composition, the composition comprising an in vitro transcribed mRNA encoding the amino acid sequence of SEQ ID NO: 1. In another embodiment, the in vitro transcribed mRNA comprises a coding sequence which encodes an amino acid sequence at least about 70%, 75%, 80%, 85%, 90%, 95%, 96%, 97%, 98%, or 99% identical to SEQ ID NO: 1.

In another embodiment, the invention provides a non-naturally occurring mRNA molecule comprising a coding sequence, a 5'-UTR, and a 3'-UTR, wherein the coding sequence encodes the amino acid sequence of SEQ ID NO: 1 and the coding sequence is at least 80% identical to SEQ ID NO: 3. In another embodiment, the coding sequence encodes the amino acid sequence at least about 70%, 75%, 80%, 85%, 90%, 95%, 96%, 97%, 98%, or 99% identical to SEQ ID NO: 1 and/or the coding sequence is about 50%, 55%, 60%, 65%, 70%, 75%, 80%, 85%, 90%, 95%, 96%, 97%, 98%, or 99% identical to SEQ ID NO: 3.

In another embodiment, the invention provides a non-naturally occurring mRNA molecule comprising a coding sequence, a 5'-UTR, and a 3'-UTR, wherein the coding sequence encodes the amino acid sequence of SEQ ID NO: 1 and the coding sequence comprises at least 50%, at least 55%, at least 60%, at least 65%, at least 70%, at least 75%, at least 80%, at least 85%, at least 90%, or at least 95% of the non-wild-type bases listed in Table 1 at the positions of the coding sequence listed in Table 1 relative to the wild-type coding sequence of SEQ ID NO: 2.

In another embodiment, the invention provides a non-naturally occurring mRNA molecule comprising a coding sequence, a 5'-UTR, and a 3'-UTR, wherein the coding sequence encodes the amino acid sequence of SEQ ID NO: 1 and the coding sequence comprises at least 50%, at least 55%, at least 60%, at least 65%, at least 70%, at least 75%, at least 80%, at least 85%, at least 90%, or at least 95% of the non-wild-type bases listed in Table 2 at the corresponding positions of the coding sequence listed in Table 2 relative to the wild-type coding sequence of SEQ ID NO: 2.

In some embodiments, the invention provides a non-naturally occurring mRNA molecule comprising a coding sequence for a signal peptide. In a particular embodiment, the invention provides a non-naturally occurring mRNA comprising a coding sequence for a growth hormone leader sequence. In certain embodiments, the invention provides a non-naturally occurring mRNA comprising a coding sequence of SEQ ID NO:18 or SEQ ID NO:19. In some embodiments, the invention provides a non-naturally occurring mRNA comprising a coding sequence at least about 50%, 55%, 60%, 65%, 70%, 75%, 80%, 85%, 90%, 95%, 96%, 97%, 98%, or 99% to SEQ ID NO:18 or SEQ ID NO:19.

In some embodiments, the invention provides a non-naturally occurring mRNA molecule comprising a sequence of SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17. In some embodiments, the invention provides a non-naturally occurring mRNA molecule comprising a sequence at least about 50%, 55%, 60%, 65%, 70%, 75%, 80%, 85%, 90%, 95%, 96%, 97%, 98%, or 99% to any of SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

In another embodiment, the invention provides a polynucleotide comprising a sequence complementary to the sequence of an mRNA according to the invention.

In another embodiment, the invention provides a composition comprising the polynucleotide according to the invention, an RNA polymerase, and nucleoside triphosphates.

In another embodiment, the invention provides a pharmaceutical composition comprising an mRNA according to the invention.

In another embodiment, the invention provides a nebulization or aerosolization apparatus loaded with a pharmaceutical composition according to the invention.

In another embodiment, the invention provides a cultured cell comprising an mRNA according to the invention and functional CFTR expressed from the mRNA.

In another embodiment, the invention provides a use of a pharmaceutical composition according to the invention for the induction of expression of functional CFTR.

In another embodiment, the invention provides a method of inducing CFTR expression in epithelial cells in a lung of a mammal, the method comprising contacting the epithelial cells with a composition, wherein the composition is a pharmaceutical composition comprising an mRNA according to the invention.

In another embodiment, the invention provides a method of inducing CFTR expression in a mammalian target cell, the method comprising contacting the mammalian target cell with a composition, the composition comprising an mRNA according to the invention.

In another embodiment, the present invention provides a method of treating cystic fibrosis by administering to a subject in need of treatment an mRNA encoding a CFTR protein as described herein. In one embodiment, the mRNA is administered to the lung of the subject. In one embodiment, the mRNA is administered by inhalation, nebulization, intranasal administration or aerosolization. In various embodiments, administration of the mRNA results in expression of CFTR in the lung of the subject.

In a particular embodiment, the present invention provides a method of treating cystic fibrosis by administering to the lung of a subject in need of treatment an mRNA comprising a coding sequence which encodes SEQ ID NO: 1. In some embodiments, the present invention provides a method of treating cystic fibrosis by administering to the lung of a subject in need of treatment an mRNA comprising a coding sequence which encodes an amino acid sequence at least about 70%, 75%, 80%, 85%, 90%, 95%, 96%, 97%, 98%, or 99% identical to the wild-type human CFTR protein (SEQ ID NO: 1). In another particular embodiment, the present invention provides a method of treating cystic fibrosis by administering to the lung of a subject in need of treatment an mRNA comprising a coding sequence of SEQ ID NO:3. In some embodiments, the present invention provides a method of treating cystic fibrosis by administering to the lung of a subject in need of treatment an mRNA comprising a coding sequence at least about 50%, 55%, 60%, 65%, 70%, 75%, 80%, 85%, 90%, 95%, 96%, 97%, 98%, or 99% identical to SEQ ID NO:3.

In yet another aspect, the present invention provides methods for making an mRNA encoding a CFTR protein as described herein. In one embodiment, the invention provides a method of making CFTR mRNA in vitro, comprising contacting an isolated polynucleotide with an RNA polymerase in the presence of nucleoside triphosphates, wherein: the isolated polynucleotide and RNA polymerase are not contained within a cell; the isolated polynucleotide is a template for the RNA polymerase; the isolated polynucleotide comprises a promoter operably linked to a template sequence; the template sequence comprises a coding sequence complement which is complementary to a sequence encoding SEQ ID NO: 1; and: (a) the template sequence comprises fewer cryptic promoters than the complement of SEQ ID NO: 2, (b) the template sequence comprises fewer direct and/or inverted repeats than SEQ ID NO: 2, (c) the template sequence comprises complements of fewer disfavored codons than SEQ ID NO: 2, or (d) the GC content of the coding sequence complement is lower than the GC content of SEQ ID NO: 2.

In another embodiment, the invention provides a method of making CFTR mRNA in vitro, comprising contacting an isolated polynucleotide according to the invention with an RNA polymerase in the presence of nucleoside triphosphates, wherein: the isolated polynucleotide and RNA polymerase are not contained within a cell; the isolated polynucleotide is a template for the RNA polymerase; and the isolated polynucleotide comprises a promoter operably linked to a template sequence, and the RNA polymerase synthesizes mRNA comprising a coding sequence encoding SEQ ID NO: 1.

In some embodiments of such uses and methods of treatment, the in vitro transcribed mRNA is a naturally occurring or wild-type mRNA encoding human CFTR (SEQ ID NO: 2) modified to include non-naturally occurring UTRs. In other embodiments, the in vitro transcribed mRNA is a non-naturally occurring mRNA as described above.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

The foregoing aspects and advantages of this invention may become apparent from the following detailed description with reference to the accompanying drawings.

FIGS. 12A-12B. Screening of different cell lines for hCFTR expression. Immunoblot of CHO and COS-7 (12A) and BHK and PKC (12B) cells transfected with hCFTR coding constructs. Protein lysates were prepared 24 hrs post transfection and screened using MA1-935 as primary antibody. Arrow indicates putative CFTR. See the discussion of MA1-935 specificity in Example 6.

FIGS. 13A-13D. Cross reactivity of different anti-human CFTR antibodies. (13A)—Mouse anti-human CFTR MA1-935 (Chemicon): (13B)—Mouse anti-human CFTR AB570 (Cystic Fibrosis Foundation): (13C)—Mouse anti-human CFTR AB596 (Cystic Fibrosis Foundation): (13D) Rabbit anti-human CFTR G449 (Rockefeller University). Arrow indicates CFTR.

Figure 36:
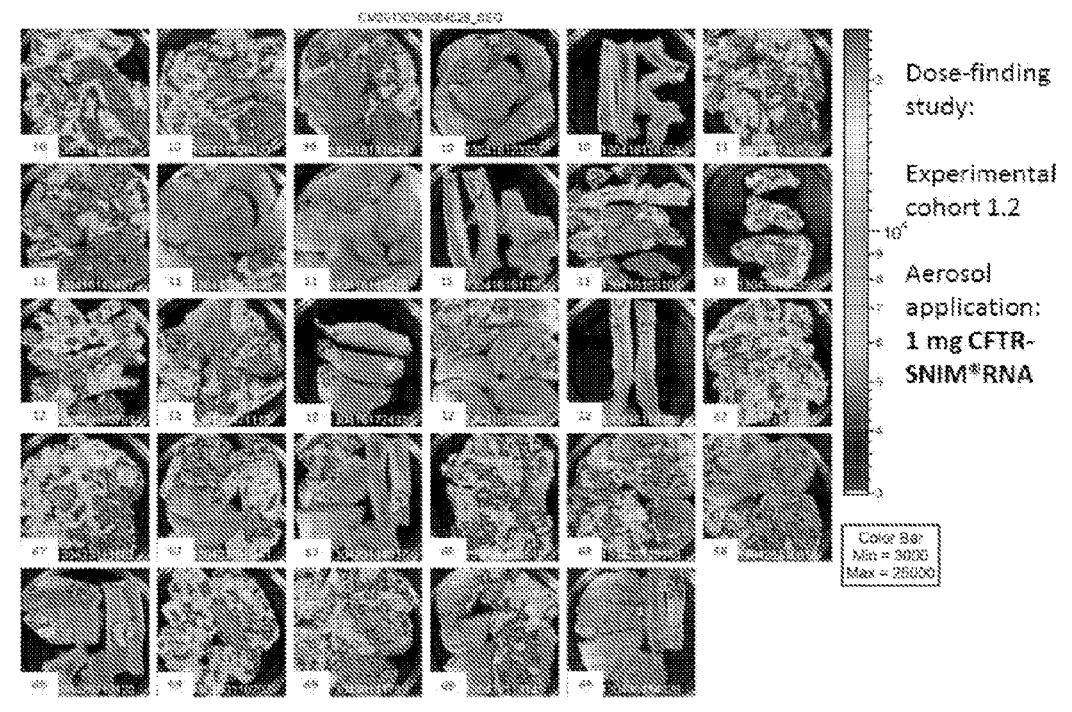

FIG. 36. Bioluminescent detection of FFL expression in porcine lung samples collected following nebulization with 1 mg FFL SNIM RNA+1 mg CO-CFTR SNIM RNA in a branched 25 kDa PEI formulation.

FIGS. 47A-47B. Illustrates multiplex nucleic acid in situ detection of (47A) ubiquitin C and (47B) dap B in porcine lung, post aerosol delivery of water for injection by nebulizer.

FIGS. 48A-48B. Illustrates multiplex nucleic acid in situ detection of (48A) ubiquitin C and (48B) dap B in porcine lung, post aerosol delivery of 1 mg FFL SNIM RNA+10 mg CO-CFTR SNIM RNA in a branched 25 kDa PEI formulation.

FIGS. 49A-49B. Illustrates multiplex nucleic acid in situ detection of (49A) right cranialis and (49B) left cranialis in porcine, post aerosol delivery of water for injection by nebulizer.

FIGS. 50A-50B. Illustrates multiplex nucleic acid in situ detection of (50A) right cranialis and (50B) left cranialis in porcine, post aerosol delivery of 1 mg FFL SNIM RNA+1 mg CO-CFTR SNIM RNA in a branched 25 kDa PEI formulation.

FIGS. 51A-51B. Illustrates multiplex nucleic acid in situ detection of (51A) right cranialis and (51B) left cranialis in porcine, post aerosol delivery of 1 mg FFL SNIM RNA+5 mg CO-CFTR SNIM RNA in a branched 25 kDa PEI formulation.

FIGS. 52A-52B. Illustrates multiplex nucleic acid in situ detection of (52A) right cranialis and (52B) left cranialis in porcine, post aerosol delivery of 1 mg FFL SNIM RNA+10 mg CO-CFTR SNIM RNA in a branched 25 kDa PEI formulation.

FIGS. 53A-53B. Illustrates positive detection of active firefly luciferase (FFL) protein in a treated pig lung via luminescence upon exposure to FFL/CO-CFTR-C-$His_{10}$ mRNA encapsulated cKK-E12 lipid nanoparticles. Pigs were treated with 1 mg FFL+9 mg CO-CFTR-C-His10 mRNA encapsulated lipid nanoparticles via nebulization using a Pari jet nebulizer and sacrificed 24 hours post-treatment. FFL luminescence was visualized using an IVIS bioluminometer.

DETAILED DESCRIPTION OF THE INVENTION

Definitions

Figure 1A:
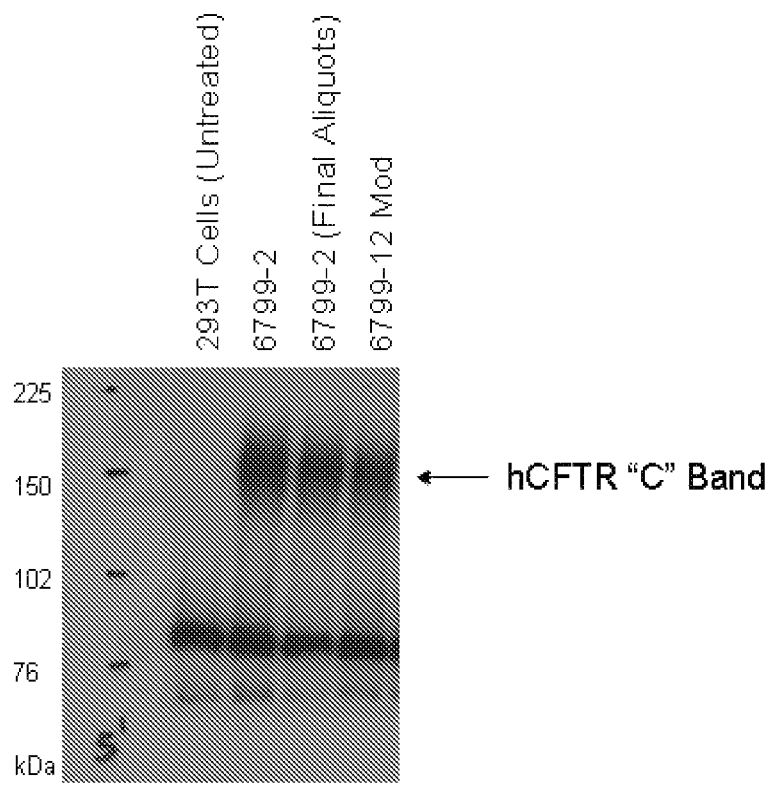
FIG. 1A. Detection of mature "C" band for human CFTR protein 24 hours after transfection with human CFTR mRNA. Successful protein production was observed for both unmodified and modified (SNIM) mRNA (comprising 25% of 2-thiouridine and 5-methylcytidine). Immunoprecipitation was performed using R&D Systems MAB25031 antibody and detection using Ab570.

As used herein, the term "polynucleotide" is generally used to refer to a nucleic acid (e.g., DNA or RNA). The terms polynucleotide, nucleic acid, DNA, RNA, and mRNA include such molecules that are comprised of: standard or unmodified residues; nonstandard or modified residues; and mixtures of standard and nonstandard residues.

As used herein, the term "mRNA" is used to refer to modified and unmodified RNA including both a coding region and a noncoding region.

As used herein, the phrase "coding region" of an mRNA generally refers to that portion that when translated results in the production of an expression product, such as a polypeptide, protein, or enzyme.

A "nonstandard nucleobase" is a base moiety other than the natural bases adenine (A), cytosine (C), guanine (G), thymine (T), or uracil (U). The nonstandard nucleobase is an analog of a specific nucleobase (A, C, G, T, or U) when its base pairing properties in a nucleic acid double helix and locus of incorporation by DNA or RNA polymerases in a nucleic acid double helix (including a local RNA-DNA helix such as that formed during transcription of a DNA template by RNA polymerase) are most similar to one of the five previously listed nucleobases, with the exception that analogs of T will generally also be analogs of U and vice versa. For purposes of determining percentage identity of a first sequence relative to a second sequence, an analog of a base is not a mismatch to the natural base; for example, pseudouridine matches uridine, 5-methylcytidine matches cytidine, etc.

The term "nonstandard" used in conjunction with terms including but not limited to "nucleoside", "base", "nucleotide", or "residue" is to be interpreted in the same manner as if it were used in conjunction with "nucleobase."

"GC content" is the fraction or percentage of total nucleobase residues in a nucleic acid sequence that are guanine residues, cytosine residues, or analogs thereof. For example, a 100 nt sequence that contains exactly 30 cytosines, exactly 30 guanines, exactly one cytosine analog, and exactly one guanine analog has a GC richness of 62%.

As used herein, a "disfavored codon" refers to a codon which is translated less efficiently or rapidly by mammalian cells than another codon for the same amino acid residue. Disfavored codons generally include codons with an A or U in the 3rd or "wobble" position of the codon. For a discussion of disfavored codons, see, e.g., U.S. Patent Publication 2009/0069256 A1.

A "non-naturally occurring mRNA molecule" is an mRNA that is not produced through normal transcription and splicing processes of wild-type cells. An mRNA may qualify as non-naturally occurring by virtue of its sequence (e.g., a series of codons and/or one or more UTRs that do not present in any naturally-occurring CFTR mRNA) and/or because it includes nonstandard nucleotide residues. A non-naturally occurring mRNA molecule may be in vitro synthesized.

In each of Tables 1 and 2 below, the NWT column indicates the non-wild-type base at the position (Pos.) in the CFTR coding sequence (see, e.g., SEQ ID NO: 3), and the WT column indicates the wild-type base at the same position (see, e.g., SEQ ID NO: 2 or the RefSeq entry for human CFTR (accession no. NM_000492.3, Feb. 10, 2013, version, available from GenBank; note that the sequence of NM_000492.3 contains noncoding sequence such that the coding sequence occurs at position 133 to 4575, such that, for example, position 7 in the tables below corresponds to position 139 of the NM_000492.3 sequence).

Non-Naturally Occurring CFTR mRNA

In addition to providing methods of producing functional CFTR in vivo using naturally occurring or wild-type CFTR mRNA (and compositions comprising that mRNA), the invention also provides non-naturally occurring CFTR mRNA that encodes CFTR protein (e.g., SEQ ID NO: 1). In some embodiments, the non-naturally occurring CFTR mRNA is purified or isolated.

In other embodiments, the non-naturally occurring CFTR mRNA is present in a cell. In some embodiments, the cell comprising the non-naturally occurring CFTR mRNA did not synthesize the non-naturally occurring CFTR mRNA and/or does not comprise DNA complementary to the non-naturally occurring CFTR mRNA and/or a functional CFTR gene; the cell may optionally comprise an inactive CFTR gene, such as a CFTR gene with a nonsense, missense, frameshift, insertion, or deletion mutation that renders the expression product of the gene nonfunctional. In some embodiments, the cell comprising the non-naturally occurring CFTR mRNA further comprises functional CFTR protein translated from the non-naturally occurring CFTR mRNA. The cell may be, e.g., a lung epithelial cell, a liver cell, or a kidney cell. In some embodiments, the cell is in a cell culture.

CFTR Coding Sequence

In some embodiments, CFTR mRNA according to the invention comprises a coding sequence with fewer complements of cryptic promoters than SEQ ID NO: 2 (i.e., the coding sequence of wild-type human CFTR), fewer direct and/or inverted repeats than SEQ ID NO: 2, fewer disfavored codons than SEQ ID NO: 2, and/or the GC content of the coding sequence is lower than the GC content of SEQ ID NO: 2.

Cryptic promoters, direct and/or inverted repeats and/or disfavored codons of a sequence may be recgnized by one skilled in the art using routine methods. For example, the direct and/or inverted repeat content of a sequence can be determined by sequence analysis (Liu et al., *Journal of Theoretical Biology* (2014) 344: 19-30). The cryptic promoter content of a sequence can also be determined by sequence analysis, e.g., presence of Shine-Dalgarno sequences within construct or the like.

In some embodiments, CFTR mRNA according to the invention is in vitro-transcribed, i.e., the mRNA was synthesized in an artificial setting not within a biological cell (e.g., a cell free in vitro transcription system). Generally, in vitro transcription involves providing a DNA template comprising a promoter and a sequence complementary to the desired mRNA (which may be circular or linear), an RNA polymerase, and nucleoside triphosphates in suitable reaction conditions (salts, buffers, and temperature). RNase inhibitors, reducing agents, and/or pyrophosphatase may be present in the reaction mixture. In some embodiments, the RNA polymerase is T7 RNA polymerase.

In some embodiments, the CFTR mRNA according to the invention comprises a coding sequence comprising at least 50%, at least 55%, at least 60%, at least 65%, at least 70%, at least 75%, at least 80%, at least 85%, at least 90%, or at least 95% of the non-wild-type bases listed in Table 1 at the positions of the coding sequence listed in Table 1 relative to the wild-type coding sequence of SEQ ID NO: 2.

TABLE 1

Non-wild-type bases that can be used in the coding sequence of mRNA encoding CFTR.

| Pos. | NWT | WT |
| --- | --- | --- |
| 7 | c | a |
| 12 | c | g |
| 15 | g | u |
| 18 | c | g |
| 30 | u | c |
| 33 | c | u |
| 36 | g | c |
| 45 | c | u |
| 48 | c | u |
| 52 | u | a |
| 53 | c | g |
| 54 | a | c |
| 60 | u | c |
| 61 | c | a |
| 63 | g | a |
| 66 | u | a |
| 69 | c | u |
| 70 | c | u |
| 72 | u | g |
| 75 | a | g |
| 78 | g | a |
| 81 | g | a |
| 84 | u | c |
| 85 | c | a |
| 87 | g | a |
| 91 | a | c |
| 93 | g | c |
| 96 | u | g |
| 99 | g | a |
| 105 | u | a |
| 111 | c | a |
| 117 | g | a |
| 123 | c | u |
| 126 | g | u |
| 129 | a | u |
| 135 | g | u |
| 138 | g | u |
| 141 | u | c |
| 144 | c | u |
| 147 | c | a |
| 150 | g | u |
| 153 | g | a |
| 156 | g | a |
| 157 | c | u |
| 159 | c | g |
| 163 | c | a |
| 165 | g | a |
| 174 | c | u |
| 175 | c | a |
| 177 | c | a |
| 180 | a | g |
| 183 | c | g |
| 186 | g | u |
| 189 | u | a |
| 198 | c | u |
| 201 | g | u |
| 204 | g | a |
| 210 | c | u |
| 213 | c | u |
| 216 | a | c |
| 219 | g | u |

TABLE 1-continued

Non-wild-type bases that can be used in the coding sequence of mRNA encoding CFTR.

| Pos. | NWT | WT |
| --- | --- | --- |
| 220 | a | c |
| 222 | a | g |
| 223 | a | c |
| 225 | g | a |
| 228 | c | u |
| 231 | c | u |
| 238 | c | a |
| 240 | g | a |
| 243 | c | u |
| 252 | c | u |
| 255 | u | a |
| 261 | c | u |
| 264 | g | a |
| 268 | c | u |
| 270 | c | a |
| 276 | g | a |
| 282 | a | c |
| 291 | c | a |
| 294 | a | g |
| 297 | c | u |
| 300 | g | c |
| 303 | g | a |
| 304 | u | c |
| 309 | u | a |
| 310 | c | a |
| 312 | c | a |
| 315 | u | c |
| 318 | c | a |
| 321 | c | u |
| 324 | g | c |
| 327 | c | u |
| 333 | c | g |
| 342 | a | g |
| 345 | a | g |
| 351 | g | c |
| 352 | a | u |
| 353 | g | c |
| 354 | c | u |
| 363 | c | u |
| 366 | c | u |
| 369 | c | a |
| 372 | g | c |
| 375 | c | a |
| 378 | a | c |
| 379 | c | u |
| 381 | g | a |
| 384 | u | c |
| 385 | u | c |
| 387 | g | u |
| 390 | u | c |
| 393 | c | u |
| 396 | c | u |
| 399 | c | g |
| 402 | a | g |
| 408 | u | g |
| 409 | u | c |
| 411 | g | c |
| 412 | u | c |
| 414 | g | a |
| 417 | u | c |
| 423 | a | c |
| 426 | c | u |
| 429 | c | u |
| 435 | c | u |
| 444 | c | u |
| 447 | u | a |
| 457 | c | a |
| 462 | c | a |
| 474 | c | u |
| 480 | c | u |
| 483 | c | u |
| 486 | a | g |
| 492 | a | u |
| 493 | c | u |
| 495 | g | a |

TABLE 1-continued

Non-wild-type bases that can be used in the coding sequence of mRNA encoding CFTR.

| Pos. | NWT | WT |
|---|---|---|
| 498 | a | g |
| 501 | c | g |
| 504 | g | a |
| 505 | u | a |
| 506 | c | g |
| 507 | g | c |
| 510 | g | u |
| 513 | g | u |
| 514 | u | c |
| 516 | g | a |
| 522 | g | a |
| 525 | u | a |
| 526 | u | a |
| 527 | c | g |
| 528 | c | u |
| 531 | c | u |
| 534 | u | a |
| 537 | g | a |
| 538 | u | c |
| 540 | g | u |
| 543 | g | u |
| 544 | u | a |
| 545 | c | g |
| 546 | c | u |
| 549 | g | c |
| 553 | a | u |
| 554 | g | c |
| 555 | u | c |
| 558 | u | c |
| 564 | c | g |
| 573 | c | u |
| 579 | g | a |
| 585 | g | u |
| 588 | g | a |
| 589 | c | u |
| 609 | u | c |
| 612 | c | u |
| 615 | g | u |
| 624 | c | g |
| 627 | c | a |
| 630 | u | c |
| 631 | u | c |
| 633 | g | c |
| 639 | c | g |
| 642 | u | a |
| 645 | u | c |
| 652 | c | u |
| 657 | g | a |
| 663 | a | g |
| 672 | u | c |
| 678 | c | a |
| 681 | g | u |
| 684 | a | u |
| 687 | u | c |
| 693 | u | a |
| 696 | g | c |
| 697 | u | c |
| 699 | g | u |
| 702 | a | c |
| 703 | u | c |
| 705 | g | u |
| 720 | u | a |
| 724 | c | a |
| 726 | g | a |
| 741 | u | c |
| 742 | c | a |
| 744 | c | a |
| 747 | c | u |
| 756 | g | u |
| 759 | u | g |
| 762 | a | g |
| 766 | u | a |
| 767 | c | g |
| 768 | g | u |
| 777 | c | u |
| 780 | c | g |
| 783 | c | u |
| 786 | u | c |
| 789 | g | a |
| 798 | c | u |
| 804 | c | u |
| 810 | g | a |
| 813 | g | u |
| 816 | c | u |
| 819 | a | g |
| 822 | c | a |
| 825 | u | c |
| 840 | u | a |
| 846 | g | a |
| 849 | g | a |
| 862 | c | u |
| 864 | c | a |
| 865 | c | a |
| 867 | c | a |
| 873 | u | a |
| 876 | g | a |
| 888 | c | u |
| 891 | c | g |
| 897 | g | a |
| 900 | g | c |
| 906 | c | g |
| 907 | c | a |
| 909 | g | a |
| 912 | u | c |
| 919 | u | a |
| 920 | c | g |
| 921 | g | c |
| 927 | g | c |
| 936 | u | c |
| 939 | c | a |
| 948 | c | u |
| 951 | u | g |
| 954 | c | g |
| 958 | c | u |
| 960 | c | a |
| 963 | g | u |
| 966 | u | g |
| 967 | u | c |
| 969 | g | u |
| 972 | u | c |
| 978 | c | a |
| 979 | u | c |
| 981 | g | a |
| 984 | u | c |
| 987 | g | a |
| 990 | g | a |
| 993 | u | c |
| 1002 | c | g |
| 1005 | g | a |
| 1008 | u | a |
| 1017 | g | c |
| 1020 | u | c |
| 1023 | g | a |
| 1035 | a | u |
| 1036 | u | c |
| 1047 | a | g |
| 1050 | g | c |
| 1053 | a | u |
| 1065 | g | c |
| 1071 | c | u |
| 1074 | g | a |
| 1077 | g | a |
| 1092 | g | u |
| 1101 | g | a |
| 1104 | c | a |
| 1113 | c | a |
| 1116 | a | g |
| 1119 | c | u |
| 1125 | g | a |
| 1137 | g | a |

TABLE 1-continued

Non-wild-type bases that can be used in the coding sequence of mRNA encoding CFTR.

| Pos. | NWT | WT |
|------|-----|-----|
| 1140 | c | u |
| 1146 | c | a |
| 1147 | c | u |
| 1152 | g | a |
| 1155 | c | u |
| 1158 | u | c |
| 1159 | c | u |
| 1161 | u | a |
| 1164 | u | g |
| 1170 | g | a |
| 1173 | g | a |
| 1179 | a | g |
| 1191 | g | a |
| 1194 | g | a |
| 1197 | u | c |
| 1200 | u | c |
| 1206 | a | g |
| 1212 | u | a |
| 1218 | a | g |
| 1222 | c | u |
| 1224 | g | a |
| 1239 | g | a |
| 1242 | g | a |
| 1245 | u | c |
| 1248 | c | u |
| 1254 | c | u |
| 1255 | c | a |
| 1257 | c | a |
| 1260 | g | a |
| 1263 | c | u |
| 1266 | a | u |
| 1272 | g | u |
| 1275 | c | u |
| 1278 | u | c |
| 1279 | u | a |
| 1280 | c | g |
| 1284 | g | c |
| 1287 | u | c |
| 1291 | u | a |
| 1292 | c | g |
| 1293 | g | u |
| 1296 | c | u |
| 1302 | c | a |
| 1305 | g | u |
| 1308 | c | u |
| 1311 | a | u |
| 1314 | a | u |
| 1317 | c | u |
| 1320 | g | c |
| 1321 | u | c |
| 1326 | g | a |
| 1329 | c | u |
| 1332 | c | u |
| 1344 | u | a |
| 1347 | g | a |
| 1350 | g | a |
| 1357 | c | u |
| 1359 | u | g |
| 1360 | c | u |
| 1362 | c | g |
| 1368 | a | u |
| 1371 | g | u |
| 1375 | a | u |
| 1376 | g | c |
| 1383 | u | a |
| 1386 | g | a |
| 1389 | a | c |
| 1392 | a | g |
| 1396 | a | u |
| 1397 | g | c |
| 1398 | c | a |
| 1401 | c | u |
| 1402 | u | c |
| 1404 | g | a |
| 1419 | g | a |
| 1422 | g | a |
| 1425 | u | g |
| 1431 | c | u |
| 1432 | a | u |
| 1433 | g | c |
| 1434 | c | a |
| 1440 | g | u |
| 1443 | g | a |
| 1449 | a | g |
| 1453 | u | a |
| 1454 | c | g |
| 1455 | c | u |
| 1458 | g | a |
| 1459 | c | a |
| 1461 | u | a |
| 1464 | c | u |
| 1474 | a | u |
| 1475 | g | c |
| 1476 | c | u |
| 1485 | a | c |
| 1491 | c | u |
| 1497 | c | u |
| 1500 | a | c |
| 1512 | g | a |
| 1515 | c | u |
| 1521 | u | c |
| 1524 | c | u |
| 1527 | a | u |
| 1530 | a | u |
| 1542 | g | a |
| 1545 | c | u |
| 1546 | c | a |
| 1555 | u | a |
| 1556 | c | g |
| 1557 | g | c |
| 1563 | u | c |
| 1566 | g | a |
| 1569 | g | a |
| 1575 | g | a |
| 1576 | u | c |
| 1578 | g | a |
| 1590 | u | c |
| 1593 | u | c |
| 1599 | c | u |
| 1602 | c | a |
| 1608 | g | a |
| 1611 | u | c |
| 1614 | c | u |
| 1617 | c | a |
| 1620 | c | u |
| 1621 | u | c |
| 1623 | g | u |
| 1632 | g | u |
| 1635 | u | a |
| 1638 | u | c |
| 1642 | u | c |
| 1645 | u | a |
| 1646 | c | g |
| 1647 | g | u |
| 1653 | g | u |
| 1656 | g | a |
| 1662 | g | a |
| 1663 | c | a |
| 1665 | g | a |
| 1668 | c | u |
| 1669 | a | u |
| 1670 | g | c |
| 1671 | c | u |
| 1672 | c | u |
| 1674 | c | a |
| 1677 | g | a |
| 1683 | g | a |
| 1698 | a | u |
| 1708 | c | u |
| 1710 | g | a |

TABLE 1-continued

Non-wild-type bases that can be used in the coding sequence of mRNA encoding CFTR.

| Pos. | NWT | WT |
|------|-----|-----|
| 1711 | c | u |
| 1713 | u | a |
| 1716 | u | c |
| 1719 | a | u |
| 1722 | g | u |
| 1734 | c | a |
| 1737 | c | u |
| 1740 | a | u |
| 1743 | g | a |
| 1758 | c | a |
| 1761 | c | u |
| 1764 | g | a |
| 1765 | u | a |
| 1766 | c | g |
| 1767 | g | c |
| 1770 | c | u |
| 1773 | g | c |
| 1782 | u | g |
| 1791 | u | c |
| 1794 | g | a |
| 1797 | g | u |
| 1800 | a | g |
| 1803 | c | u |
| 1804 | c | u |
| 1809 | g | c |
| 1812 | a | u |
| 1815 | a | u |
| 1827 | c | u |
| 1828 | c | u |
| 1830 | u | a |
| 1836 | g | a |
| 1839 | g | u |
| 1845 | g | a |
| 1848 | c | a |
| 1849 | c | u |
| 1851 | g | a |
| 1854 | c | u |
| 1855 | c | u |
| 1857 | c | g |
| 1860 | c | u |
| 1866 | a | u |
| 1867 | u | a |
| 1868 | c | g |
| 1869 | g | c |
| 1870 | u | a |
| 1871 | c | g |
| 1875 | c | u |
| 1881 | c | u |
| 1884 | c | g |
| 1887 | u | a |
| 1890 | c | u |
| 1896 | g | a |
| 1897 | u | c |
| 1899 | g | c |
| 1905 | c | u |
| 1906 | u | c |
| 1908 | g | a |
| 1914 | g | a |
| 1920 | c | u |
| 1921 | u | a |
| 1922 | c | g |
| 1923 | a | c |
| 1924 | a | u |
| 1925 | g | c |
| 1926 | c | a |
| 1938 | g | a |
| 1944 | c | u |
| 1947 | a | u |
| 1956 | g | a |
| 1959 | c | u |
| 1962 | c | u |
| 1965 | g | a |
| 1969 | c | a |
| 1971 | g | a |
| 1972 | c | a |
| 1974 | g | a |
| 1977 | c | u |
| 1980 | g | a |
| 1984 | u | c |
| 1986 | g | a |
| 1989 | g | u |
| 1992 | a | g |
| 1995 | g | c |
| 1996 | c | u |
| 1998 | g | a |
| 2004 | a | u |
| 2010 | g | a |
| 2011 | c | u |
| 2013 | u | a |
| 2016 | g | a |
| 2019 | u | a |
| 2025 | c | u |
| 2028 | g | u |
| 2031 | a | c |
| 2034 | g | c |
| 2040 | c | a |
| 2043 | g | a |
| 2049 | g | a |
| 2052 | g | a |
| 2055 | g | a |
| 2058 | g | u |
| 2064 | g | a |
| 2070 | a | u |
| 2076 | a | g |
| 2082 | u | g |
| 2085 | g | a |
| 2091 | a | g |
| 2097 | c | u |
| 2098 | a | u |
| 2099 | g | c |
| 2103 | c | u |
| 2104 | u | c |
| 2106 | g | c |
| 2112 | u | a |
| 2115 | u | c |
| 2121 | a | u |
| 2124 | u | a |
| 2127 | c | a |
| 2130 | g | a |
| 2133 | c | u |
| 2136 | a | c |
| 2139 | c | u |
| 2142 | c | g |
| 2145 | g | a |
| 2148 | a | g |
| 2154 | a | c |
| 2155 | c | u |
| 2157 | g | a |
| 2160 | g | a |
| 2169 | a | c |
| 2172 | u | c |
| 2184 | g | u |
| 2187 | c | u |
| 2190 | a | g |
| 2193 | c | u |
| 2194 | c | u |
| 2196 | g | a |
| 2200 | c | a |
| 2202 | c | a |
| 2208 | u | g |
| 2209 | a | u |
| 2210 | g | c |
| 2212 | c | u |
| 2214 | c | a |
| 2217 | g | a |
| 2220 | g | a |
| 2226 | a | u |
| 2232 | a | g |
| 2235 | g | a |
| 2241 | c | g |

TABLE 1-continued

Non-wild-type bases that can be used in the coding sequence of mRNA encoding CFTR.

| Pos. | NWT | WT |
|---|---|---|
| 2244 | u | a |
| 2247 | u | g |
| 2250 | c | u |
| 2253 | g | c |
| 2256 | u | c |
| 2257 | u | a |
| 2258 | c | g |
| 2259 | g | c |
| 2265 | u | c |
| 2266 | u | a |
| 2

TABLE 1-continued

Non-wild-type bases that can be used in the coding sequence of mRNA encoding CFTR.

| Pos. | NWT | WT |
|------|-----|-----|
| 2817 | c | u |
| 2820 | g | u |
| 2823 | u | a |
| 2829 | u | a |
| 2832 | c | g |
| 2835 | c | g |
| 2838 | g | a |
| 2842 | c | u |
| 2844 | c | a |
| 2850 | u | c |
| 2853 | g | a |
| 2857 | c | u |
| 2859 | u | a |
| 2863 | a | u |
| 2864 | g | c |
| 2865 | c | u |
| 2868 | a | u |
| 2871 | g | u |
| 2874 | g | a |
| 2877 | u | a |
| 2880 | c | u |
| 2886 | c | a |
| 2890 | u | c |
| 2892 | g | c |
| 2895 | u | c |
| 2899 | c | u |
| 2901 | c | g |
| 2904 | g | a |
| 2907 | g | a |
| 2910 | a | u |
| 2913 | u | g |
| 2917 | u | c |
| 2919 | g | u |
| 2923 | c | a |
| 2925 | c | a |
| 2931 | a | c |
| 2940 | u | a |
| 2964 | c | u |
| 2967 | g | u |
| 2970 | g | c |
| 2973 | c | a |
| 2976 | c | u |
| 2994 | g | a |
| 2995 | c | u |
| 2997 | g | a |
| 3000 | c | u |
| 3009 | g | a |
| 3015 | u | a |
| 3021 | a | u |
| 3027 | u | a |
| 3030 | c | u |
| 3031 | c | u |
| 3033 | c | a |
| 3036 | g | a |
| 3039 | u | c |
| 3045 | u | c |
| 3051 | c | u |
| 3054 | g | a |
| 3057 | c | a |
| 3060 | u | g |
| 3063 | g | a |
| 3069 | c | a |
| 3075 | g | u |
| 3081 | c | u |
| 3085 | c | u |
| 3088 | c | a |
| 3090 | g | a |
| 3093 | c | a |
| 3100 | u | c |
| 3102 | g | c |
| 3105 | g | a |
| 3108 | g | c |
| 3117 | g | a |
| 3120 | u | c |
| 3123 | g | a |
| 3132 | g | a |
| 3141 | g | c |
| 3145 | u | a |
| 3146 | c | g |
| 3147 | g | u |
| 3150 | u | a |
| 3153 | c | u |
| 3156 | u | c |
| 3159 | g | u |
| 3168 | g | u |
| 3171 | c | a |
| 3174 | u | c |
| 3177 | g | a |
| 3180 | g | a |
| 3184 | u | c |
| 3186 | g | a |
| 3192 | g | a |
| 3193 | u | c |
| 3195 | g | u |
| 3198 | c | u |
| 3204 | u | c |
| 3207 | c | a |
| 3208 | a | c |
| 3216 | c | u |
| 3228 | a | u |
| 3243 | g | u |
| 3250 | c | u |
| 3252 | c | a |
| 3258 | g | u |
| 3261 | a | c |
| 3264 | u | c |
| 3270 | u | c |
| 3276 | u | c |
| 3277 | u | c |
| 3280 | a | u |
| 3281 | g | c |
| 3282 | u | a |
| 3285 | c | a |
| 3288 | c | g |
| 3291 | a | c |
| 3297 | u | c |
| 3300 | g | a |
| 3304 | c | a |
| 3306 | c | a |
| 3309 | u | a |
| 3312 | g | a |
| 3324 | g | c |
| 3333 | u | c |
| 3336 | c | u |
| 3339 | g | u |
| 3342 | g | u |
| 3345 | u | c |
| 3348 | u | c |
| 3351 | c | u |
| 3357 | c | u |
| 3360 | g | a |
| 3363 | c | a |
| 3366 | g | a |
| 3372 | g | a |
| 3375 | c | a |
| 3378 | g | a |
| 3382 | c | a |
| 3384 | g | a |
| 3387 | c | u |
| 3402 | a | u |
| 3403 | c | u |
| 3405 | c | a |
| 3414 | c | u |
| 3417 | u | c |
| 3423 | c | u |
| 3426 | u | a |
| 3438 | a | u |
| 3441 | g | a |
| 3445 | a | u |
| 3446 | g | c |

TABLE 1-continued

Non-wild-type bases that can be used in the coding sequence of mRNA encoding CFTR.

| Pos. | NWT | WT |
|---|---|---|
| 3448 | u | a |
| 3449 | c | g |
| 3450 | g | c |
| 3453 | u | a |
| 3466 | c | u |
| 3472 | a | c |
| 3474 | g | a |
| 3477 | c | u |
| 3480 | u | g |
| 3481 | u | a |
| 3482 | c | g |
| 3483 | g | c |
| 3484 | a | c |
| 3486 | g | a |
| 3501 | c | u |
| 3510 | g | a |
| 3513 | g | a |
| 3516 | g | a |
| 3

TABLE 1-continued

Non-wild-type bases that can be used in the coding sequence of mRNA encoding CFTR.

| Pos. | NWT | WT |
|---|---|---|
| 3996 | g | u |
| 3999 | a | g |
| 4002 | a | g |
| 4005 | c | u |
| 4020 | a | g |
| 4029 | a | c |
| 4032 | c | u |
| 4038 | g | a |
| 4039 | u | a |
| 4040 | c | g |
| 4041 | g | c |
| 4047 | g | c |
| 4057 | c | u |
| 4059 | c | g |
| 4066 | c | u |
| 4071 | g | u |
| 4072 | c | a |
| 4077 | c | u |
| 4080 | c | u |
| 4084 | u | a |
| 4085 | c | g |
| 4089 | a | g |
| 4095 | a | g |
| 4098 | u | c |
| 4099 | c | u |
| 4101 | u | g |
| 4104 | c | g |
| 4105 | u | c |
| 4107 | g | u |
| 4116 | u | c |
| 4117 | u | a |
| 4118 | c | g |
| 4119 | g | u |
| 4122 | c | u |
| 4126 | c | u |
| 4131 | c | u |
| 4134 | g | a |
| 4140 | g | a |
| 4143 | u | c |
| 4146 | g | a |
| 4149 | c | a |
| 4152 | c | u |
| 4158 | g | a |
| 4161 | a | u |
| 4164 | u | a |
| 4167 | g | a |
| 4170 | g | a |
| 4173 | g | a |
| 4179 | c | u |
| 4182 | c | u |
| 4188 | g | a |
| 4191 | g | a |
| 4203 | g | a |
| 4206 | u | c |
| 4207 | c | a |
| 4209 | u | g |
| 4212 | c | a |
| 4215 | g | a |
| 4218 | c | a |
| 4224 | c | g |
| 4233 | g | a |
| 4240 | c | u |
| 4242 | u | g |
| 4248 | c | a |
| 4257 | u | c |
| 4260 | g | a |
| 4263 | c | g |
| 4266 | c | g |
| 4275 | c | u |
| 4287 | g | a |
| 4293 | u | g |
| 4296 | u | c |
| 4302 | a | g |
| 4303 | u | a |
| 4304 | c | g |
| 4305 | a | c |
| 4306 | u | c |
| 4308 | g | c |
| 4317 | g | a |
| 4320 | g | c |
| 4323 | u | c |
| 4324 | u | a |
| 4325 | c | g |
| 4326 | a | c |
| 4329 | a | c |
| 4335 | u | c |
| 4344 | a | g |
| 4347 | u | c |
| 4353 | a | c |
| 4357 | a | c |
| 4359 | a | g |
| 4362 | u | c |
| 4365 | g | a |
| 4366 | u | a |
| 4367 | c | g |
| 4368 | g | c |
| 4380 | c | u |
| 4383 | a | g |
| 4386 | g | c |
| 4392 | c | u |
| 4395 | g | u |
| 4398 | c | u |
| 4399 | u | c |
| 4407 | a | g |
| 4413 | u | a |
| 4422 | a | g |
| 4425 | u | g |
| 4431 | c | u |
| 4434 | g | a |
| 4435 | c | a |
| 4437 | u | g |
| 4443 | a | g |

In some embodiments, the CFTR mRNA according to the invention comprises a coding sequence comprising at least 50%, at least 55%, at least 60%, at least 65%, at least 70%, at least 75%, at least 80%, at least 85%, at least 90%, or at least 95% of the non-wild-type bases listed in Table 2 at the corresponding positions of the coding sequence listed in Table 2 relative to the wild-type coding sequence of SEQ ID NO: 2.

TABLE 2

Subset of non-wild-type bases that can be used in the coding sequence of mRNA encoding CFTR.

| Pos. | NWT | WT |
|---|---|---|
| 7 | c | a |
| 15 | g | u |
| 18 | c | g |
| 33 | c | u |
| 45 | c | u |
| 54 | a | c |
| 60 | u | c |
| 61 | c | a |
| 63 | g | a |
| 66 | u | a |
| 72 | u | g |
| 81 | g | a |
| 84 | u | c |
| 85 | c | a |
| 87 | g | a |
| 93 | g | c |
| 96 | u | g |
| 126 | g | u |

TABLE 2-continued

Subset of non-wild-type bases that can be used in the coding sequence of mRNA encoding CFTR.

| Pos. | NWT | WT |
|---|---|---|
| 129 | a | u |
| 135 | g | u |
| 138 | g | u |
| 141 | u | c |
| 147 | c | a |
| 150 | g | u |
| 159 | c | g |
| 163 | c | a |
| 165 | g | a |
| 175 | c | a |
| 177 | c | a |
| 180 | a | g |
| 183 | c | g |
| 186 | g | u |
| 189 | u | a |
| 201 | g | u |
| 213 | c | u |
| 216 | a | c |
| 225 | g | a |
| 238 | c | a |
| 240 | g | a |
| 252 | c | u |
| 255 | u | a |
| 270 | c | a |
| 282 | a | c |
| 291 | c | a |
| 294 | a | g |
| 304 | u | c |
| 309 | u | a |
| 310 | c | a |
| 312 | c | a |
| 315 | u | c |
| 318 | c | a |
| 324 | g | c |
| 327 | c | u |
| 333 | c | g |
| 342 | a | g |
| 345 | a | g |
| 351 | g | c |
| 369 | c | a |
| 372 | g | c |
| 375 | c | a |
| 378 | a | c |
| 384 | u | c |
| 385 | u | c |
| 390 | u | c |
| 396 | c | u |
| 399 | c | g |
| 409 | u | c |
| 412 | u | c |
| 417 | u | c |
| 423 | a | c |
| 429 | c | u |
| 435 | c | u |
| 444 | c | u |
| 447 | u | a |
| 457 | c | a |
| 462 | c | a |
| 492 | a | u |
| 498 | a | g |
| 501 | c | g |
| 504 | g | a |
| 507 | g | c |
| 510 | g | u |
| 514 | u | c |
| 525 | u | a |
| 526 | u | a |
| 527 | c | g |
| 531 | c | u |
| 534 | u | a |
| 538 | u | c |
| 544 | u | a |
| 545 | c | g |
| 555 | u | c |
| 558 | u | c |
| 564 | c | g |
| 573 | c | u |
| 588 | g | a |
| 615 | g | u |
| 624 | c | g |
| 631 | u | c |
| 642 | u | a |
| 645 | u | c |
| 663 | a | g |
| 672 | u | c |
| 684 | a | u |
| 697 | u | c |
| 702 | a | c |
| 703 | u | c |
| 720 | u | a |
| 724 | c | a |
| 726 | g | a |
| 741 | u | c |
| 742 | c | a |
| 744 | c | a |
| 756 | g | u |
| 759 | u | g |
| 762 | a | g |
| 768 | g | u |
| 777 | c | u |
| 780 | c | g |
| 786 | u | c |
| 789 | g | a |
| 798 | c | u |
| 813 | g | u |
| 816 | c | u |
| 819 | a | g |
| 825 | u | c |
| 840 | u | a |
| 864 | c | a |
| 865 | c | a |
| 867 | c | a |
| 873 | u | a |
| 891 | c | g |
| 897 | g | a |
| 900 | g | c |
| 906 | c | g |
| 907 | c | a |
| 909 | g | a |
| 912 | u | c |
| 921 | g | c |
| 927 | g | c |
| 939 | c | a |
| 948 | c | u |
| 951 | u | g |
| 954 | c | g |
| 960 | c | a |
| 963 | g | u |
| 966 | u | g |
| 967 | u | c |
| 972 | u | c |
| 979 | u | c |
| 984 | u | c |
| 990 | g | a |
| 993 | u | c |
| 1002 | c | g |
| 1008 | u | a |
| 1017 | g | c |
| 1020 | u | c |
| 1023 | G | a |
| 1035 | a | u |
| 1036 | u | c |
| 1047 | a | g |
| 1053 | a | u |
| 1065 | g | c |
| 1071 | c | u |
| 1092 | g | u |
| 1101 | g | a |
| 1116 | a | g |
| 1158 | u | c |

TABLE 2-continued

Subset of non-wild-type bases that can be used in the coding sequence of mRNA encoding CFTR.

| Pos. | NWT | WT |
|------|-----|-----|
| 1161 | u

TABLE 2-continued

Subset of non-wild-type bases that can be used in the coding sequence of mRNA encoding CFTR.

| Pos. | NWT | WT |
|------|-----|-----|
| 2265 | u | c |
| 2266 | u | a |
| 2267 | c | g |
| 2268 | a | c |
| 2271 | c | u |
| 2274 | a | c |
| 2277 | u | c |
| 2280 | a | g |
| 2289 | g | a |
| 2301 | a | g |
| 2304 | c | u |
| 2310 | c | g |
| 2316 | c | g |
| 2322 | g | a |
| 2325 | u | c |
| 2328 | g | a |
| 2331 | a | u |
| 2340 | g | u |
| 2343 | a | g |
| 2355 | c | a |
| 2358 | a | g |
| 2361 | g | a |
| 2364 | g | a |
| 2370 | a | c |
| 2373 | g | a |
| 2388 | u | g |
| 2391 | a | c |
| 2400 | g | a |
| 2403 | u | c |
| 2415 | c | g |
| 2428 | c | a |
| 2430 | u | a |
| 2436 | u | a |
| 2439 | g | u |
| 2448 | c | u |
| 2451 | a | c |
| 2454 | u | g |
| 2463 | c | u |
| 2484 | u | c |
| 2490 | a | g |
| 2514 | a | g |
| 2515 | u | a |
| 2516 | c | g |
| 2517 | a | c |
| 2526 | g | a |
| 2532 | a | u |
| 2535 | g | a |
| 2548 | u | c |
| 2553 | u | a |
| 2562 | g | u |
| 2572 | u | a |
| 2573 | c | g |
| 2583 | c | u |
| 2586 | c | g |
| 2589 | c | a |
| 2598 | u | c |
| 2601 | c | a |
| 2613 | c | g |
| 2622 | c | g |
| 2625 | a | u |
| 2628 | g | u |
| 2631 | a | u |
| 2634 | u | g |
| 2640 | c | g |
| 2643 | c | g |
| 2655 | u | a |
| 2658 | u | c |
| 2661 | g | u |
| 2665 | u | c |
| 2683 | u | a |
| 2684 | c | g |
| 2688 | a | u |
| 2694 | a | u |
| 2703 | u | c |
| 2704 | u | a |
| 2705 | c | g |
| 2712 | c | a |
| 2724 | u | c |
| 2725 | u | a |
| 2726 | c | g |
| 2727 | u | c |
| 2730 | a | c |
| 2742 | c | u |
| 2760 | a | g |
| 2781 | c | u |
| 2784 | g | u |
| 2802 | a | u |
| 2805 | c | a |
| 2811 | c | g |
| 2814 | u | g |
| 2820 | g | u |
| 2823 | u | a |
| 2829 | u | a |
| 2832 | c | g |
| 2844 | c | a |
| 2850 | u | c |
| 2859 | u | a |
| 2865 | c | u |
| 2868 | a | u |
| 2877 | u | a |
| 2890 | u | c |
| 2895 | u | c |
| 2901 | c | g |
| 2907 | g | a |
| 2910 | a | u |
| 2913 | u | g |
| 2917 | u | c |
| 2923 | c | a |
| 2925 | c | a |
| 2931 | a | c |
| 2970 | g | c |
| 2976 | c | u |
| 3000 | c | u |
| 3021 | a | u |
| 3030 | c | u |
| 3033 | c | a |
| 3039 | u | c |
| 3045 | u | c |
| 3051 | c | u |
| 3054 | g | a |
| 3060 | u | g |
| 3063 | g | a |
| 3069 | c | a |
| 3075 | g | u |
| 3088 | c | a |
| 3090 | g | a |
| 3108 | g | c |
| 3120 | u | c |
| 3141 | g | c |
| 3145 | u | a |
| 3146 | c | g |
| 3147 | g | u |
| 3150 | u | a |
| 3156 | u | c |
| 3159 | g | u |
| 3174 | u | c |
| 3184 | u | c |
| 3192 | g | a |
| 3193 | u | c |
| 3198 | c | u |
| 3228 | a | u |
| 3243 | g | u |
| 3252 | c | a |
| 3258 | g | u |
| 3261 | a | c |
| 3264 | u | c |
| 3270 | u | c |
| 3276 | u | c |
| 3277 | u | c |
| 3282 | u | a |

TABLE 2-continued

Subset of non-wild-type bases that can be used in the coding sequence of mRNA encoding CFTR.

| Pos. | NWT | WT |
|---|---|---|
| 3288 | c | g |
| 3297 | u | c |
| 3304 | c | a |
| 3306 | c | a |
| 3336 | c | u |
| 3339 | g | u |
| 3345 | u | c |
| 3348 | u | c |
| 3366 | g | a |
| 3375 | c | a |
| 3382 | c | a |
| 3387 | c | u |
| 3402 | a | u |
| 3405 | c | a |
| 3417 | u | c |
| 3426 | u | a |
| 3438 | a | u |
| 3448 | u | a |
| 3449 | c | g |
| 3450 | g | c |
| 3474 | g | a |
| 3477 | c | u |
| 3480 | u | g |
| 3481 | u | a |
| 3482 | c | g |
| 3483 | g | c |
| 3486 | g | a |
| 3501 | c | u |
| 3510 | g | a |
| 3513 | g | a |
| 3519 | a | u |
| 3528 | a | c |
| 3531 | a | g |
| 3534 | u | a |
| 3537 | g | c |
| 3546 | u | c |
| 3555 | g | c |
| 3559 | u | c |
| 3564 | u | g |
| 3570 | a | u |
| 3579 | c | u |
| 3588 | u | a |
| 3615 | u | c |
| 3624 | u | c |
| 3633 | c | u |
| 3648 | g | a |
| 3660 | c | a |
| 3666 | a | u |
| 3669 | g | a |
| 3672 | c | u |
| 3675 | a | c |
| 3681 | u | a |
| 3684 | a | g |
| 3693 | g | c |
| 3702 | u | a |
| 3711 | u | c |
| 3717 | u | g |
| 3723 | g | c |
| 3724 | u | c |
| 3729 | c | g |
| 3732 | g | a |
| 3741 | g | a |
| 3747 | a | g |
| 3750 | a | g |
| 3751 | u | a |
| 3752 | c | g |
| 3753 | g | u |
| 3756 | g | u |
| 3765 | g | a |
| 3786 | u | c |
| 3795 | u | a |
| 3810 | c | u |
| 3813 | c | u |
| 3816 | u | g |
| 3819 | g | u |
| 3847 | c | a |
| 3855 | g | c |
| 3864 | a | g |
| 3873 | a | g |
| 3879 | c | a |
| 3889 | a | u |
| 3890 | g | c |
| 3891 | c | u |
| 3901 | c | a |
| 3912 | c | g |
| 3918 | u | c |
| 3933 | a | u |
| 3945 | u | a |
| 3954 | c | u |
| 3957 | g | a |
| 3960 | c | u |
| 3972 | u | c |
| 3981 | a | g |
| 3984 | c | a |
| 3996 | g | u |
| 3999 | a | g |
| 4002 | a | g |
| 4005 | c | u |
| 4020 | a | g |
| 4029 | a | c |
| 4032 | c | u |
| 4039 | u | a |
| 4040 | c | g |
| 4041 | g | c |
| 4047 | g | c |
| 4059 | c | g |
| 4071 | g | u |
| 4072 | c | a |
| 4077 | c | u |
| 4080 | c | u |
| 4084 | u | a |
| 4085 | c | g |
| 4089 | a | g |
| 4095 | a | g |
| 4098 | u | c |
| 4104 | c | g |
| 4105 | u | c |
| 4116 | u | c |
| 4119 | g | u |
| 4134 | g | a |
| 4140 | g | a |
| 4143 | u | c |
| 4158 | g | a |
| 4161 | a | u |
| 4164 | u | a |
| 4173 | g | a |
| 4179 | c | u |
| 4188 | g | a |
| 4206 | u | c |
| 4207 | c | a |
| 4209 | u | g |
| 4212 | c | a |
| 4224 | c | g |
| 4242 | u | g |
| 4248 | c | a |
| 4257 | u | c |
| 4263 | c | g |
| 4266 | c | g |
| 4293 | u | g |
| 4303 | u | a |
| 4304 | c | g |
| 4305 | a | c |
| 4306 | u | c |
| 4320 | g | c |
| 4323 | u | c |
| 4324 | u | a |
| 4325 | c | g |
| 4326 | a | c |
| 4329 | a | c |
| 4335 | u | c |

TABLE 2-continued

Subset of non-wild-type bases that can be used in the coding sequence of mRNA encoding CFTR.

| Pos. | NWT | WT |
|------|-----|-----|
| 4344 | a | g |
| 4347 | u | c |
| 4353 | a | c |
| 4362 | u | c |
| 4365 | g | a |
| 4366 | u | a |
| 4367 | c | g |
| 4368 | g | c |
| 4383 | a | g |
| 4386 | g | c |
| 4392 | c | u |
| 4395 | g | u |
| 4399 | u | c |
| 4407 | a | g |
| 4413 | u | a |
| 4422 | a | g |
| 4425 | u | g |
| 4434 | g | a |
| 4435 | c | a |
| 4437 | u | g |

In some embodiments, the present invention comprises a non-naturally occurring CFTR mRNA comprising a coding sequence of SEQ ID NO: 3. Additional exemplary non-naturally occurring CFTR mRNA coding sequences are described in the Brief Description of Sequences section, such as, for example, SEQ ID NOs:9, 10, 11, 12, 13, 14, 15, 16, or 17. In some embodiments, the present invention provides a CFTR mRNA comprising a coding sequence at least 50%, 55%, 60%, 65%, 70%, 75%, 80%, 85%, 90%, 95%, 96%, 97%, 98%, or 99% identical to any of SEQ ID NO: 3, 9, 10, 11, 12, 13, 14, 15, 16, or 17. In some embodiments, a non-naturally occurring CFTR mRNA comprises a 5'UTR, 3'UTR, a signal peptide coding sequence or a cap or tail structure as described below.

The above-described CFTR mRNAs comprising coding sequence which differs from wild-type CFTR coding sequence can provide advantages with respect to efficacy and ease of preparation. For example, in vitro transcription reactions using a polynucleotide comprising template sequence complementary to the CFTR coding sequence can give greater RNA yield; a polynucleotide comprising said template sequence can be more stable (i.e., less prone to mutation) during growth in a host cell, reducing the amount of purification needed to generate template usable in a reaction; and the in vivo translation of an mRNA comprising the coding sequence can be higher.

Signal Peptide Sequence

In some embodiments, an mRNA encoding a CFTR protein incorporates a nucleotide sequence encoding a signal peptide. As used herein, the term "signal peptide" refers to a peptide present at a newly synthesized protein that can target the protein towards the secretory pathway. In some embodiments, the signal peptide is cleaved after translocation into the endoplasmic reticulum following translation of the mRNA. Signal peptide is also referred to as signal sequence, leader sequence or leader peptide. Typically, a signal peptide is a short (e.g., 5-30, 5-25, 5-20, 5-15, or 5-10 amino acids long) peptide. A signal peptide may be present at the N-terminus of a newly synthesized protein. Without wishing to be bound by any particular theory, the incorporation of a signal peptide encoding sequence on a CFTR encoding mRNA may facilitate the secretion and/or production of the CFTR protein in vivo.

A suitable signal peptide for the present invention can be a heterogeneous sequence derived from various eukaryotic and prokaryotic proteins, in particular secreted proteins. In some embodiments, a suitable signal peptide is a leucine-rich sequence. See Yamamoto Y et al. (1989), Biochemistry, 28:2728-2732, which is incorporated herein by reference. A suitable signal peptide may be derived from a human growth hormone (hGH), serum albumin preproprotein, Ig kappa light chain precursor, Azurocidin preproprotein, cystatin-S precursor, trypsinogen 2 precursor, potassium channel blocker, alpha conotoxin lp1.3, alpha conotoxin, alfa-galactosidase, cellulose, aspartic proteinase nepenthesin-1, acid chitinase, K28 prepro-toxin, killer toxin zygocin precursor, and Cholera toxin. Exemplary signal peptide sequences are described in Kober, et al., Biotechnol. Bioeng., 110: 1164-73, 2012, which is incorporated herein by reference.

In some embodiments, a CFTR encoding mRNA may incorporate a sequence encoding a signal peptide derived from human growth hormone (hGH), or a fragment thereof. A non-limiting nucleotide sequence encoding a hGH signal peptide is show below.

```
5' human growth hormone (hGH) sequence
(SEQ ID NO: 18):
AUGGCCACUGGAUCAAGAACCUCACUGCUGCUCGCUUUUGGACUGC

UUUGCCUGCCCUGGUUGCAAGAAGGAUCGGCUUUCCCGACCAUCCC

ACUCUCC

Alternative 5' human growth hormone (hGH)
sequence (SEQ ID NO: 19):
AUGGCAACUGGAUCAAGAACCUCCCUCCUGCUCGCAUUCGGCCUGC

UCUGUCUCCCAUGGCUCCAAGAAGGAAGCGCGUUCCCCACUAUCCC

CCUCUCG
```

In some embodiments, an mRNA according to the present invention may incorporate a signal peptide encoding sequence having at least 50%, 55%, 60%, 65%, 70%, 75%, 80%, 85%, 90%, 95%, 96%, 97%, 98%, 99% or more identity to SEQ ID NO:18 or SEQ ID NO:19.

5'-UTR, 3'-UTR, Poly-A Tail, Cap, and Nonstandard Nucleotide Residues

In some embodiments, the mRNA comprises a sequence in its 5'-UTR which is identical to SEQ ID NO: 4 or is at least 50%, at least 55%, at least 60%, at least 65%, at least 70%, at least 75%, at least 80%, at least 85%, at least 90%, at least 95%, at least 98%, or at least 99% identical to SEQ ID NO: 4.

In some embodiments, the mRNA comprises a sequence in its 3'-UTR which is identical to SEQ ID NO: 5 or is at least 50%, at least 55%, at least 60%, at least 65%, at least 70%, at least 75%, at least 80%, at least 85%, at least 90%, at least 95%, at least 98%, or at least 99% identical to SEQ ID NO: 5.

In some embodiments, the mRNA comprises a poly-A tail. In some embodiments, the poly-A tail has a length of at least 70, 100, 120, 150, 200, 250, 300, 400, or 500 residues. In some embodiments, the poly-A tail has a length ranging from 70 to 100, 100 to 120, 120 to 150, 150 to 200, or 200 to 300, 300 to 400, or 400 to 500 residues. Poly A tails can be added using a variety of art-recognized techniques. For example, long poly A tails can be added to synthetic or in vitro transcribed RNA using poly A polymerase (Yokoe, et al. Nature Biotechnology. 1996; 14: 1252-1256). A transcription vector can also encode long poly A tails. In addition, poly A tails can be added by transcription directly from PCR products. Poly A may also be ligated to the 3' end of a sense RNA with RNA ligase (see, e.g., Molecular Cloning A Laboratory Manual, 2nd Ed., ed. by Sambrook, Fritsch and Maniatis (Cold Spring Harbor Laboratory Press: 1991 edition)). In some embodiments, a poly-U or poly-C tail may be used instead or in addition to a poly-A tail. For example, CFTR encoding mRNAs may include a 3' poly(C) tail structure. A suitable poly-C tail on the 3' terminus of mRNA typically include about 10 to 200 cytosine nucleotides (e.g., about 10 to 150 cytosine nucleotides, about 10 to 100 cytosine nucleotides, about 20 to 70 cytosine nucleotides, about 20 to 60 cytosine nucleotides, or about 10 to 40 cytosine nucleotides). The poly-C tail may be added to the poly-A tail or may substitute the poly-A tail.

In some embodiments, the mRNA comprises a 5'-cap, for example, a cap1 structure. For mRNA capping enzymes and procedures, see, e.g., Fechter, P.; Brownlee, G. G. "Recognition of mRNA cap structures by viral and cellular proteins" *J. Gen. Virology* 2005, 86, 1239-1249; European patent publication 2 010 659 A2; U.S. Pat. No. 6,312,926. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G (5')ppp(5')A and G(5')ppp(5')G.

In some embodiments, the mRNA comprises one or more nonstandard nucleotide residues. The nonstandard nucleotide residues may include, e.g., 5-methyl-cytidine ("5 mC"), pseudouridine ("yWU"), and/or 2-thio-uridine ("2 sU"). See, e.g., U.S. Pat. No. 8,278,036 or WO2011012316 for a discussion of such residues and their incorporation into mRNA. In some embodiments, mRNA may be SNIM RNA. As used herein, SNIM RNA is an acronym of Stabilized Non-Immunogenic Messenger RNA, designating messenger RNAs produced by in vitro transcription (IVT) including certain percentages of modified nucleotides in the IVT reaction as described in PCT Publication WO 2011/012316. SNIM RNA used in the Examples disclosed herein was produced by IVT in which 25% of U residues were 2-thio-uridine and 25% of C residues were 5-methylcytidine. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Certain embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In certain embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

Compositions Comprising CFTR mRNA

In certain embodiments, the mRNA molecules of the invention may be administered as naked or unpackaged mRNA. In some embodiments, the administration of the mRNA in the compositions of the invention may be facilitated by inclusion of a suitable carrier. In certain embodiments, the carrier is selected based upon its ability to facilitate the transfection of a target cell with one or more mRNAs.

As used herein, the term "carrier" includes any of the standard pharmaceutical carriers, vehicles, diluents, excipients and the like which are generally intended for use in connection with the administration of biologically active agents, including mRNA.

In certain embodiments, the carriers employed in the compositions of the invention may comprise a liposomal vesicle, or other means to facilitate the transfer of a mRNA to target cells and/or tissues. Suitable carriers include, but are not limited to, polymer based carriers, such as polyethyleneimine (PEI) and multi-domain-block polymers, lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, dry powders, poly(D-arginine), nanodendrimers, starch-based delivery systems, micelles, emulsions, sol-gels, niosomes, plasmids, viruses, calcium phosphate nucleotides, aptamers, peptides, peptide conjugates, small-molecule targeted conjugates, and other vectorial tags. Also contemplated is the use of bio-nanocapsules and other viral capsid proteins assemblies as a suitable carrier. (Hum. Gene Ther. 2008 September; 19(9): 887-95).

In some embodiments, the carrier comprises an organic cation, such as a cationic lipid or a cationic organic polymer. If present, the cationic lipid may be a component of liposomal vesicles encapsulating the mRNA.

In certain embodiments of the invention, the carrier is formulated using a polymer as a carrier, alone or in combination with other carriers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727). Additional exemplary polymers suitable for the present invention include those described in PCT Publication WO2013182683, the contents of which is hereby incorporated by reference.

The use of liposomal carriers to facilitate the delivery of polynucleotides to target cells is contemplated by the present invention. Liposomes (e.g., liposomal lipid nanoparticles) are generally useful in a variety of applications in research, industry, and medicine, particularly for their use as carriers of diagnostic or therapeutic compounds in vivo (Lasic, *Trends Biotechnol.*, 16: 307-321, 1998; Drummond et al., *Pharmacol. Rev.*, 51: 691-743, 1999) and are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, *Trends Biotechnol.*, 16: 307-321, 1998). Bilayer membranes of the liposomes can also be formed by amphiphilic polymers and surfactants (e.g., polymerosomes, niosomes, etc.).

In certain embodiments, the mRNA is complexed with lipid nanoparticles to facilitate delivery to the target cell. In certain embodiments, the compositions of the invention may be combined with a multi-component lipid mixture employing one or more cationic lipids, additional lipids such as non-cationic lipids (also referred to as helper lipids), cholesterol-based lipids, and/or PEGylated lipids for mRNA encapsulation.

Cationic Lipids

In some embodiments, a suitable lipid nanoparticle contains a cationic lipid. As used herein, the phrase "cationic lipid" refers to any of a number of lipid species that have a net positive charge at a selected pH, such as physiological pH. Some cationic lipids, in particular, those known as titratable or pH-titratable cationic lipids are particularly effective in delivering mRNA. Several cationic (e.g., titratable) lipids have been described in the literature, many of which are commercially available. Particularly suitable cationic lipids for use in the compositions and methods of the invention include those described in international patent publications WO 2010/053572 (and particularly, C12-200 described at paragraph [00225]) and WO 2012/170930, both of which are incorporated herein by reference. In some embodiments, the cationic lipid cKK-E12 is used (disclosed in WO 2013/063468), the teachings of which are incorporated herein by reference in their entirety. In some embodiments, the cationic lipid N-[1-(2,3-dioleyloxy)propyl]-N,N,N-trimethylammonium chloride or "DOTMA" is used. (Feigner et al. (*Proc. Nat'l Acad. Sci.* 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2 (spermine-carboxamido)ethyl]-N,N-dimethyl-1-propanaminium or "DOSPA" (Behr et al. *Proc. Nat. 'l Acad. Sci.* 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethyl-arnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28: 172-176 (2010)), or mixtures thereof. (Heyes, J., et al., *J Controlled Release* 107: 276-287 (2005); Morrissey, D V., et al., *Nat. Biotechnol.* 23(8): 1003-1007 (2005); PCT Publication WO2005/121348A1).

In certain embodiments, the compositions and methods of the invention employ a lipid nanoparticles comprising an ionizable cationic lipid described in U.S. provisional patent application 61/617,468, filed Mar. 29, 2013 (incorporated herein by reference), such as, e.g., (15Z,18Z)—N,N-dimethyl-6-(9Z,12Z)-octadeca-9, 12-dien-1-yl)tetracosa-15,18-dien-1-amine (HGT5000), (15Z,18Z)—N,N-dimethyl-6-((9Z,12Z)-octadeca-9, 12-dien-1-yl)tetracosa-4,15,18-trien-1-amine (HGT5001), and (15Z,18Z)—N,N-dimethyl-6-((9Z,12Z)-octadeca-9, 12-dien-1-yl)tetracosa-5, 15, 18-trien-1-amine (HGT5002).

In some embodiments, one or more of the cationic lipids present in such a composition comprise at least one of an imidazole, dialkylamino, or guanidinium moiety. In a preferred embodiment, one or more of the cationic lipids does not comprise a quaternary amine.

Non-Cationic/Helper Lipids

In some embodiments, a suitable lipid nanoparticle contains one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. In some embodiments, a non-cationic lipid is a neutral lipid, i.e., a lipid that does not carry a net charge in the conditions under which the composition is formulated and/or administered. Non-cationic lipids include, but are not limited to, distearoylphosphatidylcholine (DSPC), dioleoylphosphatidylcholine (DOPC), dipalmitoyl-phosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

Cholesterol-Based Lipids

In some embodiments, a suitable lipid nanoparticle comprises one or more cholesterol-based lipids. For example, suitable cholesterol-based cationic lipids include, for example, cholesterol, PEGylated cholesterol, DC-Choi (N,N-dimethyl-N-ethylcarboxamidocholesterol), 1,4-bis(3-N-oleylamino-propyl)piperazine (Gao, et al. *Biochem. Biophys. Res. Comm.* 179, 280 (1991); Wolf et al. BioTechniques 23, 139 (1997); U.S. Pat. No. 5,744,335), or ICE.

PEGylated Lipids

In some embodiments, a suitable lipid nanoparticle comprises one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl (Methoxy Polyethylene Glycol)-2000] (C8 PEG-2000 ceramide) is contemplated by the present invention in combination with one or more of the cationic and, in some embodiments, other lipids. In some embodiments, suitable PEGylated lipids comprise PEG-ceramides having shorter acyl chains (e.g., $C_{14}$ or $C_{18}$). In some embodiments, the PEGylated lipid DSPE-PEG-Maleimide-Lectin may be used. Other contemplated PEG-modified lipids include, but are not limited to, a polyethylene glycol chain of up to 5 kDa in length covalently attached to a lipid with alkyl chain(s) of $C_6$-$C_{20}$ length. Without wishing to be bound by a particular theory, it is contemplated that the addition of PEGylated lipids may prevent complex aggregation and increase circulation lifetime to facilitate the delivery of the lipsome encapsulated mRNA to the target cell.

In certain embodiments, the composition comprises one of the following combinations of lipids:

C12-200, DOPE, cholesterol, DMG-PEG2K;
DODAP, DOPE, cholesterol, DMG-PEG2K;
HGT5000, DOPE, cholesterol, DMG-PEG2K;
HGT5001, DOPE, cholesterol, DMG-PEG2K;
XTC, DSPC, cholesterol, PEG-DMG;
MC3, DSPC, cholesterol, PEG-DMG;
ALNY-100, DSPC, cholesterol, PEG-DSG;
cKK-E12, DOPE, Chol, PEGDMG2K.

In some embodiments, lipid:mRNA ratios can be 5:1 (mg:mg), 6:1, 7:1, 8:1, 9:1, 10:1 and greater up to 30:1 (mg:mg) or more. N/P ratios can be in the range of 1.1:1 up to 10:1 or higher. Example lipid ratios are 40:30:20:10, 55:20:20:5, 50:25:20:5 (cationic lipid:helper lipid:chol:PEG lipid).

In some embodiments, the pharmaceutical compositions according to the invention do not comprise a mucolytic agent (e.g., N-acetylcysteine, erdosteine, bromheksin, carbocysteine, guiafenesin, or iodinated glycerol).

Apparatuses Loaded with a Pharmaceutical Composition

In some embodiments, a pharmaceutical composition according to the invention, such as a cationic lipid-based or PEI-based composition comprising a non-naturally occurring CFTR mRNA, is provided within an apparatus for administration to the respiratory system of a subject. The apparatus can be, e.g., an instillation, aerosolization, or nebulization apparatus. Suitable apparatuses include, for example, a PARI Boy jet nebulizer, Aeroneb® Lab nebulizer, MicroSprayer®, or EFlow mesh nebulizer. Alternatively, dry powder inhalers or aerosolization apparatuses such as portable inhalers may be used.

Uses and Methods mRNA for Uses and Methods According to the Invention

Among other things, the present invention provides methods for in vivo production of a CFTR protein, in particular, in a lung of a mammal. In some embodiments, the invention provides methods of inducing CFTR expression in epithelial cells in a lung of a mammal, comprising contacting the epithelial cells with a pharmaceutical composition comprising an in vitro transcribed mRNA, wherein the in vitro transcribed mRNA comprises a coding sequence encoding SEQ ID NO: 1 (the amino acid sequence of wild-type human CFTR). The invention also provides uses of pharmaceutical compositions comprising an in vitro transcribed mRNA, wherein the in vitro transcribed mRNA comprises a coding sequence encoding SEQ ID NO: 1, for the induction of CFTR expression in epithelial cells in a lung of a mammal.

The invention further provides methods of inducing CFTR expression in a mammalian target cell, the method comprising contacting the mammalian target cell with a composition, the composition comprising an in vitro transcribed mRNA encoding the amino acid sequence of SEQ ID NO: 1. The invention further provides a use of composition, the composition comprising an in vitro transcribed mRNA encoding the amino acid sequence of SEQ ID NO: 1, for the induction of CFTR expression in a mammalian target cell.

In some embodiments of such uses and methods of treatment, the in vitro transcribed mRNA is a naturally occurring or wild-type mRNA encoding human CFTR (SEQ ID NO: 2). In other embodiments, the in vitro transcribed mRNA is a non-naturally occurring mRNA as described above.

In certain embodiments, the in vitro transcribed mRNA comprises a coding sequence encoding SEQ ID NO: 1 which is at least 65%, 70%, 75%, 80%, 85%, 88%, 90%, 92% 95%, or 100% identical to SEQ ID NO: 2 (wild-type human CFTR mRNA coding sequence).

mRNA comprising a coding sequence encoding SEQ ID NO: 1 which is at least 65%, 70%, 75%, 80%, 85%, 90%, 95%, 99%, or 100% identical to SEQ ID NO: 2 may have greater cryptic promoter, direct and inverted repeat, and/or GC content than the mRNA discussed above. It was observed that vectors comprising SEQ ID NO: 2 frequently underwent insertion/deletion/rearrangement mutations in host cells under typical growth conditions, resulting in a heterogeneous population of vectors that could not be used directly for in vitro transcription. It was found that growing host cells under conditions such as lower temperature, subdued light and/or low copy cells such as CopyCutter® reduced, but did not eliminate, the occurrence of mutation. Accordingly, it can be advisable for in vitro transcription reactions of mRNA comprising a coding sequence at least 65%, 70%, 75%, 80%, 85%, 90%, 95%, 99%, or 100% identical to SEQ ID NO: 2 to use a template obtained by growing the vector as described above, harvesting and linearizing the vector, and purifying the desired species for use in the transcription reaction. The purification step can be, e.g., size exclusion chromatography or weak anion exchange.

The in vitro transcribed mRNA for uses and methods according to the invention can comprise a 5'-UTR, 3'UTR, poly-A, poly-U and/or poly-C tail, cap, and/or nonstandard nucleotide residues, as discussed in the section above concerning such features.

Pharmaceutical Compositions for Uses and Methods

Pharmaceutical compositions for use according to the invention may comprise mRNA for uses and methods according to the invention as discussed in the preceding section and additional ingredients as discussed in the section above regarding compositions comprising CFTR mRNA. Thus, use and/or administration of pharmaceutical compositions comprising any of the carriers discussed above is contemplated.

In some preferred embodiments, pharmaceutical compositions comprise PEI, such as branched PEI having a molecular weight ranging from 10-40 kDa, for example, 25 kDa.

In other preferred embodiments, pharmaceutical compositions comprise a cationic lipid, a pegylated lipid, and an additional lipid (such as a neutral lipid). The cationic lipid, pegylated lipid, and/or additional lipid may be chosen from those listed in the section above regarding compositions comprising CFTR mRNA.

Routes of Administration for Induction of Expression in Lung

In some embodiments of methods and uses for induction of CFTR expression in a lung of a mammal, a pharmaceutical composition as described above is administered by a route chosen from intratracheal instillation, nebulization, and aerosolization. The apparatus for administering the composition can be chosen from the apparatuses listed in the section above regarding apparatuses loaded with a pharmaceutical composition.

In preferred embodiments, the composition is administered via nebulization or aerosolization. Some lipid formulations may have a tendency to aggregate when nebulization is attempted but it is generally possible to solve aggregation issues by adjusting the formulation, e.g., by substituting the cationic lipid.

Treatment of Cystic Fibrosis

Among other things, the present invention can be used for treating cystic fibrosis. In some embodiments, the present invention provides a method of treating cystic fibrosis by administering to a subject in need of treatment an mRNA encoding a CFTR protein as described herein or a pharmaceutical composition containing the mRNA. The mRNA or a pharmaceutical composition containing the mRNA may be administered directly to the lung of the subject. Various administration routes for pulmonary delivery may be used. In some embodiments, an mRNA or a composition containing an mRNA described herein is administered by inhalation, nebulization or aerosolization. In various embodiments, administration of the mRNA results in expression of CFTR in the lung of the subject (e.g., epithelial cells of the lung).

In a particular embodiment, the present invention provides a method of treating cystic fibrosis by administering to the lung of a subject in need of treatment an mRNA comprising a coding sequence which encodes SEQ ID NO:1. In certain embodiments, the present invention provides a method of treating cystic fibrosis by administering to the lung of a subject in need of treatment an mRNA comprising a coding sequence which encodes an amino acid sequence at least about 70%, 75%, 80%, 85%, 90%, 95%, 96%, 97%, 98%, or 99% identical to SEQ ID NO: 1. In another particular embodiment, the present invention provides a method of treating cystic fibrosis by administering to the lung of a subject in need of treatment an mRNA comprising a coding sequence of SEQ ID NO: 3. In other embodiments, the present invention provides a method of treating cystic fibrosis by administering to the lung of a subject in need of treatment an mRNA comprising a coding sequence at least 65%, 70%, 75%, 80%, 85%, 90%, 95%, or 99% identical to SEQ ID NO: 3. Additional exemplary non-naturally occurring CFTR mRNAs that can be used for treating cystic fibrosis are described in the Brief Description of Sequences section, such as, for example, SEQ ID NOs:9, 10, 11, 12, 13, 14, 15, 16, or 17. In some embodiments, non-naturally occurring CFTR mRNAs that can be used for treating cystic fibrosis comprises a coding sequence at least about 50%, 55%, 60%, 65%, 70%, 75%, 80%, 85%, 90%, 95%, 96%, 97%, 98%, or 99% identical to any of SEQ ID NO: 3, 9, 10, 11, 12, 13, 14, 15, 16, or 17.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent.

Unless otherwise indicated, CFTR mRNA and SNIM RNA used in the Examples disclosed herein comprised a 5' UTR with the sequence of SEQ ID NO: 4, a coding sequence (CDS) with the sequence of SEQ ID NO: 3, and a 3' UTR with the sequence of SEQ ID NO: 5. FFL mRNA and SNIM RNA used in the Examples disclosed herein comprised a 5' UTR, CDS, and 3' UTR with the sequences of SEQ ID NOS: 6, 7, and 8, respectively.

Example 1: In Vitro Synthesized mRNA Encoding CFTR

Messenger RNA Synthesis. Human cystic fibrosis transmembrane conductance regulator (CFTR) mRNA and firefly luciferase (FFL) mRNA were synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" *J. Gen. Virology* 2005, 86, 1239-1249) and a 3' poly(A) tail of approximately 200 nucleotides in length as determined by gel electrophoresis. 5' and 3' untranslated regions were present in each mRNA product.

Exemplary non-naturally occurring CFTR mRNAs include SEQ ID NO:9, SEQ ID NO:10, SEQ ID NO:11, SEQ ID NO:12, SEQ ID NO:13, SEQ ID NO:14, SEQ ID NO:15, SEQ ID NO: 16, or SEQ ID NO: 17 described in the Brief Description of Sequences section.

Example 2: CFTR Expression and Activity in HEK Cells

This example demonstrates that fully functional CFTR protein is expressed from synthetic human CFTR mRNA delivered to cells.

Cells and CFTR Transfection.

Human embryonic kidney HEK293T cells were grown in DMEM (Invitrogen Cat #11965-092) supplemented with 10% fetal bovine serum, 2 mM L-Glutamine, 100 U/ml penicillin and 100 μg/ml streptomycin. The day before transfection, cells were plated on 6-well plates at 50-60% confluence and incubated under normal tissue culture conditions (36° C. in a humidified atmosphere of 5% CO2, 95% air). 60 μl Lipofectamine 2000 (Invitrogen Cat #11668019) was diluted in 900 μl OptiMem reduced serum media (Invitrogen Cat #31985-062) and gently vortexed. 24 μg CFTR mRNA (4 μg per plate) was diluted in 900 μl OptiMem media. The mRNA was immediately added to the diluted Lipofectamine and incubated at room temperature for 30 minutes. The plating media was gently aspirated from the HEK293T cells and replaced with 1 ml OptiMem Reduced Serum Medium. 300 μl of mRNA/Lipofectamine complex was added to each well and the cells allowed to rest under normal tissue culture conditions for 24 hrs before being re-plated by mechanical detachment on poly-L-Lysine coated glass cover slips (BD Biosciences, BD Biocoat) so that the cells could be easily transferred to a recording chamber for electrophysiological recording. Cells were incubated under standard tissue culture conditions for a minimum of a further 24 hours and were used within 48 hours of final plating.

Electrophysiological Recording.

Whole-cell patch-clamp recordings were conducted at room temperature using an Axopatch 200B amplifier with 5-8 MS electrodes. Data were digitized (50 kHz) and filtered (5 kHz) appropriately. Series resistance was compensated (70-80%) to minimize voltage errors. Voltage-clamp recordings were performed with pipette solution of the following composition: 140 mM NMDG-Cl; 5 mM EGTA; 1 mM MgCl2; 10 mM HEPES; pH 7.2; 310 mOsm/l. The bathing solution contained: 140 mM NaCl, 3 mM KCl, 2 mM MgCl2, 2 mM CaCl2, and 10 mM HEPES; pH 7.3, adjusted to 315 mOsm/l with D-glucose. Voltage clamp recordings commenced 3-5 minutes after establishing whole-cell configuration.

Cells were voltage-clamped at a holding potential of either −60 mV or 0 mV and a series of positive and negative voltage steps (either −80 mV to +80 mV or −100 to +100 mV in 20 mV increments) injected into the recorded HEK293T cells to evoke CFTR-induced whole-cell chloride (Cl−) currents. The membrane permeable analogue of cAMP, 8-Br-cAMP (500 µM, Sigma Aldrich) was applied for 4 mins to recorded cells to facilitate CFTR currents. The 'gold-standard' CFTR blocker, CFTRinh-172 (10 µM, Sigma) was applied at the end of each recording to block the CFTR induced Cl− current. Control recordings were performed in non-transfected HEK293T cells.

Test Compounds.

Test compounds were applied using a DAD-16VC fast perfusion system (ALA Scientific Instruments, USA) with the ejection pipette placed approximately 200 µm from the recorded cell. 8-Br-cAMP was made as a 500 mM stock concentration in ddH20. CFTRinh-172 was made as a 10 mM stock in DMSO. All compounds were stored at −20° C. and were rapidly defrosted and diluted to the desired final concentration immediately prior to use.

Analysis.

All analysis was conducted using Clampfit (MDS Analytical Technologies) and Excel (Microsoft) software. All values are maximum evoked-peak current amplitude. Statistical differences in the data were evaluated by Student's t-test, paired or un-paired as appropriate and considered significant at $P<0.05$.

In Vitro Human CFTR Protein Production.

The production of human CFTR protein via hCFTR mRNA was accomplished via transfection of human CFTR mRNA in HEK293T cells described herein. Treated and untreated cells were harvested and subjected to immunoprecipitation methods 24 hours post-transfection. Detection of human CFTR protein via Western blot analysis demonstrates that the fully complex glycosylated CFTR protein (designated as "C" band) was produced from the synthetic messenger RNA (FIG. 1A).

In Vitro Human CFTR Protein Activity.

To determine the activity of the synthetic human CFTR mRNA-derived CFTR protein produced after transfection, whole cell patch clamp assays were performed in both HEK 293 and HEK 293T cells. Treated cells as well as control cells (untreated and mock transfected) were subjected to activator (8-Br-cAMP, forskolin) and inhibitor (CFTRinh-172, GlyH-101) substrates to help determine changes in current flow (chloride ion transport).

Figure 2:
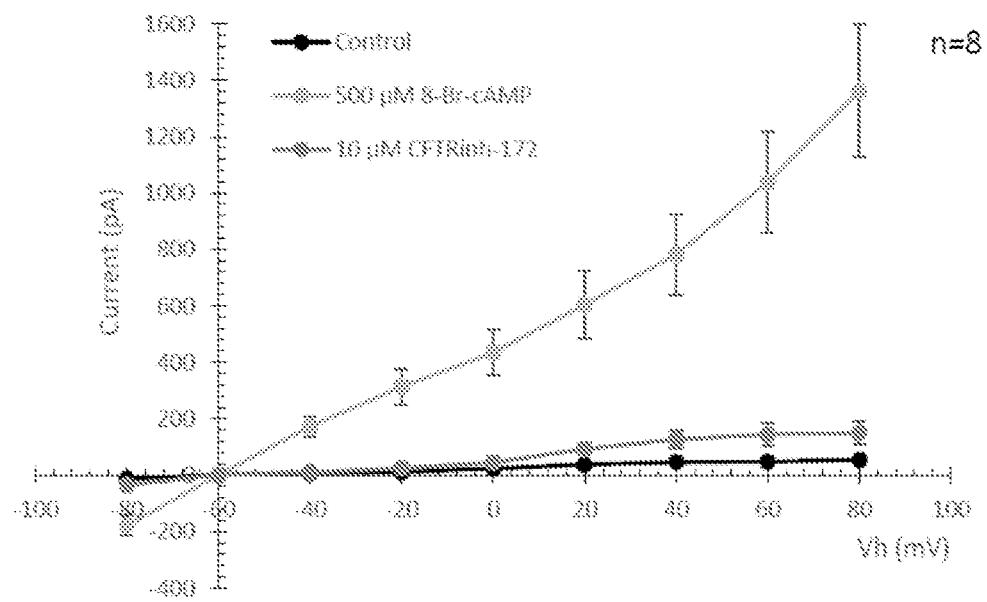
FIG. 2. Current-voltage plot of 8-Br-cAMP evoked currents of treated (4 ug hCFTR mRNA) and untreated HEK293T cells. A large current is induced within the hCFTR mRNA transfected cells as compared to the untreated cells. Treated cells that were exposed to a specific CFTR protein inhibitor, CFTRinh-172, show a marked reduction (~89%) in Cl− ion current flow.
Figure 3:
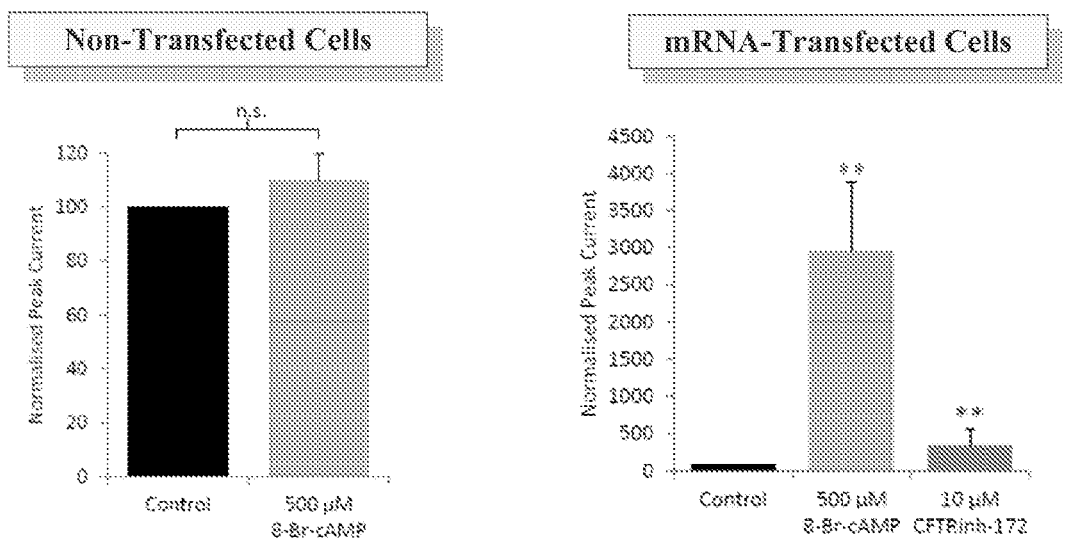
FIG. 3. Histogram plots of 8-Br-cAMP evoked currents of treated (4 ug hCFTR mRNA) and untreated HEK293T cells upon application of a +80 mV membrane potential. A large current is induced within the hCFTR mRNA transfected cells as compared to the untreated cells. Treated cells that were exposed to a specific CFTR protein inhibitor, CFTRinh-172, show a marked reduction (~89%) in Cl− ion current flow.

HEK293T cells were transfected with 4 ug of hCFTR mRNA and analyzed 24 hours post transfection. Whole cell clamp assays were conducted to measure current flow, as represented by chloride ion transport upon application of a set voltage. A plot of current vs voltage as a result of a voltage ramp of −80 mV to +80 mV (depicted in FIG. 2) demonstrates substantial differences in current when comparing untreated versus hCFTR mRNA-treated cells. This increase in current after exposure to 8-Br-cAMP, a known activator of CFTR protein, is suggestive that human CFTR protein is present in these cells. Upon treatment of these previously transfected cells with a known specific CFTR inhibitor, CFTRinh-172, the respective current drops back down to near control levels (~89% decrease). Such a decrease after exposure of this inhibitor strongly supports the presence of human CFTR protein. These results in sum demonstrate that synthetic hCFTR mRNA can produce active human CFTR protein.

Separately, CFTR whole cell activity assays were performed using an automated system (IonWorks) within HEK293 cells. As described above, treated cells as well as control cells (untreated and mock transfected) were subjected to activator and inhibitor substrates to help determine changes in current flow (chloride ion transport). In these studies, forskolin was employed as the CFTR protein activator and a portion of the hCFTR mRNA-transfected cells were further exposed to a different specific CFTR inhibitor, GlyH-101. GlyH-101 is believed to act as a CFTR pore blocker which acts upon the extracellular membrane side of the protein. Notably, this action of mechanism is different from that of CFTRinh-172, which is reported to function from the intracellular side of the CFTR protein.

Figure 4:
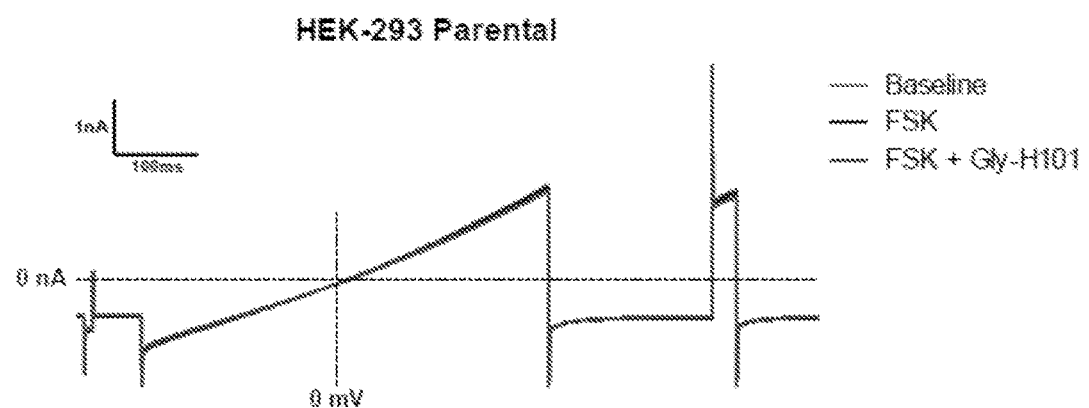
FIG. 4. Current-voltage plot comparing profiles of HEK 293 cells of native, forskolin and GlyH-101 exposure. No significant changes in current were observed in any scenario.

FIG. 4 represents a current-voltage plot of the parental HEK293 cell line treated with forskolin as well as GlyH-101. No significant change in current was observed, suggesting that these specific CFTR activators/inhibitors have no effect on the endogenous proteins present in the cell line.

Figure 5:
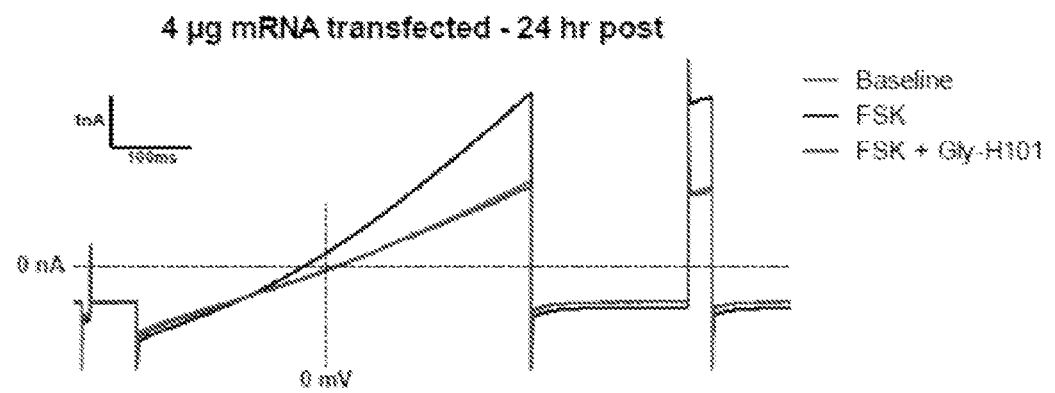
FIG. 5. Current-voltage plot of forskolin-evoked currents of treated (4 ug hCFTR mRNA) and untreated HEK293 cells. A large current is induced within the hCFTR mRNA transfected cells as compared to the untreated cells. Treated cells that were exposed to a specific CFTR protein inhibitor, GlyH-101, show a marked reduction (~95%) in Cl− ion current flow as demonstrated in the step plot (+100 mV) on the right side of the graph.

A plot of current vs. voltage as a result of a voltage ramp of −100 mV to +100 mV (depicted in FIG. 5) demonstrates substantial differences in current when comparing untreated HEK293 cells versus hCFTR mRNA-treated cells. This increase in current after exposure to forskolin a known activator of CFTR protein, is indicative that human CFTR protein is present in these cells. Upon treatment of these previously transfected cells with a different known specific CFTR inhibitor, GlyH-101, the respective current drops back down to near control levels (~95% decrease). Such a decrease after exposure of this inhibitor strongly supports the presence of human CFTR protein.

In total, these inhibition data which are a result of two distinct mechanisms strongly support the identity of a fully functional CFTR protein derived from the synthetic human CFTR messenger RNA.

Example 3: In Vivo Expression of CFTR

This example demonstrates that CFTR protein is effectively expressed in vivo from a CFTR encoding mRNA delivered through pulmonary administration.

Formulation Protocol 1.

Aliquots of 50 mg/mL ethanolic solutions of C12-200, DOPE, Chol and DMG-PEG2K were mixed and diluted with ethanol to 3 mL final volume. Separately, an aqueous buffered solution (10 mM citrate/150 mM NaCl, pH 4.5) of CFTR mRNA was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), followed by water, concentrated and stored at 2-8° C. Final concentration=1.09 mg/mL CFTR mRNA (encapsulated). $Z_{ave}$=80.2 nm ($Dv_{(50)}$=55.5 nm; $Dv_{(90)}$=99.6 nm).

Formulation Protocol 2.

Aliquots of a 2.0 mg/mL aqueous solution PEI (branched, 25 kDa) were mixed with aqueous solution of CFTR mRNA (1.0 mg/mL). The resulting complexed mixture was pipetted up and down several times and put aside for 20 minutes prior to injection. Final concentration=0.60 mg/mL CFTR mRNA (encapsulated). $Z_{ave}$=75.9 nm ($Dv_{(50)}$=57.3 nm; $Dv_{(90)}$=92.1 nm).

Analysis of FFL and CFTR Protein Produced Via Intratracheal Administered mRNA-Loaded Nanoparticles.

All studies were performed using either female BALB/C mice or CFTR KO mice. FFL samples were introduced via either direct instillation (MicroSprayer®) or nebulization (PARI Boy or Aeroneb) respective dose of encapsulated FFL mRNA. CFTR mRNA was introduced using a PARI Boy jet nebulizer. Mice were sacrificed and perfused with saline after allowing time for expression.

Intratracheal Administration of FFL mRNA.

FFL test materials were administered by a single intratracheal aerosol administration via a Microsprayer™ (50 µL/animal) while animals are anesthetized with intraperitoneal injection of a mixture of ketamine 50-100 mg/kg and xylazine 5-15 mg/kg.

Nebulization (Aerosol) Administration of FFL mRNA.

FFL test materials were administered by a single aerosol inhalation via Aeroneb® Lab nebulizer (nominal dose volume of up to 8 mL/group). The test material was delivered to a box containing the whole group of animals (n=4) and connected to oxygen flow and scavenger system.

Administration of CFTR mRNA.

CFTR mRNA was prepared in the manner described in Example 6 below. Four CFTR knockout mice were placed in an aerosol chamber box and exposed to 2 mg total codon optimized unmodified human CFTR mRNA (comprising the coding sequence of SEQ ID NO: 3) via nebulization (Pari Boy jet nebulizer) over the course of approximately one hour. Mice were sacrificed 24 hours post-exposure.

Euthanasia.

Animals were euthanized by $CO_2$ asphyxiation at representative times post-dose administration (±5%) followed by thoracotomy and exsanguinations. Whole blood (maximal obtainable volume) was collected via cardiac puncture and discarded.

Perfusion.

Following exsanguination, all animals underwent cardiac perfusion with saline. In brief, whole body intracardiac perfusion was performed by inserting 23/21 gauge needle attached to 10 mL syringe containing saline set into the lumen of the left ventricle for perfusion. The right atrium was incised to provide a drainage outlet for perfusate. Gentle and steady pressure was applied to the plunger to perfuse the animal after the needle had been positioned in the heart. Adequate flow of the flushing solution was ensured when the exiting perfusate flows clear (free of visible blood) indicating that the flushing solution has saturated the body and the procedure was complete.

Tissue Collection.

Following perfusion, all animals had the liver and lungs (right and left) harvested. Select groups were subjected to approximately one half of the liver and both (right and left) lungs snap frozen in liquid nitrogen and stored separately at nominally −70° C. Select groups were subjected to approximately half of the liver placed in one histology cassette per animal. Additionally, the lungs were inflated with 10% NBF through a cannula that was inserted into the trachea. The trachea was tied off with a ligature and the lungs (right and left) and trachea were placed intact in one histology cassette per animal. All histology cassettes were stored ambient in 10% NBF for 24 hours and transferred to 70% ethanol.

Expression of FFL in FFL-Treated Mice.

Upon analysis of the tissue samples, FFL expression was detected in FFL-treated mice (data not shown).

Expression of CFTR in CFTR Knockout Mice.

Figure 1B:
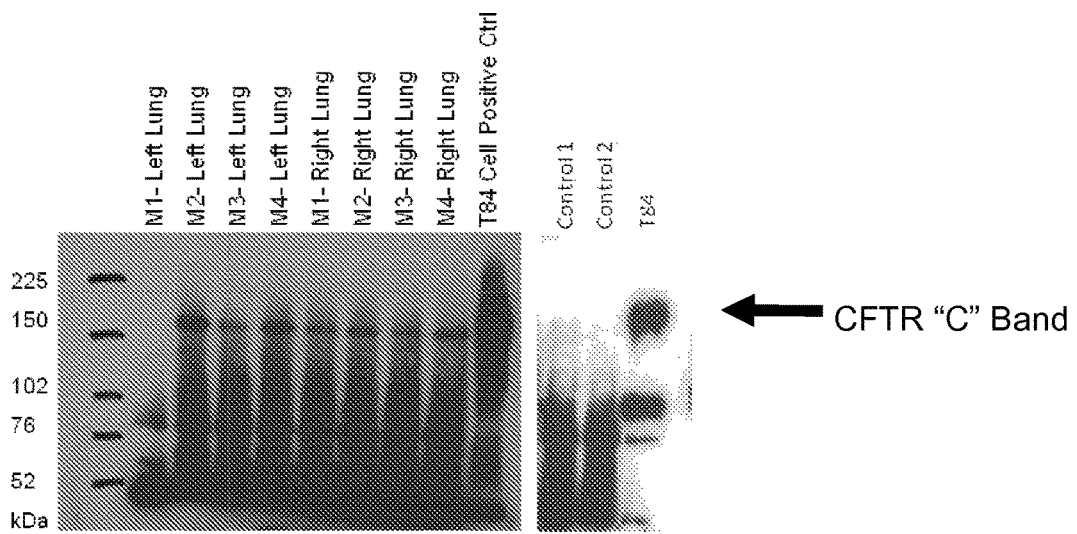
FIG. 1B. Western Blot analysis of CFTR KO mouse lungs 24 hour post-exposure of PEI/unmodified human CFTR mRNA nanoparticles. Mice were treated via nebulization (Pari Boy jet nebulizer) over the course of approximately one hour. Immunoprecipitation of human CFTR protein derived according to provided methods was performed. Mature "C" band is detected in all treated mice while unobserved in control mice.

CFTR expression was detected by immunoprecipitation-Western blot analysis of CFTR mRNA-treated mouse lungs. Mature "C" band was detected in left and right lungs of all treated mice while unobserved in control mice (FIG. 1B). Antibodies used were MAB25031 (R&D Systems) for immunoprecipitation and SAB4501942 (Sigma) for detection via Western blot analysis.

The results shown here indicate that a CFTR protein can be successfully expressed in vivo based on lung delivery of mRNA. Furthermore, the fact that CFTR mRNA has been successfully delivered to the lung of CFTR knock out mice and resulted in effective protein production in the lung indicates that CFTR mRNA based in vivo protein production may be used to treat the CFTR protein deficiency.

Example 4: Lung Delivery of CFTR mRNA Using Polymeric Nanoparticles

The delivery of human CFTR messenger RNA to the lungs of a mouse can be accomplished via either direct inhillation as well as nebulization. Using in situ hybridization methods, one can successful detect human CFTR mRNA after intratracheal administration of human CFTR mRNA-loaded nanoparticles to mice. Administration may be accomplished employing lipid-based nanoparticles (eg. C12-200) as well as polymeric nanoparticles (eg. Polyethyleneimine, PEI).

Administration of CFTR mRNA Using Polymeric Nanocarriers.

Figure 6:
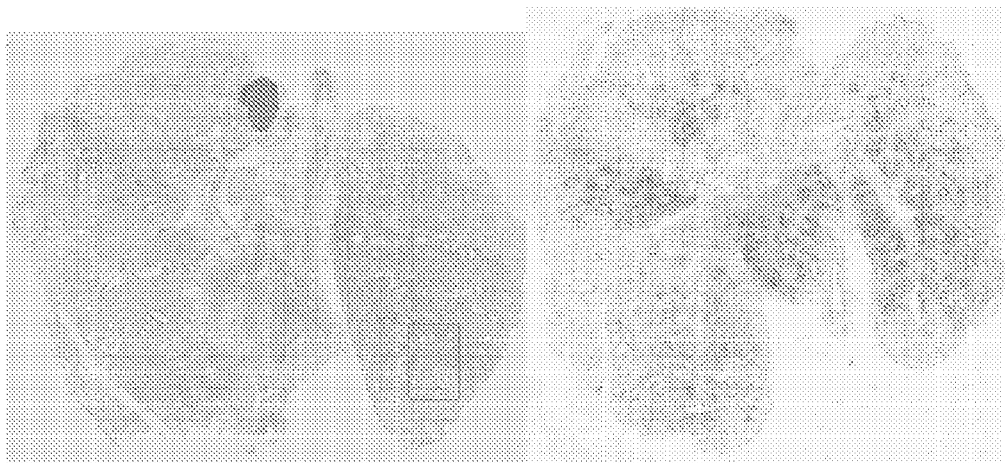
FIG. 6. In situ hybridization of human CFTR mRNA in untreated (PBS) (left) and treated (right) CFTR KO mouse lungs. Mice were exposed to 30 ug of encapsulated unmodified hCFTR mRNA in PEI nanoparticles via intratracheal administration. Substantial positive staining is observed throughout both lungs at 24 hours post-administration.

CFTR KO mice were treated with polyethyleneimine (PEI)-based CFTR mRNA loaded nanoparticles via intratracheal administration (30 ug encapsulated mRNA). The treated mice were sacrificed six hours and twenty-four hours post-administration and the lungs were harvested and fixed in 10% neutral buffered formalin (NBF). In situ hybridization was employed for detection of the exogenous human CFTR mRNA (FIG. 6). Substantial staining was observed 24 hours post-administration with widespread distribution in both mouse lungs of the treated CFTR KO mice while no staining was observed for PBS-treated control mice.

Figure 7:
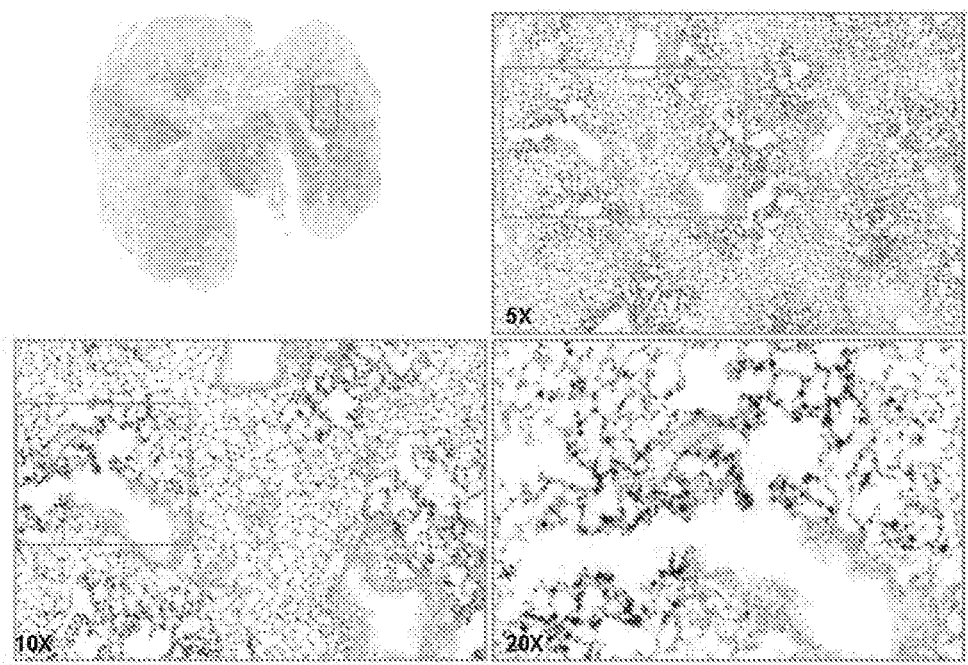
FIG. 7. In situ hybridization of human CFTR mRNA treated CFTR KO mouse lungs at different magnification views (up to 20× magnification). Mice were exposed to 30 ug of encapsulated unmodified hCFTR mRNA in PEI nanoparticles via intratracheal administration.
Figure 8:
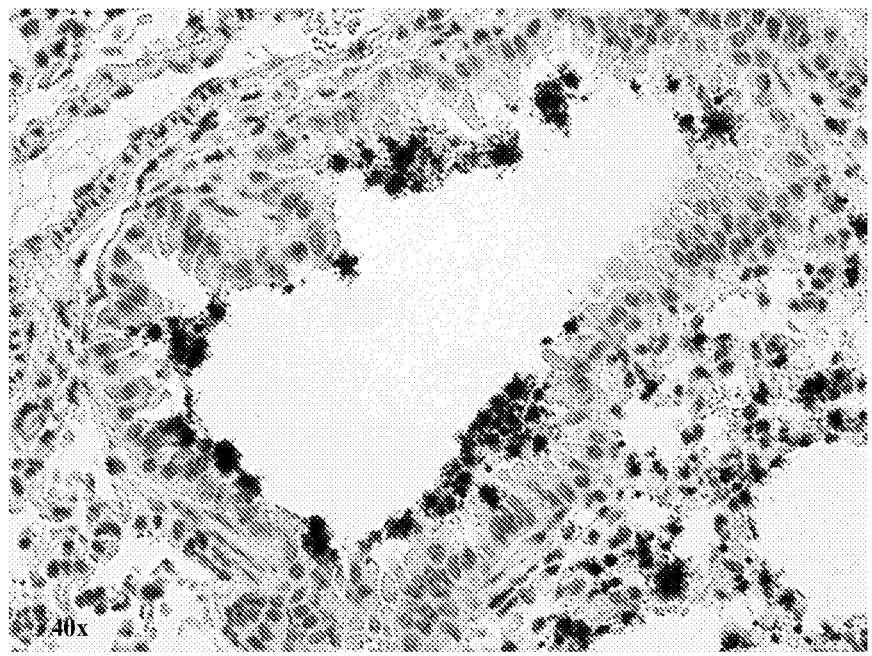
FIG. 8. High magnification (40×) representative lung section demonstrating in situ hybridization of human CFTR mRNA treated (right) CFTR KO mouse lungs. Human CFTR mRNA was detected in the apical cytoplasm of target bronchial epithelial cells 24 hours post administration. Mice were exposed to 30 ug of encapsulated unmodified hCFTR mRNA in PEI nanoparticles via intratracheal administration.
Figure 9:
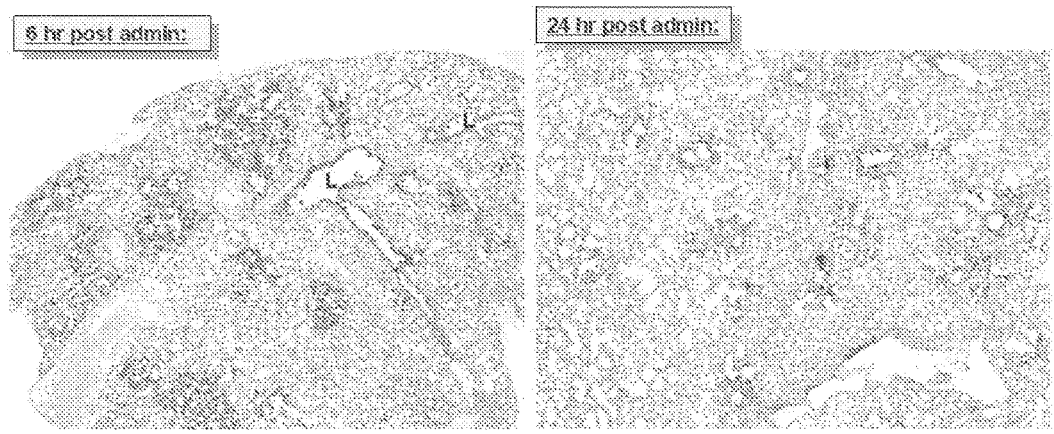
FIG. 9. Comparison of in situ hybridization staining of human CFTR mRNA treated CFTR KO mouse lungs at six hours (left) and 24 hours (right) post-administration. Mice were exposed to 30 ug of encapsulated unmodified hCFTR mRNA in PEI nanoparticles via intratracheal administration. Intense positive intracellular staining is observed within six hours throughout both lungs within bronchial and alveolar regions while substantial positive staining is still observed at 24 hours post-administration.

Analysis of the treated lungs at higher magnifications (up to 20× magnification) revealed extensive positive intracellular staining throughout the bronchial and alveolar regions of both lungs (FIG. 7). Upon further magnification (40×), positive staining within the cytoplasm of target apical bronchial epithelial cells was observed (FIG. 8). Thus, one can conclude that the messenger RNA API was successfully delivered to the target apical bronchial epithelial cells. Further, while substantial staining can be observed at 6 hours post-administration, significant positive detection of hCFTR mRNA was still observed after 24 hours (FIG. 9).

Substantial positive intracellular staining was observed throughout both lungs within bronchial and alveolar regions at 24 hours post-administration.

Example 5: Lung Delivery of CFTR mRNA Using Lipid-Based Nanoparticles

Administration of CFTR mRNA Using Lipid-Based Nanocarriers.

As mentioned above, successful lung delivery of human CFTR mRNA can be accomplished via lipid nanoparticle based delivery vehicles. Disclosed here are examples of hCFTR mRNA-loaded cationic lipid nanoparticles utilizing C12-200 as the cationic lipid component.

Figure 10:
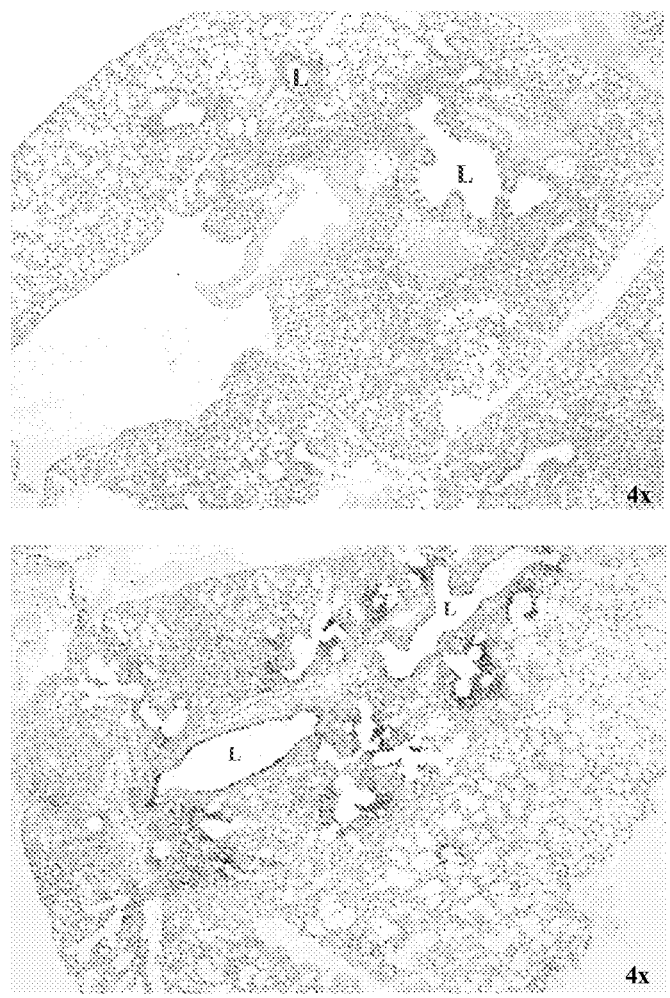
FIG. 10. In situ hybridization of human CFTR mRNA in untreated (PBS) (top) and treated (bottom) CFTR KO mouse lungs. Mice were exposed to 15 ug of encapsulated unmodified hCFTR mRNA in C12-200 lipid nanoparticles via intratracheal administration. Substantial positive staining is observed throughout both lungs at 6 hours post-administration.

Successful detection of human CFTR mRNA within the lungs of CFTR KO mice was achieved via in situ hybridization. Knockout mice were treated with 15 ug of hCFTR mRNA encapsulated in C12-200-based lipid nanoparticles and sacrificed 6 hours post-administration. Positive detection of hCFTR mRNA was observed throughout the bronchial and alveolar regions of both lungs when compared to PBS-treated control mice (FIG. 10).

Figure 11:
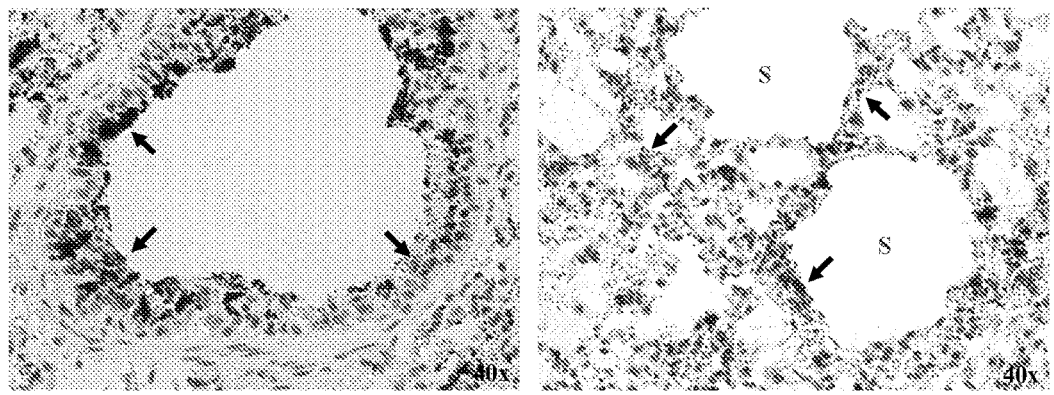
FIG. 11. High magnification (40×) representative lung sections demonstrating in situ hybridization of human CFTR mRNA treated CFTR KO mouse lungs. Human CFTR mRNA was detected in the apical cytoplasm of target bronchial epithelial (left) as well as intracellular alveolar regions (right) six hours post administration. Mice were exposed to 15 ug of encapsulated unmodified hCFTR mRNA in C12-200 lipid nanoparticles via intratracheal administration.

Upon further magnification (40×), positive detection of human CFTR mRNA was observed within the apical cytoplasm of bronchial epithelial cells and well as intracellular terminal alveolar regions (FIG. 11).

In total, successful delivery of synthetic human CFTR messenger RNA can be achieved utilizing both polymeric (PEI) and lipid nanoparticle-based (C12-200) delivery systems. These systems afforded intracellular accumulation of the drug substance within the target cells of the mice. Further, substantial amounts of hCFTR mRNA were present in these target cells 24 hours post-administration.

Example 6: Validation of Human CFTR Expression Using Specific Antibody

Antibody Validation for Human CFTR Protein Detection in Mouse, Pig, and Cultured Cells.

Experiments were performed to identify an antibody which is specific for the hCFTR protein, which does not cross-react with the mouse and swine analogue and which is available in sufficient supply for future experiments. Briefly, testing of various anti-hCFTR antibodies from academic and commercial sources led to identification of a combination of anti-hCFTR antibodies which were capable of detecting human CFTR protein after immunoprecipitation and Western blotting (IP/WB) without cross-reactivity for either murine or porcine CFTR. Thus, suitable anti-hCFTR antibodies for detection of hCFTR protein without cross-reactivity for either murine or porcine CFTR were identified based on IP/WB results.

Cells were transfected with hCFTR mRNA and protein lysates were prepared using ProteoExtract Transmembrane Kit (Merck) at 24 hrs post transfection and transmembrane fraction was screened by Western blotting for hCFTR using mouse anti-human CFTR antibody (MA1-935). Lysates from 16HBE cells were used as positive control. FIG. 12A presents the data from CHO and COS-7 cells.

Baby Hamster Kidney cells (BHK), described as CFTR-negative in the literature, were transfected similar to CHO and COS-7 cells and protein lysates screened by Western blot. In contrast to the previously published reports, a clear positive signal for CFTR could be observed using the mouse monoclonal anti-CFTR antibody (FIG. 12B). To test the specificity of antibody used in Western blot analysis, Pig Kidney Cells from CFTR-knockout pig (PKC), kindly provided by Prof. Eckhardt Wolf (Ludwig Maximilians University, Munich), were used in transfection experiments and protein lysates screened for CFTR expression. As was evident in FIG. 12B, no signal for CFTR could be detected in PKC cells. However, transfection did not result in any detectable hCFTR expression either. Using luciferase as a control for transfection, PKC cells were found to express luciferase several fold less efficient when compared to CHO or COS-7 cells. As no significant difference in the intensity of hCFTR band could be detected in any of the screened cell lines post transfection, extensive screening for other hCFTR antibodies with higher sensitivities and specificity towards hCFTR was performed.

Antibody Screening Via Western Blots.

Protein lysates were prepared from human bronchial epithelial cell line (BEAS-2B), human embryonic kidney cell line (HEK), mouse lungs and pig lungs using Proteo-Extract Transmembrane Kit (Merck) and transmembrane fraction used for immunoblotting using different primary antibodies (MA1-935 from Thermo Scientific Pierce Antibodies, Rockford, Ill., USA, AB596 from the Cystic Fibrosis Consortium, University of Pennsylvania, PA, USA, and AB570 from the Cystic Fibrosis Consortium, University of Pennsylvania, PA, USA). The data are summarized as FIGS. 13A-13D.

Whereas MA1-935 detected CFTR in all the three species, AB596 detects human and murine CFTR but not porcine and antibody G449 detects only human CFTR specifically. With AB570, it was not clear if the slightly low molecular weight bands observed with murine and porcine samples are indeed CFTR or non-specific products. In subsequent experiments (data not shown), it was found that MA1-935 recognizes a band which is not CFTR. Therefore, in general, MA1-935 results were considered as confirming results generated using other antibodies, but experiments in which the only anti-CFTR antibody used was MA1-935 were not considered conclusive.

Immunoprecipitation of hCFTR (IP-hCFTR) from Tissue Samples.

Given that all the screened antibodies produced several non-specific bands and none of them produced the characteristic banding pattern of hCFTR (C-band representing the fully glycosylated protein and B-band representing the core mannosylated form), immunoprecipitation (IP) of hCFTR and subsequent detection by Western blot was established to increase the sensitivity and specificity of detection thereby increasing the signal to noise ratio.

Initial IP experiments were performed in collaboration with Prof. Burkhard Tümmler (Medizinsche Hochschule Hannover) using protocols and antibodies published by van Barneveld et al. 2012, Immunochemical analysis of Mutant CFTR in Lung explants, *Cell Physiol. Biochem.* 30, 587-595 (2012)). Human colon carcinoma cells (T84) which overexpress hCFTR were used as positive controls for IP experiments.

Figure 14:
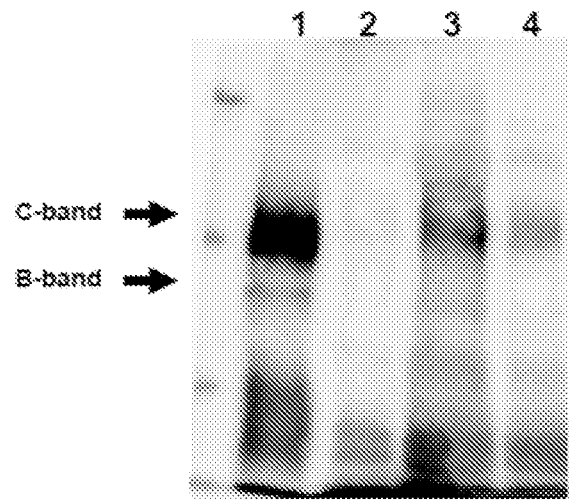
FIG. 14. Immunoprecipitation of human CFTR using three different antibodies (R29, R66/17 and R66/16) followed by immunodetection using AB596. Lane 1: T84 cells (positive control), Lane 2: untreated pig lung tissue (300 mg), Lane 3: treated pig lung tissue (697 mg), Lane 4: treated pig lung tissue (163 mg).

Immunoprecipitation of hCFTR using three different antibodies (R29, R66/17 and R66/16) followed by immunodetection with AB596 resulted in specific detection of hCFTR in protein lysates from lungs of pigs treated with an aerosol of hCFTR SNIM RNA as described in Example 8 below (FIG. 14).

HGT5001 Formulation.

Figure 15:
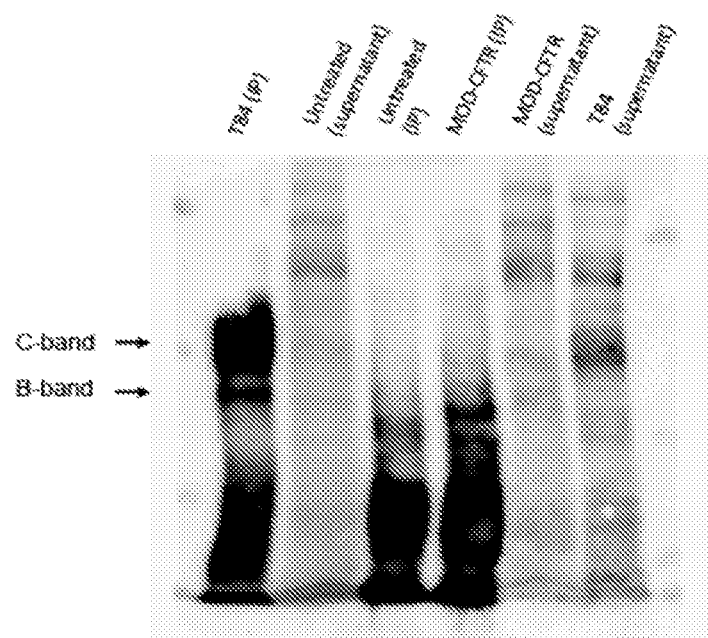
FIG. 15. Immunoprecipitation and Western blotting of a mouse at 24 hrs post IT spray application of 20 μg hCFTR SNIM RNA/10 μg FFL SNIM RNA each in the HGT5001 Formulation of Example 6. T84 cells served a positive control showing the mature glycosylated C-band and the mannosylated B-band of hCFTR. "supernatant" remaining cellular extract fraction without immunoprecipitated fraction. "IP" immunoprecipitated fraction.

Aerosol experiments using hCFTR SNIM RNA in a formulation of HGT5001:DOPE; Chol; PEGDMG2K (relative amounts 50:25:20:5 (mg:mg:mg:mg)) ("HGT5001 Formulation") were performed in mice and protein lysates from the isolated lungs at 24 hrs post mRNA delivery were also analysed by IP using the same antibodies and conditions as for the pig lysates. However, no characteristic mature CFTR banding pattern could be detected for mouse samples (FIG. 15).

Immunoprecipitation of hCFTR (IP-hCFTR) from In Vitro-Transfected Cells.

Initial IP results using tissue material from pigs provided the evidence for the technical feasibility of hCFTR detection post transcript delivery in vivo. However, as none of the antibodies used in immunoprecipitating CFTR (R29, R66/17 and R66/16) are commercially available, other commercially available antibodies were screened for their efficacy in IP reactions. Two antibodies from R&D systems (MAB25031 and MAB1660) were tested.

Figure 16:
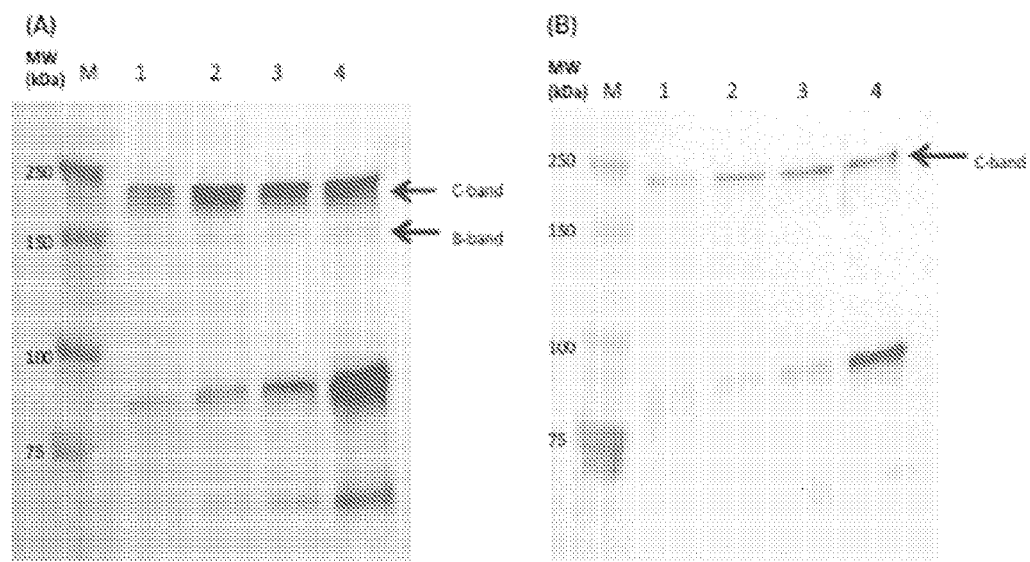
FIGS. 16A-16B. Immunoprecipitation of hCFTR from T84 cells using MAB25031 followed by immunodetection using AB570 (16A) and MAB1660 (16B).

Protein lysates were prepared from T84 cells and 500 µg of total protein was used in the IP reaction using different concentrations of MAB25031 antibody. The amount of hCFTR protein immunoprecipitated was then detected by immunobloting using AB570 (Cystic Fibrosis Foundation). AB596 under these conditions resulted in much higher background and so was not tested further. As revealed in FIG. 16A, there was no further increase in the amount of CFTR protein precipitated when the concentration of IP antibody was increased from 2 µg/ml to 4 µg/ml. Both the fully glycosylated and only core glycosylated forms (C- and B-band, respectively) were detected. The same immunoprecipitates were also screened using MAB1660 as primary antibody in western blot. With this antibody however, only band-C was visible (FIG. 16B).

Figure 17:
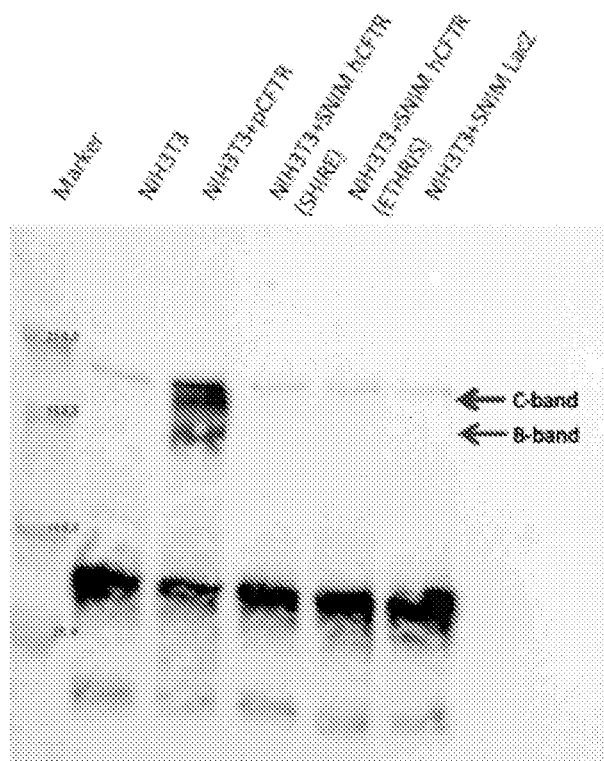
FIG. 17. Immunoprecipitation of CFTR from NIH3T3 cells at 72 hrs post transfection with different constructs.

After the successful detection of endogenous hCFTR from T84 immunoprecipitates using MAB25031 antibody, experiments were performed in NIH3T3 cells with the aim to detect hCFTR protein post transfection. NIH3T3 cells were transfected with hCFTR SNIM RNA. Protein lysates were prepared at 72 hrs post transfection and protein amounts quantified using BCA method. Human CFTR protein was immunoprecipitated from 500 µg of total protein lysate using MAB25031 antibody at 2 µg/ml followed by immunoblotting using AB570 (FIG. 17). However, no CFTR could be detected. Cells transfected with LacZ encoding mRNA were analysed as control samples for the effect of transfection per se on amount of CFTR protein.

Figure 18:
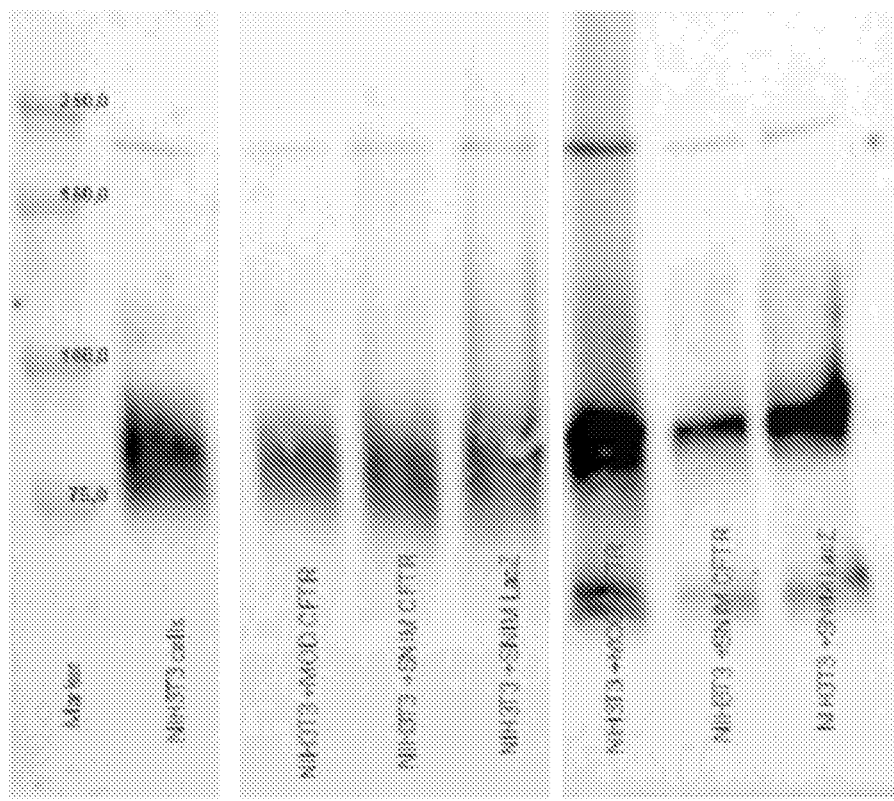
FIG. 18. Immunoprecipitation of CFTR from NIH3T3 cells at 72 hrs post transfection with different constructs using 500 ug protein and MAB1660 (left and center panels) and increased amount of total protein (8 mg) using MAB25031 (right panel).

Increasing the amount of total protein used in immunoprecipitation from 500 µg to 8 mg did not result in any detectable hCFTR protein post immunodetection with AB570. Another hCFTR specific antibody, MAB1660 (R&D Systems), was also screened for immunoprecipitation (FIG. 18). However, this antibody does not precipitate CFTR as effectively as MAB25031. Therefore all future immunoprecipitations were performed with MAB25031.

Lack of hCFTR detection in mRNA transfected samples may not necessarily mean lack of functionality of the tested mRNAs as kinetic experiments using luciferase as marker gene have shown that maximum expression with mRNA is observed at 24 hrs post transfection. Lack of hCFTR detection is rather due to insufficient hCFTR concentration in the tested samples or lack of specificity of the applied antibodies.

PEI Formulation.

Figure 19:
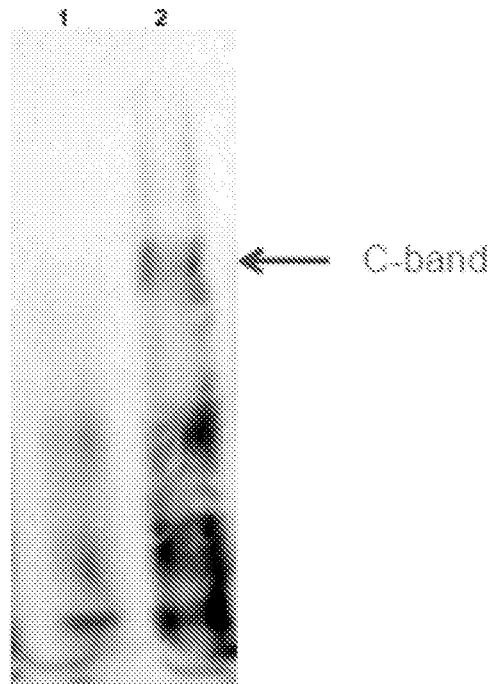
FIG. 19. Immunoprecipitation of hCFTR using MAB25031 and subsequent immunodetection using AB570 from pig lung samples post hCFTR SNIM RNA delivery in the PEI Formulation of Example 6. Lane 1: sample from luciferase-negative left caudal lobe of pig #2, Lane 2: sample from luciferase-positive lung regions of pig #1.

The established conditions were tested for their feasibility to detect hCFTR after hCFTR SNIM RNA in delivery to pigs (see Example 7) of a nanoparticle formulation with 25 kDa branched PEI ("PEI Formulation") prepared as follows. The required amount of SNIM RNA was diluted just before application in water for injection (Braun, Melsungen) to a total volume of 4 ml and added quickly to 4 ml of an aqueous solution of branched PEI 25 kDa using a pipette at an N/P ratio of 10. The solution was mixed by pipetting up and down ten times and nebulized as two separate 4.0 ml fractions one after another to the pig lungs using the indicated nebulizer. One sample from the luciferase expressing lung areas from pig #1 and another from the caudal lobe of pig #2, where no luciferase activity could be detected, thus indicating lack of mRNA delivery and/or expression, were selected as positive and negative controls. Protein lysates prepared from these samples were immunoprecipitated using MAB25031 (R&D Systems) and hCFTR protein detected using AB570. As shown in FIG. 19, luciferase expression correlated with the expression of hCFTR mRNA. Sample from the left caudal lobe from pig #2 where no luciferase activity was detectable, was also negative for hCFTR (lane 1) whereas hCFTR could be detected in samples from pig #1 which were positive for luciferase (lane 2).

Example 7: Aerosol Delivery of mRNA

Establishment of Encapsulated mRNA Aerosol Delivery to the Lungs of Pigs.

Aerosol administration of firefly luciferase (FFL) SNIM RNA to the pig lungs was established by a stepwise experimental procedure. In a first step FFL SNIM RNA formulations were nebulized to anaesthetized pigs during controlled ventilation. In a second step lungs were excised immediately after aerosol administration was completed and lung specimens were incubated in cell culture medium overnight before ex vivo luciferase measurement was performed on lung specimens by BLI.

Pigs of the German Landrace were obtained from Technical University Munich, Weihenstephan, Germany. The pigs had a body weight ranging from 35-90 kg. Each treatment was performed on one pig. In total five pigs were treated. The first pig (90 kg weight) was treated with FFL SNIM RNA in the PEI Formulation of Example 6 using an EFlow mesh nebulizer and measurement of luciferase activity in lung homogenates. The second pig (60 kg weight) was treated with FFL SNIM RNA in the PEI Formulation of Example 6 using an EFlow mesh nebulizer and measurement of luciferase activity in lung specimens by BLI. The third pig (80 kg weight) was treated with FFL SNIM RNA in the PEI Formulation of Example 6 using a PARI BOY jet nebulizer and measurement of luciferase activity in lung specimens by BLI. The fourth pig (60 kg weight) was treated with FFL SNIM RNA/hCFTR mRNA in the PEI Formulation of Example 6 using an Aeroneb mesh nebulizer and measurement of luciferase activity in lung specimens by BLI. The fifth pig (35 kg weight) was treated with FFL SNIM RNA in the HGT5001 Formulation of Example 6 using an Aeroneb mesh nebulizer and measurement of luciferase activity in lung specimens by BLI.

Sedation in pigs was initiated by premedication with azaperone 2 mg/kg body weight, ketamine 15 mg/kg body weight, atropine 0.1 mg/kg body weight and followed by insertion of an intravenous line to the lateral auricular vein. Pigs were anesthetized by intravenous injection of propofol 3-5 mg/kg body weight as required. Anesthesia was maintained by isoflurane (2-3%) with 1% propofol bolus injection at 4 to 8 mg/kg body weight to enhance anesthesia as required. Duration of the anesthesia was approximately 1-3 hrs. Pigs were killed with bolus injection of pentobarbital (100 mg/kg body weight) and potassium chloride via the lateral ear vein. Lungs were excised and tissue specimens were collected from various lung regions followed by incubation in cell culture medium overnight. For measurement of luciferase activity tissue specimens were either homogenized and analyzed in a tube luminometer or incubated in a medium bath comprising D-Luciferin substrate and subjected to ex vivo luciferase BLI.

Details and Results for Pig #1.

Figure 20:
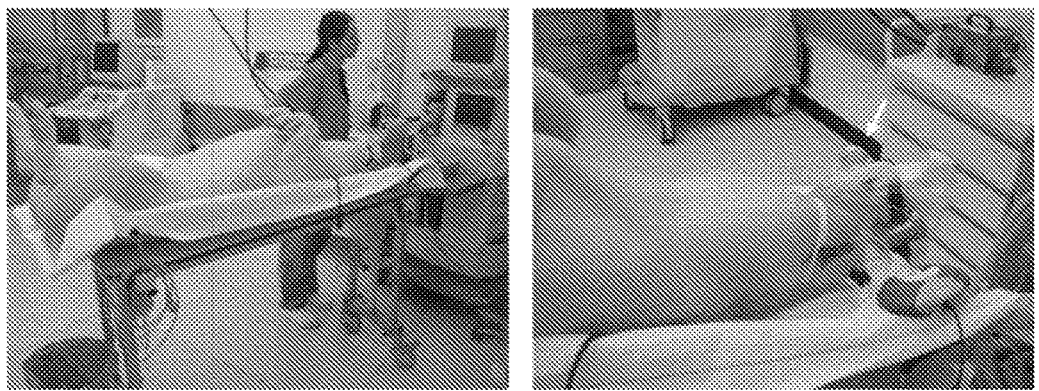
FIG. 20. Nebulisation was performed on anesthetized and ventilated pigs (left). The nebulizer was connected in-line to the ventilation system (right, see white arrow).
Figure 21:
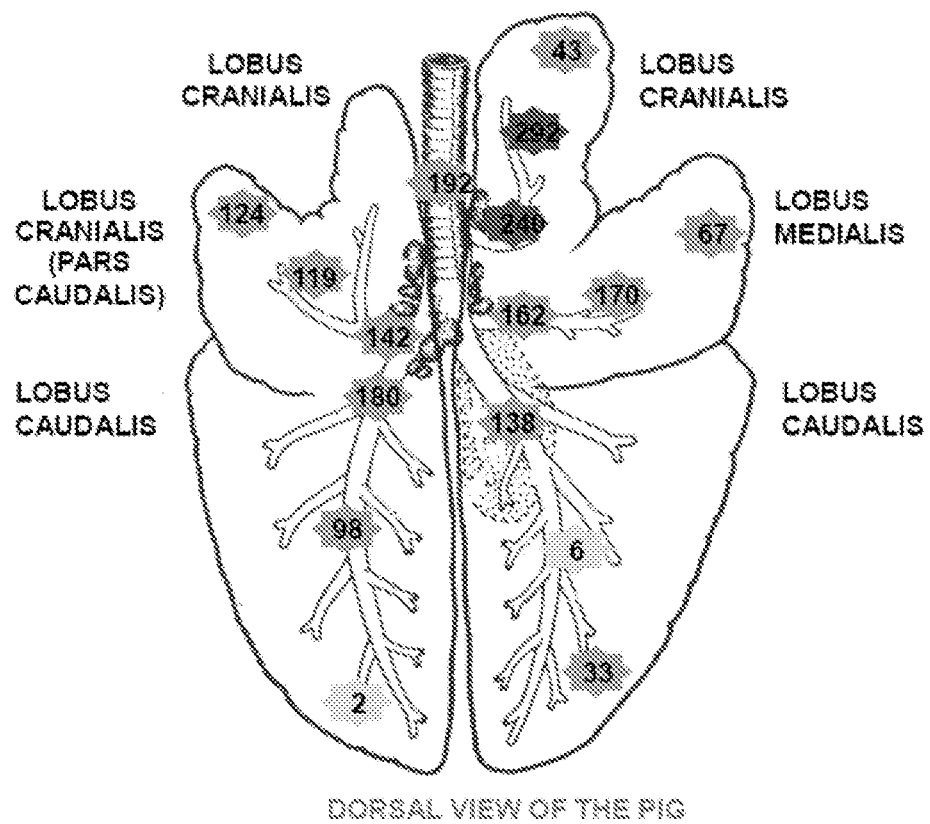
FIG. 21. Luciferase expression measured in homogenates of pig tissue specimens from different lung regions after aerosol administration of 1 mg FFL SNIM RNA in the PEI Formulation of Example 6 with the EFlow mesh nebulizer. Lung specimens were ex vivo cultured overnight before luciferase measurements (pg luciferase/mg lung tissue).

The experimental set up is illustrated in FIG. 20. For aerosol administration an EFlow mesh nebulizer was connected in-line to the ventilation tubing of the respirator. Aerosol administration took approximately 60 min and was longer than expected from control experiments with an open system. This was apparently caused by increased back pressure during nebulisation as evidenced by aerosol outflow at the reservoir of the mesh nebulizer. Eight milliliters of the PEI Formulation of Example 6 comprising 1 mg FFL SNIM RNA in water for injection were prepared as described in WP5 and were nebulized in two separate 4 ml portions one after another. Luciferase measurement was performed in tissue homogenates of excised lung specimens of various lung regions after overnight incubation in cell culture medium. Expression values were mapped according to the origin of the lung specimens (FIG. 21).

The results showed successful luciferase expression in pig lung tissue. Luciferase expression was highest in central parts of the lung and declined towards more distal regions of the lung. The expression pattern correlated with the expected deposition pattern of the inhaled FFL SNIM RNA-PEI nanoparticles according to the chosen ventilation parameters. Levels of luciferase expression were in the same range as observed in mouse experiments in WP5 using the same the PEI Formulation of Example 6.

Details and Results for Pig #2.

Figure 22:
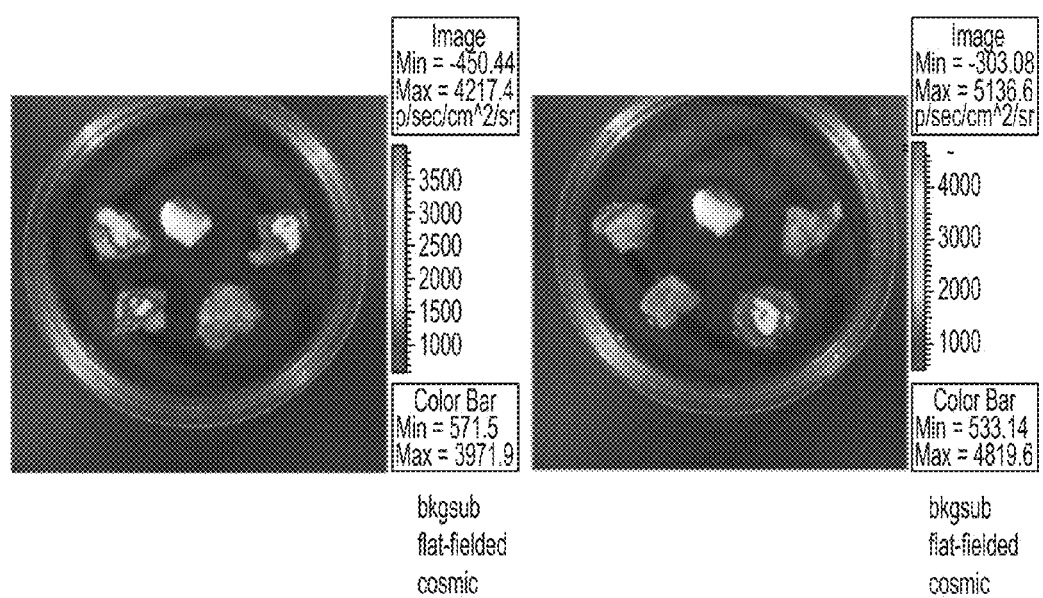
FIG. 22. BLI of luciferase expression in representative pig tissue specimens from different lung regions after aerosol administration of 1 mg FFL SNIM RNA in the PEI Formulation of Example 6. Lung specimens were ex vivo cultured overnight before measurements.

Aerosol administration of FFL SNIM RNA in the PEI Formulation of Example 6 in pig #2 was performed as in pig #1 but luciferase activity was measured on lung specimens by bioluminescent imaging (BLI). This experiment was performed to establish ex vivo luciferase measurement of organ cultured lung specimens by BLI. Luciferase measurement was clearly observed in individual tissue specimens of different lung regions of the treated pig (FIG. 22). The experiment confirmed results obtained from pig #1.

Details and Results for Pig #3.

Figure 23:
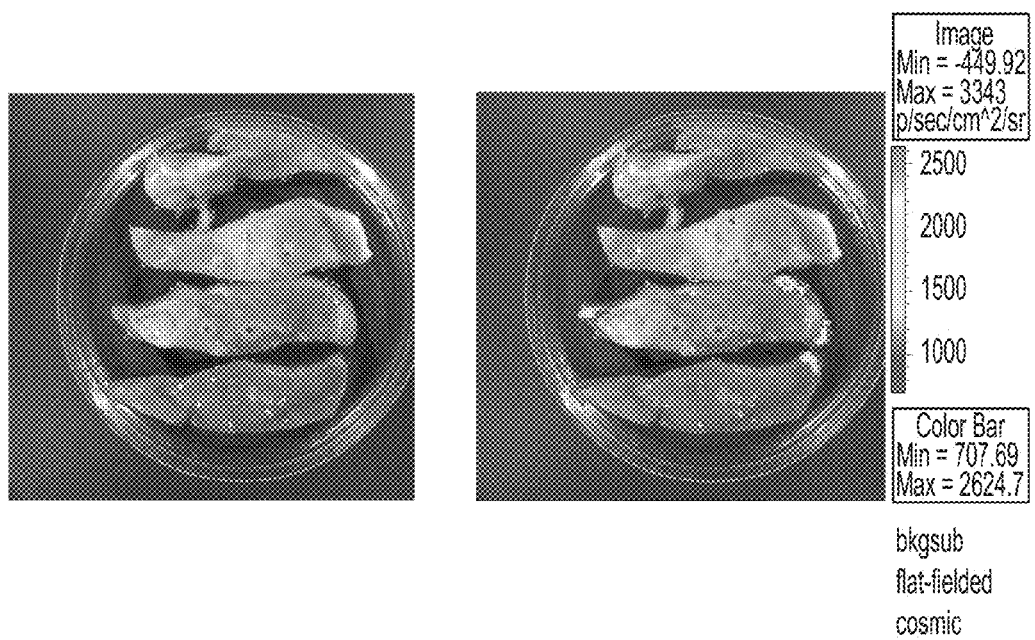
FIG. 23. BLI imaging of luciferase expression in representative pig tissue specimens from different lung regions after aerosol administration of 1 mg FFL SNIM RNA in the PEI Formulation of Example 6 using a PARI BOY jet nebulizer. Lung specimens were ex vivo cultured overnight before measurements.

Aerosol administration in pig #1 and #2 using the EFlow mesh nebulizer revealed some technical difficulties and inadequate nebulisation time. Therefore, pig #3 was treated using the PARI BOY jet nebulizer which was connected to the ventilation tubing via a T-connector. Aerosol administration lasted longer (approximately 80 min) than with the EFlow mesh nebulizer and aerosol administration was non-satisfying. Very low luciferase activity was detected in sliced lung samples from different lung regions of the treated pig (FIG. 23).

Details and Results for Pig #4.

Figure 24:
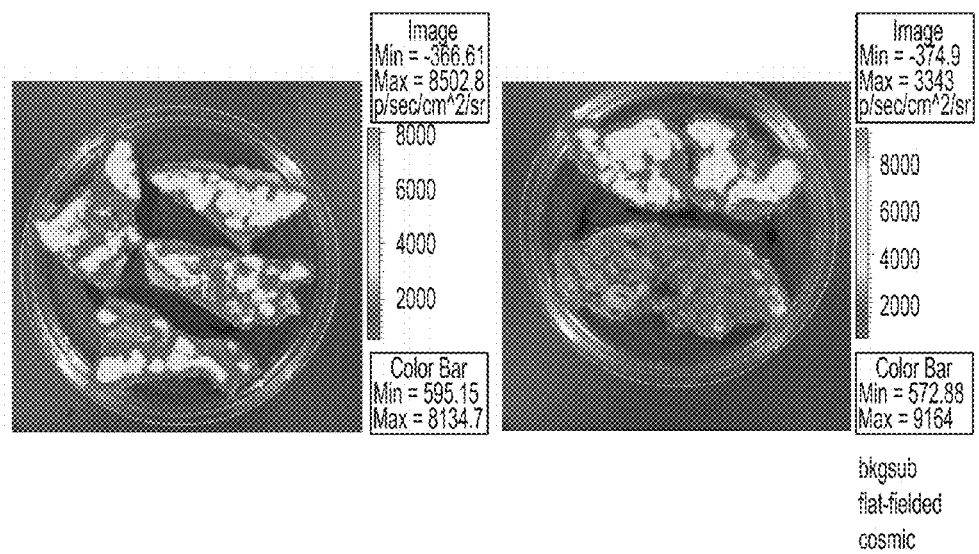
FIG. 24. BLI of luciferase expression in representative pig tissue specimens from different lung regions after aerosol administration of each 1 mg FFL SNIM RNA and hCFTR mRNA in the PEI Formulation of Example 6 using an Aeroneb mesh nebulizer. Lung specimens were ex vivo cultured overnight before measurements.

The results of the previous experiments demonstrated that a mesh nebulizer is more suitable for aerosol administration to the lungs of pigs in the chosen set up than a jet nebulizer. For this reason, another mesh nebulizer was tested for this purpose which satisfactorily nebulized the PEI Formulation of Example 6 when tested in an open system. Pig #4 was treated using the Aeroneb mesh nebulizer which was connected in-line to the tubing of the respirator. In this experiment, 1 mg of hCFTR mRNA was co-delivered together with 1 mg of FFL SNIM RNA in the PEI Formulation of Example 6. This was done to test formulation stability and nebulisability of co-formulated FFL SNIM RNA/hCFTR mRNA-PEI nanoparticles with respect to repeated dosing in to be performed in Example 8. The formulation was stable and did not reveal incompatibility with nebulisation. Luciferase activity was clearly observed in individual tissue specimens of different lung regions of the treated pig (FIG. 24).

The experiment confirmed results obtained from pig #1 and pig #2, although higher expression levels were obtained. The experiment showed that the Aeroneb mesh nebulizer was best suited for delivery of the PEI Formulation of Example 6 to the lungs of pigs. Moreover, the experiment demonstrated FFL SNIM RNA was still active when co-delivered together with hCFTR mRNA.

Details and Results for Pig #5.

Figure 25:
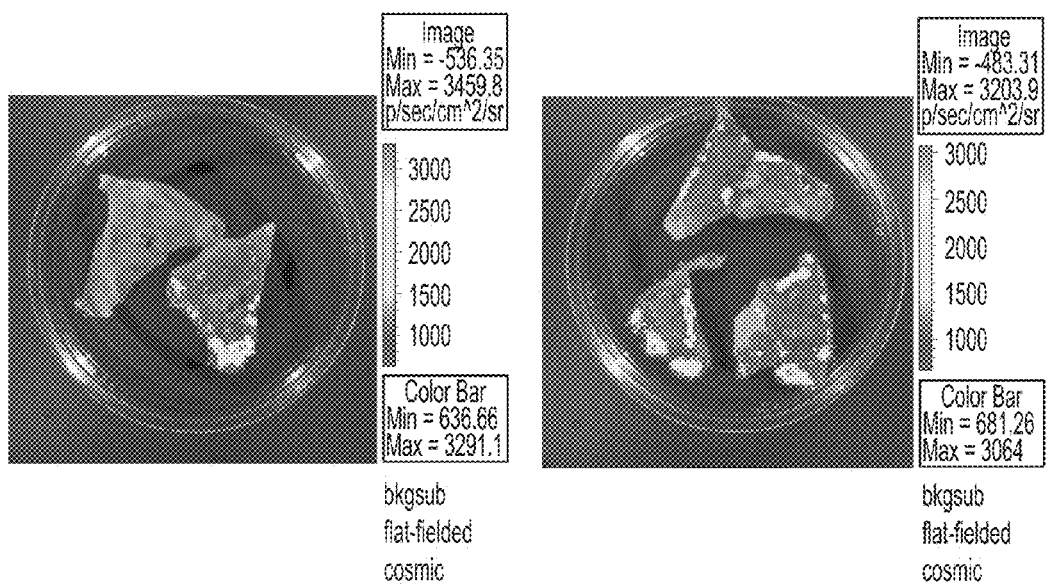
FIG. 25. BLI of luciferase expression in representative pig tissue specimens from different lung regions after aerosol administration of 1 mg FFL SNIM RNA in "SHIRE Formulation #3" (HGT5001:DOPE:Chol:DMGPEG2K (50:25:20:5) (mol ratio) using an Aeroneb mesh nebulizer. Lung specimens were ex vivo cultured overnight before measurements.

Pig #5 was treated with 1 mg of FFL SNIM RNA in the HGT5001 Formulation of Example 6 aerosolized with the Aeroneb mesh nebulizer. The formulation could be aerosolized without technical difficulties. Luciferase activity was clearly observed in individual tissue specimens of different lung regions of the treated pig (FIG. 25).

The experiment showed that aerosolized FFL SNIM RNA in the HGT5001 Formulation of Example 6 is active in pig lung tissue, although expression levels were approximately 15-20-fold lower than in pigs treated with the PEI Formulation of Example 6.

Conclusion.

Successful results were obtained using the Aeroneb mesh nebulizer with the PEI Formulation of Example 6. Four pigs were treated with the PEI Formulation of Example 6 to identify the optimal experimental setup for aerosol delivery. The results demonstrated that luciferase expression could be detected in pig lung homogenates and by BLI. Luciferase expression was highest in central parts of the lungs and hardly seen in the distal areas of the lungs. The Aeroneb mesh nebulizer was found to give the best results together with the shortest delivery time. According to these experiments another pig was treated with FFL SNIM RNA encapsulated in the HGT5001 Formulation of Example 6. Although luciferase expression was clearly observed in some parts of the pig lungs, expression levels were lower than for FFL SNIM RNA in the PEI Formulation of Example 6. The results from this work package clearly demonstrated that SNIM RNA delivery to the lungs of pigs as a large preclinical animal model was feasible using various formulations such as polymer (e.g., PEI) based Formulation and lipid (e.g., HGT5001) based formulations. The results of this example provided proof of concept for successful SNIM RNA delivery to the lungs of a large animal which closely mimics the situation in human patients by nebulizer used in clinical practice.

Example 8: In Vivo mRNA Delivery (Weekly Dose)

A trial was performed to evaluate practicability of an aerosol application once a week in pigs. Practicability was defined as performing three aerosol applications of modified mRNA in intervals of one week without induction of lung disease (absence of adverse events higher than grade 2). Additional objectives were to evaluate i) grade of distress of the animals, ii) adverse events occurring during laboratory or clinical assessment of the pigs, and iii) measurement of the induced proteins (luciferase and hCFTR).

Repeated aerosol administration of SNIM RNA in the PEI Formulation to the lungs of pigs was established. Groups of two pigs were treated one, two, or three times at weakly intervals with FFL SNIM RNA/hCFTR SNIM RNA in the PEI Formulation of Example 6. Two untreated pigs served as controls. Lungs were excised 24 hrs after treatment and ex vivo luciferase activity was measured in isolated lung specimens by BLI. Expression of hCFTR protein was analysed using IP/WB. Immunohistochemistry (IHC) was performed for detection of luciferase expression on the cellular level. Toxicology was investigated by measurement of inflammatory cytokines in serum and blood chemistry. Histopathology was performed on lung samples. The study protocol "Pilot project: Repeated application of modified mRNA to establish an animal model for aerosol therapy of cystic fibrosis in pigs" was approved by the local authorities before the start of the experiments (Animal experiments license Nr.: 0-045-12).

Experimental Design.

Pigs, German Landrace, female approximately 6 weeks old (~25 kg body mass in average) at nebulisation, were purchased from Technical University Munich, Weihenstephan, Germany. Pigs were randomized and treated according to the scheme below (Table 3). Treatment groups of each two pigs were as follows:

Group 0—Control group without treatment

Group I—Aerosol administration of 1 mg FFL SNIM RNA and 1 mg hCFTR SNIM RNA in the PEI Formulation of Example 6 on day 1.

Group II—Aerosol administration of 2 mg hCFTR SNIM RNA in the PEI Formulation of Example 6 on day 1 and 1 mg FFL SNIM RNA and 1 mg hCFTR SNIM RNA in the PEI Formulation of Example 6 on day 8.

Group III—Aerosol administration of 2 mg hCFTR SNIM RNA (6379-186) in the PEI Formulation of Example 6 on day 1 and day 8, aerosol administration of 1 mg FFL SNIM RNA and 1 mg hCFTR SNIM RNA in the PEI Formulation of Example 6 on day 15.

The scheme for treatment and evaluation of each group is shown in Table 3. In addition to the illustrated interventions, physical examination of the pigs was done on a daily basis.

TABLE 3

Time-line diagram of different treatment groups.

(Abbreviations used:
AA Aerosol application
Bw Blood work D day
Euth. Euthanasia of the animal)
Group 0 (untreated animals):

| 1st |
| Euth. |
| |
| Bw |
| ↓ |
| d1 |

Group 1 (1 aerosol application; survival 1d):

| 1st 1st |
| Bw Bw |
| AA Euth. |
| ↓ ↓ |
| d1, d2 |

Group 2 (2 aerosol applications; survival 8d):

| 1st 1st 2nd 2nd |
| Bw Bw Bw Bw |
| AA AA Euth |
| ↓↓ ↓↓ |
| d1, d2, d3, d4, d5, d6, d7, d8, d9 |

Group 3 (3 aerosol applications; survival 15d):

| 1st 1st 2nd 2nd 3rd 3rd |
| Bw Bw Bw Bw Bw Bw |
| AA AA AA Euth |
| ↓↓↓↓↓↓ |
| d1, d2, d3, d4, d5, d6, d7, d8, d9, d10, d11, d12, d13, d14, d15, d16 |

Experimental Procedure.

Sedation in pigs was initiated by premedication with azaperone 2 mg/kg body weight, ketamine 15 mg/kg body weight, atropine 0.1 mg/kg body weight and followed by insertion of an intravenous line to the lateral auricular vein. Pigs were anesthetized by intravenous injection of propofol 3-5 mg/kg body weight as required. Anesthesia was maintained with continuous intravenous infusion of 1% propofol as required. Ventilation parameters were matched with end-expiratory carbon dioxide and adjusted if necessary. Anesthesia, respiratory and cardiovascular parameters were monitored continuously using pulse oximetry, capnography, rectal temperature probe and reflex status. Animals received infusion of balanced electrolyte solution at 10 ml/kg/h. Duration of the anesthesia was approximately 80-120 min. Pigs were extubated after onset of sufficient spontaneous breathing. Pigs were killed with bolus injection of pentobarbital 100 mg/kg of body weight via the lateral ear vein after sedation. Lungs were excised and sliced approximately 1 cm thick tissue specimens were collected from various lung regions followed by incubation in cell culture. For measurement of luciferase activity tissue specimens were incubated in a medium bath comprising D-Luciferin substrate and subjected to ex vivo luciferase BLI.

Luciferase Expression in Treatment Groups by BLI.

Figure 26:
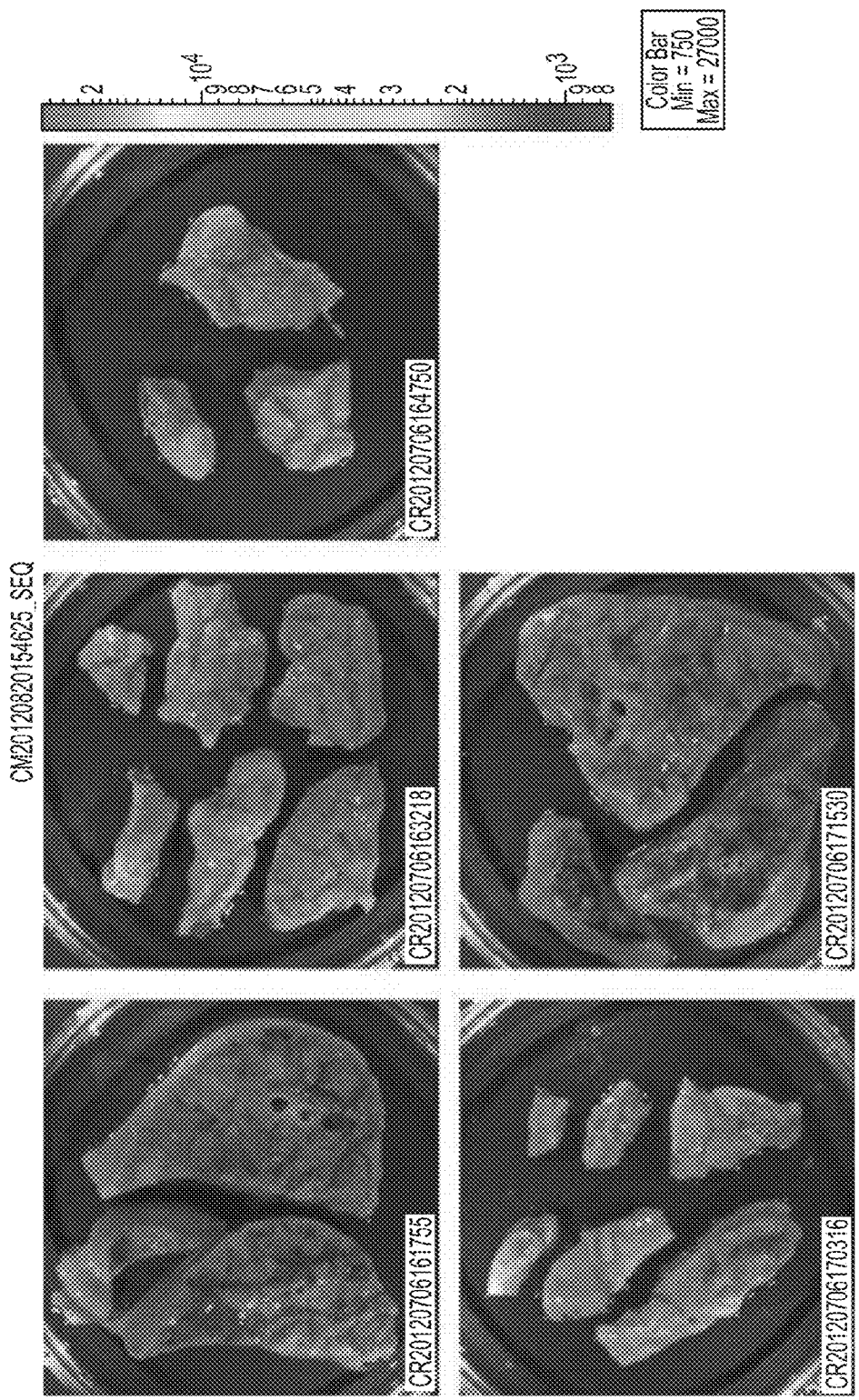
FIG. 26. BLI of luciferase expression in pig tissue specimens from different lung regions from one untreated control pig. The other untreated control pig showed the same result (data not shown).

For Group 0 (Control group without treatment), no luciferase activity was observed in lung slices (FIG. 26).

Figure 27:
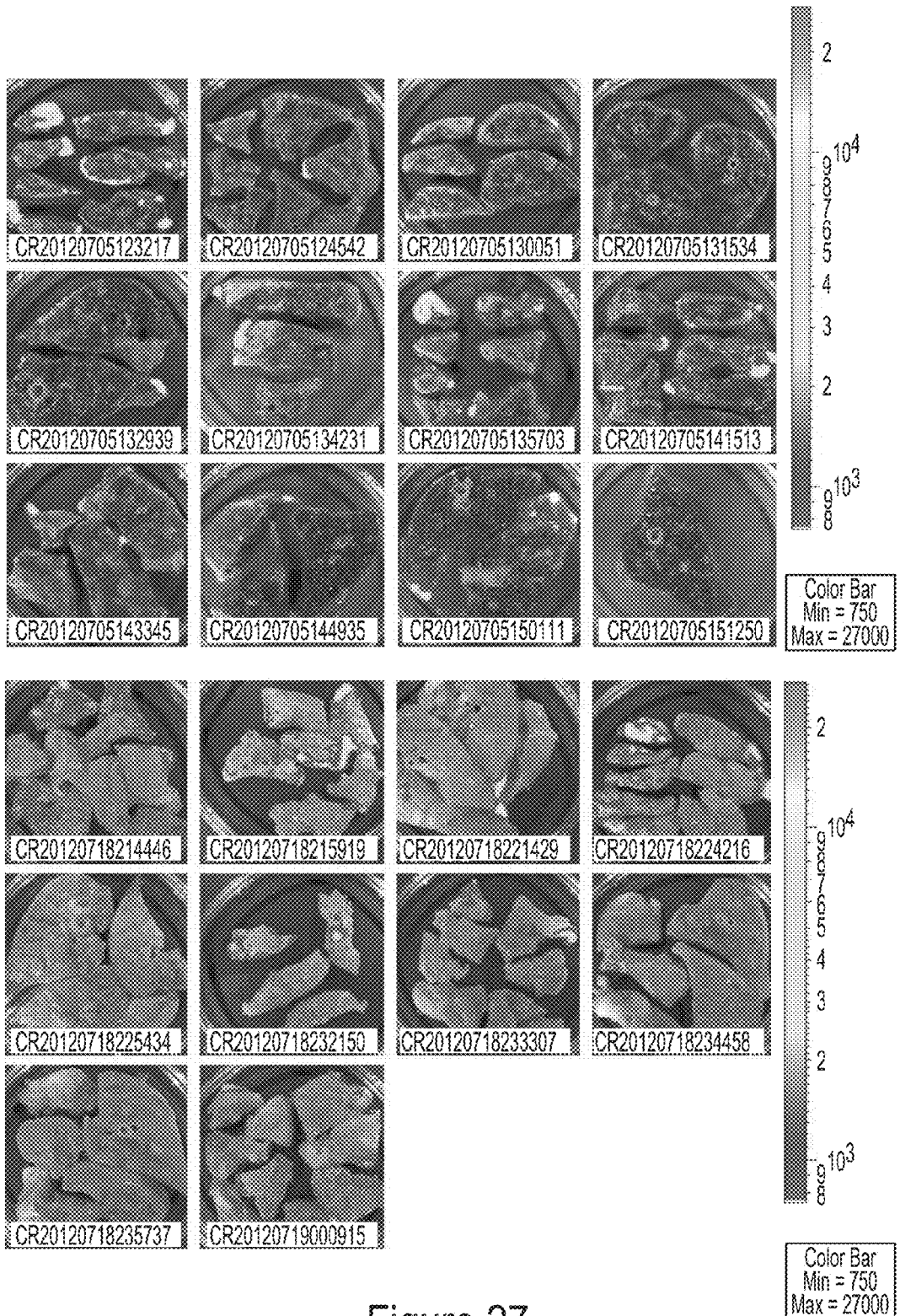
FIG. 27. BLI of luciferase expression in lung specimens of once-treated pigs #3 and #6. Aerosol administration of each 1 mg FFL SNIM RNA and hCFTR SNIM RNA in the PEI Formulation of Example 6 was performed using an Aeroneb mesh nebulizer. Slices of the entire pig lung are shown. Upper three rows: pig #3, lower three rows: pig #6.

For Group I (Aerosol administration of 1 mg FFL SNIM RNA and 1 mg hCFTR SNIM RNA in the PEI Formulation of Example 6), Luciferase activity was clearly detected in lung specimens of one time treated pigs #3 and #6 (FIG. 27). Luciferase expression was highest in central parts of the lungs.

Figure 28:
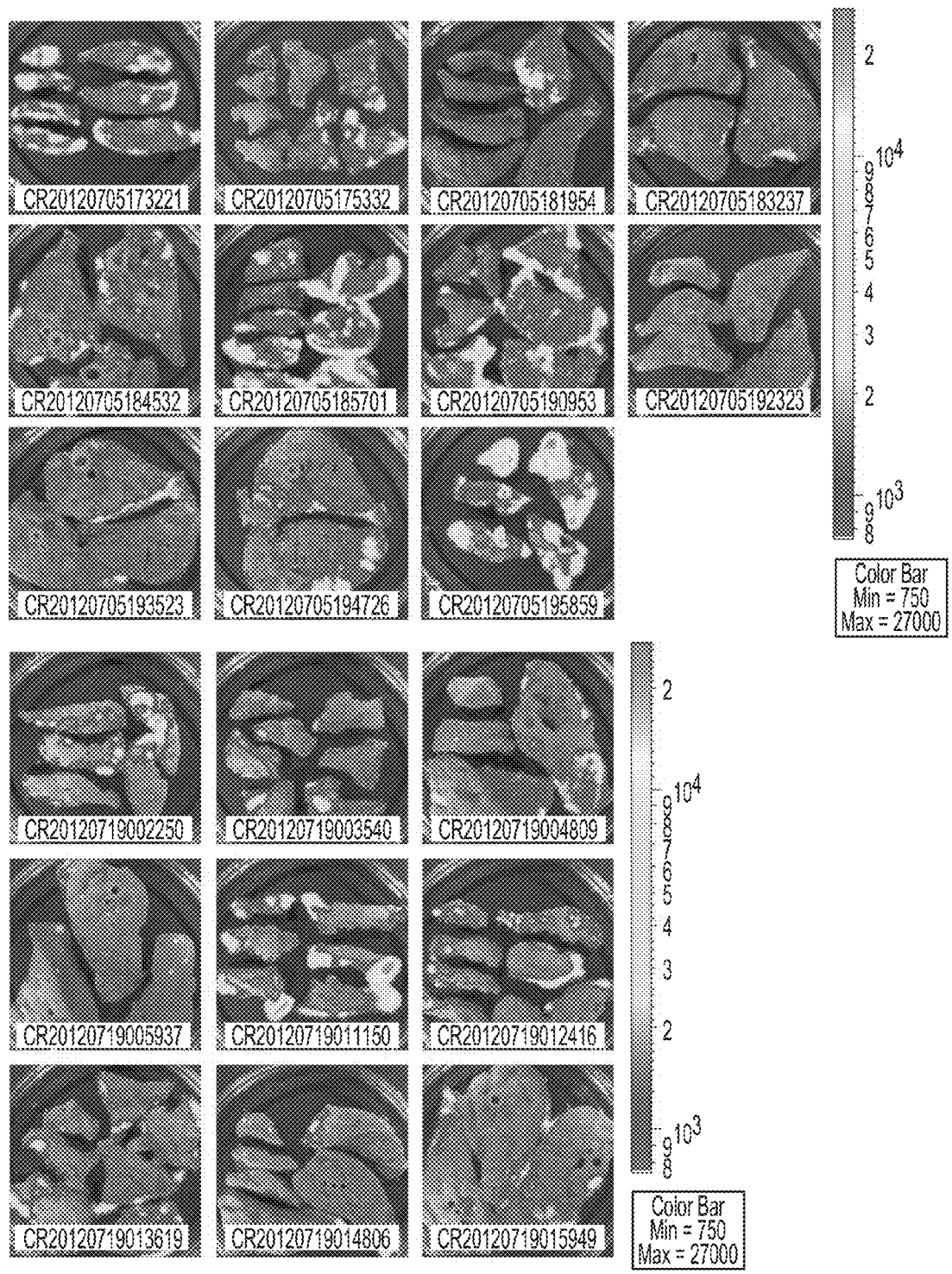
FIG. 28. BLI of luciferase expression in lung specimens of twice-treated pigs #4 and #8. Aerosol administration of each 1 mg FFL SNIM RNA and hCFTR SNIM RNA in the PEI Formulation of Example 6 was performed using an Aeroneb mesh nebulizer. Slices of the entire pig lung are shown. Upper three rows: pig #4, lower three rows: pig #8.

For Group II (Aerosol administration of 2 mg hCFTR SNIM RNA in the PEI Formulation of Example 6 on day 1 and 1 mg FFL SNIM RNA and 1 mg hCFTR SNIM RNA in the PEI Formulation of Example 6 on day 8), Luciferase activity was clearly detected in lung specimens of twice-treated pigs #4 and #8 (FIG. 28). Luciferase expression was highest in central parts of the lungs. It has to be considered that samples were stored for additional 10 hours in cell culture medium before measurement because of a power blackout on the day of the measurements and resulting technical problems with the BLI system.

Figure 29:
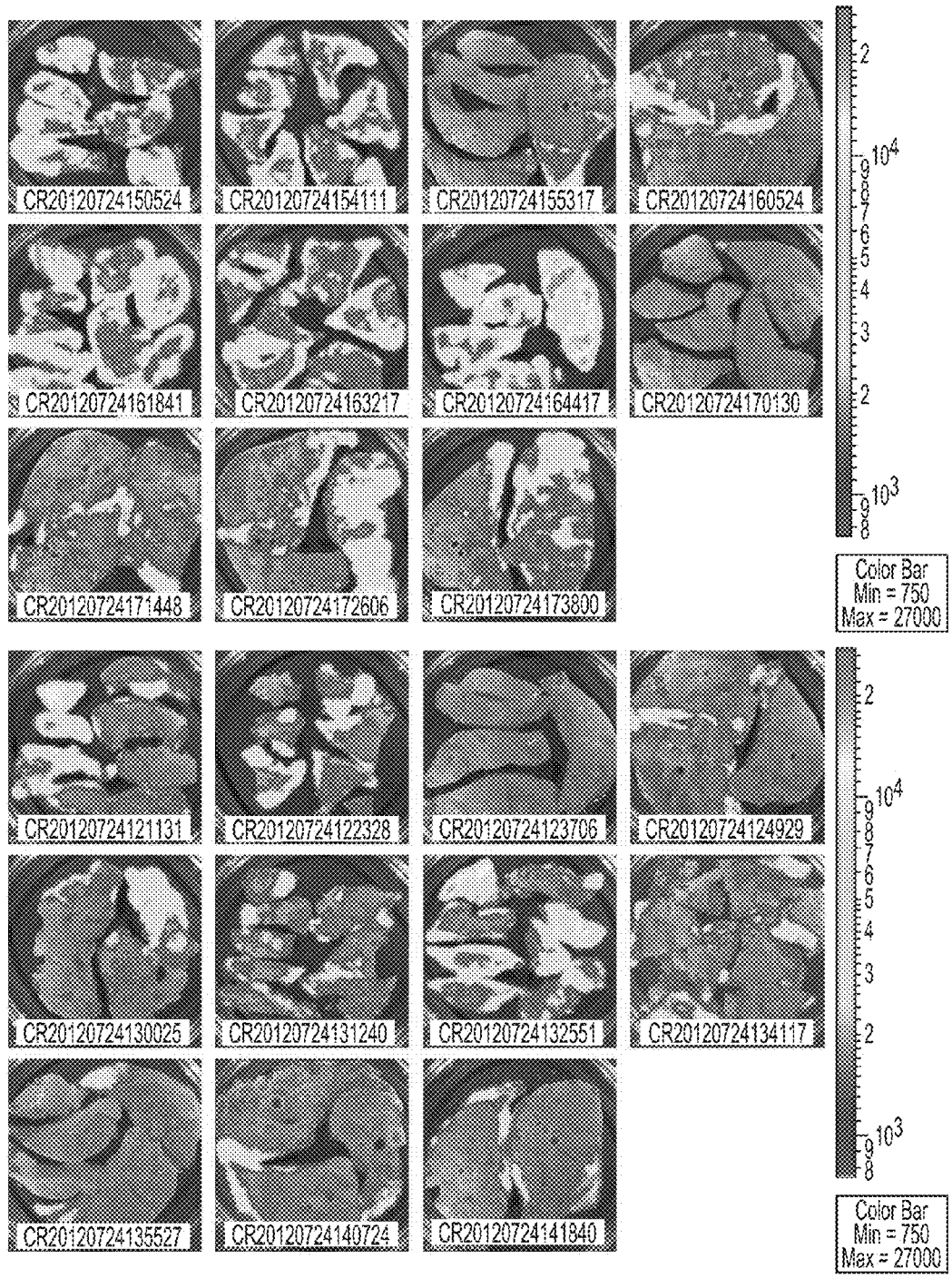
FIG. 29. BLI of luciferase expression in lung specimens of three times-treated pigs #1 and #2. Aerosol administration of each 1 mg FFL SNIM RNA and hCFTR-mRNA SNIM RNA in the PEI Formulation of Example 6 were performed using an Aeroneb mesh nebulizer. Slices of the entire pig lung are shown. Upper three rows: pig #1, lower three rows: pig #2.

For Group III (Aerosol administration of 2 mg hCFTR SNIM RNA in the PEI Formulation of Example 6 on day 1 and day 8, aerosol administration of 1 mg FFL SNIM RNA and 1 mg hCFTR SNIM RNA in the PEI Formulation of Example 6 on day 15), Luciferase activity was clearly detected in lung specimens of thrice-treated pigs #1 and #2 (FIG. 29). Luciferase expression was highest in central parts of the lungs.

Properties of SNIM RNA-PEI Nanoparticles.

Particle size and zeta potential was measured for SNIM RNA-PEI formulations before nebulisation (Table X1). The SNIM RNA-PEI nanoparticles could be reproducibly formed with a size ranging from 25-37 nm and zeta potentials ranging from 30-49 mV.

TABLE X1

Particle size and Zeta Potential measurements

| Pig # | Treatment # | Radius ± S.D. (nm) | Zeta potential ± S.D. (mV) |
|---|---|---|---|
| 1 | 1 | 26.7 ± 0.3 | 36.9 ± 5.9 |
|   | 2 | 33.3 ± 0.6 | 42.5 ± 5.5 |
|   | 3 | 31.6 ± 0.4 | 41.3 ± 3.4 |
| 2 | 1 | 24.7 ± 0.5 | 32.9 ± 3.3 |
|   | 2 | 34.9 ± 0.2 | 41.5 ± 1.4 |
|   | 3 | 32.5 ± 0.4 | 29.1 ± 1.1 |
| 3 | 1 | 35.2 ± 0.8 | 42.9 ± 1.9 |
| 4 | 1 | 36.9 ± 1.1 | 45.4 ± 0.6 |
| 6 | 1 | 27.5 ± 0.1 | 30.5 ± 6.6 |
|   | 2 | 33.0 ± 0.8 | 49.1 ± 3.0 |
| 8 | 1 | 25.5 ± 0.1 | 44.0 ± 2.1 |
|   | 2 | 33.3 ± 0.3 | 45.9 ± 9.5 |

Luciferase Expression in Treatment Groups by IHC.

Figure 30:
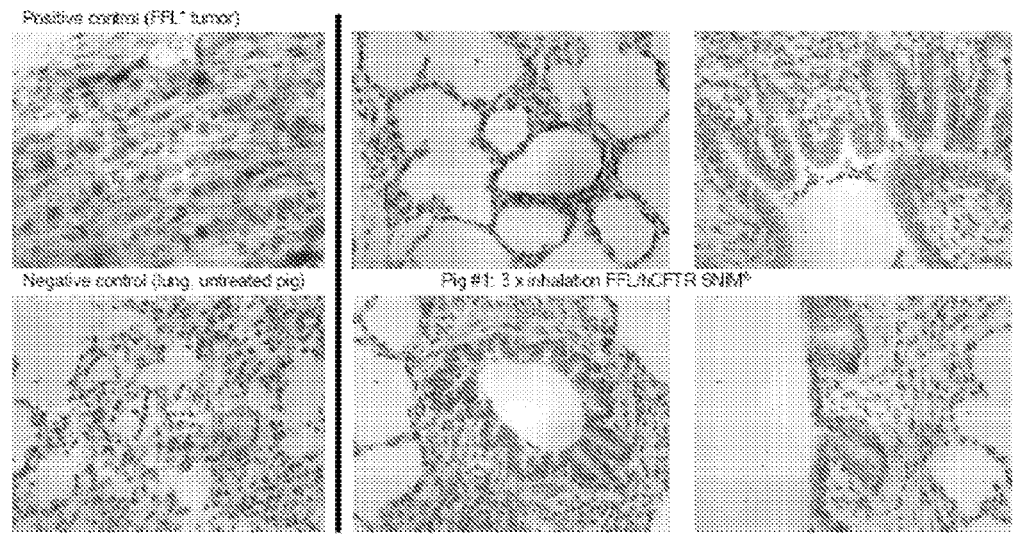
FIG. 30. Luciferase IHC on lung tissue of three times treated pig #1. Aerosol administration of each 1 mg FFL SNIM RNA and hCFTR SNIM RNA in the PEI Formulation of Example 6 was performed using an Aeroneb mesh nebulizer. Luciferase expression appeared in reddish-pink colour (Anti-Luciferase pAb 1:300, G7451, Promega, Refine AP-Kit, chromogen: New fuchsine).

IHC for FFL was performed on tissue specimens of lung slices (Sophistolab AG, Eglisau, Switzerland) which were positive by BLI and compared with lung tissue of an untreated pig and luciferase-positive mouse tumor tissue as positive control. As expected a strong signal was seen in the luciferase-positive mouse tumor tissue, whereas lung tissue of the untreated pig did not show specific staining. A clearly detectable staining pattern could be observed in the lung tissue of pig #1 which received three treatments. FFL expression was most prominent in the bronchial epithelium of large and small airways (FIG. 30).

Detection of hCFTR Protein in Lung Tissue of Treated Pig by IP/WB.

Figure 31:
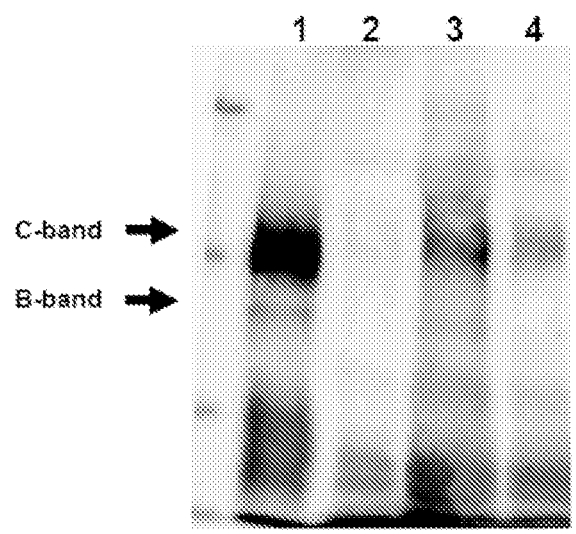
FIG. 31. Highly BLI-positive lung tissue of threefold treated pig #1 was subjected to hCFTR IP/WB. Lane 1:T84 cells (positive control), Lane 2: untreated pig lung tissue (300 mg), Lane 3: treated pig lung tissue (697 mg), Lane 4: treated pig lung tissue (163 mg). Mature complex-glycosylated hCFTR appeared as the disperse so-called C-band. Mannose-rich hCFTR appeared as the more dense so-called B-band. hCFTR expression was observed in T84 cells and pig lung tissue of hCFTR SNIM RNA treated pig #1, whereas no hCFTR expression was observed in untreated pigs.

Highly BLI-positive lung tissue of three times treated pig #1 was subjected to hCFTR IP/WB according to the protocol described by van Barneveld A et al., Cell Physiol Biochem. 30, 587-95 (2012) (FIG. 31). Mature complex-glycosylated hCFTR appears as the disperse so-called C-band. Mannose-rich hCFTR appears as the more dense so-called B-band. Clearly hCFTR expression is observed in T84 positive control cells and lung tissue of pig #1 treated with hCFTR SNIM RNA in the PEI Formulation of Example 6. Expression of hCFTR protein was not observed in untreated pigs. A comparison of hCFTR protein expression in human lung tissue from a published study using the identical protocol (van Barneveld A et al., supra) suggested that expression of hCFTR in pig lung tissue after hCFTR SNIM aerosol treatment was similar to hCFTR expression in healthy human lung.

Figure 32:
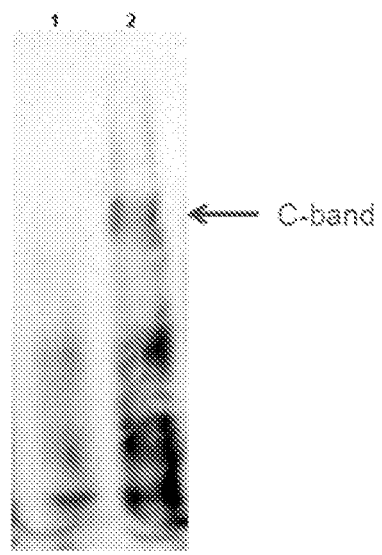
FIG. 32. Immunoprecipitation of hCFTR using MAB25031 and subsequent immunodetection using AB570 from pig lung samples post hCFTR SNIM RNA delivery in the PEI Formulation of Example 6. Lane 1: sample from luciferase-negative left caudal lobe of pig #2, Lane 2: sample from luciferase-positive lung regions of pig #1.

This finding was further confirmed by using a different set of antibodies for detection of hCFTR protein by IP/WB in treated pig lung (see Example 6). One sample from the luciferase expressing lung areas from pig #1 and another from the caudal lobe of pig #2, where no luciferase activity could be detected, thus indicating lack of mRNA delivery and/or expression were selected as positive and negative controls. Protein lysates prepared from these samples were immunoprecipitated using MAB25031 (R&D Systems) and hCFTR protein detected using AB570. As shown in FIG. 32, luciferase expression correlated with the expression of hCFTR mRNA. Sample from the left caudal lobe from pig #2 where no luciferase activity was detectable, was also negative for hCFTR (lane 1), whereas hCFTR could be detected in samples from pig #1 which were positive for luciferase (lane 2).

Toxicology: Preliminary Histological Assessment of Lung Samples.

A histological assessment of samples of the lungs taken after the euthanasia of three animals was performed. After embedding in paraffin sections lung samples were stained with Hematoxiline-Eosine for morphological evaluation. The findings were consistent across the samples from the three pigs, two of which (pig #1 and pig #2) received three aerosol applications and the third (pig #7) was an untreated control with no aerosol application.

Toxicology: Distress.

Only pig #2 and pig #1 showed mild signs of distress on day 2-4 after the first treatment. Thus, three aerosol applications within three weeks caused only mild distress Toxicology: Adverse Events.

Kind and frequency of adverse events (AE) were analyzed by laboratory parameters (blood, MBS and BAL) and by physical examination of the pigs (defined as a secondary objective in this trial).

Serum and whole blood samples were taken at the time points defined by the study protocol. Twelve representative parameters (haemoglobin, hematocrit, AP, ALT, AST, CK, bilirubin, creatinine, glucose, potassium, thrombocytes, and white blood cells) being indicative to show organ specific pathology (blood, bone marrow, liver, muscle, and kidney) were selected and the test results obtained from the Vet-MedLab, Ludwigsburg, Germany classified according to VCOG, version 2011.

The results showed that no severe adverse events (AE) were observed in the pigs (an AE of grade 3, 4, or 5 would have qualified as severe). There was no impairment of laboratory parameters after aerosol application of SNIM RNA in the PEI Formulation of Example 6. For the slight changes in some parameters (e.g. CK or liver enzymes) it is more likely that these changes were caused by the experimental procedure per se (e.g. i.m. injections and anaesthesia). Also no negative effect from repeated application could be detected—even after the third application, the pigs of group 3 show no AE higher than AE grade 2. Even AE grade 1 or 2 were rare and showed no correlation to the aerosol application of SNIM RNA in the PEI Formulation of Example 6.

Besides the repeated blood samples two other parameters were assessed to evaluate pathological processes in the lung: i) Brocho-Alveolar-Lavage fluid (BALF)—taken after euthanasia, and ii) microbiology samples (MBS) (smear form the trachea—taken during the anaesthesia). BALF was taken from each pig during autopsy and was stored at −80° C. for further examination. Tracheal smears were taken prior to each aerosol application and microbiologically examined. These examinations revealed a broad spectrum of pathogens including *Bordetella bronchiospectica* (a common pathogen of the respiratory tract of the pig) and *Escherichia coli*. Pigs were once treated with tulathromycin i.m.-injection (1 ml Draxxin® 10%).

Physical Examination.

In addition to the laboratory parameters, physical examinations of the pigs were performed in the observation periods between the aerosol applications (for details see 1.1.2 of annex 1 and annex 4 of the study protocol). As no system for documenting, grading and assigning the attribution of the AE, either to the intervention or something else is defined for pigs, the common toxicology criteria (CTC)-system established for dogs and cats was used (published by VOCG in 2011). To grade the laboratory parameters, species specific ULN (upper limits of normal) and LLN (lower limits of normal) were used. Clinical assessments were made within the following six AE categories:

(1) allergic/immunologic events; (2) pulmonary/respiratory; (3) constitutional clinical signs; (4) dermatologic/skin; (5) gastrointestinal; and (6) pulmonary/respiratory.

The results showed that no severe AE (no grade 3, 4, or 5) were observed in the pigs. There was no impairment of parameters assessed by physical examination after the aerosol application of SNIM RNA in the PEI Formulation. The two pigs of group 3 showed grade 1 and 2 AE in three of the respiratory parameters (bronchospasm/wheezing, larynx oedema, and dyspnoea) but these mild or moderate findings were restricted to one or two days. As these observations only occurred after the first anaesthesia/intubation/aerosol application in these two pigs but not after the second or third aerosol application in these two pigs or in any other pig, it is unlikely that these findings are caused by the substance under investigation.

Conclusion.

The results of this example demonstrated that the PEI Formulation encoding FFL and hCFTR SNIM RNA could be successfully aerosolized repeatedly to the lungs of pigs without loss of activity after each treatment cycle and without adverse events. Luciferase expression was found in central parts of the lung tissue but hardly detected in distal lung areas. The regional pattern of luciferase expression correlated with the expected deposition pattern of the PEI Formulation of Example 6 according to settings used for controlled ventilation. Immunohistochemistry on selected lung samples form treated pigs showed luciferase expression predominantly in the bronchial epithelium of large and small airways. IP/WB clearly demonstrated expression of complex-glycosylated C-band of mature human CFTR in treated pig lung which was absent in untreated pig lung and luciferase-negative lung specimens. Expression of hCFTR in pig lung tissue after hCFTR SNIM RNA aerosol treatment was comparable to the hCFTR expression in healthy human lung when compared to published reports using the identical protocol for hCFTR protein detection. Adverse events grade 1 or 2 were very rare and showed no correlation to the aerosol application of SNIM RNA in the PEI Formulation. Thus, expression of hCFTR protein was successfully demonstrated in lungs of pigs treated with SNIM hCFTR mRNA.

Example 9: CFTR Encoding mRNA Containing Signal Peptide

This example demonstrates that a CFTR protein may be effectively expressed from a CFTR encoding mRNA with a signal peptide encoding sequence.

Messenger RNA Synthesis.

For the experiment, C-terminal $His_{10}$ tagged codon optimized human cystic fibrosis transmembrane conductance regulator (CO-CFTR-C-$His_{10}$)(SEQ ID NO: 15), a codon optimized human CFTR with a growth hormone signal sequence leader (GH-CO-CFTR)(SEQ ID NO: 16) and codon optimized human CFTR (CO-CFTR)(SEQ ID NO: 17) SNIM RNA were synthesized by in vitro transcription from a plasmid DNA template using standard methods. Cells and CFTR transfection. Human embryonic kidney HEK293T cells were grown in DMEM (Invitrogen Cat #11965-092) supplemented with 10% fetal bovine serum, 2 mM L-Glutamine, 100 U/ml penicillin and 100 µg/ml streptomycin. The day before transfection, cells were plated on 6-well plates at 50-60% confluence and incubated under normal tissue culture conditions (36° C. in a humidified atmosphere of 5% C02, 95% air). In preparation for transfection, 60 µl Lipofectamine 2000 (Invitrogen Cat #11668019) was diluted in OptiMem reduced serum media (Invitrogen Cat #31985-062) and gently vortexed. For the experiment 4 µg of either CO-CFTR, GH-CO-CFTR or CO-CFTR-C-$His_{10}$ SNIM RNA was diluted in 900 µl OptiMem media. The mRNA was immediately added to the diluted Lipofectamine® and incubated at room temperature for 30 minutes. The plating media was gently aspirated and replaced with 1 ml OptiMem Reduced Serum Medium and 300 µl of each respective mRNA/Lipofectamine® complex. Cells were incubated under standard tissue culture conditions.

Western Analysis.

Figures 33A, 33B, 33C:
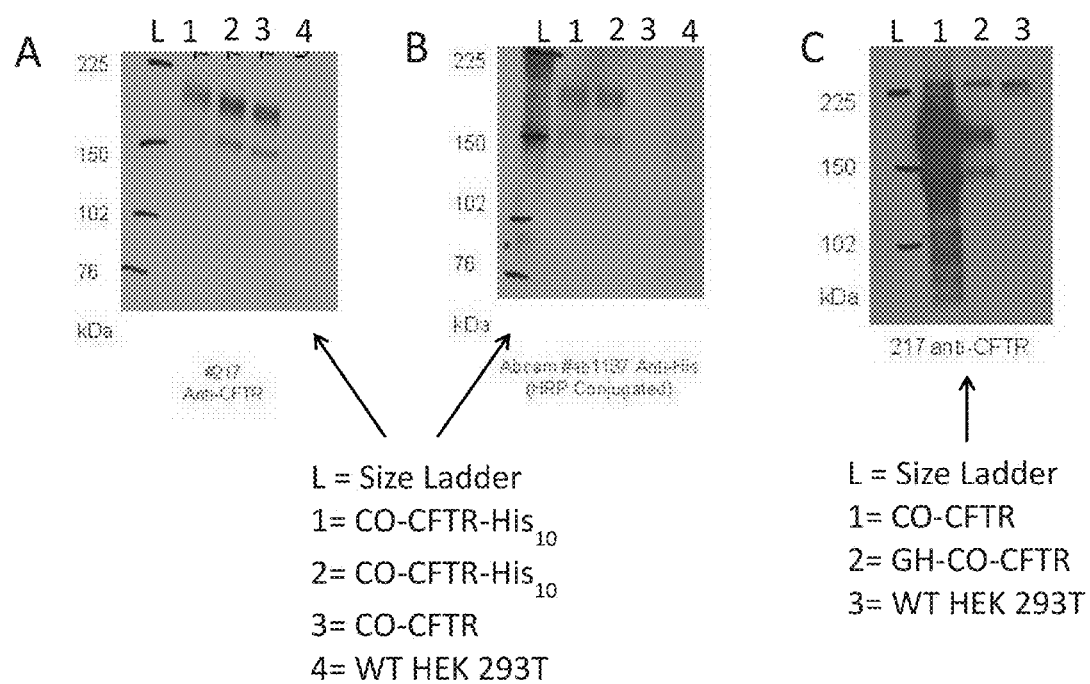
FIGS. 33A & 33B. In vitro transfection of HEK 293T cells with C-terminal $His_{10}$ tagged (CO-CFTR-C-$His_{10}$) and non-tagged (CO-CFTR) codon optimized human CFTR SNIM RNA. Following transfection, whole cell lysate was collected and analyzed for human CFTR expression by Western blot using (33A) anti-CFTR antibody #217 and (33B) anti-His antibody 1187. Transfected samples were compared to non-transfection HEK 293T control lysate (Lane 3).
FIG. 33C. In vitro transfection of HEK 293T cells with SNIM RNA encoding codon optimized human CFTR with a growth hormone leader sequence and a (GH-CO-CFTR) or SNIM RNA encoding a C-terminal $His_{10}$ tagged codon optimized human CFTR (CO-CFTR-C-$His_{10}$). Following transfection, whole cell lysate was collected and analyzed for human CFTR expression by Western blot using anti-CFTR antibody #217. Transfected samples were compared to non-transfection HEK 293T control lysate (Lane 3).

Approximately 48 post transfection, cells were removed from their respective plates and lysed. Whole cell lysate was subjected to separation by SDS-PAGE and probed by Western blot. As shown in FIGS. 33A-33C, robust expression of human CFTR protein was detected following CO-CFTR, GH-CO-CFTR and human CO-CFTR-C-$His_{10}$ mRNA transfection, by anti-CFTR (33A & 33B) or anti-His (33C) antibodies (FIGS. 33A-33C).

Example 10: In Vivo CO-CFTR-C-His10 mRNA Delivery to CFTR Knockout Mice

Analysis of Human CFTR Protein Produced Via Intratracheal Administered mRNA-Loaded Nanoparticles.

All studies were performed using CFTR KO mice. CFTR mRNA formulation or vehicle control was introduced using a PARI Boy jet nebulizer. Mice were sacrificed and perfused with saline, after a predetermined period of time, to allow for protein expression from the mRNA.

Messenger RNA Synthesis.

In the example, C-terminal $His_{10}$ tagged codon optimized human cystic fibrosis transmembrane conductance regulator (CO-CFTR-C-$His_{10}$) SNIM RNA and codon-optimized FFL SNIM RNA were synthesized by in vitro transcription from plasmid DNA templates.

PEI Formulation.

For the approach, delivery and expression of CO-CFTR-C-$His_{10}$ mRNA in the lungs of CFTR knockout mice was evaluated using both polymeric and lipid-based nanoparticle formulations. Polymeric nanoparticle formulations with 25 kDa branched PEI prepared as follows. The required amount of SNIM RNA was diluted just before application in water for injection (Braun, Melsungen) to a total volume of 4 ml and added quickly to 4 ml of an aqueous solution of branched PEI 25 kDa using a pipette at an N/P ratio of 10. The solution was mixed by pipetting up and down ten times and nebulized as two separate 4.0 ml fractions one after another to the mouse lungs using the indicated nebulizer.

cKK-E12 Formulation.

For the lipid-based nanoparticle experiment, a lipid formulation was created using CO-CFTR-C-$His_{10}$ SNIM RNA in a formulation of cKK-E12:DOPE:Chol:PEGDMG2K (relative amounts 50:25:20:5 (mg:mg:mg:mg). The solution was nebulized to the mouse lungs using the indicated nebulizer.

Nebulization (Aerosol) Administration of Human CO-CFTR-C-$His_{10}$ mRNA.

CFTR test materials were administered by a single aerosol inhalation via PARI Boy jet nebulizer (nominal dose volume of up to 8 mL/group). The test material was delivered to a box containing the whole group of animals (n=4) and connected to oxygen flow and scavenger system.

Administration of Human CO-CFTR-C-$His_{10}$ mRNA.

CFTR mRNA was prepared in the manner described above. Four CFTR knockout mice were placed in an aerosol chamber box and exposed to 2 mg total codon optimized unmodified human CFTR mRNA (comprising the coding sequence of SEQ ID NO: 3) via nebulization (Pari Boy jet nebulizer) over the course of approximately one hour. Mice were sacrificed 24 hours post-exposure.

Euthanasia.

Animals were euthanized by CO2 asphyxiation at representative times post-dose administration (±5%) followed by thoracotomy and exsanguinations. Whole blood (maximal obtainable volume) was collected via cardiac puncture and discarded.

Perfusion.

Following exsanguination, all animals underwent cardiac perfusion with saline. In brief, whole body intracardiac perfusion was performed by inserting 23/21 gauge needle attached to 10 mL syringe containing saline set into the lumen of the left ventricle for perfusion. The right atrium was incised to provide a drainage outlet for perfusate. Gentle and steady pressure was applied to the plunger to perfuse the animal after the needle had been positioned in the heart. Adequate flow of the flushing solution was ensured when the exiting perfusate flows clear (free of visible blood) indicating that the flushing solution has saturated the body and the procedure was complete.

Tissue Collection.

Following perfusion, all animals had their lungs (right and left) harvested. Both (right and left) lungs were snap frozen in liquid nitrogen and stored separately at nominally −70° C.

Expression of Human CFTR from CO-CFTR-C-his$_{10}$ mRNA in CFTR Knockout Mice.

Figure 34:
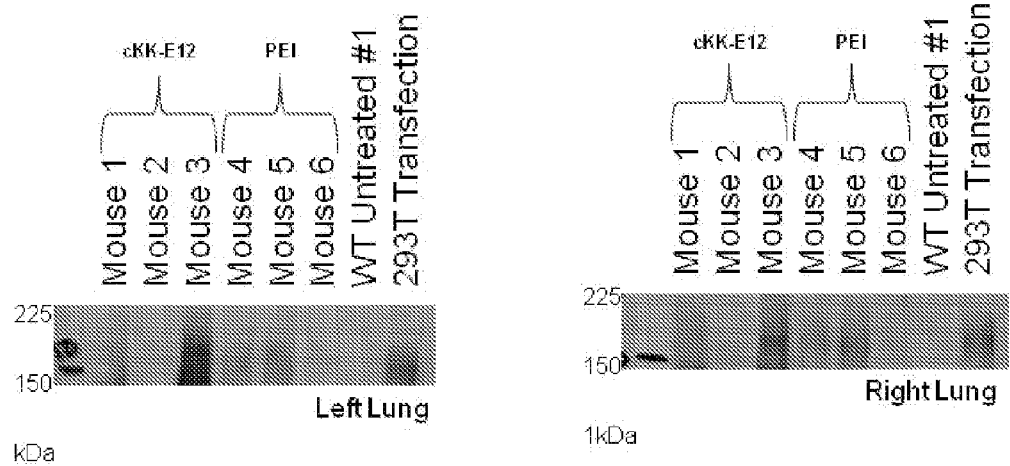
FIG. 34. In vivo transfection of CFTR knockout mice with C-terminal $His_{10}$ tagged codon optimized human CFTR SNIM RNA encapsulated within either a lipid (cKK-E12) or polymeric (PEI) nanoparticle formulation. Following nebulized delivery of each respective mRNA formulation, Right and Left lung tissue lysate was collected and analyzed for CFTR expression by Western blot using anti-His antibody 1187. Control CFTR knockout lung tissue and CFTR-$His_{10}$ HEK293 lysate was used as a negative and positive controls respectively.
Figure 35:
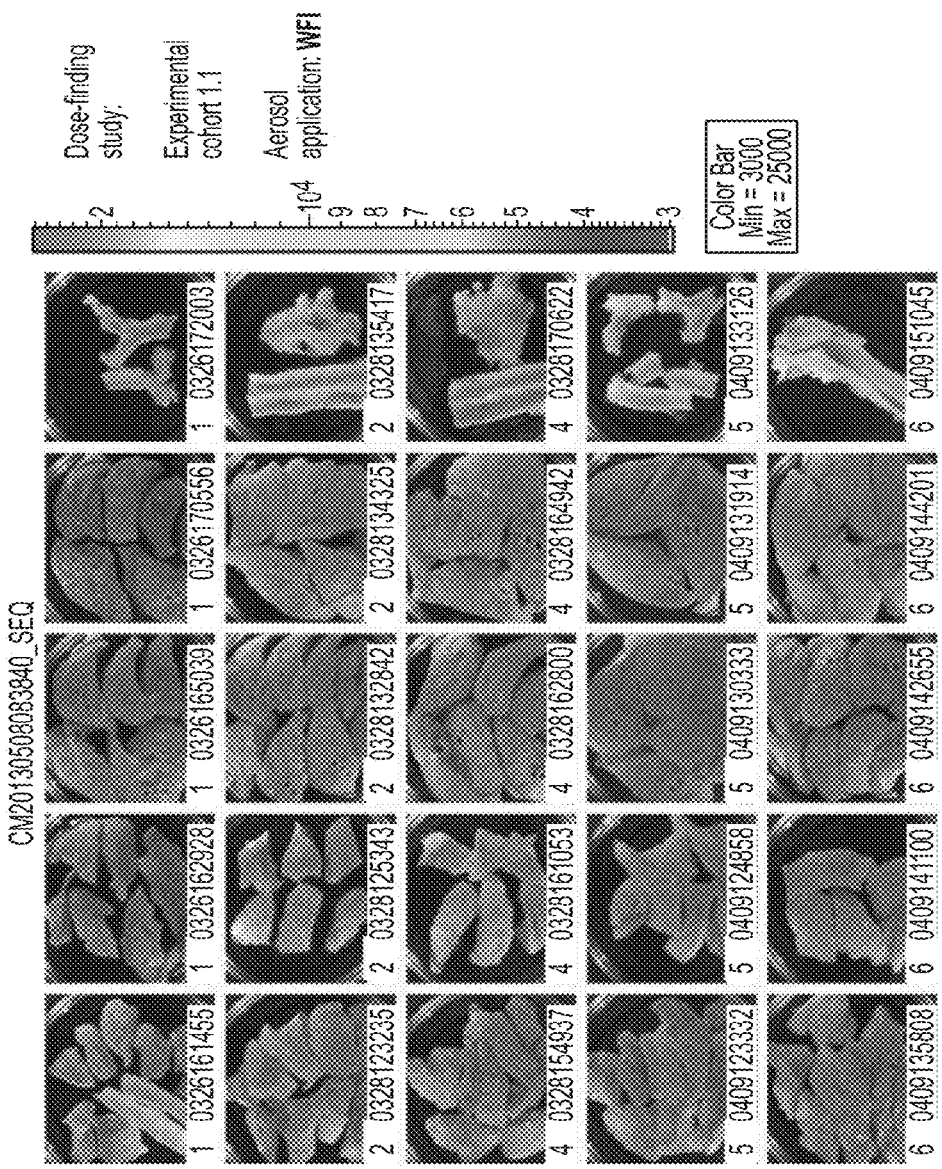
FIG. 35. Bioluminescent detection of FFL expression in porcine lung samples collected following nebulization with water for injection.
Figure 37:
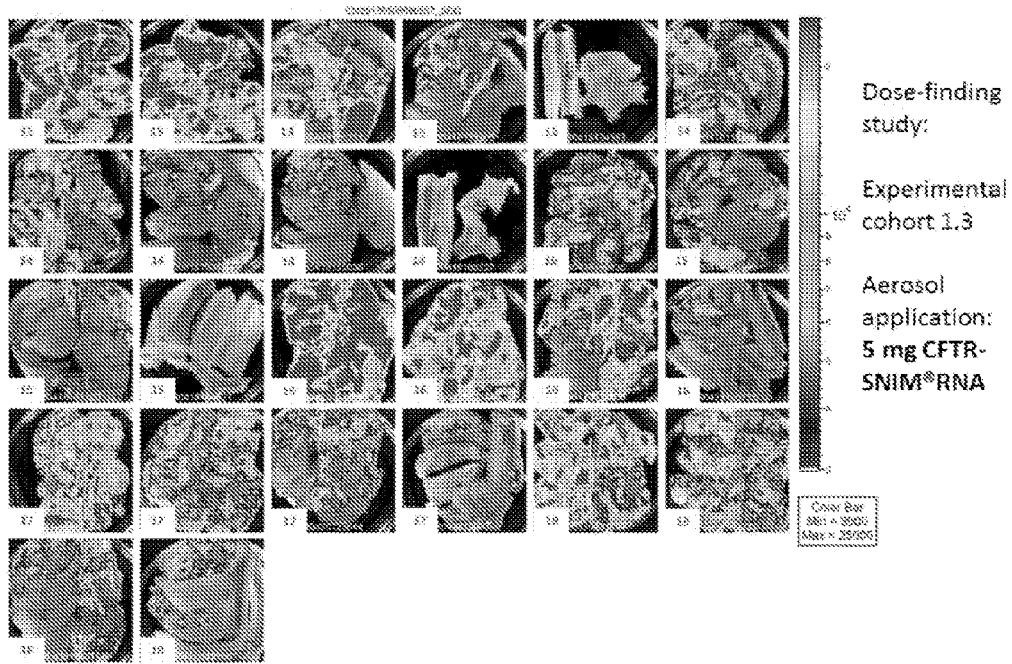
FIG. 37. Bioluminescent detection of FFL expression in porcine lung samples collected following nebulization with 1 mg FFL SNIM RNA+5 mg CO-CFTR SNIM RNA in a branched 25 kDa PEI formulation.
Figure 38:
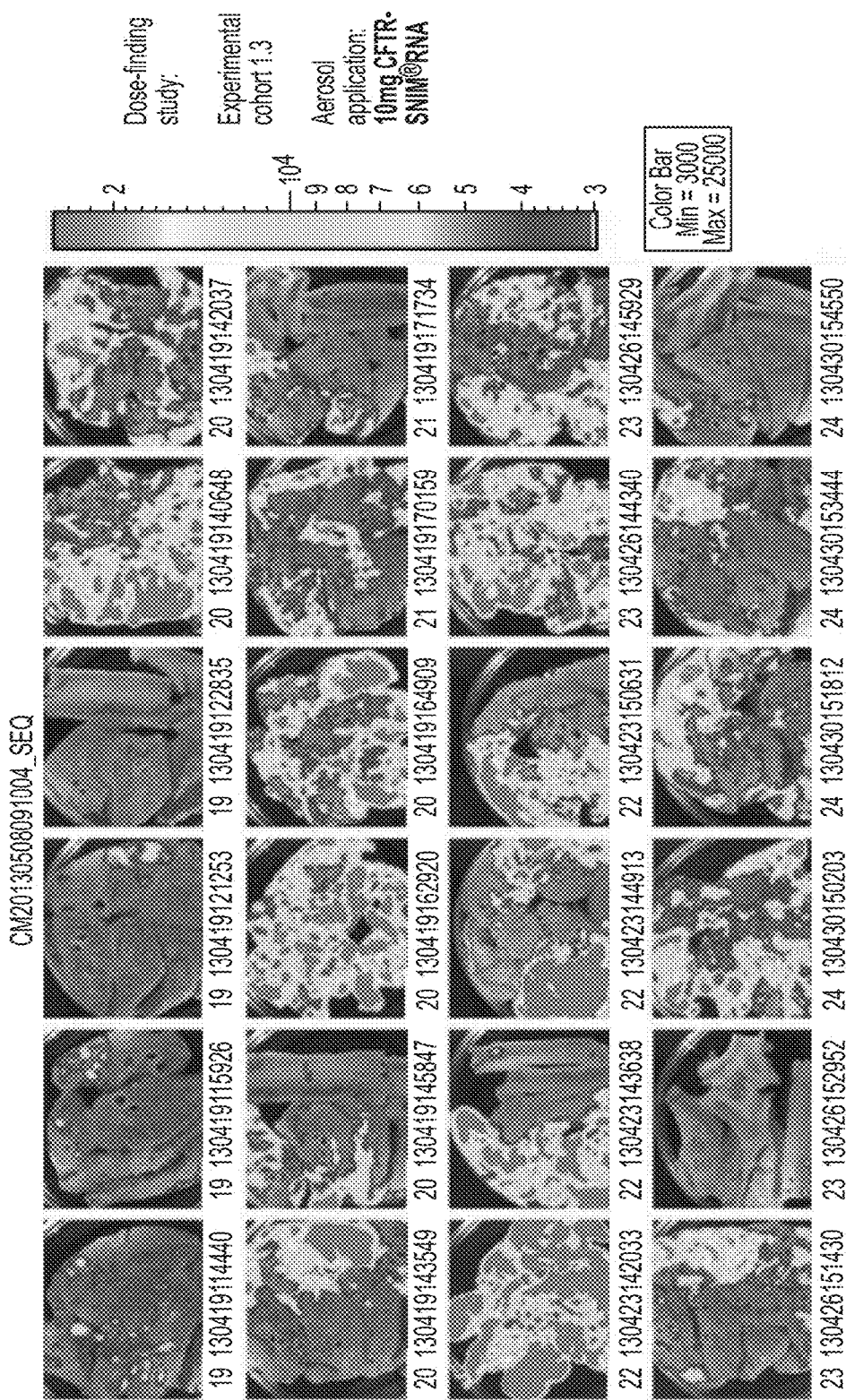
FIG. 38. Bioluminescent detection of FFL expression in porcine lung samples collected following nebulization with 1 mg FFL SNIM RNA+10 mg CO-CFTR SNIM RNA in a branched 25 kDa PEI formulation.

CFTR expression was detected by Western blot analysis of tissue lysate collected from CFTR mRNA-treated mouse lungs. Mature "C" band was detected in left and right lungs of all treated mice, for both the lipid-based and polymeric-based formulations (FIG. 34). Expression of the mature "C" band was verified by comparison with lysate collected from HEK 293T human CO-CFTR-C-His$_{10}$ positive cells as described in Example 9. In contrast, no detectable signal was observed in lysate collected from wild type untreated control mice (FIG. 34). Taken together, these data suggest that both polymeric and lipid based formulations (such as the cKK-E12 formulation listed above) are effective for lung delivery of CFTR mRNA, e.g., via inhalation, and that once delivered, the codon optimized CFTR mRNA can effectively express human CFTR protein.

Example 11: In Vivo Dose Escalation Study

Dose Escalation of PEI Encapsulated mRNA Aerosol Delivery to the Lungs of Pigs.

Aerosol administration of a combination of firefly luciferase (FFL) SNIM RNA and codon optimized human CFTR (CO-CFTR) SNIM RNA at varying concentrations to pig lungs was established by a stepwise experimental procedure. In a first step the FFL/CO-CFTR SNIM RNA formulation was nebulized to anaesthetized pigs during controlled ventilation. In a second step, the animals were sacrificed by bolus injection of pentobarbital (100 mg/kg of body weight) and potassium chloride via the lateral ear vein after sedation 24 hours after aerosol administration was completed. Lungs were excised and sliced to approximately 1 cm thick tissue specimens. For measurement of luciferase activity, tissue specimens were incubated in a medium bath comprising D-Luciferin substrate and subjected to ex vivo luciferase BLI. After BLI, samples from luciferase-positive and luciferase-negative regions were taken for histopathology, immunohistochemistry and in situ hybridization. The residual specimens were shock-frozen in liquid nitrogen and subsequently stored at −80° C. until analysis by IP/WB and Elisa.

Messenger RNA Synthesis.

In the example, codon optimized human cystic fibrosis transmembrane conductance regulator (CO-CFTR) SNIM RNA, codon-optimized FFL mRNA SNIM RNA were synthesized by in vitro transcription from plasmid DNA templates using standard methods.

Experimental Design.

Pigs of the German Landrace were obtained from Technical University Munich, Weihenstephan, Germany. The pigs had a body weight ranging from 35-90 kg. The study was designed using both age and weight-matched pigs to control for variability. A single cohort of 6 pigs (3 male and 3 female) was established for each experimental group of the 4-arm study. The first cohort was treated with water for injection (WFI) alone, which was administered using a Aeroneb mesh nebulizer. The second cohort was treated with a solution of 1 mg FFL SNIM RNA and 1 mg of codon optimized human CFTR (CO-CFTR) SNIM RNA in the PEI Formulation described below, using an Aeroneb mesh nebulizer. The third cohort received 1 mg of FFL SNIM RNA and 5 mg of codon optimized human CFTR (CO-CFTR) SNIM RNA in the PEI Formulation described below. The fourth cohort was treated with 1 mg of FFL SNIM RNA and 10 mg of codon optimized human CFTR (CO-CFTR) SNIM RNA in the PEI Formulation described below. The scheme for treatment and evaluation of each group is shown in Table 4 below.

TABLE 4

Experimental Design for Dose Escalation Study

| Cohort | Pigs (No. and Sex) | Treatment | Formulation |
| --- | --- | --- | --- |
| 1 | 6 (3 male + 3 female) | N/A | WFI |
| 2 | 6 (3 male + 3 female) | 1 mg FFL + 1 mg CO-CFTR | Branched 25 kDa PEI + WFI |
| 3 | 6 (3 male + 3 female) | 1 mg FFL + 5 mg CO-CFTR | Branched 25 kDa PEI + WFI |
| 4 | 6 (3 male + 3 female) | 1 mg FFL + 10 mg CO-CFTR | Branched 25 kDa PEI + WFI | mRNA-PEI Formulation.

An exemplary standardized formulation procedure described below was performed just before treatment of the animals.

Materials:
Syringe Pump (Mixing Device):
Manufacturer: KD Scientific
Type: KDS-210-CE
Syringe:
Manufacturer: B.Braun
Type: Omnifix, 20 mL or 30 mL/Luer Lock Solo
Ref.: 4617207V
Tubing:
Manufacturer: B.Braun
Type: Safeflow Extension Set
Ref.: 4097154
Needle:
Manufacturer: B.Braun
Type: Sterican, 20G×1½"
Ref.: 4657519
Mixing Valve:
Manufacturer: B.Braun
Type: Discofix C 3SC
Ref.: 16494C
Water for injection:
Manufacturer: B.Braun
Type: Aqua
Ref.: 82423E Examplary method for the preparation of polyplexes containing 1 mg hCFTR SNIM RNA and 1 mg FFL SNIM RNA N/P 10 in a volume of 8 mL: 3 mL water for injection and 3 mL RNA stock solution (c: 1 mg/mL in water; 1.5 mL FFL mRNA+1.5 mL CFTR mRNA) were filled into a 15 mL falcon tube. In a second falcon tube 5.61 mL water for injection were mixed with 0.39 mL brPEI stock solution (c: 10 mg/mL in water). Two 20 mL syringes were fixed in the mixing device. Each of them was connected to a needle via a tubing. One syringe was filled with the RNA- and the other with the PEI-solution using the withdrawal function of the syringe pump. (Settings: Diameter: 20.1 mm, Flow: 5 mL/min, Volume: 5.9 mL). The needles were removed and the tubes connected to the mixing valve. It was important to connect the syringe containing the RNA-solution to the angled position of the valve. To control the outlet diameter, a needle was connected. The mixing was performed using the infusion function of the syringe pump (Settings: Diameter: 20.1 mm, Flow: 40 mL/min, Volume: 5.8 mL). To achieve a reproducible polydispersity index, the samples were fractionated manually during mixing. The first few µL until the flow was stable (100-200 µL) and the last few µL sometimes containing air bubbles were collected in a separate tube. The mixture was incubated for 30 min at room temperature for polyplex formation and afterwards stored on ice. For different doses, the parameters were modified and adapted as shown in Table 5.

TABLE 5

Exemplary volumes and settings for different mixing volumes

| | mRNA component | | | PEI component | | |
|---|---|---|---|---|---|---|
| Cohort | V (FFL SNIM RNA 1 mg/ mL) (mL) | V (hCFTR SNIM RNA 1 mg/ mL) (mL) | Water (mL) | V (brPEI stock; 10 mg/ mL) (mL) | Water (mL) | Aerosolized volume (ml) |
| 2 | 1.5 | 1.5 | 3 | 0.39 | 5.61 | 8 |
| 3 | 1.17 | 5.83 | 7 | 0.91 | 13.09 | 24 |
| 4 | 1.09 | 10.91 | 12 | 1.56 | 22.44 | 44 |

| Cohort | V (withdrawal) (ml) | V (infusion) (ml) |
|---|---|---|
| 2 | 5.9 | 5.8 |
| 3 | 13.9 | 13.8 |
| 4 | 23.9 | 23.8 |

V (withdrawal) and V (infusion) designate the setting on the syringe pump for aspiration and dispension, respectively, of the mRNA and PEI components.

Transfection of HEK Cells to Check the Functionality of the Nebulized Complexes.

Post nebulization, an aliquot of complexes (80 al) was used to transfect HEK cells. One day prior to transfection, $1\times10^6$ cells were plated in 6 well plates. At the day of transfection, medium was removed from the cells, cells were washed with PBS once following which 80 µl of complexes together with 920 µl of serum free MEM medium was added per well. For each complex, three replicate wells were prepared. The cells were incubated with the complexes for 4 hours under standard cell culture conditions. At the end of incubation, complex containing medium was removed and serum containing MEM medium (1 ml) was added per well. Plates were incubated under standard cell culture conditions. At 24 hours post transfection, protein lysates were prepared using the same protocol and buffers used for animal tissues with exclusion of homogenization step. Cells from three wells were pooled for analysis. Expression of human CFTR was detected using immunoprecipitation with R24.1 antibody (R&D Systems) and Western Blot with a combination of 217, 432 and 596 antibodies (all from Cystic Fibrosis Consortium, University of Pennsylvania, PA, USA). hCFTR could be detected for all of complexes nebulized in pigs (see FIGS. 54-57).

Aerosol Application.

The aerosol (WFI alone 44 ml; modified mRNA PEI formulation in WFI: 8, 24 and 44 ml) was nebulized and inhaled into the anaesthetized pig via an Aeroneb® mesh nebulizer. Sedation in pigs was initiated by premedication with azaperone 2 mg/kg body weight, ketamine 15 mg/kg body weight, atropine 0.1 mg/kg body weight and followed by insertion of an intravenous line to the lateral auricular vein. Pigs were anesthetized by intravenous injection of propofol 3-5 mg/kg body weight as required. Anesthesia was maintained by isoflurane (2-3%) with 1% propofol bolus injection at 4 to 8 mg/kg body weight to enhance anesthesia as required. Duration of the anesthesia was approximately 1-3 hrs. Pigs were sacrificed with bolus injection of pentobarbital (100 mg/kg body weight) and potassium chloride via the lateral ear vein 24 hours after completion of aerosolization. Lungs were excised and tissue specimens were collected from various lung regions. The stored samples were subjected to different assessment methods such as bioluminescence, histopathology, IP/Western Blot and Elisa.

Bioluminescence Analysis.

For measurement of luciferase activity tissue specimens were either homogenized and analyzed in a tube luminometer or incubated in a medium bath comprising D-Luciferin substrate and subjected to ex vivo luciferase BLI. The data illustrates that a strong bioluminescence signal was observed for each of cohorts 2-4 (1 mg, 5, mg and 10 mgs respectively), when compared to control lung tissue samples from cohort 1 (WFI vehicle control) (FIGS. 35-38).

CFTR Expression Analysis by Western Blot and Immunohistochemistry.

Figure 39:
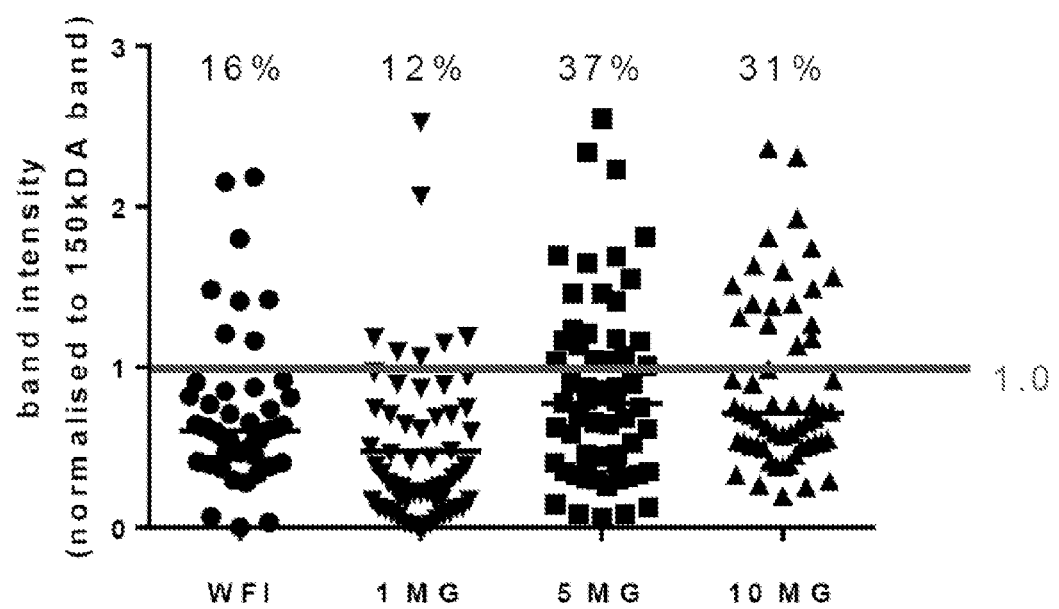
FIG. 39. Relative quantification of CFTR expression in different chorots. Band intensities were normalized to 150 kDa band in the protein ladder.

FFL positive tissues samples were excised (minimum of 10 samples for each pig within a cohort) and analyzed by immunoprecipitation/Western blot (IP-WB) and immunohistochemistry for human CFTR. Briefly, protein lysates were prepared from pig lungs as follows: Between 300-400 mg of lung tissue was used for analysis. The tissue was homogenized in basis buffer (20 mM Tris, 150 mM NaCl, pH 8.0) containing protease inhibitors using LysingMatrixA (MP-Biomedicals, Ref:6910-500) and Homogeniser "Fast-Prep24" (MP Biomedicals). The whole tissue mix was transferred to a new 2 ml safe lock pre-cooled Eppendorf tube and 25 µl iodoacetamide (Sigma: 16125) and 1 µl Omni cleave (1:5 diluted in Omni cleave buffer) (Epicenter: OC7810K) was added. The samples were then incubated on ice for 5 minutes, followed by addition of 26 µl of 10% SDS solution. Samples were further incubated at 4° C. for 60 min on a shaker. Post incubation, 260 µl of lysis buffer (850 µl basis buffer+10% TritonX-100+5% Sodium deoxcholate) was added to the samples and they were incubated at 4° C. on a shaker for 90 minutes. Finally, protein lysates were centrifuged at 13,000 rpm at 4° C. for 10-20 min and the supernatant was transferred into a new Eppendorf tube. Protein concentration was quantified using the BCA Protein Assay (Pierce). Samples were aliquoted containing 10 mg of total protein and end volumes were adjusted with basis buffer to 1 ml per sample. Based on the data presented in Example 6, immunoprecipitation of CFTR was carried out using antibody R24.1 and was followed by Western blot immunodetection of CFTR using a triple combination of three different antibodies obtained from Cystic Fibrosis Consortium, University of Pennsylvania, PA, USA (antibodies 217, 432, 596). To control for intra-group variability among different animals and variability in CFTR expression, the markers band in protein size standard corresponding to 150 kDa was set as reference and the band instensities of different groups were normalized to this value. As demonstrated in FIG. 39, only 16% of the tissues sample analysed form the control pigs of cohort 1 resulted in a CFTR expression level greater than baseline. In contrast, cohorts 3 and 4, which represent the 5 mg and 10 mg treatment groups respectively, each resulted in greater than 30% of their lung tissue samples testing positive for a CFTR expression level higher than baseline (FIG. 39). Furthermore, the increase in CFTR expression observed within cohorts 3 and 4, was almost two fold greater than that of control.

Figure 40:
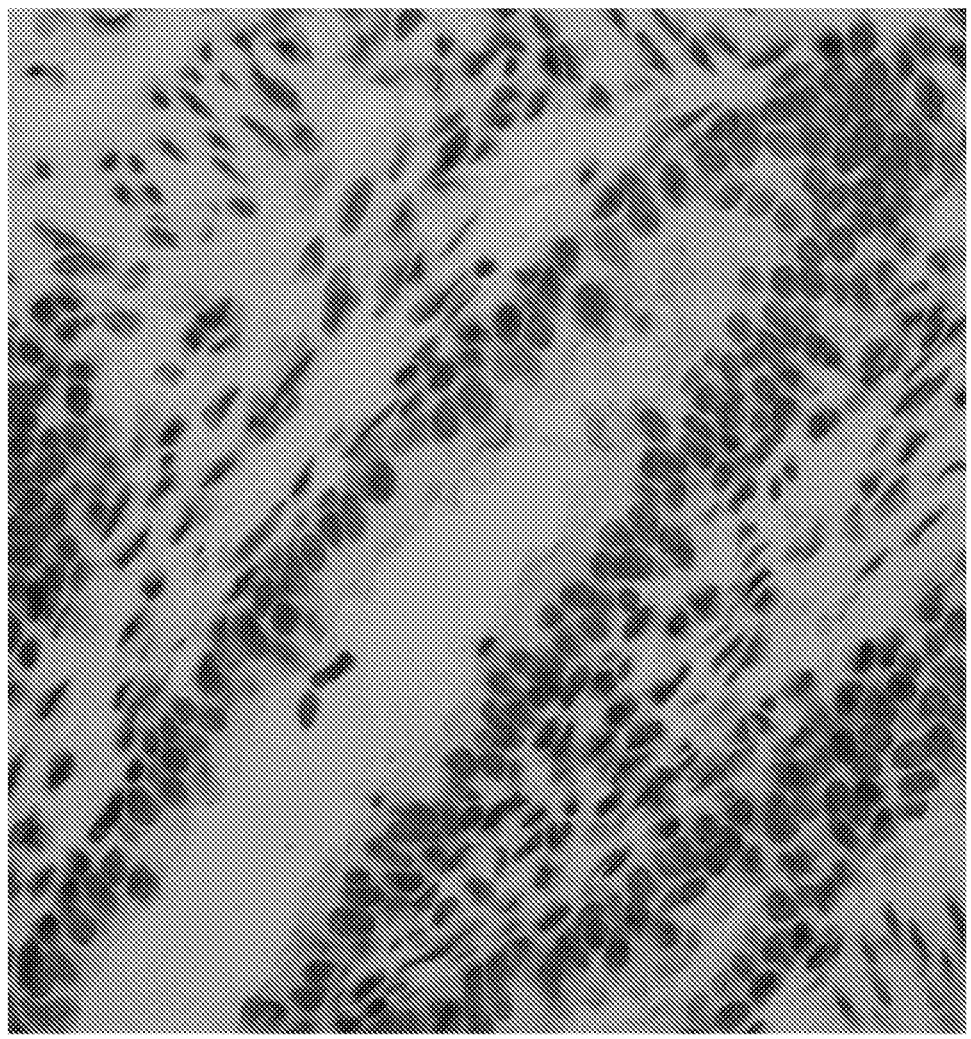
FIG. 40. Representative example of a "CFTR-positive" bronchi with at least one epithelial cell detected within the epithelial cell layer and displaying a clear membrane localized CFTR signal via CFTR immunohistochemical staining using an anti-CFTR antibody.
Figure 41:
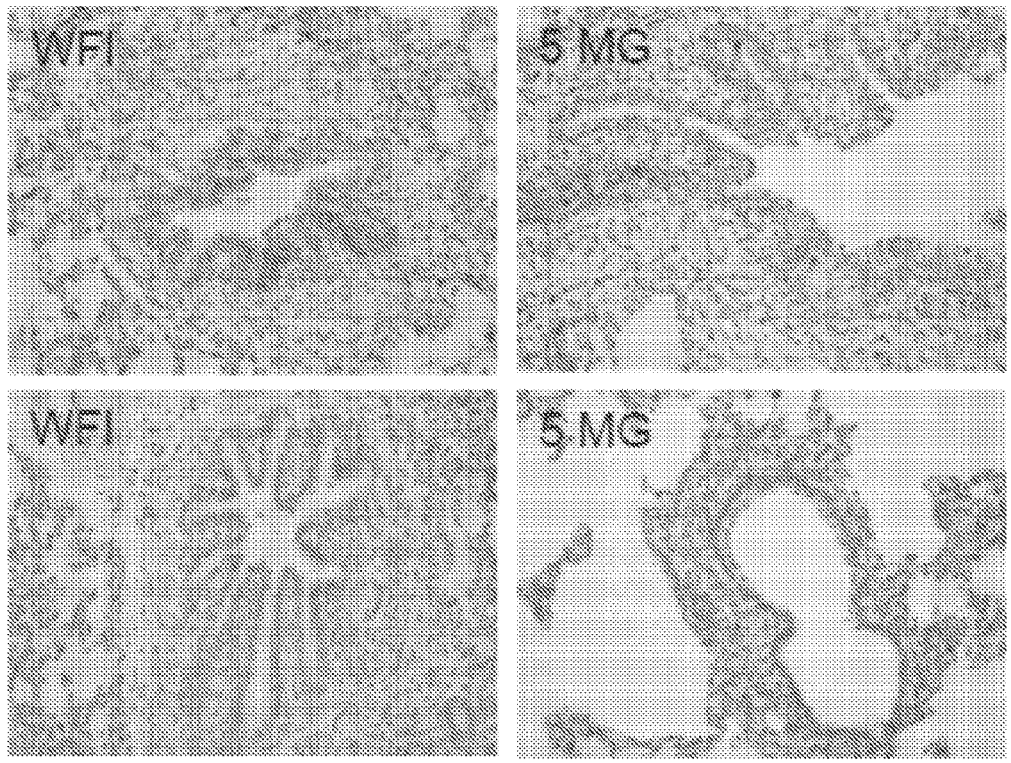
FIG. 41. Immunohistochemical staining of CFTR in porcine lung following aerosol delivery of control (WFI) or 5 mg CO-CFTR SNIM RNA.
Figure 42:
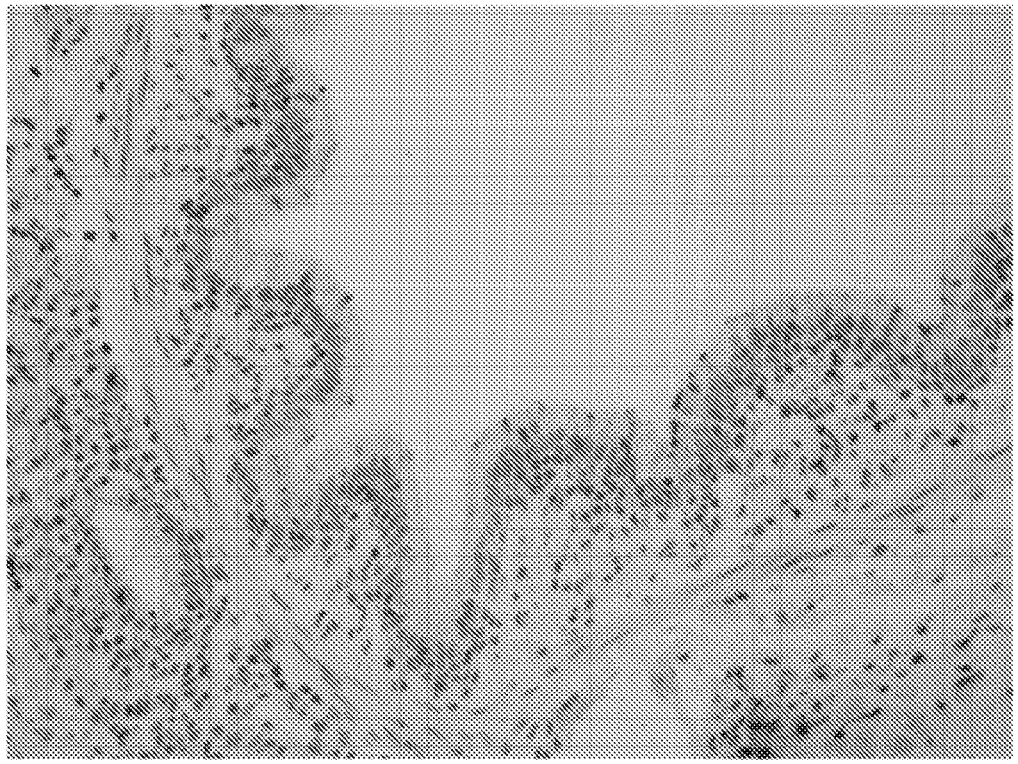
FIG. 42. Represents a "low" CFTR expression level, assayed in porcine lung by immunohistochemical staining with anti-CFTR following aerosol delivery of 5 mg CO-CFTR SNIM RNA.
Figure 43:
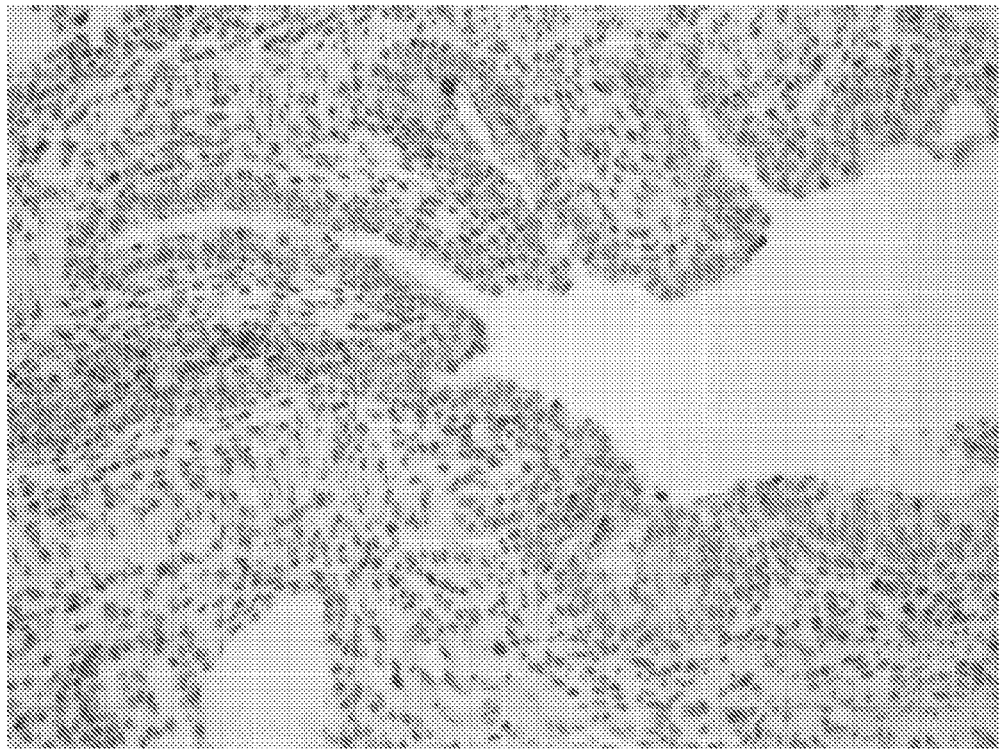
FIG. 43. Represents a "medium" CFTR expression level, assayed in porcine lung by immunohistochemical staining with anti-CFTR following aerosol delivery of 5 mg CO-CFTR SNIM RNA.
Figure 44:
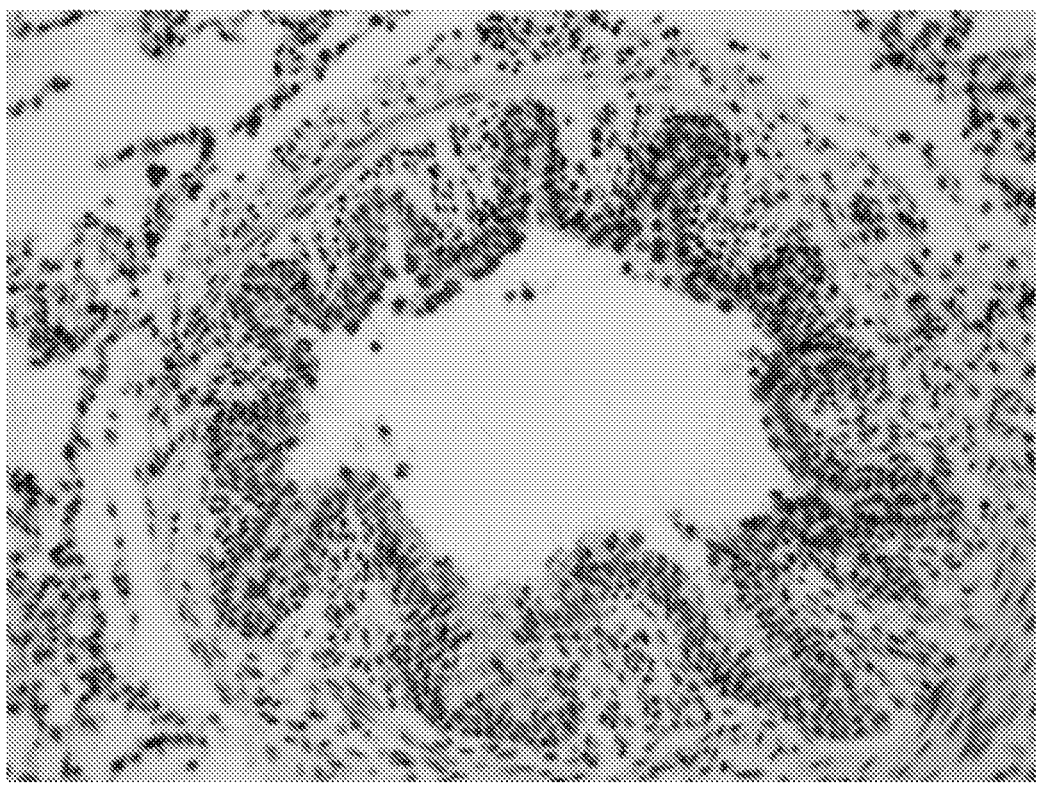
FIG. 44. Represents a "high" CFTR expression level, assayed in porcine lung by immunohistochemical staining with anti-CFTR following aerosol delivery of 5 mg CO-CFTR SNIM RNA.
Figure 45:
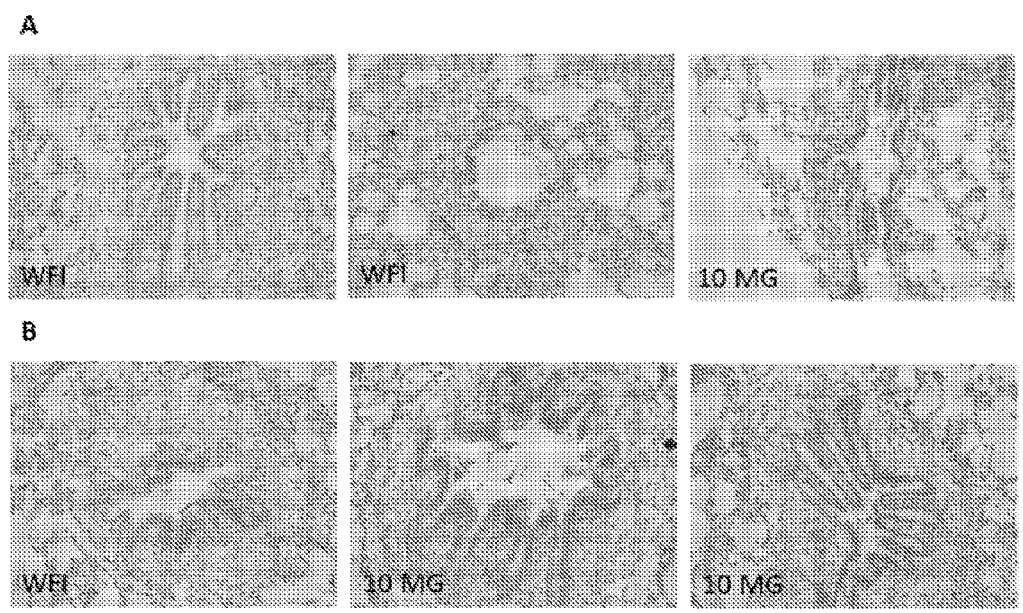
FIG. 45. Immunohistochemical staining of CFTR in porcine lung following aerosol delivery of control (WFI) or 10 mg CO-CFTR SNIM RNA.
Figure 46:
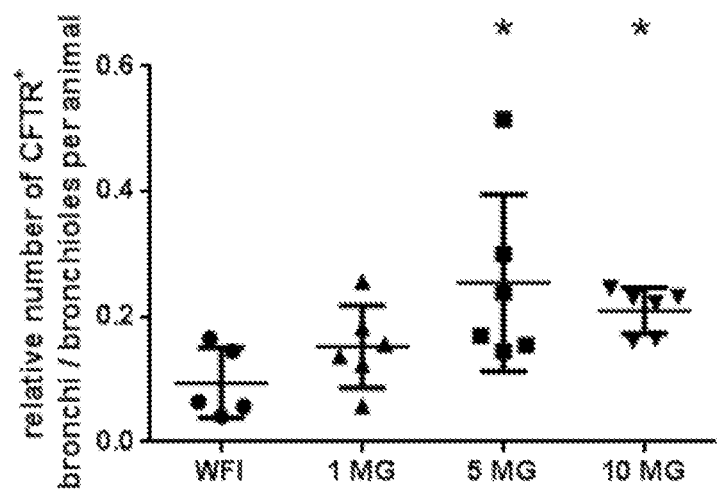
FIG. 46. Quantification of relative numbers of CFTR-positive bronchi/bronchioles per animal. Analysis of each cohort (WFI; and 1 mg, 5 mg, 10 mg human CFTR SNIM RNA) 24 hours post aerosol administration. CFTR expression normalized to signal intensity for 150 kDa protein standard. (WFI=9.4±5.6%, 1 MG=15.2±6.6%, 5 MG=25.4±14.1%, 10 MG=20.9±3.7%; WFI vs 5 MG p=0.0281, WFI vs 10 MG p=0.0174)
Figure 54:
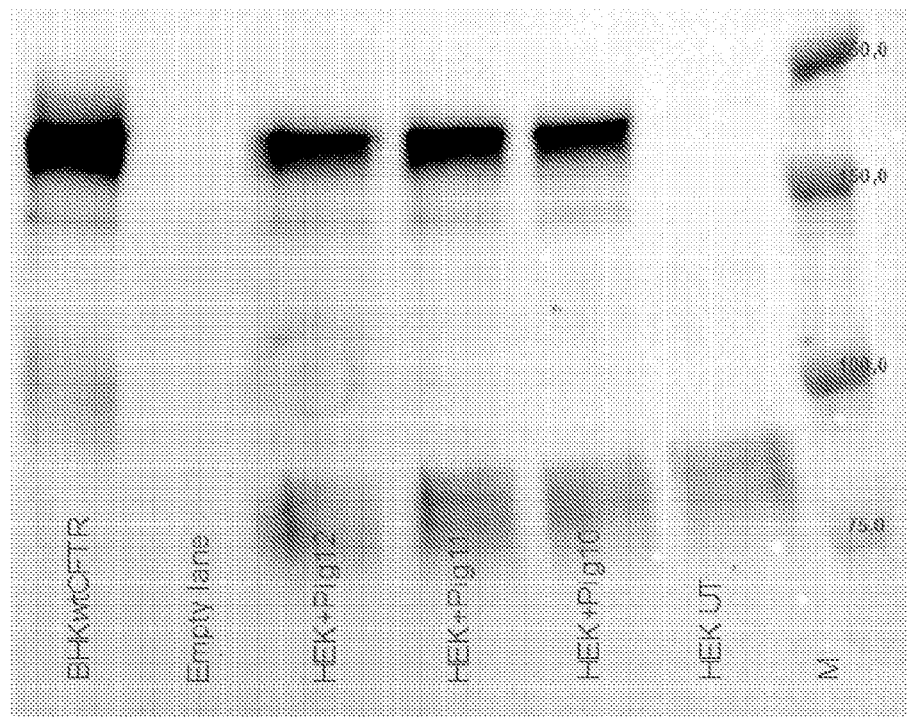
FIG. 54. Illustrates exemplary results of hCFTR expression in HEK cells transfected using neubilized complexes given to pigs 10, 11 and 12 (1 mg dose).
Figure 55:
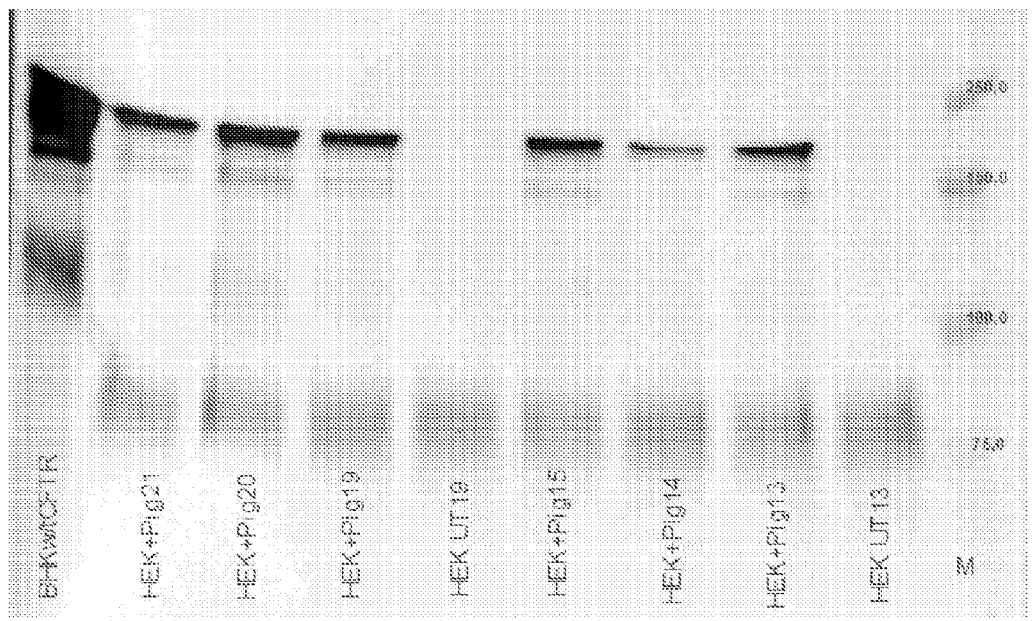
FIG. 55. Illustrates exemplary results of hCFTR expression in HEK cells transfected using neubilized complexes given to pigs 13, 14 and 15 (5 mg dose) and in HEK cells transfected using neubilized complexes given to pigs 19, 20 and 21 (10 mg dose).
Figure 56:
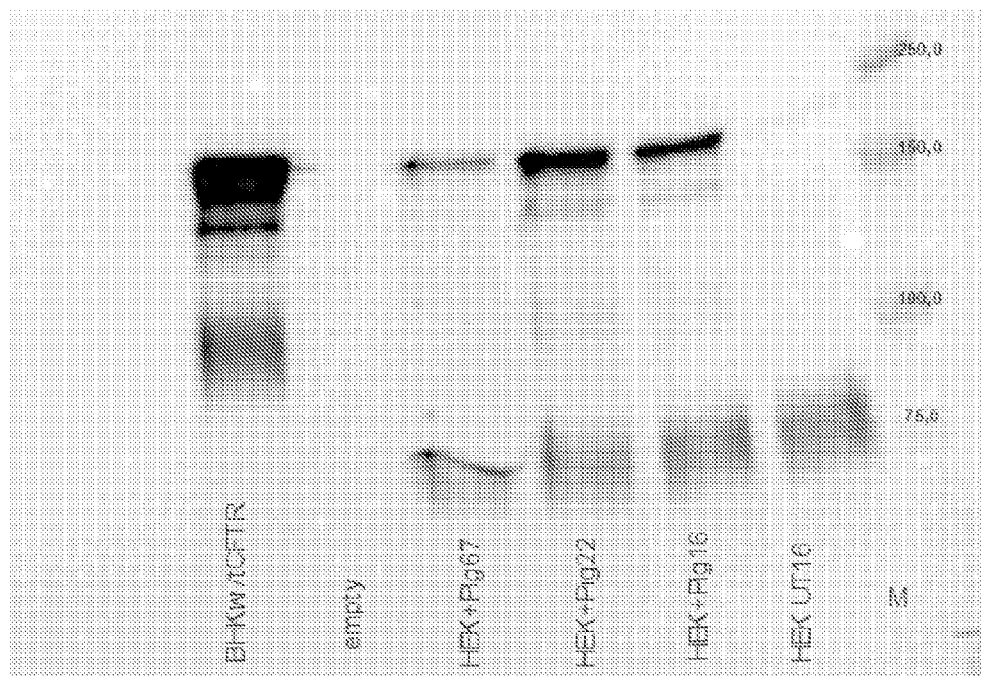
FIG. 56. Illustrates exemplary results of hCFTR expression in HEK cells transfected using neubilized complexes given to pig 16 (5 mg dose), 22 (10 mg dose) and 67 (1 mg dose).
Figure 57:
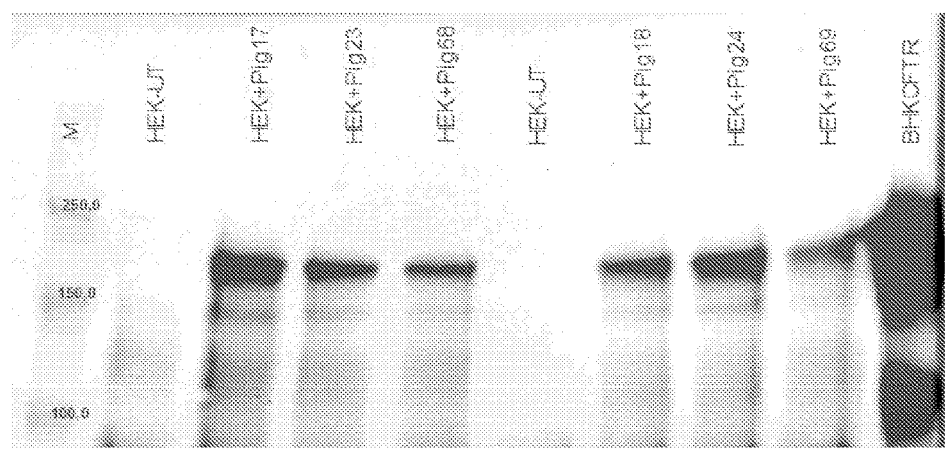
FIG. 57. Illustrates exemplary results of hCFTR expression in HEK cells transfected using neubilized complexes given to pigs 17, 18 (5 mg dose), 23, 24 (10 mg dose) and 68, 69 (1 mg dose).

Analysis of CFTR immunohistochemistry was performed by quantification of CFTR-positive bronchi and bronchioles. A bronchus/bronchiole was regarded as positive if at least one epithelial cell was detected within the epithelial cell layer displaying a clear membrane-localized CFTR signal. A representative image of a "positive" sample is depicted in FIG. 40. Conditions for CFTR immunohistochemistry were optimized by assessing specificity of available antibodies against CFTR utilizing single antibody or combinations of up to three antibodies respectively. Clear CFTR-specific signals were observed after incubation of antibody 596. The data demonstrates, that CFTR-positive epithelial cells were detected in lung tissue sections of all four cohorts, demonstrating detection of human and porcine CFTR by the immunohistochemistry procedure (FIGS. 41 and 45). While low (FIG. 42), medium (FIG. 43) and high (FIG. 44) CFTR expression levels were observed for cohort 3, the overall finding demonstrates that the 5 mg treatment of codon optimized human CFTR SNIM RNA resulted in a greater number of CFTR positive cells and overall CFTR signal intensity compared to vehicle control. The data also illustrates a yet further enhancement of CFTR expression following 10 mg treatment, thus demonstrating a clear dose response effect (FIG. 45). Quantification of absolute and relative numbers of CFTR-positive bronchi/bronchioles further support these findings, revealing a significant higher numbers in animals which were treated with 5 or 10 mg of human CFTR SNIM RNA compared to vehicle control (FIG. 46). Indicating an overall elevation in CFTR expression levels following treatment with human CFTR SNIM RNA.

CFTR Expression Analysis by In Situ Hybridization (ISH).

FFL positive tissues samples were excised (minimum of 10 samples for each pig within a cohort) and subjected to manual in situ hybridization analysis using the RNAscope® (Advanced Cell Diagnostic) "ZZ" probe technology. Probes were generated based on the codon-optimized sequence of codon optimized human CFTR SNIM RNA (SEQ ID NO:17). Briefly, the RNAscope® assay is an in situ hybridication assay designed to visualize single RNA molecules per cell in formalin-fixed, paraffin-embedded (FFPE) tissue mounted on slides. Each embedded tissue sample was pretreated according to the manufacturers protocol and incubated with a target specific human CFTR specific RNA probe. The hCFTR probe was shown bind CFTR, with cross reactivity to human, mouse, rat, pig and monkey. Once bound, the probe is hybridized to a cascade of signal amplification molecules, through a series of 6 consecutive rounds of amplification. The sample was then treated with an HRP-labeled probe specific to the signal amplification cassette and assayed by chromatic visualization using 3,3'-diaminobenzidine (DAB). A probe specific for Ubiquitin C was used as the positive control (FIGS. 47A and 48A), while dapB was used as the negative control (FIGS. 47B and 48B). Positive CFTR signal was compared to that of untreated and vehicle control treated porcine lung tissue (FIGS. 49A and 49B). Stained samples were visualized under a standard bright field microscope. The data demonstrates that treatment with 1 mg of codon optimized human CFTR SNIM RNA resulted in a dramatic increase in CFTR expression in both the right (A) and left (B) lung tissue of corhort 2, when compared to vehicle control (FIGS. 49A-49B and 50A & 50B) Furthermore, a further increase in CFTR expression was observed for the 5 mg and 10 mg treatment groups, as demonstrated by a dramatic increase staining observed within the right (A) and left (B) lung samples analyzed for cohorts 3 and 4 (FIGS. 51A-51B and 52A & 52B). Taken together, these data strongly supports the effective delivery of mRNA via inhalation and expression of human CFTR within both lobes of the lung and their various tissues.

Conclusion.

The results demonstrated that both luciferase and CFTR mRNA can be effectively delivered in vivo to lung tissues. Luciferase expression was observed throughout various tissue samples collected from different regions within both the right and left lobs of the lungs. Thus suggestions, that nebulization is an effective approach for administering mRNA and results in fairly uniform distribution. Furthermore, in addition to luciferase, CFTR mRNA was also efficiently delivered to the lungs, resulting in enhanced protein expression. Expression and protein activity was verified by IP-WB, immunohistochemistry and in situ hybridization. Each approach clearly demonstrated a dose dependent increase in mRNA delivery and CFTR expression and/or activity, within the tissues of the lung. Taken together, the experiments highlight the overall practicality and feasibility for delivering CFTR mRNA to the lung of a human subject and demonstrate the effectiveness of in vivo CFTR protein production for therapeutic use.

Example 12: In Vivo Expression in the Lung

This example desmonstrates successful in vivo expression in the lung following aerosol delivery of mRNA-loaded nanoparticles. All studies were performed using pigs of the German Landrace, obtained from Technical University Munich, Weihenstephan, Germany. The pigs had a body weight ranging from 35-90 kg. FFL/CO-CFTR-C-His10 mRNA formulation or vehicle control was introduced using a Pari jet nebulizer. Pigs were sacrificed and perfused with saline, after a predetermined period of time, to allow for protein expression from the mRNA.

Messenger RNA Synthesis.

In the example, codon optimized fire fly luciferase (CO-FFL) mRNA was synthesized by in vitro transcription from plasmid DNA templates.

cKK-E12 Formulation.

For the lipid-based nanoparticle experiment, a lipid formulation was created using 1 mg FFL+9 mg of CO-CFTR-C-His$_{10}$ mRNA encapsulated in a formulation of cKK-E12:DOPE:Chol:PEGDMG2K (relative amounts 40:30:25:5 (mol ratio). The solution was nebulized to the Pig lungs using the indicated nebulizer.

Aerosol Application.

The aerosol (Saline or CO-FFL cKK-E12 formulation) was nebulized and inhaled into the anaesthetized pig. Sedation in pigs was initiated by premedication with azaperone 2 mg/kg body weight, ketamine 15 mg/kg body weight, atropine 0.1 mg/kg body weight and followed by insertion of an intravenous line to the lateral auricular vein. Pigs were anesthetized by intravenous injection of propofol 3-5 mg/kg body weight as required. Anesthesia was maintained by isoflurane (2-3%) with 1% propofol bolus injection at 4 to 8 mg/kg body weight to enhance anesthesia as required. Duration of the anesthesia was approximately 1-3 hrs. Pigs were killed with bolus injection of pentobarbital (100 mg/kg body weight) and potassium chloride via the lateral ear vein. Lungs were excised and tissue specimens were collected from various lung regions followed by incubation in cell culture medium overnight. The stored samples were subjected to bioluminescence detection.

Bioluminescence Analysis.

For measurement of luciferase activity tissue specimens were either homogenized and analyzed in a tube luminometer or incubated in a medium bath comprising D-Luciferin substrate and subjected to ex vivo luciferase BLI. A strong bioluminescence signal was observed for each of the (A) FFL/CO-CFTR-C-His10 mRNA treated pigs, when compared to (B) control lung tissue samples from control pigs (Saline vehicle control) (FIGS. 53 A&B).

These data illustrate that FFL/CFTR mRNA were successfully delivered to and expressed in the lung by aerosol administration.

BRIEF DESCRIPTION OF SEQUENCES

SEQ ID NO 1. Wild-type CFTR amino acid sequence.
SEQ ID NO 2. Wild-type CFTR mRNA coding sequence.
SEQ ID NO 3. Non-naturally occurring CFTR mRNA coding sequence #1.
SEQ ID NO 4. CFTR mRNA 5'-UTR.
SEQ ID NO 5. CFTR mRNA 3'-UTR #1.
SEQ ID NO 6. FFL 5' UTR.
SEQ ID NO 7. FFL coding sequence.
SEQ ID NO 8. FFL 3' UTR.
SEQ ID NO 9. Non-naturally occurring CFTR mRNA coding sequence #2.
SEQ ID NO 10. Non-naturally occurring CFTR mRNA coding sequence #3.
SEQ ID NO 11. Non-naturally occurring CFTR mRNA coding sequence #4.
SEQ ID NO 12. Non-naturally occurring CFTR mRNA coding sequence #5.
SEQ ID NO 13. Non-naturally occurring CFTR mRNA coding sequence #6.
SEQ ID NO 14. Non-naturally occurring CFTR mRNA coding sequence #7.
SEQ ID NO 15. Codon Optimized Human CFTR C-terminal $His_{10}$ fusion mRNA coding sequence.
SEQ ID NO 16. Codon Optimized Human CFTR mRNA coding sequence with a Growth Hormone Leader Sequence.
SEQ ID NO 17. Codon Optimized Human CFTR mRNA
SEQ ID NO 18. mRNA Leader Sequence #1
SEQ ID NO 19. mRNA Leader Sequence #2
SEQ ID NO 20. CFTR mRNA 3'-UTR #2.

```
SEQ ID NO: 1
                                                     (SEQ ID NO: 1)
MQRSPLEKASVVSKLFFSWTRPILRKGYRQRLELSDIYQIPSVD

SADNLSEKLEREWDRELASKKNPKLINALRRCFFWRFMFYGIFLYLGEVTKAVQPLLL

GRIIASYDPDNKEERSIAIYLGIGLCLLFIVRTLLLHPAIFGLHHIGMQMRIAMFSLI

YKKTLKLSSRVLDKISIGQLVSLLSNNLNKFDEGLALAHFVWIAPLQVALLMGLIWEL

LQASAFCGLGFLIVLALFQAGLGRMMMKYRDQRAGKISERLVITSEMIENIQSVKAYC

WEEAMEKMIENLRQTELKLTRKAAYVRYFNSSAFFFSGFFVVFLSVLPYALIKGIILR

KIFTTISFCIVLRMAVTRQFPWAVQTWYDSLGAINKIQDFLQKQEYKTLEYNLTTTEV

VMENVTAFWEEGFGELFEKAKQNNNNRKTSNGDDSLFFSNFSLLGTPVLKDINFKIER

GQLLAVAGSTGAGKTSLLMVIMGELEPSEGKIKHSGRISFCSQFSWIMPGTIKENIIF

GVSYDEYRYRSVIKACQLEEDISKFAEKDNIVLGEGGITLSGGQRARISLARAVYKDA

DLYLLDSPFGYLDVLTEKEIFESCVCKLMANKTRILVTSKMEHLKKADKILILHEGSS

YFYGTFSELQNLQPDFSSKLMGCDSFDQFSAERRNSILTETLHRFSLEGDAPVSWTET

KKQSFKQTGEFGEKRKNSILNPINSIRKFSIVQKTPLQMNGIEEDSDEPLERRLSLVP

DSEQGEAILPRISVISTGPTLQARRRQSVLNLMTHSVNQGQNIHRKTTASTRKVSLAP

QANLTELDIYSRRLSQETGLEISEEINEEDLKECFFDDMESIPAVTTWNTYLRYITVH

KSLIFVLIWCLVIFLAEVAASLVVLWLLGNTPLQDKGNSTHSRNNSYAVIITSTSSYY

VFYIYVGVADTLLAMGFFRGLPLVHTLITVSKILHHKMLHSVLQAPMSTLNTLKAGGI

LNRFSKDIAILDDLLPLTIFDFIQLLLIVIGAIAVVAVLQPYIFVATVPVIVAFIMLR

AYFLQTSQQLKQLESEGRSPIFTHLVTSLKGLWTLRAFGRQPYFETLFHKALNLHTAN

WFLYLSTLRWFQMRIEMIFVIFFIAVTFISILTTGEGEGRVGIILTLAMNIMSTLQWA

VNSSIDVDSLMRSVSRVFKFIDMPTEGKPTKSTKPYKNGQLSKVMIIENSHVKKDDIW

PSGGQMTVKDLTAKYTEGGNAILENISFSISPGQRVGLLGRTGSGKSTLLSAFLRLLN

TEGEIQIDGVSWDSITLQQWRKAFGVIPQKVFIFSGTFRKNLDPYEQWSDQEIWKVAD

EVGLRSVIEQFPGKLDFVLVDGGCVLSHGHKQLMCLARSVLSKAKILLLDEPSAHLDP

VTYQIIRRTLKQAFADCTVILCEHRIEAMLECQQFLVIEENKVRQYDSIQKLLNERSL

FRQAISPSDRVKLFPHRNSSKCKSKPQIAALKEETEEEVQDTRL
```

-continued

SEQ ID NO: 2

(SEQ ID NO: 2)
AUGCAGAGGUCGCCUCUGGAAAAGGCCAGCGUUGUCUCCAAACUUUUUUCAGCUGGACC

AGACCAAUUUUGAGGAAAGGAUACAGACAGCGCCUGGAAUUGUCAGACAUAUACCAAAU

CCCUUCUGUUGAUUCUGCUGACAAUCUAUCUGAAAAAUUGGAAAGAGAAUGGGAUAGAG

AGCUGGCUUCAAAGAAAAAUCCUAAACUCAUUAAUGCCCUUCGGCGAUGUUUUUUCUGG

AGAUUUAUGUUCUAUGGAAUCUUUUUAUAUUUAGGGGAAGUCACCAAAGCAGUACAGCC

UCUCUUACUGGGAAGAAUCAUAGCUUCCUAUGACCCGGAUAACAAGGAGGAACGCUCUA

UCGCGAUUUAUCUAGGCAUAGGCUUAUGCCUUCUCUUUAUUGUGAGGACACUGCUCCUAC

ACCCAGCCAUUUUUGGCCUUCAUCACAUUGGAAUGCAGAUGAGAAUAGCUAUGUUUAGU

UUGAUUUAUAAGAAGACUUUAAAGCUGUCAAGCCGUGUUCUAGAUAAAAUAAGUAUUGG

ACAACUUGUUAGUCUCCUUUCCAACAACCUGAACAAAUUUGAUGAAGGACUUGCAUUGG

CACAUUUCGUGUGGAUCGCUCCUUUGCAAGUGGCACUCCUCAUGGGGCUAAUCUGGGAGU

UGUUACAGGCGUCUGCCUUCUGUGGACUUGGUUUCCUGAUAGUCCUUGCCCUUUUUCAGG

CUGGGCUAGGGAGAAUGAUGAUGAAGUACAGAGAUCAGAGAGCUGGGAAGAUCAGUGAA

AGACUUGUGAUUACCUCAGAAAUGAUUGAAAAUAUCCAAUCUGUUAAGGCAUACUGCUG

GGAAGAAGCAAUGGAAAAAAUGAUUGAAAACUUAAGACAAACAGAACUGAAACUGACUC

GGAAGGCAGCCUAUGUGAGAUACUUCAAUAGCUCAGCCUUCUUCUUCUCAGGGUUCUUU

GUGGUGUUUUUAUCUGUGCUUCCCUAUGCACUAAUCAAAGGAAUCAUCCUCCGGAAAAU

AUUCACCACCAUCUCAUUCUGCAUUGUUCUGCGCAUGGCGGUCACUCGGCAAUUUCCCUG

GCUGUACAAACAUGGUAUGACUCUCUUGGAGCAAUAAACAAAAUACAGGAUUUCUUAC

AAAAGCAAGAAUAUAAGACAUUGGAAUAUAACUUAACGACUACAGAAGUAGUGAUGGAG

AAUGUAACAGCCUUCUGGGAGGAGGGAUUUGGGGAAUUAUUUGAGAAAGCAAAACAAAA

CAAUAACAAUAGAAAAACUUCUAAUGGUGAUGACAGCCUCUUCUUCAGUAAUUUCUCAC

UUCUUGGUACUCCUGUCCUGAAAGAUAUUAAUUUCAAGAUAGAAAGAGGACAGUUGUUG

GCGGUUGCUGGAUCCACUGGAGCAGGCAAGACUUCACUUCUAAUGAUGAUUAUGGGAGA

ACUGGAGCCUUCAGAGGGUAAAAUUAAGCACAGUGGAAGAAUUUCAUUCUGUUCUCAGU

UUUCCUGGAUUAUGCCUGGCACCAUUAAAGAAAAUAUCAUCUUUGGUGUUUCCUAUGAU

GAAUAUAGAUACAGAAGCGUCAUCAAAGCAUGCCAACUAGAAGAGGACAUCUCCAAGUU

UGCAGAGAAAGACAAUAUAGUUCUUGGAGAAGGUGGAAUCACACUGAGUGGAGGUCAAC

GAGCAAGAAUUUCUUUAGCAAGAGCAGUAUACAAAGAUGCUGAUUUGUAUUUAUUAGAC

UCUCCUUUUGGAUACCUAGAUGUUUUAACAGAAAAGAAAUAUUUGAAAGCUGUGUCUG

UAAACUGAUGGCUAACAAAACUAGGAUUUUGGUCACUUCUAAAAUGGAACAUUUAAAGA

AAGCUGACAAAAUAUUAAUUUUGAAUGAAGGUAGCAGCUAUUUUUAUGGGACAUUUUCA

GAACUCCAAAAUCUACAGCCAGACUUUAGCUCAAAACUCAUGGGGAUGUGAUUCUUUCGAC

CAAUUUAGUGCAGAAAGAAGAAAUUCAAUCCUAACUGAGACCUUACACCGUUUCUCAUU

AGAAGGAGAUGCUCCUGUCUCCUGGACAGAAACAAAAAAACAAUCUUUUAAACAGACUG

GAGAGUUUGGGAAAAAGGAAGAAUUCUAUUCUCAAUCCAAUCAACUCUAUACGAAAA

UUUUCCAUUGUGCAAAAGACUCCCUUACAAAUGAAUGGCAUCGAAGAGGAUUCUGAUGA

GCCUUUAGAGAAGGCUGUCCUUAGUACCAGAUUCUGAGCAGGGAGAGGCGAUACUGC

CUCGCAUCAGCGUGAUCAGCACUGGCCCCACGCUUCAGGCACGAAGGAGGCAGUCUGUCC

UGAACCUGAUGACACACUCAGUUAACCAAGGUCAGAACAUUCACCGAAAGACAACAGCAU

-continued

```
CCACACGAAAAGUGUCACUGGCCCCUCAGGCAAACUUGACUGAACUGGAUAUAUAUUCAA

GAAGGUUAUCUCAAGAAACUGGCUUGGAAAUAAGUGAAGAAAUUAACGAAGAAGACUUA

AAGGAGUGCCUUUUUGAUGAUAUGGAGAGCAUACCAGCAGUGACUACAUGGAACACAUA

CCUUCGAUAUAUUACUGUCCACAAGAGCUUAAUUUUUGUGCUAAUUUGGUGCUUAGUAA

UUUUUCUGGCAGAGGUGGCUGCUUCUUUGGUUGUGCUGUGGCUCCUUGGAAACACUCCU

CUUCAAGACAAAGGGAAUAGUACUCAUAGUAGAAAUAACAGCUAUGCAGUGAUUAUCAC

CAGCACCAGUUCGUAUUAUGUGUUUUACAUUUACGUGGGAGUAGCCGACACUUUGCUUG

CUAUGGGAUUCUUCAGAGGUCUACCACUGGUGCAUACUCUAAUCACAGUGUCGAAAAUU

UUACACCACAAAAUGUUACAUUCUGUUCUUCAAGCACCUAUGUCAACCCUCAACACGUUG

AAAGCAGGUGGGAUUCUUAAUAGAUUCUCCAAAGAUAUAGCAAUUUUGGAUGACCUUCU

GCCUCUUACCAUAUUUGACUUCAUCCAGUUGUUAUUAAUUGUGAUUGGAGCUAUAGCAG

UUGUCGCAGUUUUACAACCCUACAUCUUUGUUGCAACAGUGCCAGUGAUAGUGGCUUUU

AUUAUGUUGAGAGCAUAUUUCCUCCAAACCUCACAGCAACUCAAACAACUGGAAUCUGAA

GGCAGGAGUCCAAUUUUCACUCAUCUUGUUACAAGCUUAAAAGGACUAUGGACACUUCG

UGCCUUCGGACGGCAGCCUUACUUUGAAACUCUGUUCCACAAAGCUCUGAAUUUACAUAC

UGCCAACUGGUUCUUGUACCUGUCAACACUGCGCUGGUUCCAAAUGAGAAUAGAAAUGA

UUUUUGUCAUCUUCUUCAUUGCUGUUACCUUCAUUUCCAUUUUAACAACAGGAGAAGGA

GAAGGAAGAGUUGGUAUUAUCCUGACUUUAGCCAUGAAUAUCAUGAGUACAUUGCAGUG

GGCUGUAAACUCCAGCAUAGAUGUGGAUAGCUUGAUGCGAUCUGUGAGCCGAGUCUUUA

AGUUCAUUGACAUGCCAACAGAAGGUAAACCUACCAAGUCAACCAAACCAUACAAGAAUG

GCCAACUCUCGAAAGUUAUGAUUAUUGAGAAUUCACACGUGAAGAAAGAUGACAUCUGG

CCCUCAGGGGGCCAAAUGACUGUCAAAGAUCUCACAGCAAAAUACACAGAAGGUGGAAA

UGCCAUAUUAGAGAACAUUUCCUUCUCAAUAAGUCCUGGCCAGAGGGUGGGCCUCUUGG

GAAGAACUGGAUCAGGGAAGAGUACUUUGUUAUCAGCUUUUUUGAGACUACUGAACACU

GAAGGAGAAAUCCAGAUCGAUGGUGUGUCUUGGGAUUCAAUAACUUUGCAACAGUGGAG

GAAAGCCUUUGGAGUGAUACCACAGAAAGUAUUUAUUUUUUCUGGAACAUUUAGAAAAA

ACUUGGAUCCCUAUGAACAGUGGAGUGAUCAAGAAAUAUGGAAAGUUGCAGAUGAGGUU

GGGCUCAGAUCUGUGAUAGAACAGUUUCCUGGGAAGCUUGACUUUGUCCUUGUGGAUGG

GGGCUGUGUCCUAAGCCAUGGCCACAAGCAGUUGAUGUGCUUGGCUAGAUCUGUUCUCA

GUAAGGCGAAGAUCUUGCUGCUUGAUGAACCCAGUGCUCAUUUGGAUCCAGUAACAUAC

CAAAUAAUUAGAAGAACUCUAAAAACAAGCAUUUGCUGAUUGCACAGUAAUUCUCUGUGA

ACACAGGAUAGAAGCAAUGCUGGAAUGCCAACAAUUUUUGGUCAUAGAAGAGAACAAAG

UGCGGCAGUACGAUUCCAUCCAGAAACUGCUGAACGAGAGGAGCCUCUUCCGGCAAGCCA

UCAGCCCCUCCGACAGGGUGAAGCUCUUUCCCCACCGGAACUCAAGCAAGUGCAAGUCUA

AGCCCCAGAUUGCUGCUCUGAAAGAGGAGACAGAAGAAGAGGUGCAAGAUACAAGGCUU

UAG
```

SEQ ID NO: 3

(SEQ ID NO: 3)
```
AUGCAGCGGUCCCCGCUCGAAAAGGCCAGUGUCGUGUCCAAACUCUUCUUCUCAUGGACU

CGGCCUAUCCUUAGAAAGGGGUAUCGGCAGAGGCUUGAGUUGUCUGACAUCUACCAGAU

CCCCUCGGUAGAUUCGGCGGAUAACCUCUCGGAGAAGCUCGAACGGGAAUGGGACCGCGA

ACUCGCGUCUAAGAAAAACCCGAAGCUCAUCAACGCACUGAGAAGGUGCUUCUUCUGGCG
```

```
GUUCAUGUUCUACGGUAUCUUCUUGUAUCUCGGGGAGGUCACAAAAGCAGUCCAACCCCU

GUUGUUGGGUCGCAUUAUCGCCUCGUACGACCCCGAUAACAAAGAAGAACGGAGCAUCGC

GAUCUACCUCGGGAUCGGACUGUGUUUGCUUUUCAUCGUCAGAACACUUUUGUUGCAUCC

AGCAAUCUUCGGCCUCCAUCACAUCGGUAUGCAGAUGCGAAUCGCUAUGUUUAGCUUGAU

CUACAAAAGACACUGAAACUCUCGUCGCGGGUGUUGGAUAAGAUUUCCAUCGGUCAGU

UGGUGUCCCUGCUUAGUAAUAACCUCAACAAAUUCGAUGAGGGACUGGCGCUGGCACAU

UUCGUGUGGAUUGCCCCGUUGCAAGUCGCCCUUUUGAUGGGCCUUAUUUGGGAGCUGUU

GCAGGCAUCUGCCUUUUGUGGCCUGGGAUUUCUGAUUGUGUUGGCAUUGUUUCAGGCUG

GGCUUGGGCGGAUGAUGAUGAAGUAUCGCGACCAGAGAGCGGGUAAAAUCUCGGAAAGA

CUCGUCAUCACUUCGGAAAUGAUCGAAAACAUCCAGUCGGUCAAAGCCUAUUGCUGGGAA

GAAGCUAUGGAGAAGAUGAUUGAAAACCUCCGCCAAACUGAGCUGAAACUGACCCGCAA

GGCGGCGUAUGUCCGGUAUUUCAAUUCGUCAGCGUUCUUCUUUUCCGGGUUCUUCGUUG

UCUUUCUCUCGGUUUUGCCUUAUGCCUUGAUUAAGGGGAUUAUCCUCCGCAAGAUUUUC

ACCACGAUUUCGUUCUGCAUUGUAUUGCGCAUGGCAGUGACACGGCAAUUUCCGUGGGCC

GUGCAGACAUGGUAUGACUCGCUUGGAGCGAUCAACAAAAUCCAAGACUUCUUGCAAAA

GCAAGAGUACAAGACCCUGGAGUACAAUCUUACUACUACGGAGGUAGUAAUGGAGAAUG

UGACGGCUUUUUGGGAAGAGGGUUUUGGAGAACUGUUUGAGAAAGCAAAGCAGAAUAAC

AACAACCGCAAGACCUCAAAUGGGGACGAUUCCCUGUUUUUCUCGAACUUCUCCCUGCUC

GGAACACCCGUGUUGAAGGACAUCAAUUUCAAGAUUGAGAGGGGACAGCUUCUCGCGGU

AGCGGGAAGCACUGGUGCGGGAAAAACUAGCCUCUUGAUGGUGAUUAUGGGGGAGCUUG

AGCCCAGCGAGGGGAAGAUUAAACACUCCGGGCGUAUCUCAUUCUGUAGCCAGUUUUCAU

GGAUCAUGCCCGGAACCAUUAAAGAGAACAUCAUUUUCGGAGUAUCCUAUGAUGAGUAC

CGAUACAGAUCGGUCAUUAAGGCGUGCCAGUUGGAAGAGGACAUUUCUAAGUUCGCCGA

GAAGGAUAACAUCGUCUUGGGAGAAGGGGGUAUUACAUUGUCGGGAGGGCAGCGAGCGC

GGAUCAGCCUCGCGAGAGCGGUAUACAAAGAUGCAGAUUUGUAUCUGCUUGAUUCACCG

UUUGGAUACCUCGACGUAUUGACAGAAAAAGAAAUCUUCGAGUCGUGCGUGUGUAAACU

UAUGGCUAAUAAGACGAGAAUCCGGUGCAUCAAAAAUGGAACACCUUAAGAAGGCGG

ACAAGAUCCUGAUCCUCCACGAAGGAUCGUCCUACUUUUACGGCACUUUCUCAGAGUUGC

AAAACUUGCAGCCGGACUUCUCAAGCAAACUCAUGGGGUGUGACUCAUUCGACCAGUUCA

GCGCGGAACGGCGGAACUCGAUCUUGACGGAAACGCUGCACCGAUUCUCGCUUGAGGGUG

AUGCCCCGGUAUCGUGGACCGAGACAAAGAAGCAGUCGUUUAAGCAGACAGGAGAAUUU

GGUGAGAAAAGAAAGAACAGUAUCUUGAAUCCUAUUAACUCAAUUCGCAAGUUCUCAAU

CGUCCAGAAAACUCCACUGCAGAUGAAUGGAAUUGAAGAGGAUUCGGACGAACCCCUGG

AGCGCAGGCUUAGCCUCGUGCCGGAUUCAGAGCAAGGGGAGGCCAUUCUUCCCCGGAUUU

CGGUGAUUUCAACCGGACCUACACUUCAGGCGAGGCGAAGGCAAUCCGUGCUCAACCUCA

UGACGCAUUCGGUAAACCAGGGGCAAAACAUUCACCGCAAAACGACGGCCUCAACGAGAA

AAGUGUCACUUGCACCCCAGGCGAAUUUGACUGAACUCGACAUCUACAGCCGUAGGCUUU

CGCAAGAAACCGGACUUGAGAUCAGCGAAGAAAUCAAUGAAGAAGAUUUGAAAGAGUGU

UUCUUUGAUGACAUGGAAUCAAUCCCAGCGGUGACAACGUGGAACACAUACUUGCGUUA

CAUCACGGUGCACAAGUCCUUGAUUUUCGUCCUCAUCGGUGUCUCGUGAUCUUUCUCGC

UGAGGUCGCAGCGUCACUUGUGGUCCUCUGGCUGCUUGGUAAUACGCCCUUGCAAGACAA
```

-continued

AGGCAAUUCUACACACUCAAGAAACAAUUCCUAUGCCGUGAUUAUCACUUCUACAAGCUC
GUAUUACGUGUUUUACAUCUACGUAGGAGUGGCCGACACUCUGCUCGCGAUGGGUUUCU
UCCGAGGACUCCCACUCGUUCACACGCUUAUCACUGUCUCCAAGAUUCUCCACCAUAAGA
UGCUUCAUAGCGUACUGCAGGCUCCCAUGUCCACCUUGAAUACGCUCAAGGCGGGAGGUA
UUUUGAAUCGCUUCUCAAAAGAUAUUGCAAUUUGGAUGACCUUCUGCCCCUGACGAUC
UUCGACUUCAUCCAGUUGUUGCUGAUCGUGAUUGGGCUAUUGCAGUAGUCGCUGUCCU
CCAGCCUUACAUUUUUGUCGCGACCGUUCCGGUGAUCGUGGCGUUUAUCAUGCUGCGGGC
CUAUUUCUUGCAGACGUCACAGCAGCUUAAGCAACUGGAGUCUGAAGGGAGGUCGCCUA
UCUUUACGCAUCUUGUGACCAGUUUGAAGGGAUUGUGGACGUUGCGCGCCUUUGGCAGG
CAGCCCUACUUUGAAACACUGUUCCACAAAGCGCUGAAUCUCCAUACGGCAAAUUGGUUU
UUGUAUUUGAGUACCCUCCGAUGGUUUCAGAUGCGCAUUGAGAUGAUUUUUGUGAUCUU
CUUUAUCGCGGUGACUUUUAUCUCCAUCUUGACCACGGGAGAGGGCGAGGGACGGGUCG
GUAUUAUCCUGACACUCGCCAUGAACAUUAUGAGCACUUUGCAGUGGGCAGUGAACAGC
UCGAUUGAUGUGGAUAGCCUGAUGAGGUCCGUUUCGAGGGUCUUUAAGUUCAUCGACAU
GCCGACGGAGGGAAAGCCCACAAAAAGUACGAAACCCUAUAAGAAUGGGCAAUUGAGUA
AGGUAAUGAUCAUCGAGAACAGUCACGUGAAGAAGGAUGACAUCUGGCCUAGCGGGGGU
CAGAUGACCGUGAAGGACCUGACGGCAAAAUACACCGAGGGAGGGAACGCAAUCCUUGA
AAACAUCUCGUUCAGCAUUAGCCCCGGUCAGCGUGUGGGUUGCUCGGGAGGACCGGGUC
AGGAAAAUCGACGUUGCUGUCGGCCUUCUUGAGACUUCUGAAUACAGAGGGUGAGAUCC
AGAUCGACGGCGUUUCGUGGGAUAGCAUCACCUUGCAGCAGUGGCGGAAAGCGUUUGGA
GUAAUCCCCCAAAAGGUCUUUAUCUUUAGCGGAACCUUCCGAAAGAAUCUCGAUCCUUAU
GAACAGUGGUCAGAUCAAGAGAUUUGGAAAGUCGCGGACGAGGUUGGCCUUCGGAGUGU
AAUCGAGCAGUUUCCGGGAAAACUCGACUUUGUCCUUGUAGAUGGGGGAUGCGUCCUGU
CGCAUGGGCACAAGCAGCUCAUGUGCCUGGCGCGAUCCGUCCUCUCUAAAGCGAAAAUUC
UUCUCUUGGAUGAACCUUCGGCCCAUCUGGACCCGGUAACGUAUCAGAUCAUCAGAAGGA
CACUUAAGCAGGCGUUUGCCGACUGCACGGUGAUUCUCUGUGAGCAUCGUAUCGAGGCCA
UGCUCGAAUGCCAGCAAUUUCUUGUCAUCGAAGAGAAUAAGGUCCGCCAGUACGACUCCA
UCCAGAAGCUGCUUAAUGAGAUCAUUGUUCCGGCAGGCGAUUUCACCAUCCGAUAGG
GUGAAACUUUUCCACACAGAAAUUCGUCGAAGUGCAAGUCCAAACCGCAGAUCGCGGCC
UUGAAAGAAGAGACUGAAGAAGAAGUUCAAGACACGCGUCUUUAA

SEQ ID NO: 4
(SEQ ID NO: 4)
GGACAGAUCGCCUGGAGACGCCAUCCACGCUGUUUUGACCUCCAUAGAAGACACCGGGAC
CGAUCCAGCCUCCGCGGCCGGGAACGGUGCAUUGGAACGCGGAUUCCCCGUGCCAAGAGU
GACUCACCGUCCUUGACACG

SEQ ID NO: 5
(SEQ ID NO: 5)
CGGGUGGCAUCCCUGUGACCCCUCCCCAGUGCCUCUCCUGGCCCUGGAAGUUGCCACUCC
AGUGCCCACCAGCCUUGUCCUAAUAAAAUUAAGUUGCAUC

SEQ ID NO: 6
(SEQ ID NO: 6)
GGGAUCCUACC

-continued

SEQ ID NO: 7

(SEQ ID NO: 7)
AUGGAAGAUGCCAAAAACAUUAAGAAGGGCCCAGCGCCAUUCUACCCACUCGAAGACGGG

ACCGCCGGCGAGCAGCUGCACAAAGCCAUGAAGCGCUACGCCCUGGUGCCCGGCACCAUC

GCCUUUACCGACGCACAUAUCGAGGUGGACAUUACCUACGCCGAGUACUUCGAGAUGAGC

GUUCGGCUGGCAGAAGCUAUGAAGCGCUAUGGGCUGAAUACAAACCAUCGGAUCGUGGU

GUGCAGCGAGAAUAGCUUGCAGUUCUUCAUGCCCGUGUUGGGUGCCCUGUUCAUCGGUG

UGGCUGUGGCCCCAGCUAACGACAUCUACAACGAGCGCGAGCUGCUGAACAGCAUGGGCA

UCAGCCAGCCCACCGUCGUAUUCGUGAGCAAGAAAGGGCUGCAAAAGAUCCUCAACGUGC

AAAAGAAGCUACCGAUCAUACAAAAGAUCAUCAUCAUGGAUAGCAAGACCGACUACCAG

GGCUUCCAAAGCAUGUACACCUUCGUGACUUCCCAUUUGCCACCCGGCUUCAACGAGUAC

GACUUCGUGCCCGAGAGCUUCGACCGGGACAAAACCAUCGCCCUGAUCAUGAACAGUAGU

GGCAGUACCGGAUUGCCCAAGGGCGUAGCCCUACCGCACCGCACCGCUUGUGUCCGAUUC

AGUCAUGCCCGCGACCCCAUCUUCGGCAACCAGAUCAUCCCCGACACCGCUAUCCUCAGC

GUGGUGCCAUUUCACCACGGCUUCGGCAUGUUCACCACGCUGGGCUACUUGAUCUGCGGC

UUUCGGGUCGUGCUCAUGUACCGCUUCGAGGAGGAGCUAUUCUUGCGCAGCUUGCAAGAC

UAUAAGAUUCAAUCUGCCCUGCUGGUGCCCACACUAUUUAGCUUCUUCGCUAAGAGCACU

CUCAUCGACAAGUACGACCUAAGCAACUUGCACGAGAUCGCCAGCGGCGGGGCGCCGCUC

AGCAAGGAGGUAGGUGAGGCCGUGGCCAAACGCUUCCACCUACCAGGCAUCCGCCAGGGC

UACGGCCUGACAGAAACAACCAGCGCCAUUCUGAUCACCCCCGAAGGGGACGACAAGCCU

GGCGCAGUAGGCAAGGUGGUGCCCUUCUUCGAGGCUAAGGUGGUGGACUUGGACACCGG

UAAGACACUGGGUGUGAACCAGCGCGGCGAGCUGUGCGUCCGUGGCCCCAUGAUCAUGAG

CGGCUACGUUAACAACCCCGAGGCUACAAACGCUCUCAUCGACAAGGACGGCUGGCUGCA

CAGCGGCGACAUCGCCUACUGGGACGAGGACGAGCACUUCUUCAUCGUGGACCGGCUGAA

GAGCCUGAUCAAAUACAAGGGCUACCAGGUAGCCCCAGCCGAACUGGAGAGCAUCCUGCU

GCAACACCCCAACAUCUUCGACGCCGGGGUCGCCGGCCUGCCCGACGACGAUGCCGGCGA

GCUGCCCGCCGCAGUCGUCGUGCUGGAACACGGUAAAACCAUGACCGAGAAGGAGAUCGU

GGACUAUGUGGCCAGCCAGGUUACAACCGCCAAGAAGCUGCGCGGUGGUGUUGUGUUCG

UGGACGAGGUGCCUAAAGGACUGACCGGCAAGUUGGACGCCCGCAAGAUCCGCGAGAUUC

UCAUUAAGGCCAAGAAGGGCGGCAAGAUCGCCGUGUA

SEQ ID NO: 8

(SEQ ID NO: 8)
UUUGAAUU

SEQ ID NO: 9

(SEQ ID NO: 9)
AUGCAGAGAAGCCCCCUGGAAAAGGCCAGCGUGGUGUCCAAGCUGUUCUUCAGCUGGACC

AGACCCAUCCUGAGAAAGGGCUACAGACAGAGACUGGAACUGAGCGACAUCUACCAGAUC

CCCAGCGUGGACAGCGCCGACAACCUGAGCGAGAAGCUGGAAAGAGAGUGGGACAGAGA

GCUGGCUAGCAAGAAGAACCCCAAGCUGAUCAACGCCCUGAGGCGGUGCUUCUUCUGGCG

GUUUAUGUUCUACGGCAUCUUCCUGUACCUGGGCGAAGUGACAAAGGCCGUGCAGCCCCU

GCUCCUGGGCAGAAUCAUUGCCAGCUACGACCCCGACAACAAAGAGGAAAGAUCUAUCGC

CAUCUACCUGGGCAUCGGCCUGUGCCUGCUGUUCAUCGUGCGGACACUGCUGCUGCACCC

CGCCAUCUUCGGCCUGCACCACAUCGGCAUGCAGAUGAGAAUCGCCAUGUUCAGCCUGAU

CUACAAGAAAACCCUGAAGCUGAGCAGCAGGGUGCUGGACAAGAUCAGCAUCGGACAGCU

-continued

```
GGUGUCCCUGCUGAGCAACAACCUGAACAAGUUCGACGAGGGACUGGCCCUGGCUCACUU
CGUGUGGAUCGCUCCACUGCAGGUCGCCCUGCUGAUGGGCCUGAUCUGGGAGCUGCUGCA
GGCCAGCGCUUUCUGCGGCCUGGGCUUUCUGAUUGUGCUGGCCCUGUUUCAGGCUGGCCU
GGGCAGGAUGAUGAUGAAGUACAGGGACCAGAGAGCCGGCAAGAUCAGCGAGAGACUGG
UCAUCACCAGCGAGAUGAUCGAGAACAUCCAGAGCGUGAAGGCCUACUGCUGGGAAGAG
GCCAUGGAAAAGAUGAUCGAAAACCUGAGACAGACCGAGCUGAAGCUGACCAGAAAGGC
CGCCUACGUGCGGUACUUCAACAGCAGCGCCUUCUUCUUCUCCGGCUUCUUCGUGGUGUU
CCUGUCCGUGCUGCCCUACGCCCUGAUCAAGGGCAUCAUCCUGAGGAAGAUCUUCACCAC
CAUUUCUUUCUGCAUCGUGCUGAGAAUGGCCGUGACCAGACAGUUCCCCUGGGCCGUGCA
GACUUGGUACGACAGCCUGGGCGCCAUCAACAAGAUCCAGGACUUCCUGCAGAAGCAGGA
GUACAAGACCCUCGAGUACAACCUGACCACCACCGAGGUGGUCAUGGAAAACGUGACCGC
CUUCUGGGAGGAAGGCUUCGGCGAGCUGUUCGAGAAGGCCAAGCAGAACAACAACAACA
GAAAGACCAGCAACGGCGACGACUCCCUGUUCUUCUCCAACUUCUCCCUGCUGGGCACCC
CCGUGCUGAAGGACAUCAACUUCAAGAUCGAGAGAGGCCAGCUGCUCGCCGUGGCCGGCU
CUACAGGCGCUGGCAAGACCUCUCUGCUGAUGGUCAUCAUGGGCGAGCUGGAACCCAGCG
AGGGCAAGAUCAAGCACAGCGGCAGAAUCAGCUUCUGCAGCCAGUUCAGCUGGAUCAUGC
CCGGCACCAUCAAAGAGAACAUCAUCUUCGGCGUGUCCUACGACGAGUACAGAUACAGAA
GCGUGAUCAAGGCCUGCCAGCUGGAAGAGGACAUCAGCAAGUUCGCCGAGAAGGACAACA
UCGUGCUGGGCGAGGGCGGCAUCACCCUGUCUGGCGGCCAGAGAGCCAGAAUCAGCCUGG
CCAGAGCCGUGUACAAGGACGCCGACCUGUACCUGCUGGACAGCCCCUUCGGCUACCUGG
ACGUGCUGACCGAGAAAGAGAUCUUCGAGAGCUGCGUGUGCAAGCUGAUGGCCAACAAG
ACCAGAAUCCUGGUCACCAGCAAGAUGGAACACCUGAAGAAGGCCGACAAGAUCCUGAUC
CUGCACGAGGGCAGCAGCUACUUCUACGGCACAUUCAGCGAGCUGCAGAACCUGCAGCCC
GACUUCAGCAGCAAACUGAUGGGCUGCGACAGCUUCGACCAGUUCAGCGCCGAGAGAAGA
AACAGCAUCCUGACCGAGACACUGCACAGAUUCAGCCUGGAAGGCGACGCCCCCGUGUCU
UGGACCGAGACAAAGAAGCAGAGCUUCAAGCAGACCGGCGAGUUCGGCGAGAAGAGAAA
GAACUCCAUCCUGAACCCCAUCAACAGCAUCCGGAAGUUCAGCAUCGUGCAGAAAACCCC
CCUGCAGAUGAACGGCAUCGAAGAGGACAGCGACGAGCCCCUGGAAAGACGGCUGAGCCU
GGUGCCUGACAGCGAGCAGGGCGAGGCCAUCCUGCCUAGAAUCAGCGUGAUCAGCACCGG
CCCCACCCUGCAGGCUAGAAGGCGGCAGAGCGUGCUGAACCUGAUGACCCACAGCGUGAA
CCAGGGCCAGAACAUCCACCGCAAGACCACCGCCAGCACCAGAAAGGUGUCCCUGGCUCC
UCAGGCCAACCUGACCGAGCUGGACAUCUACAGCAGAAGGCUGAGCCAGGAAACCGGCCU
GGAAAUCAGCGAGGAAAUCAACGAAGAGGACCUGAAAGAGUGCUUCUUCGACGACAUGG
AAUCCAUCCCCGCCGUGACCACCUGGAACACCUACCUGCGGUACAUCACCGUGCACAAGA
GCCUGAUCUUCGUGCUGAUCUGGUGCCUGGUCAUCUUCCUGGCCGAGGUGGCCGCCAGCC
UGGUGGUGCUGUGGCUCCUGGGAAACACCCCCUCUGCAGGACAAGGGCAACAGCACCCACA
GCAGAAACAACAGCUACGCCGUGAUCAUCACCUCCACCAGCUCCUACUACGUGUUCUACA
UCUACGUGGGCGUGGCCGACACCCUGCUGGCUAUGGGCUUCUUCAGAGGCCUGCCCCUGG
UGCACACCCUGAUCACCGUGUCCAAGAUCCUGCACCAUAAGAUGCUGCACAGCGUGCUGC
AGGCUCCCAUGAGCACCCUGAACACACUGAAGGCUGGCGGCAUCCUGAACAGGUUCAGCA
AGGAUAUCGCCAUCCUGGACGACCUGCUGCCUCUGACCAUCUUCGACUUCAUCCAGCUGC
```

-continued

UGCUGAUCGUGAUCGGCGCUAUCGCCGUGGUGGCCGUGCUGCAGCCCUACAUCUUCGUGG

CCACCGUGCCCGUGAUCGUGGCCUUCAUUAUGCUGAGAGCCUACUUUCUGCAGACCAGCC

AGCAGCUGAAGCAGCUGGAAAGCGAGGGCAGAAGCCCCAUCUUCACCCACCUCGUGACCA

GCCUGAAGGGCCUGUGGACCCUGAGAGCCUUCGGCAGACAGCCCUACUUCGAGACACUGU

UCCACAAGGCCCUGAACCUGCACACCGCCAACUGGUUUCUGUACCUGUCCACCCUGAGAU

GGUUCCAGAUGAGGAUCGAGAUGAUCUUCGUCAUCUUCUUUAUCGCCGUGACCUUCAUCU

CUAUCCUGACCACCGGCGAGGGCGAGGGAAGAGUGGGAAUCAUCCUGACCCUGGCCAUGA

ACAUCAUGAGCACACUGCAGUGGGCCGUGAACAGCAGCAUCGACGUGGACAGCCUGAUGA

GAAGCGUGUCCAGAGUGUUCAAGUUCAUCGACAUGCCUACCGAGGGCAAGCCCACCAAGA

GCACCAAGCCCUACAAGAACGGCCAGCUGAGCAAAGUGAUGAUCAUCGAGAACAGCCACG

UCAAGAAGGACGACAUCUGGCCCAGCGGCGGACAGAUGACCGUGAAGGACCUGACCGCCA

AGUACACAGAGGGCGGCAACGCUAUCCUGGAAAACAUCAGCUUCAGCAUCAGCCCAGGCC

AGAGAGUGGGCCUGCUGGGGAGAACAGGCAGCGGCAAGUCUACCCUGCUGUCCGCCUUCC

UGAGACUGCUGAACACCGAGGGCGAGAUCCAGAUCGAUGGCGUGUCCUGGGACUCCAUCA

CCCUGCAGCAGUGGCGCAAGGCCUUCGGCGUGAUCCCCCAGAAGGUGUUCAUCUUCAGCG

GCACCUUCAGAAAGAACCUGGACCCCUACGAGCAGUGGUCCGACCAGGAAAUCUGGAAGG

UCGCCGAUGAAGUGGGCCUGAGAUCCGUGAUCGAGCAGUUCCCCGGCAAGCUGGACUUCG

UGCUGGUGGACGGCGGCUGCGUGCUGAGCCACGGCCACAAGCAGCUGAUGUGUCUGGCCC

GCUCCGUGCUGAGCAAGGCUAAGAUUCUGCUGCUGGACGAGCCUAGCGCCCACCUGGACC

CUGUGACCUACCAGAUCAUCAGAAGGACCCUGAAGCAGGCCUUCGCCGACUGCACCGUGA

UCCUGUGCGAGCACAGAAUCGAGGCCAUGCUGGAAUGCCAGCAGUUCCUGGUCAUCGAAG

AGAACAAAGUGCGGCAGUACGACAGCAUCCAGAAGCUGCUGAACGAGAGAAGCCUGUUC

AGACAGGCCAUCAGCCCCAGCGACAGAGUGAAGCUGUUCCCCCACCGCAACAGCAGCAAG

UGCAAGAGCAAGCCCCAGAUCGCCGCCCUGAAAGAAGAGACUGAGGAAGAGGUGCAGGAC

ACCAGACUGUGA

SEQ ID NO: 10

(SEQ ID NO: 10)
AUGCAGCGGUCCCCGCUCGAAAAGGCCAGUGUCGUGUCCAAACUCUUCUUCUCAUGGACU

CGGCCUAUCCUUAGAAAGGGGUAUCGGCAGAGGCUUGAGUUGUCUGACAUCUACCAGAU

CCCCUCGGUAGAUUCGGCGGAUAACCUCUCGGAGAAGCUCGAACGGGAAUGGGACCGCGA

ACUCGCGUCUAAGAAAAACCCGAAGCUCAUCAACGCACUGAGAAGGUGCUUCUUCUGGCG

GUUCAUGUUCUACGGUAUCUUCUUGUAUCUCGGGGAGGUCACAAAAGCAGUCCAACCCCU

GUUGUUGGGUCGCAUUAUCGCCUCGUACGACCCCGAUAACAAAGAAGAACGGAGCAUCGC

GAUCUACCUCGGGAUCGGACUGUGUUUGCUUUUCAUCGUCAGAACACUUUUGUUGCAUCC

AGCAAUCUUCGGCCUCCAUCACAUCGGUAUGCAGAUGCGAAUCGCUAUGUUUAGCUUGAU

CUACAAAAAGACACUGAAACUCUCGUCGCGGGUGUUGGAUAAGAUUUCCAUCGGUCAGU

UGGUGUCCCUGCUUAGUAAUAACCUCAACAAAUUCGAUGAGGGACUGGCGCUGGCACAU

UUCGUGUGGAUUGCCCCGCUGCAAGUCGCACUGCUUAUGGGACUGAUUUGGGAACUGUU

GCAGGCCAGCGCCUUUUGCGGCCUGGGAUUUCUCAUUGUGCUUGCACUUUUCCAAGCAGG

GCUCGGCAGAAUGAUGAUGAAGUACAGGGACCAGAGAGCCGGAAAGAUCUCAGAACGGC

UCGUGAUUACUUCAGAAAUGAUCGAGAACAUUCAAUCGGUGAAAGCUACUGCUGGGAA

GAGGCGAUGGAAAAGAUGAUCGAAAACCUCAGACAGACCGAGUUGAAGCUGACCCGGAA

-continued

```
GGCCGCGUACGUCAGAUACUUCAACAGCAGCGCUUUCUUCUUCUCGGGCUUCUUCGUCGU

GUUCCUGUCGGUGCUGCCGUAUGCCCUCAUUAAGGGAAUUAUCUUGCGGAAGAUCUUUA

CUACUAUCUCAUUUUGCAUCGUCCUUCGGAUGGCGGUCACUCGGCAGUUCCCGUGGGCCG

UGCAGACCUGGUACGACAGCCUCGGGGCCAUCAACAAGAUCCAAGACUUUCUCCAAAAGC

AAGAGUACAAAACCCUCGAAUACAACCUCACCACUACUGAAGUGGUCAUGGAAAACGUGA

CCGCCUUUUGGGAAGAAGGCUUCGGAGAACUGUUCGAGAAGGCGAAGCAAAACAACAAU

AAUCGCAAGACUAGCAACGGGGAUGACUCACUGUUCUUCAGCAAUUUCUCACUGCUCGGC

ACCCCGGUGCUUAAGGACAUCAACUUCAAGAUUGAACGCGGACAGCUCUUGGCGGUGGCC

GGAUCCACCGGAGCAGGAAAGACUAGCCUGCUGAUGGUGAUCAUGGGUGAGCUGGAACC

GUCCGAAGGCAAAAUCAAGCACUCCGGCAGAAUCAGCUUCUGCUCGCAGUUUUCGUGGAU

CAUGCCAGGAACCAUCAAGAGAACAUCAUCUUUGGAGUCUCAUACGAUGAGUACCGCUA

CAGAAGCGUGAUUAAGGCCUGCCAGCUUGAAGAGGACAUCUCCAAGUUCGCGGAAAAGG

ACAACAUCGUGCUGGGUGAGGGAGGGAUCACGUUGUCGGGCGGUCAGAGAGCCCGCAUU

UCGCUGGCACGGGCUGUGUACAAGGAUGCGGAUCUUUACCUUCUGGACUCGCCAUUCGGU

UACCUCGACGUGCUGACCGAAAAAGAAAUCUUCGAGAGCUGCGUGUGUAAGCUGAUGGC

UAAUAAGACUAGAAUCCUCGUGACGUCCAAAAUGGAACAUCUUAAGAAGGCGGAUAAGA

UUCUCAUUCUUCACGAGGGGUCGAGCUACUUCUACGGGACUUUUAGCGAGCUGCAGAAU

UUGCAGCCGGACUUCAGCUCAAAGCUCAUGGGCUGCGACUCGUUCGAUCAGUUCAGCGCC

GAACGGCGCAAUUCGAUCUUGACGGAAACCCUGCACAGAUUCUCGCUGGAGGGAGAUGCA

CCUGUCUCGUGGACCGAAACCAAGAAGCAGUCCUUCAAGCAGACGGGAGAGUUCGGAGAA

AAGCGGAAGAACUCAAUCCUCAACCCAAUCAACUCCAUUCGCAAAUUCUCAAUCGUGCAG

AAAACUCCACUGCAGAUGAACGGUAUCGAAGAGGAUUCGGACGAGCCACUUGAGCGGAG

ACUGUCGCUGGUGCCAGAUUCAGAACAGGGGGAGGCAAUCCUGCCGCGCAUUUCCGUGAU

CAGCACUGGGCCGACCCUCCAAGCUAGACGCAGGCAAUCAGUGCUGAAUCUCAUGACCCA

CUCCGUCAACCAGGGACAGAAUAUCCACCGCAAGACCACCGCGUCGACUAGAAAGGUGUC

AUUGGCACCGCAAGCAAAUUUGACUGAACUUGACAUCUACUCACGGCGCCUCUCCCAAGA

AACCGGAUUGGAAAUCUCCGAAGAGAUUAACGAAGAAGAUUUGAAAGAGUGUUUCUUCG

ACGAUAUGGAGUCGAUCCCCGCAGUGACCACUUGGAAUACGUAUCUUCGGUACAUCACCG

UGCACAAGAGCCUGAUCUUCGUCCUCAUCGGUGCCGGUGAUCUUUCUGGCCGAAGUCG

CCGCUUCGCUGGUCGUGCUGUGGCUGCUCGGUAAUACCCCGCUCCAAGACAAAGGCAAUU

CCACUCACUCGCGCAACAACAGCUACGCUGUGAUUAUCACGUCAACCUCGUCGUACUAUG

UGUUCUACAUCUACGUGGGAGUCGCGGACACUCUGCUCGCUAUGGGCUUCUUUCGCGGAC

UGCCCCUGGUCCACACUCUCAUCACGGUGAGCAAGAUCCUCCAUCAUAAGAUGCUCCAUU

CCGUGCUGCAGGCCCCGAUGAGCACUCUCAACACUCUGAAGGCGGGUGGAAUCUUGAACA

GAUUUUCCAAAGACAUCGCGAUUCUGGACGAUCUGCUCCCACUCACUAUCUUCGACUUCA

UCCAACUGCUGCUGAUCGUCAUCGGAGCUAUCGCCGUGGUGGCUGUCCUCCAGCCGUAUA

UCUUCGUGGCCACUGUGCCGGUGAUUGUCGCUUUCAUCAUGUUGCGCGCGUACUUCUUGC

AAACCUCGCAGCAACUCAAGCAACUGGAGUCCGAGGGCCGGAGCCCAAUCUUUACCCAUC

UGGUGACUUCACUGAAAGGUCUGUGGACCCUCCGCGCCUUUGGUCGCCAGCCUUACUUCG

AAACUCUCUUUCACAAAGCACUGAAUCUCCACACUGCAAACUGGUUCUUGUACCUGUCCA

CCCUGCGGUGGUUCCAAAUGCGGAUCGAGAUGAUCUUUGUCAUCUUCUUCAUCGCCGUGA
```

-continued

CUUUUAUCUCCAUCCUCACCACCGGCGAGGGAGAGGGGAGAGUGGGAAUCAUCCUGACGC
UGGCGAUGAAUAUCAUGUCCACUUUGCAGUGGGCCGUCAAUUCGAGCAUCGACGUGGAU
UCGCUGAUGCGCAGCGUGUCGCGCGUGUUCAAGUUCAUCGAUAUGCCCACCGAAGGUAAA
CCCACCAAGAGCACGAAGCCUUACAAGAACGGGCAGCUCUCAAAGGUGAUGAUUAUCGAG
AACUCCCAUGUGAAGAAGGACGACAUCUGGCCAUCCGGAGGACAGAUGACCGUGAAGGAC
CUGACCGCCAAAUACACGGAGGGCGGAAAUGCAAUCCUCGAAAACAUCUCGUUCUCCAUC
UCGCCUGGCCAAAGGGUGGGACUUUUGGGACGCACUGGAUCCGGAAAGAGCACCCUGCUU
AGCGCCUUCUUGAGGCUCUUGAACACCGAGGGCGAAAUCCAGAUCGAUGGCGUGUCGUGG
GAUUCGAUCACCCUGCAGCAGUGGAGAAAGGCCUUCGGGGUGAUCCCGCAAAAAGUGUUC
AUCUUCUCCGGAACGUUUCGGAAAAACCUUGACCCAUACGAACAAUGGUCGGAUCAAGAG
AUUUGGAAGGUCGCCGACGAAGUGGGGCUGCGCUCCGUGAUCGAGCAGUUUCCGGGAAA
ACUGGACUUCGUCUUGGUCGACGGCGGAUGCGUCCUGUCCCACGGACAUAAGCAGCUGAU
GUGCCUGGCCCGCAGCGUCCUUUCAAAAGCUAAGAUCCUGCUGCUGGAUGAACCUUCAGC
ACACCUCGACCCGGUCACCUACCAGAUCAUCAGACGGACCCUGAAACAGGCCUUUGCGGA
UUGUACUGUGAUCUUGUGUGAACACCGCAUUGAAGCCAUGCUGGAGUGCCAGCAGUUCC
UGGUCAUCGAAGAGAACAAAGUGCGGCAGUACGAUUCCAUCCAAAAACUGCUCAAUGAG
CGGUCCCUGUUCAGACAGGCAAUUAGCCCGAGCGACAGGGUCAAAUUGUUCCCCCAUAGA
AAUUCGUCGAAAUGUAAGUCAAAGCCUCAGAUCGCGGCACUGAAAGAAGAAACUGAAGA
AGAGGUGCAAGACACCAGACUGUGA

SEQ ID NO: 11

(SEQ ID NO: 11)
AUGCAGAGAAGCCCACUGGAAAAGGCGUCGGUGGUGUCAAAGCUGUUCUUUAGCUGGAC
CAGACCUAUCUUGCGGAAGGGAUACCGCCAACGCCUGGAGCUGUCGGACAUCUACCAGAU
UCCGUCAGUGGAUUCAGCAGACAAUCUCUCCGAAAAGCUGGAACGCGAAUGGGACAGAG
AGUUGGCGUCAAAGAAGAACCCAAAGUUGAUCAAUGCCCUGCGCCGCUGCUUCUUCUGGC
GGUUCAUGUUCUACGGAAUCUUUCUGUACCUCGGCGAAGUCACCAAGGCUGUGCAACCGC
UUCUGCUGGGACGCAUCAUCGCCUCAUACGACCCGGACAACAAGGAAGAACGCUCCAUCG
CAAUCUACCUCGGGAUCGGCCUCUGCCUGCUGUUUAUCGUGCGGACGCUGCUGCUCCAUC
CAGCCAUUUUCGGACUGCACCACAUUGGCAUGCAAAUGCGGAUCGCCAUGUUCAGCCUGA
UCUACAAAAAGACCCUGAAGUUGAGCUCACGGGUGUUGGAUAAGAUUUCGAUCGGACAG
CUGGUGUCGCUGCUCUCCAACAACCUCAACAAGUUUGACGAAGGCCUGGCACUGGCCCAC
UUCGUGUGGAUUGCCCCGUUGCAAGUCGCCCUUUUGAUGGGCCUUAUUUGGGAGCUGUU
GCAGGCAUCUGCCUUUUGUGGCCUGGGAUUUCUGAUUGUGUUGGCAUUGUUUCAGGCUG
GGCUUGGGCGGAUGAUGAUGAAGUAUCGCGACCAGAGAGCGGGUAAAAAUCUCGGAAAGA
CUCGUCAUCACUUCGGAAAUGAUCGAAAACAUCCAGUCGGUCAAAGCCUAUUGCUGGGAA
GAAGCUAUGGAGAAGAUGAUUGAAAACCUCCGCCAAACUGAGCUGAAACUGACCCGCAA
GGCGGCGUAUGUCCGGUAUUUCAAUUCGUCAGCGUUCUUCUUUUCCGGGUUCUUCGUUG
UCUUUCUCUCGGUUUUGCCUUAUGCCUUGAUUAAGGGGAUUAUCCUCCGCAAGAUUUUC
ACCACGAUUUCGUUCUGCAUUGUAUUGCGCAUGGCAGUGACACGGCAAUUUCCGUGGGCC
GUGCAGACAUGGUAUGACUCGCUUGGAGCGAUCAACAAAAAUCCAAGACUUCUUGCAAAA
GCAAGAGUACAAGACCCUGGAGUACAAUCUUACUACUACGGAGGUAGUAAUGGAGAAUG
UGACGGCUUUUUGGGAGGAAGGAUUCGGCGAAUUGUUCGAAAAGGCUAAGCAGAACAAC

-continued

```
AACAAUCGGAAAACCUCCAAUGGGGACGAUUCGCUGUUCUUCUCGAAUUUCUCCCUGCUG

GGAACGCCCGUGCUUAAAGACAUCAACUUCAAGAUCGAACGGGCCAGCUGCUCGCGGUC

GCGGGCAGCACUGGAGCGGGAAAGACUUCCCUGCUCAUGGUCAUCAUGGGAGAGCUGGA

GCCCUCGGAGGGCAAAAUCAAGCACUCGGGGAGGAUCUCAUUUUGCAGCCAGUUCUCGUG

GAUCAUGCCCGGUACUAUCAAAGAAAACAUCAUCUUUGGAGUCAGCUAUGACGAGUACC

GCUACCGGUCGGUGAUCAAGGCCUGCCAGCUGGAAGAAGAUAUCUCCAAGUUCGCCGAAA

AGGACAACAUUGUGCUGGGAGAAGGUGGAAUCACUCUCUCGGGAGGCCAGCGCGCACGG

AUCUCACUCGCAAGGGCCGUGUACAAGGAUGCCGAUUUGUACCUGUUGGAUUCGCCGUUC

GGUUAUCUUGAUGUCCUCACUGAGAAAGAGAUUUUUGAGUCGUGCGUCUGUAAGCUGAU

GGCCAACAAAACCCGCAUCCUGGUGACCUCGAAGAUGGAGCACUUGAAGAAGGCCGACAA

AAUCCUUAUCCUCCAUGAGGGUAGCUCAUACUUCUACGGCACCUUUUCGGAACUGCAGAA

UCUGCAGCCCGACUUCUCAUCAAAACUGAUGGGAUGUGACUCGUUCGAUCAGUUCUCGGC

GGAGCGGCGGAACUCGAUCCUCACCGAAACUCUCCACCGGUUCAGCCUCGAGGGAGAUGC

CCCAGUCAGCUGGACCGAAACUAAGAAGCAGUCCUUCAAACAGACCGGAGAGUUCGGAGA

AAAACGCAAGAACUCCAUCCUCAAUCCAAUCAACAGCAUCCGCAAGUUCAGCAUCGUGCA

GAAAACUCCACUUCAGAUGAACGGAAUCGAAGAGGAUAGCGACGAGCCGCUUGAGCGGA

GAUUGUCACUGGUGCCGGACAGCGAGCAAGGGGAAGCGAUUCUGCCGCGGAUCUCCGUGA

UCUCGACUGGCCCUACCCUCCAAGCUCGCAGACGCCAGAGCGUGCUGAAUCUCAUGACCC

ACUCAGUCAACCAGGGACAAAACAUCCAUAGAAAGACCACCGCUUCAACCCGGAAAGUGU

CACUUGCACCGCAGGCAAACCUGACCGAACUCGACAUCUACAGCAGACGGCUCUCACAAG

AAACUGGAUUGGAGAUCAGCGAAGAGAUCAACGAAGAAGAUCUCAAAGAAUGCUUCUUC

GACGAUAUGGAGUCCAUCCCAGCAGUCACUACGUGGAAUACCUACCUCCGCUACAUCACU

GUGCACAAGAGCCUGAUUUUCGUGUUGAUCUGGUGCCUGGUCAUCUUCUUGGCCGAGGU

GGCCGCGAGCCUCGUGGUCCUCUGGCUGCUCGGCAAUACGCCGCUGCAAGAUAAGGGAAA

UUCCACGCAUAGCAGAAACAACUCAUACGCAGUGAUCAUCACUAGCACUUCAUCGUACUA

CGUGUUCUACAUCUACGUGGGGUGGCCGAUACUCUGUUGGCAAUGGGAUUCUUUAGAG

GGCUGCCUCUGGUGCAUACUCUGAUCACUGUGUCCAAGAUCCUCCACCACAAGAUGCUCC

ACUCCGUGCUUCAGGCCCCUAUGUCAACUCUCAACACCCUCAAGGCCGGAGGUAUUCUUA

AUCGCUUUUCCAAGGACAUCGCCAUUCUCGAUGACUUGCUUCCCCUGACUAUCUUCGACU

UUAUCCAGUUGCUGCUGAUUGUGAUCGGCGCUAUUGCCGUCGUCGCAGUGCUGCAACCGU

ACAUCUUUGUGGCUACCGUCCCAGUCAUUGUGGCCUUCAUCAUGCUCAGGGCAUACUUUC

UCCAGACCAGCCAGCAGCUCAAGCAGCUCGAAUCCGAAGGCAGAUCGCCGAUCUUCACCC

ACCUCGUCACUUCGCUCAAGGGCCUCUGGACCCUGCGCGCCUUCGGUCGCCAGCCGUAUU

UCGAAACCCUGUUCCAUAAAGCACUGAACCUCCAUACUGCGAACUGGUUUCUCUACCUUU

CAACCCUGAGGUGGUUCCAGAUGAGAAUCGAGAUGAUCUUUGUGAUCUUCUUUAUCGCU

GUGACGUUCAUCUCCAUUCUCACUACCGGCGAGGGAGAGGGCAGAGUGGGGAUUAUCCUC

ACGCUGGCCAUGAAUAUCAUGAGCACGCUGCAGUGGGCCGUCAAUAGCAGCAUCGACGUG

GACUCCCUGAUGCGGUCCGUGUCGAGAGUGUUUAAGUUCAUCGAUAUGCCUACUGAAGG

GAAACCGACCAAGUCGACCAAGCCGUACAAGAAUGGGCAGCUGAGCAAGGUGAUGAUUA

UUGAGAACUCCCAUGUGAAGAAGGACGACAUCUGGCCCAGCCGGAGGCCAGAUGACCGUGA

AGGACUUGACCGCUAAGUACACUGAGGGUGGAAAUGCCAUUCUUGAGAAUAUCAGCUUC
```

-continued

UCGAUCUCGCCGGGACAACGCGUGGGAUUGCUCGGGCGCACUGGCAGCGGCAAAUCCACC

CUGCUUAGCGCUUUUCUGAGGCUGCUGAACACUGAAGGUGAAAUUCAAAUCGAUGGAGU

GUCGUGGGAUAGCAUCACCCUUCAACAGUGGCGCAAGGCCUUCGGCGUGAUCCCUCAAAA

GGUCUUUAUCUUCUCGGGGACGUUCCGGAAAAAUCUCGACCCCUACGAACAGUGGUCAGA

CCAAGAGAUUUGGAAAGUCGCAGAUGAGGUCGGACUGCGCUCAGUGAUCGAACAGUUUC

CGGGUAAACUUGACUUCGUGCUCGUCGAUGGAGGUUGCGUCCUGUCCCACGGACAUAAGC

AGCUGAUGUGUCGGCGCGCUCGGUCCUCUCCAAAGCGAAGAUCCUGCUGCUCGAUGAAC

CGUCCGCCCACCUUGAUCCAGUGACCUAUCAGAUCAUUCGGAGAACUUUGAAGCAAGCCU

UCGCUGACUGCACCGUCAUCCUCUGCGAACACCGGAUCGAGGCAAUGCUGGAGUGCCAAC

AGUUUCUGGUCAUCGAAGAAAACAAAGUGCGCCAGUAUGACUCGAUCCAAAAACUUCUG

AACGAGCGCUCCCUCUUCCGGCAGGCAAUCAGCCCAUCCGACCGCGUGAAGUUGUUCCCU

CAUCGGAAUAGCUCCAAAUGCAAAUCGAAGCCGCAGAUCGCUGCCUUGAAAGAAGAAACC

GAAGAAGAAGUCCAAGACACUAGGUUGUAG

SEQ ID NO: 12

(SEQ ID NO: 12)
AUGCAGCGGUCCCCUCUGGAGAAGGCUUCCGUGGUCAGCAAGCUGUUCUUCUCGUGGACC

AGACCUAUCCUCCGCAAGGGAUACCGCCAGCGCCUGGAGCUGUCAGAUAUCUACCAGAUC

CCAAGCGUGGACUCAGCCGACAAUCUGAGCGAAAAGCUGGAACGGGAGUGGGACCGGGA

GCUCGCCUCCAAGAAGAAUCCGAAGUUGAUCAAUGCGCUGCGCAGAUGCUUCUUCUGGCG

GUUUAUGUUUUACGGCAUCUUUCUGUAUCUCGGAGAAGUGACCAAAGCCGUGCAGCCGC

UGCUCUUGGGUAGGAUCAUUGCUUCGUACGACCCGGACAACAAAGAAGAACGCUCCAUCG

CCAUCUACCUCGGAAUCGGUCUGUGCCUGCUCUUUAUCGUGCGCACUCUCCUGCUGCAUC

CGGCGAUCUUCGGACUGCACCACAUCGGCAUGCAAAUGCGGAUCGCAAUGUUCUCACUGA

UCUACAAAAGACUCUGAAGCUCAGCUCCAGAGUGCUGGAUAAGAUCUCGAUCGGGCAAC

UCGUCAGCCUGCUGUCGAACAAUCUGAAUAAGUUCGACGAAGGGUUGGCCCUCGCACAUU

UCGUGUGGAUCGCACCGCUGCAAGUGGCGCUCCUGAUGGGACUCAUUUGGGAACUGCUCC

AAGCCAGCGCGUUUUGCGGACUCGGAUUCCUGAUCGUGCUCGCCCUGUUCCAAGCCGGAC

UGGGGCGCAUGAUGAUGAAGUACCGCGAUCAGCGGGCAGGAAAGAUCUCCGAGCGGUUG

GUGAUCACUUCCGAAAUGAUCGAGAAUAUUCAGUCCGUGAAGGCCUACUGCUGGGAAGA

AGCUAUGGAAAAGAUGAUUGAAAACUUGCGGCAAACUGAGCUGAAAUUGACUCGCAAAG

CGGCAUACGUCCGCUACUUCAAUAGCAGCGCCUUCUUCUUUUCGGGCUUUUUCGUGGUGU

UUCUGAGCGUGCUGCCCUACGCUCUGAUCAAGGGAAUCAUCCUCCGGAAAAUCUUCACCA

CCAUUUCGUUCUGUAUCGUGUUGCGCAUGGCCGUGACUCGCCAGUUCCCCUGGGCGGUGC

AGACCUGGUACGACAGCUUGGGGGCAAUCAAUAAGAUUCAAGACUUCUUGCAAAAGCAG

GAGUACAAGACUCUGGAGUACAACCUGACCACCACUGAAGUCGUGAUGGAGAACGUGACC

GCCUUUUGGGAAGAGGGUUUUGGAGAACUGUUUGAGAAAGCAAAGCAGAAUAACAACAA

CCGCAAGACCUCAAAUGGGGACGAUUCCCUGUUUUUCUCGAACUUCUCCCUGCUCGGAAC

ACCCGUGUUGAAGGACAUCAAUUUCAAGAUUGAGAGGGGACAGCUUCUCGCGGUAGCGG

GAAGCACGGUGCGGGAAAAACUAGCCUCUUGAUGGUGAUUAUGGGGGAGCUUGAGCCC

AGCGAGGGGAAGAUUAAACACUCCGGGCGUAUCUCAUUCUGUAGCCAGUUUUCAUGGAU

CAUGCCCGGAACCAUUAAAGAGAACAUCAUUUUCGGAGUAUCCUAUGAUGAGUACCGAU

ACAGAUCGGUCAUUAAGGCGUGCCAGUUGGAAGAGGACAUUUCUAAGUUCGCCGAGAAG

-continued

```
GAUAACAUCGUCUUGGGAGAAGGGGGUAUUACAUUGUCGGGAGGGCAGCGAGCGCGGAU

CAGCCUCGCGAGAGCGGUAUACAAAGAUGCAGAUUUGUAUCUGCUUGAUUCACCGUUUG

GAUACCUCGACGUAUUGACAGAAAAAGAAAUCUUCGAGUCGUGCGUGUGUAAACUUAUG

GCUAAUAAGACGAGAAUCCUGGUGACUUCCAAAAUGGAGCAUCUCAAGAAGGCGGACAA

GAUCCUGAUUCUGCAUGAGGGAUCAAGCUAUUUCUACGGAACUUUUUCCGAGCUGCAGA

ACCUCCAGCCGGAUUUUAGCUCCAAGCUGAUGGGUUGCGACUCAUUCGACCAAUUCUCGG

CUGAGCGGCGGAACUCAAUCCUGACCGAAACCCUGCAUCGCUUCUCCCUUGAGGGAGAUG

CCCCGGUGUCGUGGACUGAGACUAAAAAGCAGUCGUUUAAGCAAACUGGCGAAUUCGGC

GAAAAGCGGAAGAAUAGCAUCCUCAACCCAAUCAACAGCAUUCGGAAGUUCAGCAUCGUC

CAAAAGACCCCGCUCCAGAUGAACGGCAUUGAAGAGGACUCAGACGAGCCAUUGGAAAGA

CGCCUGUCACUGGUCCCAGAUUCGGAGCAGGGUGAAGCAAUUCUGCCUCGGAUCUCGGUC

AUCUCGACUGGCCCCACUCUCCAAGCUCGGCGGAGACAGAGCGUGCUUAACUUGAUGACC

CACUCCGUGAACCAGGGUCAGAACAUCCACCGCAAAACCACCGCCUCCACCAGGAAGGUG

UCACUGGCCCCUCAAGCCAAUCUGACUGAGUUGGAUAUCUACUCCAGAAGGCUCAGCCAG

GAAACCGGACUGGAAAUCUCGGAAGAGAUCAACGAAGAGGAUCUCAAAGAGUGUUUCUU

CGACGACAUGGAAUCAAUCCCUGCUGUCACUACUUGGAACACCUAUCUCCGCUACAUUAC

CGUGCACAAGUCACUCAUCUUCGUCCUGAUCUGGUGCCUCGUGAUCUUCCUGGCCGAGGU

CGCAGCAUCGCUGGUCGUGCUGUGGCUGCUCGGCAACACCCCACUCCAAGACAAAGGCAA

CAGCACCCAUUCCCGCAACAACUCCUACGCGGUGAUCAUCACUUCAACUUCGUCCUACUA

CGUCUUUUACAUCUACGUGGGCGUGGCGGACACGCUCCUGGCUAUGGGGUUCUUUCGCGG

GCUGCCUCUUGUCCACACGCUCAUCACUGUGUCAAAGAUUCUCCACCACAAAAUGCUGCA

CUCCGUGCUCCAGGCCCCUAUGUCGACUUUGAACACGCUUAAGGCCGGAGGCAUCCUUAA

CAGAUUCUCGAAAGAUAUCGCGAUCUUGGACGAUCUUCUGCCGCUGACUAUCUUUGACUU

CAUCCAACUCCUGCUGAUCGUCAUCGGUGCCAUCGCAGUGGUCGCGGUGCUCCAACCGUA

CAUUUUCGUGGCGACUGUGCCGGUGAUCGUGGCGUUCAUCAUGCUGCGGGCUUACUUUCU

UCAGACCUCACAGCAGCUGAAGCAACUCGAAUCGGAGGGUAGAUCACCAAUCUUUACCCA

CCUCGUCACCUCGCUGAAGGGACUCUGGACCCUGCGCGCAUUUGGACGGCAACCGUACUU

CGAGACUCUCUUCCAUAAGGCCCUGAAUCUGCAUACGGCGAAUUGGUUUCUUUACCUCUC

GACGCUCCGCUGGUUCCAGAUGCGCAUUGAGAUGAUUUUCGUCAUCUUUUUCAUCGCGGU

GACCUUCAUCUCCAUCCUCACCACGGGUGAGGGAGAGGGCAGAGUCGGAAUUAUCCUCAC

UCUGGCCAUGAACAUCAUGUCCACUCUGCAGUGGGCCGUCAACUCAUCCAUUGACGUGGA

CUCGCUGAUGCGCUCCGUGUCGAGAGUGUUCAAGUUCAUCGAUAUGCCGACCGAGGGAAA

GCCAACUAAGUCGACCAAGCCGUACAAAAACGGACAGCUGAGCAAGGUCAUGAUCAUCGA

AAACUCCCACGUGAAAAAGGAUGACAUCUGGCCGUCCGGUGGACAGAUGACGGUGAAGG

AUCUGACUGCGAAGUACACUGAGGGAGGGAAUGCCAUCCUCGAAAACAUCUCAUUCUCAA

UCUCCCCUGGACAGAGGGUCGGGCUGCUGGGCCGCACUGGCUCGGGGAAGUCGACUCUUC

UUUCGGCAUUUCUGCGCUUGCUCAAUACCGAGGGAGAAAUCCAGAUCGAUGGAGUGUCA

UGGGACUCGAUCACCCUGCAGCAGUGGCGCAAGGCUUUUGGCGUCAUCCCGCAAAAGGUG

UUCAUCUUCUCGGGCACUUUUAGAAAGAAUCUGGAUCCCUACGAACAGUGGUCAGAUCA

AGAGAUUUGGAAAGUCGCAGACGAAGUGGGCCUCCGGUCCGUGAUUGAACAGUUUCCGG

GAAAGCUCGACUUCGUGCUUGUGGACGGAGGAUGUGUGCUGAGCCACGGCCACAAACAGC
```

-continued

UCAUGUGCCUGGCUCGGUCGGUCCUGUCGAAAGCAAAGAUCCUGCUGCUGGACGAACCGU

CGGCACACCUCGAUCCAGUGACGUACCAGAUCAUCCGGCGGACCCUGAAGCAGGCCUUCG

CAGACUGCACUGUCAUUUGUGUGAACACAGAAUCGAAGCUAUGUUGGAGUGCCAGCAG

UUCCUGGUCAUCGAAGAAAACAAAGUCCGCCAGUACGAUUCGAUUCAGAAGCUGCUGAAC

GAACGGAGCCUCUUCAGACAGGCGAUCAGCCCCAGCGAUCGGGUCAAGUUGUUCCCGCAU

CGGAACAGCAGCAAGUGUAAGUCAAAGCCUCAGAUCGCUGCACUCAAAGAAGAGACUGA

AGAAGAAGUGCAAGACACCAGACUCUGA

SEQ ID NO: 13

(SEQ ID NO: 13)

AUGCAGCGCUCGCCUCUGGAGAAAGCCUCAGUCGUGUCAAAACUGUUCUUUAGCUGGACU

CGCCCGAUUCUCCGGAAGGGUUAUAGACAGCGCUUGGAGCUCUCCGACAUCUACCAAAUC

CCUUCCGUGGACUCCGCCGACAACCUGUCGGAGAAGCUCGAACGCGAGUGGGACCGGGAA

CUCGCGUCCAAAAAGAAUCCAAAACUCAUUAAUGCACUGCGCCGCUGCUUCUUCUGGCGC

UUUAUGUUUUACGGUAUCUUUCUCUACCUGGGCGAGGUGACGAAAGCAGUGCAGCCGCU

CCUGCUUGGCAGAAUUAUCGCCUCGUACGAUCCGGAUAACAAAGAAGAACGCUCAAUCGC

UAUCUACCUCGGUAUCGGAUUGUGCCUGCUUUUCAUCGUGCGCACCCUGUUGCUGCACCC

GGCGAUUUUCGGACUCCACCACAUCGGAAUGCAAAUGAGAAUUGCAAUGUUCUCAUUGA

UCUACAAAAGACCCUUAAACUGUCGUCCCGCGUCCUCGACAAGAUUUCAAUCGGCCAGC

UGGUGUCGCUUCUUUCGAAUAAUCUUAACAAGUUCGAUGAAGGACUCGCGCUCGCCCAUU

UCGUGUGGAUCGCACCACUUCAAGUCGCACUGCUCAUGGGACUGAUUUGGGAGUUGCUGC

AGGCUUCCGCCUUUUGCGGCCUGGGAUUCCUGAUCGUCCUGGCUUUGUUCCAGGCUGGAC

UGGGCAGAAUGAUGAUGAAGUACCGGGACCAGCGGGCAGGAAAGAUCAGCGAAAGGCUC

GUGAUCACUAGCGAAAUGAUCGAGAACAUCCAAUCCGUCAAGGCGUACUGCUGGGAAGA

AGCGAUGGAGAAGAUGAUCGAAAAUCUUCGCCAGACCGAACUCAAACUCACUAGAAAGG

CUGCCUACGUGCGCUACUUUAACAGCUCAGCAUUUUUCUUCUCCGGAUUUUUCGUGGUGU

UCCUGUCGGUGCUGCCAUACGCCCUGAUCAAGGGGAUCAUUCUUCGCAAAAUCUUCACCA

CGAUCUCAUUCUGCAUUGUCCUCCGGAUGGCCGUGACGCGGCAGUUCCCUUGGGCAGUGC

AAACUUGGUACGAUUCGCUGGGGGCCAUUAACAAGAUUCAAGAUUUUCUUCAAAAGCAG

GAGUACAAAACCCUGGAGUACAAUCUGACCACUACGGAAGUCGUGAUGGAAAACGUGAC

UGCUUUUUGGGAGGAAGGCUUCGGCGAACUUUUUGAAAAGGCAAAGCAAAACAAUAACA

ACAGAAAGACGUCAAACGGCGAUGACUCGCUGUUCUUCUCCAAUUUCUCCCUGCUCGGCA

CCCCUGUGCUGAAGGACAUCAACUUCAAAAUUGAACGCGGACAGCUGCUGGCCGUGGCGG

GAUCGACCGGGGCUGGGAAAACCUCGUUGUUGAUGGUGAUCAUGGGAGAACUCGAACCC

UCGGAGGGAAAGAUUAAGCAUAGCGGACGGAUCAGCUUCUGUUCCCAGUUCUCGUGGAU

CAUGCCGGGAACCAUUAAGGAAAACAUCAUCUUCGGCGUGUCCUACGACGAGUACCGGUA

UAGGUCGGUGAUCAAGGCCUGCCAGUUGGAAGAGGACAUCUCCAAGUUCGCUGAGAAGG

ACAACAUCGUGCUCGGUGAAGGGGGCAUUACUCUGUCCGGUGGCCAGCGCGCGAGAAUUU

CGCUGGCUCGCGCGGUGUACAAAGAUGCGGAUCUCUAUCUGCUGGAUUCGCCCUUCGGAU

ACCUCGAUGUCCUCACGGAGAAGGAGAUCUUCGAAUCGUGCGUGUGCAAGUUGAUGGCG

AACAAGACUAGGAUCCUGGUCACUUCCAAGAUGGAGCACUUGAAGAAGGCCGAUAAGAU

CUUGAUCCUCCAUGAAGGAUCGAGCUACUUUUUACGGAACUUUCUCAGAGCUGCAGAACUU

GCAGCCGGACUUCUCAAGCAAACUGAUGGGUUGCGACUCGUUCGACCAGUUUUCGGCAGA

-continued

```
ACGGCGGAACUCGAUCCUGACUGAGACUCUGCAUCGCUUUUCGCUGGAAGGCGAUGCCCC
UGUGUCCUGGACUGAAACCAAGAAGCAAUCCUUCAAACAAACUGGAGAAUUCGGAGAAA
AGCGGAAGAACUCCAUCCUUAACCCCAUCAAUAGCAUCCGGAAGUUCUCAAUCGUCCAAA
AGACCCCGCUGCAGAUGAAUGGCAUCGAAGAAGAUAGCGACGAACCUCUUGAAAGACGGC
UGUCCUUGGUGCCAGACUCAGAACAGGGAGAAGCUAUCCUGCCGCGGAUCUCCGUGAUCA
GCACCGGACCGACUCUGCAGGCUCGCAGACGCCAGAGCGUGCUCAACCUGAUGACCCACU
CCGUGAACCAGGGACAAAACAUCCAUAGAAAGACCACGGCCUCCACCAGAAAAGUCUCCC
UGGCACCGCAAGCCAACCUGACUGAACUGGACAUCUACAGCAGAAGGCUCAGCCAAGAAA
CCGGACUGGAGAUUUCAGAAGAAAUCAACGAGGAAGAUCUUAAAGAGUGCUUCUUCGAC
GACAUGGAAUCGAUCCCAGCCGUGACCACUUGGAAUACCUAUCUGAGAUACAUCACCGUG
CACAAAUCCCUGAUCUUCGUGCUGAUCUGGUGCCUGGUGAUCUUCCUGGCUGAGGUGGCC
GCCUCACUGGUGGUGCUUUGGUUGCUGGGGAAUACGCCGCUCCAAGACAAGGGAAACUCC
ACGCACUCCAGAAACAACUCGUACGCCGUGAUCAUCACGUCGACUUCGUCGUACUACGUG
UUCUACAUCUACGUCGGUGUGGCAGACACUCUCUUGGCGAUGGGCUUUUUCCGGGGACUG
CCACUGGUCCACACCCUGAUCACCGUGUCCAAAAUCUUGCACCACAAGAUGCUCCACAGC
GUGCUGCAAGCCCCGAUGAGCACCCUGAAUACCCUCAAAGCGGGAGGCAUCCUCAACAGA
UUCAGCAAGGACAUCGCCAUCCUCGACGACCUGUUGCCCCUGACCAUCUUCGAUUUCAUC
CAGCUUCUUCUCAUCGUGAUCGGGGCAAUCGCUGUCGUGGCGGUGCUGCAGCCGUACAUC
UUCGUGGCGACUGUGCCAGUGAUCGUCGCCUUUAUCAUGCUGCGGGCCUACUUUCUCCAA
ACUUCCCAACAGCUGAAACAACUGGAGUCGGAGGGCCGCAGCCCUAUCUUCACCCAUCUG
GUGACCAGCCUCAAAGGACUGUGGACUCUGAGGGCUUUCGGGAGGCAGCCAUACUUCGAG
ACUCUCUUUCACAAGGCCCUGAAUCUCCAUACGGCAAAUUGGUUUUUGUAUUUGAGUACC
CUCCGAUGGUUUCAGAUGCGCAUUGAGAUGAUUUUUGUGAUCUUCUUUAUCGCGGUGAC
UUUUAUCUCCAUCUUGACCACGGGAGAGGGCGAGGGACGGGUCGGUAUUAUCCUGACAC
UCGCCAUGAACAUUAUGAGCACUUUGCAGUGGGCAGUGAACAGCUCGAUUGAUGUGGAU
AGCCUGAUGAGGUCCGUUUCGAGGGUCUUUAAGUUCAUCGACAUGCCGACGGAGGGAAA
GCCCACAAAAAGUACGAAACCCUAUAAGAAUGGGCAAUUGAGUAAGGUAAUGAUCAUCG
AGAACAGUCACGUGAAGAAGGAUGACAUCUGGCCUAGCGGGGGUCAGAUGACCGUGAAG
GACCUGACGGCAAAAUACACCGAGGGAGGGAACGCAAUCCUUGAAAACAUCUCGUUCAGC
AUUAGCCCCGGUCAGCGUGUGGGGUUGCUCGGGAGGACCGGGUCAGGAAAAUCGACGUU
GCUGUCGGCCUUCUUGAGACUUCUGAAUACAGAGGGUGAGAUCCAGAUCGACGGCGUUU
CGUGGGAUAGCAUCACCUUGCAGCAGUGGCGCAAGGCGUUCGGAGUCAUUCCCCAAAGG
UGUUCAUCUUUUCGGGAACCUUCCGCAAGAAUCUGGAUCCGUACGAACAGUGGAGCGACC
AAGAGAUUUGGAAAGUGGCAGAUGAAGUGGGAUUGCGGAGCGUCAUCGAACAGUUUCCG
GGAAAGCUCGAUUUCGUCCUUGUGGACGGUGGAUGUGUGCUGUCGCACGGCCAUAAGCA
GCUGAUGUGUCUCGCCCGCUCGGUGCUGUCAAAGGCGAAGAUCCUCUUGCUGGAUGAGCC
AUCAGCCCAUCUGGACCCGGUGACGUACCAGAUCAUUAGACGGACGCUGAAACAGGCAUU
CGCGGACUGCACUGUGAUCCUCUGUGAACAUCGGAUCGAGGCCAUGCUGGAGUGUCAACA
AUUCUUGGUCAUCGAAGAGAACAAAGUGCGGCAGUACGACAGCAUCCAAAAGCUGCUGA
ACGAGAGGUCCCUCUUCCGCCAGGCCAUCUCCCCAUCCGACCGGGUCAAGCUGUUCCCUC
```

-continued

ACCGCAACAGCUCAAAGUGCAAAUCCAAACCCCAGAUCGCAGCGCUGAAAGAAGAAACUG
AAGAAGAAGUGCAAGACACUAGACUGUGA

SEQ ID NO: 14

(SEQ ID NO: 14)
AUGCAAAGGUCCCCAUUGGAGAAGGCCUCAGUGGUGUCGAAGCUGUUCUUCUCGUGGACC
AGGCCUAUCCUCCGGAAGGGAUACAGACAGCGGCUGGAACUGUCCGAUAUCUACCAGAUC
CCCAGCGUGGACAGCGCCGAUAAUCUCAGCGAAAAGCUGGAACGGGAAUGGGACCGCGAA
CUCGCUUCGAAGAAGAACCCGAAGCUGAUUAAUGCUCUGCGGAGAUGUUUCUUUUGGCG
GUUCAUGUUUUACGGAAUCUUUCUGUACUUGGGAGAGGUCACGAAGGCUGUGCAGCCUC
UGCUGCUGGGACGGAUUAUCGCGUCGUAUGACCCCGACAAUAAGGAAGAACGCAGCAUCG
CAAUCUACCUGGGCAUCGGAUUGUGCCUGCUGUUCAUCGUGAGAACUCUCCUGCUGCAUC
CAGCCAUCUUCGGACUCCACCACAUUGGAAUGCAGAUGAGAAUCGCAAUGUUCUCCCUGA
UCUACAAGAAAACGCUCAAGCUCAGCAGCCGCGUGCUCGAUAAGAUCAGCAUCGGUCAAU
UGGUGUCCCUGCUGUCGAAUAACCUCAACAAGUUCGACGAAGGGUUGGCCCUCGCUCACU
UCGUGUGGAUCGCACCUCUGCAAGUGGCCCUGCUGAUGGGACUGAUUUGGGAGCUGCUGC
AGGCUUCCGCUUUCUGCGGCCUGGGAUUUCUUAUCGUGCUUGCUCUGUUCCAGGCGGGAC
UGGGACGCAUGAUGAUGAAGUACCGGGACCAACGGGCUGGAAAGAUCAGCGAACGGCUG
GUGAUCACUUCCGAAAUGAUUGAGAAUAUCCAGUCAGUCAAGGCGUACUGCUGGGAAGA
GGCUAUGGAAAAGAUGAUUGAAAAUCUGAGACAAACCGAGCUGAAGCUGACUCGGAAAG
CGGCCUACGUCAGAUACUUCAAUAGCUCAGCUUUCUUUUUCUCGGGUUUUUCGUCGUGU
UCCUGUCGGUGCUUCCCUAUGCCCUGAUUAAGGGCAUCAUUCUGCGCAAGAUCUUCACUA
CGAUCUCAUUCUGCAUCGUGCUGCGCAUGGCUGUGACCAGACAAUUCCCGUGGGCCGUGC
AAACCUGGUACGAUUCACUGGGAGCCAUCAACAAGAUCCAAGACUUUCUCCAAAAACAGG
AGUAUAAGACCCUGGAGUACAACCUGACUACUACCGAGGUGGUGAUGGAGAACGUGACU
GCGUUUUGGGAAGAAGGGUUCGGCGAACUGUUUGAAAAGGCCAAGCAGAACAAUAACAA
CAGAAAGACUUCAAACGGAGAUGACUCGCUGUUCUUUUCGAACUUCAGCCUGCUGGGUAC
CCCAGUGUUGAAAGAUAUCAACUUCAAGAUUGAGAGAGGACAGCUGCUGGCUGUGGCGG
GAUCCACCGGAGCAGGAAAAACUUCACUCCUGAUGGUGAUCAUGGGAGAACUCGAACCGU
CAGAGGGGAAGAUUAAACACUCGGGAAGAAUCUCAUUUUGCUCCCAAUUUUCAUGGAUU
AUGCCGGGAACCAUUAAAGAAAACAUUAUCUUCGGCGUGUCCUACGACGAGUACCGCUAC
AGAUCGGUGAUCAAAGCAUGCCAGCUGGAAGAGGACAUCUCGAAAUUCGCUGAAAAAGA
CAAUAUCGUGCUCGGGAAGGCGGCAUCACCCUCAGCGGAGGACAACGGGCACGGAUUUC
GCUCGCACGCGCAGUCUACAAAGACGCCGAUCUCUACCUCUUGGACAGCCCAUUCGGGUA
UCUGGACGUGCUCACCGAGAAAGAGAUCUUCGAAAGCUGCGUCUGCAAGCUCAUGGCCAA
CAAGACCCGCAUCCUCGUGACGUCGAAGAUGGAACAUCUUAAGAAGGCUGACAAGAUUCU
CAUUCUCCAUGAAGGGAGCUCAUACUUCUACGGCACCUUUUCCGAGCUCCAGAAUCUGCA
ACCGGACUUCUCGUCCAAGCUGAUGGGCUGCGAUUCGUUUGAUCAGUUCUCCGCCGAGCG
GAGAAACAGCAUUCUGACGGAAACCCUGCACCGGUUCUCGCUGGAAGGCGAUGCACCGGU
GUCGUGGACCGAAACUAAGAAGCAAUCGUUCAAGCAGACGGGAGAGUUUGGAGAGAAGC
GGAAAAACUCCAUCCUCAACCCGAUCAACAGCAUCCGGAAGUUCAGCAUCGUGCAAAAGA
CCCCGCUCCAGAUGAAUGGCAUUGAAGAGGACUCCGACGAACCUUUUGGAACGCAGACUGA
GCCUCGUGCCGGAUUCAGAACAGGGAGAAGCCAUUCUGCCACGGAUCUCCGUGAUCAGCA

-continued

CUGGGCCAACUCUCCAAGCACGGCGGAGGCAGUCCGUGCUGAAUCUUAUGACGCACAGCG

UGAACCAAGGGCAGAACAUCCAUAGAAAAACGACCGCUUCGACCAGGAAAGUCUCCCUCG

CCCCACAAGCUAACCUCACGGAACUGGAUAUCUACUCCCGCAGACUGUCGCAAGAGACUG

GCCUUGAGAUCUCCGAAGAGAUUAACGAAGAAGAUCUCAAAGAAUGUUUCUUCGAUGAU

AUGGAAUCAAUCCCGGCAGUGACCACUUGGAACACCUACUUGCGCUAUAUCACUGUGCAC

AAAAGCCUUAUCUUCGUCCUCAUCUGGUGCCUCGUCAUCUUCCUGGCUGAGGUCGCAGCC

UCGCUGGUCGUGCUCUGGUUGCUCGGAAACACUCCGCUGCAGGAUAAGGGGAAUUCGACU

CACUCGCGGAACAAUUCGUACGCUGUCAUUAUCACCUCGACGUCGUCAUACUACGUGUUU

UACAUCUACGUGGGAGUGGCUGACACUCUGUUGGCUAUGGGGUUCUUUCGCGGCCUGCCA

CUGGUCCAUACUCUCAUUACUGUGUCCAAAAUCCUUCAUCACAAGAUGUUGCAUUCAGUG

CUGCAAGCACCGAUGUCCACCCUCAAUACCCUUAAGGCUGGCGGGAUUCUCAACCGCUUC

UCGAAAGACAUCGCCAUCCUCGAUGAUCUUCUGCCUCUCACCAUCUUUGAUUUCAUCCAG

CUGCUCCUGAUCGUGAUCGGAGCGAUUGCCGUGGUGGCAGUGUUGCAGCCGUACAUCUUU

GUCGCAACUGUGCCGGUCAUCGUCGCCUUCAUCAUGCUGCGCGCCUACUUCUUGCAAACG

UCACAGCAACUGAAGCAGCUUGAAUCCGAGGGAAGAUCACCUAUCUUCACCCACCUCGUG

ACUUCGCUGAAGGGGCUGUGGACGCUGCGCGCAUUUGGAAGGCAACCGUACUUCGAGACU

UUGUUCCACAAGGCGCUCAAUCUUCACACUGCCAAUUGGUUCUUGUACCUGUCAACGCUG

AGAUGGUUUCAGAUGCGGAUCGAAAUGAUCUUCGUGAUCUUCUUUAUCGCGGUGACUUU

CAUCUCGAUCCUGACUACCGGAGAGGGAGAAGGACGGGUGGGUAUUAUCCUCACUCUGGC

GAUGAACAUCAUGUCGACGCUUCAGUGGGCGGUGAAUAGCUCAAUCGAUGUCGACUCGC

UGAUGCGCUCCGUGAGCCGGGUGUUUAAGUUCAUCGACAUGCCAACUGAAGGGAAGCCG

ACCAAGUCGACCAAACCGUACAAAAACGGACAGCUCUCCAAGGUGAUGAUUAUCGAGAAU

UCCCACGUGAAAAAGGACGACAUCUGGCCAUCCGGUGGACAGAUGACCGUGAAGGACCUG

ACCGCGAAGUACACUGAGGGAGGCAACGCAAUCCUUGAGAACAUCAGCUUCUCCAUCUCG

CCCGGUCAGAGGGUGGGCCUUCUUGGCCGGACCGGAUCGGGAAAGUCCACUCUUCUGUCG

GCCUUUCUUCGCCUCUUGAAUACUGAAGGGGAAAUCCAGAUCGACGGAGUGUCGUGGGA

UAGCAUCACUCUGCAGCAGUGGCGGAAAGCGUUUGGAGUAAUCCCCCAAAAGGUCUUUA

UCUUUAGCGGAACCUUCCGAAAGAAUCUCGAUCCUUAUGAACAGUGGUCAGAUCAAGAG

AUUUGGAAAGUCGCGGACGAGGUUGGCCUUCGGAGUGUAAUCGAGCAGUUUCCGGGAAA

ACUCGACUUUGUCCUUGUAGAUGGGGAUGCGUCCUGUCGCAUGGGCACAAGCAGCUCAU

GUGCCUGGCGCGAUCCGUCCUCUCUAAAGCGAAAAUUCUUCUCUUGGAUGAACCUUCGGC

CCAUCUGGACCCGGUAACGUAUCAGAUCAUCAGAAGGACACUUAAGCAGGCGUUUGCCGA

CUGCACGGUGAUUCUCUGUGAGCAUCGUAUCGAGGCCAUGCUCGAAUGCCAGCAAUUUCU

UGUCAUCGAAGAGAAUAAGGUCCGCCAGUACGACUCCAUCCAGAAGCUGCUUAAUGAGA

GAUCAUUGUUCCGGCAGGCGAUUUCACCAUCCGAUAGGGUGAAACUUUUUCCACACAGAA

AUUCGUCGAAGUGCAAGUCCAAACCGCAGAUCGCGGCCUUGAAAGAAGAGACUGAAGAA

GAAGUUCAAGACACGCGUCUUUAA

SEQ ID NO: 15

(SEQ ID NO: 15)
AUGCAGCGGUCCCCGCUCGAAAAGGCCAGUGUCGUGUCCAAACUCUUCUUCUCAUGGACU

CGGCCUAUCCUUAGAAAGGGGUAUCGGCAGAGGCUUGAGUUGUCUGACAUCUACCAGAU

CCCCUCGGUAGAUUCGGCGGAUAACCUCUCGGAGAAGCUCGAACGGGAAUGGGACCGCGA

-continued

```
ACUCGCGUCUAAGAAAAACCCGAAGCUCAUCAACGCACUGAGAAGGUGCUUCUUCUGGCG

GUUCAUGUUCUACGGUAUCUUCUUGUAUCUCGGGGAGGUCACAAAAGCAGUCCAACCCCU

GUUGUUGGGUCGCAUUAUCGCCUCGUACGACCCCGAUAACAAAGAAGAACGGAGCAUCGC

GAUCUACCUCGGGAUCGGACUGUGUUUGCUUUUCAUCGUCAGAACACUUUUGUUGCAUCC

AGCAAUCUUCGGCCUCCAUCACAUCGGUAUGCAGAUGCGAAUCGCUAUGUUUAGCUUGAU

CUACAAAAAGACACUGAAACUCUCGUCGCGGGUGUUGGAUAAGAUUUCCAUCGGUCAGU

UGGUGUCCCUGCUUAGUAAUAACCUCAACAAAUUCGAUGAGGGACUGGCGCUGGCACAU

UUCGUGUGGAUUGCCCCGUUGCAAGUCGCCCUUUUGAUGGGCCUUAUUUGGGAGCUGUU

GCAGGCAUCUGCCUUUUGUGGCCUGGGAUUUCUGAUUGUGUUGGCAUUGUUUCAGGCUG

GGCUUGGGCGGAUGAUGAUGAAGUAUCGCGACCAGAGAGCGGGUAAAAUCUCGGAAAGA

CUCGUCAUCACUUCGGAAAUGAUCGAAAACAUCCAGUCGGUCAAAGCCUAUUGCUGGGAA

GAAGCUAUGGAGAAGAUGAUUGAAAACCUCCGCCAAACUGAGCUGAAACUGACCCGCAA

GGCGGCGUAUGUCCGGUAUUUCAAUUCGUCAGCGUUCUUCUUUUCCGGGUUCUUCGUUG

UCUUUCUCUCGGUUUUGCCUUAUGCCUUGAUUAAGGGGAUUAUCCUCCGCAAGAUUUUC

ACCACGAUUUCGUUCUGCAUUGUAUUGCGCAUGGCAGUGACACGGCAAUUUCCGUGGGCC

GUGCAGACAUGGUAUGACUCGCUUGGAGCGAUCAACAAAAUCCAAGACUUCUUGCAAAA

GCAAGAGUACAAGACCCUGGAGUACAAUCUUACUACUACGGAGGUAGUAAUGGAGAAUG

UGACGGCUUUUUGGGAAGAGGGUUUUGGAGAACUGUUUGAGAAAGCAAAGCAGAAUAAC

AACAACCGCAAGACCUCAAAUGGGGACGAUUCCCUGUUUUUCUCGAACUUCUCCCUGCUC

GGAACACCCGUGUUGAAGGACAUCAAUUUCAAGAUUGAGAGGGGACAGCUUCUCGCGGU

AGCGGGAAGCACUGGUGCGGGAAAAACUAGCCUCUUGAUGGUGAUUAUGGGGGAGCUUG

AGCCCAGCGAGGGGAAGAUUAAACACUCCGGGCGUAUCUCAUUCUGUAGCCAGUUUUCAU

GGAUCAUGCCCGGAACCAUUAAAGAGAACAUCAUUUUCGGAGUAUCCUAUGAUGAGUAC

CGAUACAGAUCGGUCAUUAAGGCGUGCCAGUUGGAAGAGGACAUUUCUAAGUUCGCCGA

GAAGGAUAACAUCGUCUUGGGAGAAGGGGGUAUUACAUUGUCGGGAGGGCAGCGAGCGC

GGAUCAGCCUCGCGAGAGCGGUAUACAAAGAUGCAGAUUUGUAUCUGCUUGAUUCACCG

UUUGGAUACCUCGACGUAUUGACAGAAAAAGAAAUCUUCGAGUCGUGCGUGUGUAAACU

UAUGGCUAAUAAGACGAGAAUCCUGGUGACAUCAAAAAUGGAACACCUUAAGAAGGCGG

ACAAGAUCCUGAUCCUCCACGAAGGAUCGUCCUACUUUUACGGCACUUUCUCAGAGUUGC

AAAACUUGCAGCCGGACUUCUCAAGCAAACUCAUGGGGUGUGACUCAUUCGACCAGUUCA

GCGCGGAACGGCGGAACUCGAUCUUGACGGAAACGCUGCACCGAUUCUCGCUUGAGGGUG

AUGCCCCGGUAUCGUGGACCGAGACAAAGAAGCAGUCGUUUAAGCAGACAGGAGAAUUU

GGUGAGAAAAGAAAGAACAGUAUCUUGAAUCCUAUUAACUCAAUUCGCAAGUUCUCAAU

CGUCCAGAAAACUCCACUGCAGAUGAAUGGAAUUGAAGAGGAUUCGGACGAACCCCUGG

AGCGCAGGCUUAGCCUCGUGCCGGAUUCAGAGCAAGGGGAGGCCAUUCUUCCCCGGAUUU

CGGUGAUUUCAACCGGACCUACACUUCAGGCGAGGCGAAGGCAAUCCGUGCUCAACCUCA

UGACGCAUUCGGUAAACCAGGGGCAAAACAUUCACCGCAAAACGACGGCCUCAACGAGAA

AAGUGUCACUUGCACCCCAGGCGAAUUUGACUGAACUCGACAUCUACAGCCGUAGGCUUU

CGCAAGAAACCGGACUUGAGAUCAGCGAAGAAAUCAAUGAAGAAGAUUUGAAAGAGUGU

UUCUUUGAUGACAUGGAAUCAAUCCCAGCGGUGACAACGUGGAACACAUACUUGCGUUA

CAUCACGGUGCACAAGUCCUUGAUUUUCGUCCUCAUCGGUGUCUCGUGAUCUUUCUCGC
```

-continued

UGAGGUCGCAGCGUCACUUGUGGUCCUCUGGCUGCUUGGUAAUACGCCCUUGCAAGACAA

AGGCAAUUCUACACACUCAAGAAACAAUUCCUAUGCCGUGAUUAUCACUUCUACAAGCUC

GUAUUACGUGUUUUACAUCUACGUAGGAGUGGCCGACACUCUGCUCGCGAUGGGUUUCU

UCCGAGGACUCCCACUCGUUCACACGCUUAUCACUGUCUCCAAGAUUCUCCACCAUAAGA

UGCUUCAUAGCGUACUGCAGGCUCCCAUGUCCACCUUGAAUACGCUCAAGGCGGGAGGUA

UUUUGAAUCGCUUCUCAAAAGAUAUUGCAAUUUUGGAUGACCUUCUGCCCCUGACGAUC

UUCGACUUCAUCCAGUUGUUGCUGAUCGUGAUUGGGGCUAUUGCAGUAGUCGCUGUCCU

CCAGCCUUACAUUUUUGUCGCGACCGUUCCGGUGAUCGUGGCGUUUAUCAUGCUGCGGGC

CUAUUUCUUGCAGACGUCACAGCAGCUUAAGCAACUGGAGUCUGAAGGGAGGUCGCCUA

UCUUUACGCAUCUUGUGACCAGUUUGAAGGGAUUGUGGACGUUGCGCGCCUUUGGCAGG

CAGCCCUACUUUGAAACACUGUUCCACAAAGCGCUGAAUCUCCAUACGGCAAAUUGGUUU

UUGUAUUUGAGUACCCUCCGAUGGUUUCAGAUGCGCAUUGAGAUGAUUUUUGUGAUCUU

CUUUAUCGCGGUGACUUUUAUCUCCAUCUUGACCACGGGAGAGGGCGAGGGACGGGUCG

GUAUUAUCCUGACACUCGCCAUGAACAUUAUGAGCACUUUGCAGUGGGCAGUGAACAGC

UCGAUUGAUGUGGAUAGCCUGAUGAGGUCCGUUUCGAGGGUCUUUAAGUUCAUCGACAU

GCCGACGGAGGGAAAGCCCACAAAAAGUACGAAACCCUAUAAGAAUGGGCAAUUGAGUA

AGGUAAUGAUCAUCGAGAACAGUCACGUGAAGAAGGAUGACAUCUGGCCUAGCGGGGGU

CAGAUGACCGUGAAGGACCUGACGGCAAAAUACACCGAGGGAGGGAACGCAAUCCUUGA

AAACAUCUCGUUCAGCAUUAGCCCCGGUCAGCGUGUGGGGUUGCUCGGGAGGACCGGGUC

AGGAAAAUCGACGUUGCUGUCGGCCUUCUUGAGACUUCUGAAUACAGAGGGUGAGAUCC

AGAUCGACGGCGUUUCGUGGGAUAGCAUCACCUUGCAGCAGUGGCGGAAAGCGUUUGGA

GUAAUCCCCCAAAAGGUCUUUAUCUUUAGCGGAACCUUCCGAAAGAAUCUCGAUCCUUAU

GAACAGUGGUCAGAUCAAGAGAUUUGGAAAGUCGCGGACGAGGUUGGCCUUCGGAGUGU

AAUCGAGCAGUUUCCGGGAAAACUCGACUUUGUCCUUGUAGAUGGGGGAUGCGUCCUGU

CGCAUGGGCACAAGCAGCUCAUGUGCCUGGCGCGAUCCGUCCUCUCUAAAGCGAAAAUUC

UUCUCUUGGAUGAACCUUCGGCCCAUCUGGACCCGGUAACGUAUCAGAUCAUCAGAAGGA

CACUUAAGCAGGCGUUUGCCGACUGCACGGUGAUUCUCUGUGAGCAUCGUAUCGAGGCCA

UGCUCGAAUGCCAGCAAUUUCUUGUCAUCGAAGAGAAUAAGGUCCGCCAGUACGACUCCA

UCCAGAAGCUGCUUAAUGAGAGAUCAUUGUUCCGGCAGGCGAUUUCACCAUCCGAUAGG

GUGAAACUUUUUCCACACAGAAAUUCGUCGAAGUGCAAGUCCAAACCGCAGAUCGCGGCC

UUGAAAGAAGAGACUGAAGAAGAAGUUCAAGACACGCGUCUUCACCAUCACCAUCACCAU

CACCAUCACCAUUAA

SEQ ID NO: 16

(SEQ ID NO: 16)

<u>*AUGGCCACUGGAUCAAGAACCUCACUGCUGCUCGCUUUUGGACUGCUUUGCCUGCCCUGGU*</u>

<u>*UGCAAGAAGGAUCGGCUUUCCCGACCAUCCCACUCUCC*</u>AUGCAGCGGUCCCCGCUCGAAAA

GGCCAGUGUCGUGUCCAAACUCUUCUUCUCAUGGACUCGCCUAUCCUUAGAAAGGGGUA

UCGGCAGAGGCUUGAGUUGUCUGACAUCUACCAGAUCCCCUCGGUAGAUUCGGCGGAUAA

CCUCUCGGAGAAGCUCGAACGGGAAUGGGACCGCGAACUCGCGUCUAAGAAAAACCCGAA

GCUCAUCAACGCACUGAGAAGGUGCUUCUUCGGCGGUUCAUGUUCUACGGUAUCUUCUU

GUAUCUCGGGGAGGUCACAAAAGCAGUCCAACCCCUGUUGUUGGGUCGCAUUAUCGCCUC

GUACGACCCCGAUAACAAAGAAGAACGGAGCAUCGCGAUCUACCUCGGGAUCGGACUGUG

-continued

```
UUUGCUUUCAUCGUCAGAACACUUUUGUUGCAUCCAGCAAUCUUCGGCCUCCAUCACAU
CGGUAUGCAGAUGCGAAUCGCUAUGUUUAGCUUGAUCUACAAAAAGACACUGAAACUCU
CGUCGCGGGUGUUGGAUAAGAUUUCCAUCGGUCAGUUGGUGUCCCUGCUUAGUAAUAAC
CUCAACAAAUUCGAUGAGGGACUGGCGCUGGCACAUUUCGUGUGGAUUGCCCCGUUGCAA
GUCGCCCUUUUGAUGGGCCUUAUUUGGGAGCUGUUGCAGGCAUCUGCCUUUUGUGGCCU
GGGAUUUCUGAUUGUGUUGGCAUUGUUUCAGGCUGGGCUUGGGCGGAUGAUGAUGAAGU
AUCGCGACCAGAGAGCGGGUAAAAUCUCGGAAAGACUCGUCAUCACUUCGGAAAUGAUC
GAAAACAUCCAGUCGGUCAAAGCCUAUUGCUGGGAAGAAGCUAUGGAGAAGAUGAUUGA
AAACCUCCGCCAAACUGAGCUGAAACUGACCCGCAAGGCGGCGUAUGUCCGGUAUUUCAA
UUCGUCAGCGUUCUUCUUUUCCGGGUUCUUCGUUGUCUUUCUCUCGGUUUUGCCUUAUGC
CUUGAUUAAGGGGAUUAUCCUCCGCAAGAUUUUCACCACGAUUUCGUUCUGCAUUGUAU
UGCGCAUGGCAGUGACACGGCAAUUUCCGUGGGCCGUGCAGACAUGGUAUGACUCGCUUG
GAGCGAUCAACAAAAUCCAAGACUUCUUGCAAAAGCAAGAGUACAAGACCCUGGAGUAC
AAUCUUACUACUACGGAGGUAGUAAUGGAGAAUGUGACGGCUUUUUGGGAAGAGGGUUU
UGGAGAACUGUUUGAGAAAGCAAAGCAGAAUAACAACAACCGCAAGACCUCAAAUGGGG
ACGAUUCCCUGUUUUCUCGAACUUCUCCCUGCUCGGAACACCCGUGUUGAAGGACAUCA
AUUUCAAGAUUGAGAGGGGACAGCUUCUCGCGGUAGCGGGAAGCACUGGUGCGGGAAAA
ACUAGCCUCUUGAUGGUGAUUAUGGGGGAGCUUGAGCCCAGCGAGGGGAAGAUUAAACA
CUCCGGGCGUAUCUCAUUCUGUAGCCAGUUUCAUGGAUCAUGCCCGGAACCAUUAAAGA
GAACAUCAUUUUCGGAGUAUCCUAUGAUGAGUACCGAUACAGAUCGGUCAUUAAGGCGU
GCCAGUUGGAAGAGGACAUUUCUAAGUUCGCCGAGAAGGAUAACAUCGUCUUGGGAGAA
GGGGGUAUUACAUUGUCGGAGGGCAGCGAGCGCGGAUCAGCCUCGCGAGAGCGGUAUA
CAAAGAUGCAGAUUUGUAUCUGCUUGAUUCACCGUUUGGAUACCUCGACGUAUUGACAG
AAAAAGAAAUCUUCGAGUCGUGCGUGUGUAAACUUAUGGCUAAUAAGACGAGAAUCCUG
GUGACAUCAAAAAUGGAACACCUUAAGAAGGCGGACAAGAUCCUGAUCCUCCACGAAGG
AUCGUCCUACUUUUACGGCACUUUCUCAGAGUUGCAAAACUUGCAGCCGGACUUCUCAAG
CAAACUCAUGGGGUGUGACUCAUUCGACCAGUUCAGCGCGGAACGGCGGAACUCGAUCUU
GACGGAAACGCUGCACCGAUUCUCGCUUGAGGGUGAUGCCCCGGUAUCGUGGACCGAGAC
AAAGAAGCAGUCGUUUAAGCAGACAGGAGAAUUUGGUGAGAAAAGAAAGAACAGUAUCU
UGAAUCCUAUUAACUCAAUUCGCAAGUUCUCAAUCGUCCAGAAAACUCCACUGCAGAUGA
AUGGAAUUGAAGAGGAUUCGGACGAACCCCUGGAGCGCAGGCUUAGCCUCGUGCCGGAU
UCAGAGCAAGGGGAGGCCAUUCUUCCCCGGAUUUCGGUGAUUUCAACCGGACCUACACUU
CAGGCGAGGCGAAGGCAAUCCGUGCUCAACCUCAUGACGCAUUCGGUAAACCAGGGGCAA
AACAUUCACCGCAAAACGACGGCCUCAACGAGAAAAGUGUCACUUGCACCCCAGGCGAAU
UUGACUGAACUCGACAUCUACAGCCGUAGGCUUUCGCAAGAAACCGGACUUGAGAUCAGC
GAAGAAAUCAAUGAAGAAGAUUUGAAAGAGUGUUUCUUUGAUGACAUGGAAUCAAUCCC
AGCGGUGACAACGUGGAACACAUACUUGCGUUACAUCACGGUGCACAAGUCCUUGAUUU
UCGUCCUCAUCUGGUGUCUCGUGAUCUUUCUCGCUGAGGUCGCAGCGUCACUUGUGGUCC
UCUGGCUGCUUGGUAAUACGCCCUUGCAAGACAAAGGCAAUUCUACACACUCAAGAAACA
AUUCCUAUGCCGUGAUUAUCACUUCUACAAGCUCGUAUUACGUGUUUUACAUCUACGUA
GGAGUGGCCGACACUCUGCUCGCGAUGGGUUUCUUCCGAGGACUCCCACUCGUUCACACG
```

-continued

CUUAUCACUGUCUCCAAGAUUCUCCACCAUAAGAUGCUUCAUAGCGUACUGCAGGCUCCC
AUGUCCACCUUGAAUACGCUCAAGGCGGGAGGUAUUUUGAAUCGCUUCUCAAAAGAUAU
UGCAAUUUUGGAUGACCUUCUGCCCCUGACGAUCUUCGACUUCAUCCAGUUGUUGCUGAU
CGUGAUUGGGGCUAUUGCAGUAGUCGCUGUCCUCCAGCCUUACAUUUUUGUCGCGACCGU
UCCGGUGAUCGUGGCGUUUAUCAUGCUGCGGGCCUAUUUCUUGCAGACGUCACAGCAGCU
UAAGCAACUGGAGUCUGAAGGGAGGUCGCCUAUCUUUACGCAUCUUGUGACCAGUUUGA
AGGGAUUGUGGACGUUGCGCGCCUUUGGCAGGCAGCCCUACUUUGAAACACUGUUCCACA
AAGCGCUGAAUCUCCAUACGGCAAAUUGGUUUUUGUAUUUGAGUACCCUCCGAUGGUUU
CAGAUGCGCAUUGAGAUGAUUUUUGUGAUCUUCUUUAUCGCGGUGACUUUUAUCUCCAU
CUUGACCACGGGAGAGGGCGAGGGACGGGUCGGUAUUAUCCUGACACUCGCCAUGAACAU
UAUGAGCACUUUGCAGUGGGCAGUGAACAGCUCGAUUGAUGUGGAUAGCCUGAUGAGGU
CCGUUUCGAGGGUCUUUAAGUUCAUCGACAUGCCGACGGAGGGAAAGCCCACAAAAAGU
ACGAAACCCUAUAAGAAUGGGCAAUUGAGUAAGGUAAUGAUCAUCGAGAACAGUCACGU
GAAGAAGGAUGACAUCUGGCCUAGCGGGGGUCAGAUGACCGUGAAGGACCUGACGGCAA
AAUACACCGAGGGAGGGAACGCAAUCCUUGAAAACAUCUCGUUCAGCAUUAGCCCCGGUC
AGCGUGUGGGGUUGCUCGGGAGGACCGGGUCAGGAAAAUCGACGUUGCUGUCGGCCUUC
UUGAGACUUCUGAAUACAGAGGGUGAGAUCCAGAUCGACGGCGUUUCGUGGGAUAGCAU
CACCUUGCAGCAGUGGCGGAAAGCGUUUGGAGUAAUCCCCCAAAAGGUCUUUAUCUUUA
GCGGAACCUUCCGAAAGAAUCUCGAUCCUUAUGAACAGUGGUCAGAUCAAGAGAUUUGG
AAAGUCGCGGACGAGGUUGGCCUUCGGAGUGUAAUCGAGCAGUUUCCGGGAAAACUCGA
CUUUGUCCUUGUAGAUGGGGAUGCGUCCUGUCGCAUGGGCACAAGCAGCUCAUGUGCCU
GGCGCGAUCCGUCCUCUCUAAAGCGAAAAUUCUUCUCUUGGAUGAACCUUCGGCCCAUCU
GGACCCGGUAACGUAUCAGAUCAUCAGAAGGACAUUAAGCAGGCGUUUGCCGACUGCAC
GGUGAUUCUCUGUGAGCAUCGUAUCGAGGCCAUGCUCGAAUGCCAGCAAUUUCUUGUCA
UCGAAGAGAAUAAGGUCCGCCAGUACGACUCCAUCCAGAAGCUGCUUAAUGAGAGAUCA
UUGUUCCGGCAGGCGAUUUCACCAUCCGAUAGGGUGAAACUUUUUCCACACAGAAAUUCG
UCGAAGUGCAAGUCCAAACCGCAGAUCGCGGCCUUGAAAGAAGAGACUGAAGAAGAAGU
UCAAGACACGCGUCUUUAA

SEQ ID NO: 17
(SEQ ID NO: 17)
AUGCAGCGGUCCCCGCUCGAAAAGGCCAGUGUCGUGUCCAAACUCUUCUUCUCAUGGACU
CGGCCUAUCCUUAGAAAGGGGUAUCGGCAGAGGCUUGAGUUGUCUGACAUCUACCAGAU
CCCCUCGGUAGAUUCGGCGGAUAACCUCUCGGAGAAGCUCGAACGGGAAUGGGACCGCGA
ACUCGCGUCUAAGAAAAACCCGAAGCUCAUCAACGCACUGAGAAGGUGCUUCUUCUGGCG
GUUCAUGUUCUACGGUAUCUUCUUGUAUCUCGGGGAGGUCACAAAAGCAGUCCAACCCCU
GUUGUUGGGUCGCAUUAUCGCCUCGUACGACCCCGAUAACAAAGAAGAACGGAGCAUCGC
GAUCUACCUCGGGAUCGGACUGUGUUUGCUUUUCAUCGUCAGAACACUUUUGUUGCAUCC
AGCAAUCUUCGGCCUCCAUCACAUCGGUAUGCAGAUGCGAAUCGCUAUGUUUAGCUUGAU
CUACAAAAAGACACUGAAACUCUCGUCGCGGGUGUUGGAUAAGAUUUCCAUCGGUCAGU
UGGUGUCCCUGCUUAGUAAUAACCUCAACAAAUUCGAUGAGGGACUGGCGCUGGCACAU
UUCGUGUGGAUUGCCCCGUUGCAAGUCGCCCUUUUGAUGGGCCUUAUUUGGGAGCUGUU
GCAGGCAUCUGCCUUUUGUGGCCUGGGAUUUCUGAUUGUGUUGGCAUUGUUUCAGGCUG

-continued

GGCUUGGGCGGAUGAUGAUGAAGUAUCGCGACCAGAGAGCGGGUAAAAUCUCGGAAAGA

CUCGUCAUCACUUCGGAAAUGAUCGAAAACAUCCAGUCGGUCAAAGCCUAUUGCUGGGAA

GAAGCUAUGGAGAAGAUGAUUGAAAACCUCCGCCAAACUGAGCUGAAACUGACCCGCAA

GGCGGCGUAUGUCCGGUAUUUCAAUUCGUCAGCGUUCUUCUUUUCCGGGUUCUUCGUUG

UCUUUCUCUCGGUUUUGCCUUAUGCCUUGAUUAAGGGGAUUAUCCUCCGCAAGAUUUUC

ACCACGAUUUCGUUCUGCAUUGUAUUGCGCAUGGCAGUGACACGGCAAUUUCCGUGGGCC

GUGCAGACAUGGUAUGACUCGCUUGGAGCGAUCAACAAAAUCCAAGACUUCUUGCAAAA

GCAAGAGUACAAGACCCUGGAGUACAAUCUUACUACUACGGAGGUAGUAAUGGAGAAUG

UGACGGCUUUUUGGGAAGAGGGUUUUGGAGAACUGUUUGAGAAAGCAAAGCAGAAUAAC

AACAACCGCAAGACCUCAAAUGGGGACGAUUCCCUGUUUUUCUCGAACUUCUCCCUGCUC

GGAACACCCGUGUUGAAGGACAUCAAUUUCAAGAUUGAGAGGGGACAGCUUCUCGCGGU

AGCGGGAAGCACUGGUGCGGGAAAAACUAGCCUCUUGAUGGUGAUUAUGGGGGAGCUUG

AGCCCAGCGAGGGGAAGAUUAAACACUCCGGGCGUAUCUCAUUCUGUAGCCAGUUUUCAU

GGAUCAUGCCCGGAACCAUUAAAGAGAACAUCAUUUUCGGAGUAUCCUAUGAUGAGUAC

CGAUACAGAUCGGUCAUUAAGGCGUGCCAGUUGGAAGAGGACAUUUCUAAGUUCGCCGA

GAAGGAUAACAUCGUCUUGGGAGAAGGGGGUAUUACAUUGUCGGGAGGGCAGCGAGCGC

GGAUCAGCCUCGCGAGAGCGGUAUACAAAGAUGCAGAUUUGUAUCUGCUUGAUUCACCG

UUUGGAUACCUCGACGUAUUGACAGAAAAAGAAAUCUUCGAGUCGUGCGUGUGUAAACU

UAUGGCUAAUAAGACGAGAAUCCUGGUGACAUCAAAAAUGGAACACCUUAAGAAGGCGG

ACAAGAUCCUGAUCCUCCACGAAGGAUCGUCCUACUUUUACGGCACUUUCUCAGAGUUGC

AAAACUUGCAGCCGGACUUCUCAAGCAAACUCAUGGGGUGUGACUCAUUCGACCAGUUCA

GCGCGGAACGGCGGAACUCGAUCUUGACGGAAACGCUGCACCGAUUCUCGCUUGAGGGUG

AUGCCCCGGUAUCGUGGACCGAGACAAAGAAGCAGUCGUUUAAGCAGACAGGAGAAUUU

GGUGAGAAAAGAAAGAACAGUAUCUUGAAUCCUAUUAACUCAAUUCGCAAGUUCUCAAU

CGUCCAGAAAACUCCACUGCAGAUGAAUGGAAUUGAAGAGGAUUCGGACGAACCCCUGG

AGCGCAGGCUUAGCCUCGUGCCGGAUUCAGAGCAAGGGGAGGCCAUUCUUCCCCGGAUUU

CGGUGAUUUCAACCGGACCUACACUUCAGGCGAGGCGAAGGCAAUCCGUGCUCAACCUCA

UGACGCAUUCGGUAAACCAGGGGCAAAACAUUCACCGCAAAACGACGGCCUCAACGAGAA

AAGUGUCACUUGCACCCCAGGCGAAUUUGACUGAACUCGACAUCUACAGCCGUAGGCUUU

CGCAAGAAACCGGACUUGAGAUCAGCGAAGAAAUCAAUGAAGAAGAUUUGAAAGAGUGU

UUCUUUGAUGACAUGGAAUCAAUCCCAGCGGUGACAACGUGGAACACAUACUUGCGUUA

CAUCACGGUGCACAAGUCCUUGAUUUUCGUCCUCAUCGGUGUCUCGUGAUCUUUCUCGC

UGAGGUCGCAGCGUCACUUGUGGUCCUCUGGCUGCUUGGUAAUACGCCCUUGCAAGACAA

AGGCAAUUCUACACACUCAAGAAACAAUUCCUAUGCCGUGAUUAUCACUUCUACAAGCUC

GUAUUACGUGUUUACAUCUACGUAGGAGUGGCCGACACUCUGCUCGCGAUGGGUUUCU

UCCGAGGACUCCCACUCGUUCACACGCUUAUCACUGUCUCCAAGAUUCUCCACCAUAAGA

UGCUUCAUAGCGUACUGCAGGCUCCCAUGUCCACCUUGAAUACGCUCAAGGCGGGAGGUA

UUUUGAAUCGCUUCUCAAAAGAUAUUGCAAUUUUGGAUGACCUUCUGCCCCUGACGAUC

UUCGACUUCAUCCAGUUGUUGCUGAUCGUGAUUGGGCUAUUGCAGUAGUCGCUGUCCU

CCAGCCUUACAUUUUUGUCGCGACCGUUCCGGUGAUCGUGGCGUUUAUCAUGCUGCGGGC

CUAUUUCUUGCAGACGUCACAGCAGCUUAAGCAACUGGAGUCUGAAGGGAGGUCGCCUA

-continued

UCUUUACGCAUCUUGUGACCAGUUUGAAGGGAUUGUGGACGUUGCGCGCCUUUGGCAGG

CAGCCCUACUUUGAAACACUGUUCCACAAAGCGCUGAAUCUCCAUACGGCAAAUUGGUUU

UUGUAUUUGAGUACCCUCCGAUGGUUUCAGAUGCGCAUUGAGAUGAUUUUUGUGAUCUU

CUUUAUCGCGGUGACUUUUAUCUCCAUCUUGACCACGGGAGAGGGCGAGGGACGGGUCG

GUAUUAUCCUGACACUCGCCAUGAACAUUAUGAGCACUUUGCAGUGGGCAGUGAACAGC

UCGAUUGAUGUGGAUAGCCUGAUGAGGUCCGUUUCGAGGGUCUUUAAGUUCAUCGACAU

GCCGACGGAGGGAAAGCCCACAAAAAGUACGAAACCCUAUAAGAAUGGGCAAUGAGUA

AGGUAAUGAUCAUCGAGAACAGUCACGUGAAGAAGGAUGACAUCUGGCCUAGCGGGGGU

CAGAUGACCGUGAAGGACCUGACGGCAAAAUACACCGAGGGAGGGAACGCAAUCCUUGA

AAACAUCUCGUUCAGCAUUAGCCCCGGUCAGCGUGUGGGGUUGCUCGGGAGGACCGGGUC

AGGAAAAUCGACGUUGCUGUCGGCCUUCUUGAGACUUCUGAAUACAGAGGGUGAGAUCC

AGAUCGACGGCGUUUCGUGGGAUAGCAUCACCUUGCAGCAGUGGCGGAAAGCGUUUGGA

GUAAUCCCCCAAAAGGUCUUUAUCUUUAGCGGAACCUUCCGAAAGAAUCUCGAUCCUUAU

GAACAGUGGUCAGAUCAAGAGAUUUGGAAAGUCGCGGACGAGGUUGGCCUUCGGAGUGU

AAUCGAGCAGUUUCCGGGAAAACUCGACUUUGUCCUUGUAGAUGGGGAUGCGUCCUGU

CGCAUGGGCACAAGCAGCUCAUGUGCCUGGCGCGAUCCGUCCUCUCUAAAGCGAAAAUUC

UUCUCUUGGAUGAACCUUCGGCCCAUCUGGACCCGGUAACGUAUCAGAUCAUCAGAAGGA

CACUUAAGCAGGCGUUUGCCGACUGCACGGUGAUUCUCUGUGAGCAUCGUAUCGAGGCCA

UGCUCGAAUGCCAGCAAUUUCUUGUCAUCGAAGAGAAUAAGGUCCGCCAGUACGACUCCA

UCCAGAAGCUGCUUAAUGAGAGAUCAUUGUUCCGGCAGGCGAUUUCACCAUCCGAUAGG

GUGAAACUUUUUCCACACAGAAAUUCGUCGAAGUGCAAGUCCAAACCGCAGAUCGCGGCC

UUGAAAGAAGAGACUGAAGAAGAAGUUCAAGACACGCGUCUUUAA

SEQ ID NO: 18

(SEQ ID NO: 18)
AUGGCCACUGGAUCAAGAACCUCACUGCUGCUCGCUUUUGGACUGCUUUGCCUGC

CCUGGUUGCAAGAAGGAUCGGCUUUCCCGACCAUCCCACUCUCC

SEQ ID NO: 19

(SEQ ID NO: 19)
AUGGCAACUGGAUCAAGAACCUCCCUCCUGCUCGCAUUCGGCCUGCUCUGUCUCC

CAUGGCUCCAAGAAGGAAGCGCGUUCCCCACUAUCCCCCUCUCG

SEQ ID NO: 20
CGGGUGGCAUCCCUGUGACCCUCCCCAGUGCCUCUCCUGGCCCUGGAAGUUGCC

ACUCCAGUGCCCACCAGCCUUGUCCUAAUAAAAUUAAGUUGCAUCAAGCU

EQUIVALENTS

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches. The recitation of series of numbers with differing amounts of significant digits in the specification is not to be construed as implying that numbers with fewer significant digits given have the same precision as numbers with more significant digits given.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or."

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method of producing cystic fibrosis transmembrane conductance regulator (CFTR) protein in a lung of a mammal, the method comprising:

administering to the lung of the mammal by aerosolization a composition comprising an mRNA-loaded nanoparticle, wherein the nanoparticle is a liposome, wherein the mRNA is an in vitro transcribed mRNA and has a coding sequence at least 80% identical to SEQ ID NO: 3, wherein the mRNA encodes a human CFTR protein comprising the amino acid sequence of SEQ ID NO:1, and wherein the mRNA is unmodified.

2. The method of claim 1, wherein the mRNA has the coding sequence at least 90% identical to SEQ ID NO: 3.

3. The method of claim 1, wherein the mRNA has the coding sequence 100% identical to SEQ ID NO: 3.

4. The method of claim 1, wherein the mRNA comprises a 5' untranslated region (UTR) and/or a 3' UTR.

5. The method of claim 4, wherein the 5'-UTR comprises SEQ ID NO: 4 and/or the 3'-UTR comprises SEQ ID NO: 5.

6. The method of claim 4, wherein the mRNA further comprises a poly-A tail.

7. The method of claim 6, wherein the poly-A tail is of at least 70, 100, 120, 150, 200, or 250 residues in length.

8. The method of claim 4, wherein the mRNA further comprises a 5' cap.

9. The method of claim 1, wherein the aerosolization is nebulization.

10. The method of claim 1, wherein the human CFTR protein is expressed in the epithelial cells of the lung.

11. The method of claim 1, wherein the composition further comprises a pharmaceutically acceptable carrier.

12. The method of claim 1, wherein the liposome comprises one or more PEGylated lipids.

13. The method of claim 1, wherein the liposome further comprises one or more cationic lipids and one or more non-cationic lipids.

* * * * *